United States Patent
Rusche et al.

(10) Patent No.: US 9,796,664 B2
(45) Date of Patent: Oct. 24, 2017

(54) COMPOSITIONS INCLUDING 6-AMINOHEXANOIC ACID DERIVATIVES AS HDAC INHIBITORS

(71) Applicant: BIOMARIN PHARMACEUTICAL INC., Novato, CA (US)

(72) Inventors: James R. Rusche, Framingham, MA (US); Norton P. Peet, North Andover, MA (US); Allen Hopper, Katonah, NY (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 0 days.

(21) Appl. No.: 14/993,621

(22) Filed: Jan. 12, 2016

(65) Prior Publication Data

US 2016/0122290 A1  May 5, 2016

Related U.S. Application Data

(63) Continuation of application No. 13/062,030, filed as application No. PCT/US2009/055952 on Sep. 3, 2009, now Pat. No. 9,265,734.

(Continued)

(51) Int. Cl.
| | |
|---|---|
| A61K 31/166 | (2006.01) |
| C07C 233/80 | (2006.01) |
| A61K 31/00 | (2006.01) |
| A61K 31/16 | (2006.01) |
| C07C 235/16 | (2006.01) |
| C07C 237/22 | (2006.01) |
| C07C 255/57 | (2006.01) |
| C07C 311/16 | (2006.01) |
| C07C 311/19 | (2006.01) |
| C07C 317/44 | (2006.01) |
| C07C 323/62 | (2006.01) |
| C07D 209/48 | (2006.01) |
| C07D 213/30 | (2006.01) |
| C07D 231/56 | (2006.01) |
| C07D 277/56 | (2006.01) |
| C07D 295/14 | (2006.01) |
| C07D 307/84 | (2006.01) |
| C07D 409/12 | (2006.01) |
| C07D 213/81 | (2006.01) |
| C07D 217/24 | (2006.01) |
| C07D 231/12 | (2006.01) |
| C07D 237/24 | (2006.01) |
| C07D 241/24 | (2006.01) |
| C07D 241/44 | (2006.01) |
| C07D 271/12 | (2006.01) |
| C07D 295/15 | (2006.01) |
| C07D 307/85 | (2006.01) |
| C07D 333/38 | (2006.01) |

(52) U.S. Cl.
CPC ............ *C07C 233/80* (2013.01); *A61K 31/00* (2013.01); *A61K 31/16* (2013.01); *C07C 235/16* (2013.01); *C07C 237/22* (2013.01); *C07C 255/57* (2013.01); *C07C 311/16* (2013.01); *C07C 311/19* (2013.01); *C07C 317/44* (2013.01); *C07C 323/62* (2013.01); *C07D 209/48* (2013.01); *C07D 213/30* (2013.01); *C07D 213/81* (2013.01); *C07D 217/24* (2013.01); *C07D 231/12* (2013.01); *C07D 231/56* (2013.01); *C07D 237/24* (2013.01); *C07D 241/24* (2013.01); *C07D 241/44* (2013.01); *C07D 271/12* (2013.01); *C07D 277/56* (2013.01); *C07D 295/14* (2013.01); *C07D 295/15* (2013.01); *C07D 307/84* (2013.01); *C07D 307/85* (2013.01); *C07D 333/38* (2013.01); *C07D 409/12* (2013.01); *C07C 2601/02* (2017.05); *C07C 2601/14* (2017.05)

(58) Field of Classification Search
CPC .............................. A61K 31/16; A61K 31/166
USPC .................................................. 514/616, 617
See application file for complete search history.

(56) References Cited

U.S. PATENT DOCUMENTS

| | | | |
|---|---|---|---|
| 4,855,442 | A | 8/1989 | Lee et al. |
| 6,710,060 | B2 | 3/2004 | Yamamoto et al. |

(Continued)

FOREIGN PATENT DOCUMENTS

| | | |
|---|---|---|
| CN | 1632700 A | 6/2005 |
| CN | 101648922 A | 2/2010 |

(Continued)

OTHER PUBLICATIONS

Alberini, Transcription factors in long-term memory and synaptic plasticity. *Physiol Rev.* 89: 121-45 (2009).

(Continued)

*Primary Examiner* — Yong Chu
*Assistant Examiner* — Sonya Wright
(74) *Attorney, Agent, or Firm* — Marshall Gerstein & Borun LLP

(57) ABSTRACT

This invention relates to compounds of Formula (I) wherein $Cy^1$, $L^1$, Y, $R^1$, $L^2$, and Ar2 are defined herein, for the treatment of cancers, inflammatory disorders, and neurological conditions.

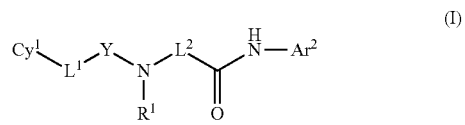

(I)

19 Claims, 4 Drawing Sheets

Related U.S. Application Data

(60) Provisional application No. 61/112,556, filed on Nov. 7, 2008, provisional application No. 61/093,927, filed on Sep. 3, 2008.

(56) References Cited

U.S. PATENT DOCUMENTS

| | | |
|---|---|---|
| 8,329,946 B2 | 12/2012 | Schreiber et al. |
| 2004/0029885 A1 | 2/2004 | Bauer et al. |
| 2004/0106599 A1 | 6/2004 | Delorme et al. |
| 2004/0142859 A1 | 7/2004 | Steffan et al. |
| 2004/0147569 A1 | 7/2004 | Suzuki et al. |
| 2005/0215601 A1 | 9/2005 | Aono et al. |
| 2006/0166990 A1 | 7/2006 | Ottosen et al. |
| 2007/0049603 A1 | 3/2007 | Miknis et al. |
| 2009/0306077 A1 | 12/2009 | Mogi et al. |
| 2010/0056522 A1 | 3/2010 | Yoneda et al. |
| 2010/0063045 A1 | 3/2010 | Mogi et al. |
| 2010/0196502 A1 | 8/2010 | Kozikowski et al. |
| 2010/0298358 A1 | 11/2010 | Lu et al. |
| 2013/0317003 A1 | 11/2013 | Jacques et al. |

FOREIGN PATENT DOCUMENTS

| | | |
|---|---|---|
| EP | 1390491 B1 | 7/2008 |
| IT | 2007RM0038 | 7/2008 |
| JP | 11269140 | 10/1999 |
| JP | 11269146 | 10/1999 |
| JP | 11302173 | 11/1999 |
| JP | 2000256194 A | 9/2000 |
| JP | 2003137866 A | 5/2003 |
| JP | 2004035485 A | 2/2004 |
| JP | 2007001885 A | 1/2007 |
| KR | 2010117391 | 11/2010 |
| WO | WO-00/35877 A1 | 6/2000 |
| WO | WO-01/38322 A1 | 5/2001 |
| WO | WO-02/18335 A1 | 3/2002 |
| WO | WO-02/090534 A1 | 11/2002 |
| WO | WO-03/011851 | 2/2003 |
| WO | WO-03/013484 A2 | 2/2003 |
| WO | WO-03/024448 A2 | 3/2003 |
| WO | WO-03/076422 A1 | 9/2003 |
| WO | WO-03/087057 A1 | 10/2003 |
| WO | WO-03/092686 A1 | 11/2003 |
| WO | WO-2004/005513 A2 | 1/2004 |
| WO | WO-2004/035525 A1 | 4/2004 |
| WO | WO-2004/039318 A2 | 5/2004 |
| WO | WO-2004/041273 A1 | 5/2004 |
| WO | WO-2004/052838 A1 | 6/2004 |
| WO | WO-2004/058234 A2 | 7/2004 |
| WO | WO-2004/069133 A2 | 8/2004 |
| WO | WO-2004/069823 A1 | 8/2004 |
| WO | WO-2004/071400 A2 | 8/2004 |
| WO | WO-2004/072068 A1 | 8/2004 |
| WO | WO-2004/087693 A1 | 10/2004 |
| WO | WO-2005/002552 A2 | 1/2005 |
| WO | WO-2005/003127 A1 | 1/2005 |
| WO | WO-2005/030144 A2 | 4/2005 |
| WO | WO-2005/030704 A1 | 4/2005 |
| WO | WO-2005/030705 A1 | 4/2005 |
| WO | WO-2005/035551 A2 | 4/2005 |
| WO | WO-2005/055928 A2 | 6/2005 |
| WO | WO-2005/058803 A1 | 6/2005 |
| WO | WO-2005/087724 A2 | 9/2005 |
| WO | WO-2005/092899 A1 | 10/2005 |
| WO | WO-2005/121073 A1 | 12/2005 |
| WO | WO-2006/001958 A2 | 1/2006 |
| WO | WO-2006/005955 A1 | 1/2006 |
| WO | WO-2006/014618 A2 | 2/2006 |
| WO | WO-2006/033943 A2 | 3/2006 |
| WO | WO-2006/062580 A1 | 6/2006 |
| WO | WO-2006/065703 A1 | 6/2006 |
| WO | WO-2006/066133 A2 | 6/2006 |
| WO | WO-2006/070192 A1 | 7/2006 |
| WO | WO-2006/097474 A1 | 9/2006 |
| WO | WO-2006/102760 A1 | 10/2006 |
| WO | WO-2006/104983 A1 | 10/2006 |
| WO | WO-2006/105979 A1 | 10/2006 |
| WO | WO-2006/115845 A1 | 11/2006 |
| WO | WO-2006/122319 A2 | 11/2006 |
| WO | WO-2007/002248 A2 | 1/2007 |
| WO | WO-2007/011626 A2 | 1/2007 |
| WO | WO-2007/022638 A1 | 3/2007 |
| WO | WO-2007/039403 A1 | 4/2007 |
| WO | WO-2007/039404 A1 | 4/2007 |
| WO | WO-2007/044565 A2 | 4/2007 |
| WO | WO-2007/045844 A1 | 4/2007 |
| WO | WO-2007/055942 A2 | 5/2007 |
| WO | WO-2007/058927 A1 | 5/2007 |
| WO | WO-2007/061880 A1 | 5/2007 |
| WO | WO-2007/082873 A1 | 7/2007 |
| WO | WO-2007/082874 A1 | 7/2007 |
| WO | WO-2007/082876 A1 | 7/2007 |
| WO | WO-2007/082878 A1 | 7/2007 |
| WO | WO-2007/082882 A1 | 7/2007 |
| WO | WO-2007/084390 A2 | 7/2007 |
| WO | WO-2007/087129 A2 | 8/2007 |
| WO | WO-2007/087130 A2 | 8/2007 |
| WO | WO-2007/100657 A2 | 9/2007 |
| WO | WO-2007/113289 A1 | 10/2007 |
| WO | WO-2007/118137 A1 | 10/2007 |
| WO | WO-2007/136605 A2 | 11/2007 |
| WO | WO-2008/006793 A1 | 1/2008 |
| WO | WO-2008/010985 A2 | 1/2008 |
| WO | WO-2008010985 | * 1/2008 |
| WO | WO-2008/033743 A1 | 3/2008 |
| WO | WO-2008/033747 A2 | 3/2008 |
| WO | WO-2008/074132 A1 | 6/2008 |
| WO | WO-2008/084218 A1 | 7/2008 |
| WO | WO-2008/089436 A2 | 7/2008 |
| WO | WO-2008/109994 A1 | 9/2008 |
| WO | WO-2008/112913 A1 | 9/2008 |
| WO | WO-2008/113255 A1 | 9/2008 |
| WO | WO-2008122115 A1 | 10/2008 |
| WO | WO-2009/002495 A1 | 12/2008 |
| WO | WO-2009/002534 A1 | 12/2008 |
| WO | WO-2009/004427 A2 | 1/2009 |
| WO | WO-2009/015237 A1 | 1/2009 |
| WO | WO-2009/020589 A1 | 2/2009 |
| WO | WO-2009/024825 A1 | 2/2009 |
| WO | WO-2009/025785 A2 | 2/2009 |
| WO | WO-2009/027746 A1 | 3/2009 |
| WO | WO-2009/033281 A1 | 3/2009 |
| WO | WO-2009/036057 A1 | 3/2009 |
| WO | WO-2009/037001 A2 | 3/2009 |
| WO | WO-2009/045440 A1 | 4/2009 |
| WO | WO-2009/053808 A2 | 4/2009 |
| WO | WO-2009/063054 A1 | 5/2009 |
| WO | WO-2009/079391 A1 | 6/2009 |
| WO | WO-2009/086012 A1 | 7/2009 |
| WO | WO-2009/112522 A1 | 9/2009 |
| WO | WO-2009/156484 A2 | 12/2009 |
| WO | WO-2010/009139 A2 | 1/2010 |
| WO | WO-2010/009155 A2 | 1/2010 |
| WO | WO-2010/009166 A1 | 1/2010 |
| WO | WO-2010/014611 A1 | 2/2010 |
| WO | WO-2010/028192 A1 | 3/2010 |
| WO | WO-2010/028213 A2 | 3/2010 |
| WO | WO-2010/031708 A2 | 3/2010 |
| WO | WO-2010/038081 A2 | 4/2010 |
| WO | WO-2010/043953 A2 | 4/2010 |
| WO | WO-2010/049182 A2 | 5/2010 |
| WO | WO-2010/094678 A1 | 8/2010 |
| WO | WO-2010/126811 A1 | 11/2010 |
| WO | WO-2010/126851 A1 | 11/2010 |
| WO | WO-2010/127152 A2 | 11/2010 |
| WO | WO-2010/131922 A2 | 11/2010 |
| WO | WO-2010/144371 A1 | 12/2010 |
| WO | WO-2010/144378 A2 | 12/2010 |

(56) References Cited

FOREIGN PATENT DOCUMENTS

| WO | WO-2012/016081 A2 | 2/2012 |
|---|---|---|
| WO | WO-2012/118782 A1 | 9/2012 |

OTHER PUBLICATIONS

Archin et al., Administration of vorinostat disrupts HIV-1 latency in patients on antiretroviral therapy. *Nature*, 487(7408): 482-5 (2012).
Ashton et al., New low-density lipoprotein receptor upregulators acting via a novel mechanism. *J. Med. Chem.* 39(17): 3343-56 (1996).
Bayomi, Synthesis and ring transformation of pyrrolo[2,3-d][1,3]oxazine to pyrrolo[2,3-d]pyrimidines. *Arch. Pharm Res.* 13(1): 97-100 (1990).
Bayomi, Synthesis and ring transformation of pyrrolo[2,3-d][1,3]oxazine to pyrrolo[2,3-d]pyrimidines. *J. Chinese Chem. Soc.* 39(1): 101-4 (1992).
Blackwell et al., Decoding products of diversity pathways from stock solutions derived from single polymeric macrobeads. *Angew. Chem. Int. Ed.* 40(18): 3421-5 (2001).
Blazkovaj et al., Effect of histone deacetylase inhibitors on HIV production in latently infected, resting CD4(+) T cells from infected individuals receiving effective antiretroviral therapy. *J. Infect. Dis.* 206(5): 765-9 (2012).
Boev et al., Synthesis of new polydentate tweezers ligands of amido-amine type. *Russian J. Org. Chem.* 43(2): 297-304 (2007).
Campuzano et al., Friedreich's ataxia: Autosomal recessive disease caused by an intronic GAA triplet repeat expansion. *Science*, 271: 1423-7 (1996).
CAS Science IP, Search Report dated Dec. 17, 2010, 125 pages.
CAS Science IP, Search Report dated Dec. 17, 2010, 97 pages.
CAS Science IP, Search Report dated Dec. 20, 2010, 284 pages.
CAS Science IP, Search Report dated Dec. 22, 2010, 860 pages.
Charles et al., Synthesis of substituted benzamides and benzimidazoles as anthelmintic and antimicrobial agents. *Pharmazie*, 37(6): 413-5 (1982).
Charrier et al., Antiproliferative activities of a library of hybrids between indanones and HDAC inhibitor SAHA and MS-275 analogues. *Bioorg. Med. Chem. Lett.* 17(22): 6142-6 (2007).
Charton et al., Synthesis and biological evaluation of benzimidazole derivatives as potent AMP-activated protein kinase activators. *Bioorg Med Chem.* 14(13): 4490-518 (2006).
Chen et al., Discovering benzamide derivatives as glycogen phosphorylase inhibitors and their binding site at the enzyme. *Bioorg. Med. Chem.* 15(21): 6763-74 (2007).
Chen et al., Pyrrolopyridazine MEK inhibitors. *Bioorg. Med. Chem. Lett.* 16(3): 628-32 (2006).
Chou et al., Pimelic diphenylamide 106 is a slow, tight-binding inhibitor of class I histone deacetylases. *J. Biol. Chem.* 283(51): 35402-9 (2008).
Coxon et al., Structure of the reaction product of 4-hydroxy-2,3-dioxo-4-phenylbutanoic acid 1,4-lactone with o-phenylenediamine. *Carbohydrate Res.* 142(1): 1-10 (1985).
Dahn et al., Reductones and tricarbonyl compds. XXI. Reactions of dehydroascorbic acid and; of other 2,3-dioxobutyrolactones with o-phenylenediamine. *Helvetica Chimica Acta*, 47(7): 1860-70 (1964) English Summary.
Dessalew, QSAR study on aminophenylbenzamides and acrylamides as histone deacetylase inhibitors: an insight into the structural basis of antiproliferative activity. *Med Chem Res.* 16(7/9): 449-60 (2007).
Dokmanovic et al., Histone deacetylase inhibitors: Overview and perspectives. *Mol Cancer Res.* 5: 981-9 (2007).
El Ashry et al., Reaction of dehydro-L-ascorbic acid analogs with o-phenylenediamine, *Carbohydrate Res.* 153(1): 146-9 (1986).
Farag et al., Studies with polyfunctionally substituted heterocycles. Novel syntheses of pyrazolyl-1,2,4-triazoles and pyrazolo[5,1-c][1,2,4]triazines. *J. Chem. Res. Synopses*, (1): 10-11 (1994).

Frechette et al., 4-(Heteroarylaminomethyl)-N-(2-aminophenyl)-benzamides and their analogs as a novel class of histone deacetylase inhibitors. *Bioorg. Med. Chem. Lett.* 18(4): 1502-6 (2008).
Gilley et al., 2-Nitrophenyl isocyanide as a versatile convertible isocyanide: Rapid access to a fused γ-lactamβ-lactone bicycle. *J. Org. Chem.* 73(11): 4198-204 (2008).
Goebel et al., Characterization of new PPARγ agonists: analysis of telmisartan's structural components. *Chem. Med. Chem.* 4(3): 445-56 (2009).
Habib et al., Synthetic approaches and biological evaluation of some new sulfonate ester-containing quinazoline derivatives as potentially active antimicrobial agents. *Bollettino Chimico Farmaceutico*, 134(4): 209-15 (1995).
Hamblett et al., The discovery of 6-amino nicotinamides as potent and selective histone deacetylase inhibitors. *Bioorg. Med. Chem. Lett.* 17(19): 5300-9 (2007).
Hasegawa et al., Novel naphthalene derivatives as inhibitors of human immunoglobulin E antibody production. *J. Med. Chem.* 40(4): 395-407 (1997).
Hassan et al., Condensed pyrroles: N1-benzyl-2,5,6-trimethylpyrrolo[2,3-4]1,3-oxazin-4-ones and N1-benzyl-2,5,6-trimethyl-3-substituted-pyrrolo[2,3-d]pyrimidin-4-ones. *Indian J. Chem.* Section B: Organic Chemistry Including Medicinal Chemistry, 39B(10): 764-8 (2000).
Heidebrecht et al., Exploring the pharmacokinetic properties of phosphorus-containing selective HDAC 1 and 2 inhibitors (SHI-1:2). *Bioorg. Med. Chem. Lett.* 19(7): 2053-8 (2009).
Herman et al., Histone deacetylase inhibitors reverse gene silencing in Friedreich's ataxia. *Nat. Chem. Biol.* 2(10): 551-8 (2006).
Huang et al., N-(2-Aminophenyl)-2-anilinobenzamide. *Acta Crystallographica*, Section E: Structure Reports Online, 65(5): o1108 (2009).
Hubbs et al., Amino acid derivatives as histone deacetylase inhibitors. *Bioorg. Med. Chem. Lett.* 18(1): 34-8 (2008).
International Preliminary Report on Patentability in International Application No. PCT/US2012/26874, issued Sep. 3, 2013, 6 pages.
International Search Report and Written Opinion in International Application No. PCT/US2009/055952, mailed Dec. 15, 2009, 9 pages.
International Search Report and Written Opinion in International Application No. PCT/US2012/26874, mailed Jun. 13, 2012.
Ismail et al., Behavior of 2-substituted 6,8-dibromo-3,1-benzoxazin-4-ones towards o-phenylenediamine and anthranilic acid; a case of unusual cleavage of 6,8-dibromo-2-methyl-3,1-benzoxazin-4-one. *Tetrahedron*, 44(12): 3757-60 (1988).
Katayev et al., Anion binding by pyrrole-pyridine-based macrocyclic polyamides. *Supramolecular Chem.* 20(7): 619-24 (2008).
Katayev et al., Bipyrrole- and dipyrromethane-based amido-imine hybrid macrocycles. New receptors for oxoanions. *J. Org. Chem.* 72(8): 2886-96 (2007).
Katayev et al., Expanding sapphyrin: Towards selective phosphate binding. *Chem. Eur. J.* 14(29): 9065-73 (2008).
Katritzky et al., Azlactones as polymer components and intermediates. *J. Polymer Sci.* Part A: Polymer Chemistry, 27: 1781-90 (1989).
Kattar et al., Parallel medicinal chemistry approaches to selective HDAC1/HDAC2 inhibitor (SHI-1:2) optimization. *Bioorg. Med. Chem. Lett.* 19(4): 1168-72 (2009).
Khan et al., Determination of the class and isoform selectivity of small-molecule histone deacetylas. *Biochem. J.* 409(2): 581-9 (2008).
Kitagawa et al., Effects of a novel histone deacetylase inhibitor, N-(2-aminophenyl) benzamide, on a reversible hypertrophy induced by isoproterenol in in situ rat hearts. *J Pharmacol. Sci.* 104(2): 167-75 (2007).
Kiyokawa et al., New orally bioavailable 2-aminobenzamide-type histone deacetylase inhibitor possessing a (2-hydroxyethyl)(4-(thiophen-2-yl)benzyl)amino group. *Bioorg Med Chem.* 18(11): 3925-33 (2010).
Korshak et al., The effect of chemical defects in macromolecules on the thermal stability of pyrrones. *Acad. Sci. USSR*, 200: 865-8 (1971).

(56) References Cited

OTHER PUBLICATIONS

Kuroda et al., Further development of a robust workup process for solution-phase high-throughput library synthesis to address environmental and sample tracking issues. *Bioorg. Med. Chem.* 8(4): 505-12 (2006).
Lu et al., Zn2+-chelating, motif-tethered, short-chain fatty acids as a novel class of histone deacetylase inhibitors. *J. Med. Chem.* 47(2): 467-74 (2004).
Mahboobi et al., Design of chimeric histone deacetylase- and tyrosine kinase-inhibitors: A series of imatinib hybrides as potent inhibitors of wild-type and mutant BCR-ABL, PDGF-Rb, and histone deacetylases. *J. Med. Chem.* 52(8): 2265-79 (2009).
Mai et al., Novel uracil-based 2-aminoanilide and 2-aminoanilide-like derivatives: Histone deacetylase inhibition and in-cell activities. *Bioorg. Med. Chem. Lett.* 18(8): 2530-5 (2008).
Malvaez et al., HDAC3-selective inhibitor enhances extinction of cocaine-seeking behavior in a persistent manner. *Proc. Natl. Acad. Sci. USA*, 110(7): 2647-52 (2013).
McQuown et al., HDAC3 is a critical negative regulator of long-term memory formation. *J. Neurosci.* 31(2): 764-74 (2011).
Methot et al., Exploration of the internal cavity of histone deacetylase (HDAC) with selective HDAC1/HDAC2 inhibitors (SHI-1:2). *Bioorg. Med. Chem. Lett.* 18(3): 973-8 (2008).
Methot et al., SAR profiles of spirocyclic nicotinamide derived selective HDAC1/HDAC2 inhibitors (SHI-1:2). *Bioorg. Med. Chem. Lett.* 18(23):6104-9 (2008).
Moradei et al., Novel aminophenyl benzamide-type histone deacetylase inhibitors with enhanced potency and selectivity. *J. Med. Chem.* 50(23): 5543-6 (2007).
Moradei et al., Substituted N-(2-aminophenyl)-benzamides, (E)-N-(2-aminophenyl)-acrylamides and their analogues: Novel classes of histone deacetylase inhibitors. *Bioorg. Med. Chem. Lett.* 16(15): 4048-52 (2006).
Nagaoka et al., Synthesis and cancer antiproliferative activity of new histone deacetylase inhibitors: hydrophilic hydroxamates and 2-aminobenzamide-containing derivatives. *Eur. J. Med. Chem.* 41(6): 697-708 (2006).
Oliva et al., Chromogenic charge transfer cleft-type tetrahydrobenzoxanthene enantioselective receptors for dinitrobenzoylamino acids. *J. Org. Chem.* 69(20): 6883-5 (2004).
Paquin et al., Design and synthesis of 4-[(s-triazin-2-ylamino)methyl]-N-(2-aminophenyl)benzamides and their analogs as a novel class of histone deacetylase inhibitors. *Bioorg. Med. Chem. Lett.* 18(3): 1067-71 (2008).
Pigro et al., Readily available carbohydrate-derived imines and amides as chiral ligands for asymmetric catalysis. *Tetrahedron*, 58(27): 5459-66 (2002).
Rabilloud et al., Condensation reactions between o-phenylenediamine and 2-substituted 1,3-benzoxazin-4-ones. *Bulletin de la Societe Chimique de France*, (11-12, Pt. 2): 2682-6 (1975) English Summary.
Raeppel et al., SAR and biological evaluation of analogues of a small molecule histone deacetylase inhibitor N-(2-aminophenyl)-44(4-(pyridin-3-yl)pyrimidin-2-ylamino)methyl)benzamide (MGCD0103). *Bioorg. Med. Chem. Lett.* 19(3): 644-9 (2009).
Rai et al., HDAC inhibitors correct frataxin deficiency in a Friedreich ataxia mouse mode. *Plos ONE*, 3(4): 1-8 (2008).
Reddy et al., Synthesis of chiral benzimidazole-pyrrolidine derivatives and their application in organocatalytic aldol and Michael addition reactions. *Synthetic Commun.* 37(24): 4289-99 (2007).

Sagara et al., Identification of a novel 4-aminomethylpiperidine class of M3 muscarinic receptor antagonists and structural insight into their M3 selectivity. *J. Med. Chem.* 49(19): 5653-63 (2006).
Salisbury et al., Optimization of activity-based probes for proteomic profiling of histone deacetylase complexes. *J. Am. Chem. Soc.* 130(7): 2184-94 (2008).
Savarino et al., "Shock and kill" effects of class I—selective histone deacetylase inhibitors in combination with the glutathione synthesis inhibitor buthionine sulfoximine in cell line models for HIV-1 quiescence. *Retrovirology*, 6: 52 (2009).
Siliphaivanh et al., Design of novel histone deacetylase inhibitors. *Bioorg. Med. Chem. Lett.* 17(16): 4619-24 (2007).
Stefanko et al., Modulation of long-term memory for object recognition via HDAC inhibition. *Proc. Natl. Acad. Sci. USA*, 106(23): 9447-52 (2009).
Katritzky et al., STN result—*Journal of Polymer Science*, Part A: Polymer Chemistry, 27(5): 1781-90 (1989).
Supplementary European Search Report, Appl. No. 09812248.4 dated Aug. 20, 2012.
Thomas et al., The HDAC inhibitor 4b ameliorates the disease phenotype and transcriptional abnormalities in Huntington's disease transgenic mice. *Proc. Natl. Acad. Sci. USA*, 105(40): 15564-9 (2008).
Tsujimoto et al., Condensation of o-phenylenediamine with dehydro-L-ascorbic acid derivatives; and analogs. *Carbohydrate Res.* 138(1): 148-52 (1985).
Vaisburg et al., N-(2-Amino-phenyl)-4-(heteroarylmethyl)-benzamides as new histone deacetylase inhibitors. *Bioorg. Med. Chem. Lett.* 17(24): 6729-33 (2007).
Valente et al., Pyrrole-based hydroxamates and 2-aminoanilides: Histone deacetylase inhibition and cellular activities. *Chem. Med. Chem.* 4(9): 1411-5 (2009).
Vannini et al., Substrate binding to histone deacetylases as shown by the crystal structure of the HDAC8-substrate complex. *EMBO Reports*, 8: 879-84 (2007).
Vattipalli et al., Synthesis and β-adrenergic blocking activity of naphthyloxypropylamines. *Indian J. Chem.* Section B: Organic Chemistry Including Medicinal Chemistry, 47B(10): 1587-90 (2008).
Wang et al., Immunomodulatory effects of deacetylase inhibitors: therapeutic targeting of FOXP3+ regulatory T cells. *Nat. Rev. Drug. Disc.* 8: 969-81 (2009).
Wang et al., Monoacylation of unprotected symmetrical diamines with resin-bound benzoic acids. *Tetrahedron Lett.* 45(35): 6645-8 (2004).
Wang et al., N-Hydroxy-1,2-disubstituted-1H-benzimidazol-5-yl acrylamides as novel histone deacetylase inhibitors: Design, synthesis, SAR studies, and in vivo antitumor activity. *Bioorg. Med. Chem. Lett.* 19(5): 1403-8 (2009).
Wang et al., Screening on in vitro anti-tumor activities of novel synthetic compounds targeting histone Deacetylase. *Jiefangjun Yaoxue Xuebao*, 25(6): 482-5 (2009) English Abstract.
Witter et al., Optimization of biaryl selective HDAC1&2 inhibitors (SHI-1:2). *Bioorg. Med. Chem.* Lett. 18(2): 726-31 (2008).
Zhu et al., Investigation on the isoform selectivity of histone deacetylase inhibitors using chemical; feature based pharmacophore and docking approaches. *Eur. J. Med. Chem.* 45(5): 1777-91 (2010).
International Preliminary Report on Patentability in International Application No. PCT/US2009/055952, Mar. 8, 2011.

\* cited by examiner

COMPOSITIONS INCLUDING 6-AMINOHEXANOIC ACID DERIVATIVES AS HDAC INHIBITORS

CROSS REFERENCE TO RELATED APPLICATIONS

This application claims the benefit of U.S. Provisional Application No. 61/093,927, filed on Sep. 3, 2008 and U.S. Provisional Application No. 61/112,556, filed on Nov. 7, 2008, each of these prior applications is incorporated herein by reference in its entirety.

TECHNICAL FIELD

This invention relates to new compounds for the treatment of cancers, inflammatory disorders, and neurological conditions.

BACKGROUND

Altering gene expression through chromatin modification can be accomplished by inhibiting histone deacetylase (HDAC) enzymes. There is evidence that histone acetylation and deacetylation are mechanisms by which transcriptional regulation in a cell—a major event in cell differentiation, proliferation, and apoptosis—is achieved. It has been hypothesized that these effects occur through changes in the structure of chromatin by altering the affinity of histone proteins for coiled DNA in the nucleosome. Hypoacetylation of histone proteins is believed to increase the interaction of the histone with the DNA phosphate backbone. Tighter binding between the histone protein and DNA can render the DNA inaccessible to transcriptional regulatory elements and machinery. HDACs have been shown to catalyze the removal of acetyl groups from the epsilon-amino groups of lysine residues present within the N-terminal extension of core histones, thereby leading to hypoacetylation of the histones and blocking of the transcriptional machinery and regulatory elements.

Inhibition of HDAC, therefore can lead to histone deacetylase-mediated transcriptional derepression of tumor suppressor genes. For example, cells treated in culture with HDAC inhibitors have shown a consistent induction of the kinase inhibitor p21, which plays an important role in cell cycle arrest. HDAC inhibitors are thought to increase the rate of transcription of p21 by propagating the hyperacetylated state of histones in the region of the p21 gene, thereby making the gene accessible to transcriptional machinery. Further, non-histone proteins involved in the regulation of cell death and cell-cycle also undergo lysine acetylation and deacetylation by HDACs and histone acetyl transferase (HATs).

This evidence supports the use of HDAC inhibitors in treating various types of cancers. For example, vorinostat (suberoylanilide hydroxamic acid (SAHA)) has been approved by the FDA to treat cutaneous T-cell lymphoma and is being investigated for the treatment of solid and hematological tumors. Further, other HDAC inhibitors are in development for the treatment of acute myelogenous leukemia, Hodgkin's disease, myelodysplastic syndromes and solid tumor cancers.

HDAC inhibitors also have been shown to inhibit pro-inflammatory cytokines, such as those involved in autoimmune and inflammatory disorders due to their ability to inhibit the expression of pro-inflammatory cytokines such as TNF-alpha. For example, the HDAC inhibitor MS275 was shown to slow disease progression and joint destruction in collagen-induced arthritis in rat and mouse models. Other HDAC inhibitors have been shown to have efficacy in treating or ameliorating inflammatory disorders or conditions in in vivo models or tests for disorders such as Crohn's disease, colitis, and airway inflammation and hyper-responsiveness. HDAC inhibitors have also been shown to ameliorate spinal cord inflammation, demyelination, and neuronal and axonal loss in experimental autoimmune encephalomyelitis.

HDACs are divided into four classes. Class I is represented by yeast RPD3-like proteins (HDAC-1, -2, -3, and -8). Class IIa (HDAC-4, -5, -7, and -9) and class IIb (HDAC-6 and -10) share domains with yeast HDAC-1. Class IV (e.g., HDAC-11) shares properties of both class I and II HDACs. HDACs are zinc dependent deacetylases. In general, HDAC inhibitors normally include a Zn-binding group, as well as a surface recognition domain. There remains a need to develop new HDAC inhibitors, which will be useful in the treatment of various neurological or inflammatory conditions.

Hence, there is a need to develop new HDAC inhibitors, which will be useful in the treatment of various neurological or inflammatory conditions.

SUMMARY

The invention is based, inter alia, on the discovery of new compounds of Formula I that serve as inhibitors of Class I HDAC enzymes. The new compounds can be used, e.g., in methods of treating cancers, inflammatory disorders, neurological conditions, and malaria.

In one aspect, this invention features compounds of Formula (I):

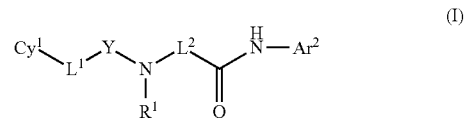

or pharmaceutically acceptable salt thereof; wherein:
Y is selected from C(=O), S(=O), and S(=O)$_2$;
$Ar^2$ is selected from $C_{6-10}$ aryl, 5-membered heteroaryl, 6-membered heteroaryl, and benzo[d][1,3]dioxolyl; wherein said $C_{6-10}$ aryl, 5-membered heteroaryl, 6-membered heteroaryl and benzo[d][1,3]dioxolyl are each substituted at one ortho position by one J group and by m independently selected $R^z$ groups;
$L^2$ is a linking group selected from ‖-A-‖, ‖-a-D-‖, ‖-D-a-‖, and ‖-b-D-b-‖; wherein said linking group is optionally substituted by 1, 2, 3, or 4 $R^x$ groups; ‖-indicates a single bond attaching the linking group to the nitrogen atom of the $N(R^1)(Y-L^1-Cy^1)$ group of Formula (I); and -‖ indicates a single bond attaching the linking group to the carbonyl group of the —C(=O)NH(Ar$^2$) moiety of Formula (I); provided that there are 4, 5, or 6 atoms connecting the shortest path from ‖- to -‖;

A is selected from straight chain $C_{4-6}$ alkylene, straight chain $C_{4-6}$ alkenylene straight chain $C_{4-6}$ alkynylene, 5-membered cycloalkylene, 6-membered cycloalkylene, 7-membered cycloalkylene, 5-membered heterocycloalkylene, 6-membered heterocycloalkylene, 7-membered heterocycloalkylene, phenylene, 5-membered heteroarylene, 6-membered heteroarylene, and 7-membered heteroarylene; wherein 1 or 2 carbon atoms of said straight chain $C_{4-6}$ alkylene, straight chain $C_{4-6}$ alkenylene, and straight chain $C_{4-6}$ alkynylene are each optionally replaced by a group independently selected from —O—, —S—, —S(=O)—, —S(=O)$_2$—, —C(=O)—, and —NR$^a$—;

D is selected from 3-membered cycloalkylene, 4-membered cycloalkylene, 5-membered cycloalkylene, 6-membered cycloalkylene, 7-membered cycloalkylene, 3-membered heterocycloalkylene, 4-membered heterocycloalkylene, 5-membered heterocycloalkylene, 6-membered heterocycloalkylene, 7-membered heterocycloalkylene, phenylene, 3-membered heteroarylene, 4-membered heteroarylene, 5-membered heteroarylene, 6-membered heteroarylene, and 7-membered heteroarylene;

a is selected from straight chain $C_{1-4}$ alkylene, straight chain $C_{1-4}$ alkenylene, and straight chain $C_{1-4}$ alkynylene; wherein 1 or 2 carbons of said straight chain $C_{1-4}$ alkylene, straight chain $C_{1-4}$ alkenylene, straight chain $C_{1-4}$ alkynylene are each optionally replaced by a group independently selected from —O—, —S—, —S(=O)—, —S(=O)$_2$—, —C(=O)—, and —NR$^a$—;

each b is independently selected from straight chain $C_{1-3}$ alkylene, straight chain $C_{1-3}$ alkenylene, and straight chain $C_{1-3}$alkynylene;

each R$^a$ is independently selected from H and $C_{1-3}$alkyl;

Cy$^1$ is selected from $C_{2-9}$ heterocycloalkyl, $C_{6-10}$ aryl, and $C_{1-9}$ heteroaryl; each of which is substituted with n independently selected R$^y$ groups;

L$^1$ is selected from a bond and $C_{1-4}$ alkylene; wherein 1 carbon atom of said straight chain $C_{1-4}$ alkylene is optionally replaced by —C(=O)—;

R$^1$ is selected from H, $C_{1-4}$ alkyl, $C_{1-4}$ haloalkyl, $C_{1-4}$ alkoxycarbonyl, carbamyl, di-$C_{1-4}$-alkyl-carbamyl, and $C_{1-4}$ alkylcarbamyl;

J is selected from amino and hydroxyl;

each R$^x$ is independently selected from halogen, hydroxyl, cyano, nitro, $C_{1-4}$ alkyl, $C_{1-4}$ alkoxy, $C_{1-4}$ haloalkyl, $C_{1-4}$ haloalkoxy, amino, $C_{1-4}$ alkylamino, and di-$C_{1-4}$-alkylamino;

each R$^y$ is independently selected from halogen, cyano, nitro, hydroxyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$alkylcarbonyl, $C_{1-6}$haloalkylcarbonyl, $C_{6-10}$ arylcarbonyl, $C_{1-6}$ alkylsulfonyl, sulfonamido, $C_{1-6}$ alkylthio, carbamyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, amino, $C_{1-6}$alkylamino, di-$C_{1-6}$alkylamino, $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$alkylcarbonyl, $C_{1-6}$ alkylcarbamyl, di-$C_{1-6}$ alkylcarbamyl, $C_{1-6}$ alkylcarbonylamino, $C_{1-6}$alkylcarbonyl-($C_{1-4}$-alkyl)amino, $C_{1-6}$ alkoxycarbonylamino, $C_{1-6}$ alkylamino, di-$C_{1-6}$alkylamino are each optionally substituted by 1, 2, or 3 independently selected R$^{y'}$ groups; and wherein said $C_{3-7}$cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1, 2, or 3 independently selected R$^{y''}$ groups;

provided that only one R$^y$ is selected from optionally substituted $C_{3-7}$cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;

each R$^z$ is independently selected from halogen, cyano, nitro, hydroxyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{6-10}$ aryloxy, $C_{1-6}$ alkoxycarbonyl, $C_{1-6}$alkylcarbonyl, carbamyl, $C_{1-6}$ alkylcarbamyl, di-$C_{1-6}$ alkylcarbamyl, $C_{1-6}$alkylcarbonylamino, $C_{1-6}$ alkylcarbonyl-($C_{1-4}$-alkyl)amino, $C_{1-6}$ alkoxycarbonylamino, amino, $C_{1-6}$ alkylamino, di-$C_{1-6}$ alkylamino, $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$ alkylcarbonyl, $C_{1-6}$ alkylcarbamyl, di-$C_{1-6}$ alkylcarbamyl, $C_{1-6}$ alkylcarbonylamino, $C_{1-6}$alkylcarbonyl-($C_{1-4}$-alkyl) amino, $C_{1-6}$ alkoxycarbonylamino, $C_{1-6}$ alkylamino, di-$C_{1-6}$alkylamino are each optionally substituted by 1, 2, or 3 independently selected R$^{z'}$ groups; and wherein said $C_{3-7}$ cycloalkyl, $C_{2-6}$ heterocycloalkyl, phenyl, $C_{1-6}$ heteroaryl, $C_{3-7}$cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1, 2, or 3 independently selected R$^{z''}$ groups;

provided that only one R$^z$ is selected from optionally substituted $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;

each R$^{y'}$ and R$^{z'}$ is independently selected from hydroxyl, cyano, nitro, $C_{1-4}$ alkoxy, $C_{1-4}$ haloalkoxy, amino, $C_{1-4}$ alkylamino, and di-$C_{1-4}$-alkylamino;

each R$^{y''}$ and R$^{z''}$ is independently selected from halogen, hydroxyl, cyano, nitro, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

n is an integer selected from 0, 1, 2, 3, and 4; and m is an integer selected from 0, 1, 2, and 3.

In one aspect, the invention features compounds of Formula (I):

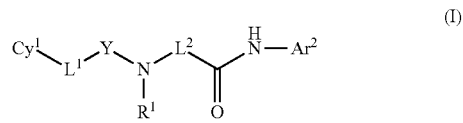

and pharmaceutically acceptable salts, hydrates, and solvates thereof; wherein:

Y is selected from C(=O), S(=O), and S(=O)$_2$;

Ar$^2$ is selected from phenyl, 5-membered heteroaryl, and 6-membered heteroaryl; wherein said phenyl, 5-membered heteroaryl, and 6-membered heteroaryl are each substituted at one ortho position by one J group and by m independently selected R$^z$ groups;

L$^2$ is a linking group selected from ||-A-||, ||-a-D-||, ||-D-a-||, and ||-b-D-b-||; wherein said linking group is optionally substituted by 1, 2, 3, or 4 R$^x$ groups; ||-indicates a single bond attaching the linking group to the nitrogen atom of the N(R$^1$)(Y-L$^1$-Cy$^1$) group of Formula (I); and -|| indicates a single bond attaching the linking group to the carbonyl group of the —C(=O)NH(Ar$^2$) moiety of Formula (I); provided that there are 4, 5, or 6 atoms connecting the shortest path from ||- to -||;

A is selected from straight chain $C_{4-6}$ alkylene, straight chain $C_{4-6}$ alkenylene, straight chain $C_{4-6}$ alkynylene, 5-membered cycloalkylene, 6-membered cycloalkylene, 7-membered cycloalkylene, 5-membered heterocycloalkylene, 6-membered heterocycloalkylene, 7-membered heterocycloalkylene, phenylene, 5-membered heteroarylene, 6-membered heteroarylene, and 7-membered heteroarylene; wherein 1 or 2 carbon atoms of said straight chain $C_{4-6}$ alkylene, straight chain $C_{4-6}$ alkenylene, and straight chain $C_4$-6 alkynylene are each optionally replaced by a group independently selected from —O—, —S—, —S(=O)—, —S(=O)$_2$—, —C(=O)—, and —NR$^a$—;

D is selected from 3-membered cycloalkylene, 4-membered cycloalkylene, 5-membered cycloalkylene, 6-membered cycloalkylene, 7-membered cycloalkylene, 3-membered heterocycloalkylene, 4-membered heterocycloalkylene, 5-membered heterocycloalkylene, 6-membered heterocycloalkylene, 7-membered heterocycloalkylene, phenylene, 3-membered heteroarylene, 4-membered heteroarylene, 5-membered heteroarylene, 6-membered heteroarylene, and 7-membered heteroarylene;

a is selected from straight chain $C_{1-4}$ alkylene, straight chain $C_{1-4}$ alkenylene, and straight chain $C_{1-4}$ alkynylene; wherein 1 or 2 carbons of said straight chain $C_{1-4}$ alkylene, straight chain $C_{1-4}$ alkenylene, and straight chain $C_{1-4}$ alkynylene are each optionally replaced by a group independently selected from —O—, —S—, —S(=O)—, —S(=O)$_2$—, —C(=O)—, and —NR$^a$—;

each b is independently selected from straight chain $C_{1-3}$ alkylene, straight chain $C_{1-3}$ alkenylene, and straight chain $C_{1-3}$ alkynylene;

each R$^a$ is independently selected from H and $C_{1-3}$alkyl;

Cy$^1$ is selected from $C_{2-9}$ heterocycloalkyl, $C_{6-10}$ aryl, and $C_{1-9}$ heteroaryl; each of which is substituted with n independently selected R$^y$ groups;

L$^1$ is selected from a bond and $C_{1-4}$ alkylene;

R$^1$ is selected from H, $C_{1-4}$ alkyl, $C_{1-4}$ haloalkyl, $C_{1-4}$alkoxycarbonyl, carbamyl, di-$C_{1-4}$-alkyl-carbamyl, and $C_{1-4}$ alkylcarbamyl;

J is selected from amino and hydroxyl;

each R$^x$ is independently selected from halogen, hydroxyl, cyano, nitro, $C_{1-4}$ alkyl, $C_{1-4}$ alkoxy, $C_{1-4}$ haloalkyl, $C_{1-4}$ haloalkoxy, amino, $C_{1-4}$ alkylamino, and di-$C_{1-4}$-alkylamino;

each R$^y$ is independently selected from halogen, cyano, nitro, hydroxyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$ alkylcarbonyl, carbamyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, amino, $C_{1-6}$ alkylamino, di-$C_{1-6}$alkylamino, $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$ alkylcarbonyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, $C_{1-6}$ alkylamino, di-$C_{1-6}$ alkylamino are each optionally substituted by 1, 2, or 3 independently selected R$^{y'}$ groups; and wherein said $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1, 2, or 3 independently selected R$^{y''}$ groups;

provided that only one R$^y$ is selected from optionally substituted $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;

each R$^z$ is independently selected from halogen, cyano, nitro, hydroxyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$haloalkoxy, $C_{1-6}$ alkoxycarbonyl, $C_{1-6}$ alkylcarbonyl, carbamyl, $C_{1-6}$ alkylcarbamyl, di-$C_{1-6}$ alkylcarbamyl, $C_{1-6}$alkylcarbonylamino, $C_{1-6}$ alkylcarbonyl-($C_{1-4}$alkyl)amino, $C_{1-6}$ alkoxycarbonylamino, amino, $C_{1-6}$ alkylamino, di-$C_{1-6}$alkylamino, $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$alkylcarbonyl, $C_{1-6}$ alkylcarbamyl, di-$C_{1-6}$ alkylcarbamyl, $C_{1-6}$ alkylcarbonylamino, $C_{1-6}$alkylcarbonyl-($C_{1-4}$-alkyl)amino, $C_{1-6}$ alkoxycarbonylamino, $C_{1-6}$ alkylamino, di-$C_{1-6}$alkylamino are each optionally substituted by 1, 2, or 3 independently selected R$^{z'}$ groups; and wherein said $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1, 2, or 3 independently selected R$^{z''}$ groups;

provided that only one R$^z$ is selected from optionally substituted $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;

each R$^{y'}$ and R$^{z'}$ is independently selected from hydroxyl, cyano, nitro, $C_{1-4}$ alkoxy, $C_{1-4}$ haloalkoxy, amino, $C_{1-4}$ alkylamino, and di-$C_{1-4}$-alkylamino;

each R$^{y''}$ and R$^{z''}$ is independently selected from halogen, hydroxyl, cyano, nitro, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

n is an integer selected from 0, 1, 2, 3, and 4; and m is an integer selected from 0, 1, 2, and 3.

In some embodiments, the compound is not selected from N-(7-(2-aminophenylamino)-7-oxoheptyl)biphenyl-3-carboxamide, N-(7-(2-aminophenylamino)-7-oxoheptyl)biphenyl-4-carboxamide, and N-(7-(2-aminophenylamino)-7-oxoheptyl)-6-phenylnicotinamide, and pharmaceutically acceptable salts thereof.

In some embodiments, it is provided that the compound is not selected from N-(7-(2-aminophenylamino)-7-oxoheptyl) biphenyl-3-carboxamide; N-(7-(2-aminophenylamino)-7-oxoheptyl)biphenyl-4-carboxamide; N-(7-(2-aminophenylamino)-7-oxoheptyl)-6-phenylnicotinamide; (2S,3S, 4R)—N-[5-[(2-aminophenyl)amino]-5-oxopentyl]-2-ethoxy-3,4-dihydro-3-(3-hydroxypropyl)-4-(1-methylethyl)-2H-pyran-6-carboxamide; (2R,3S,4S)—N-[5-[(2-aminophenyl)amino]-5-oxopentyl]-2-ethoxy-3,4-dihydro-3-(3-hydroxypropyl)-4-(1-methylethyl)-2H-pyran-6-carboxamide; (2S,3R,4R)—N-[5-[(2-aminophenyl)amino]-5-oxopentyl]-2-ethoxy-3,4-dihydro-3-(3-hydroxypropyl)-4-(1-methylethyl)-2H-pyran-6-carboxamide; (2R,4S)—N-(5-(2-aminophenylamino)-5-oxopentyl)-2-(3-hydroxypropoxy)-4-isopropyl-3,4-dihydro-2H-pyran-6-carboxamide; (2S,4R)—N-(5-(2-aminophenylamino)-5-oxopentyl)-2-(3-hydroxypropoxy)-4-isopropyl-3,4-dihydro-2H-pyran-6-carboxamide; (2R,3R, 4S)—N-[5-[(2-aminophenyl)amino]-5-oxopentyl]-2-ethoxy-3,4-dihydro-3-(3-hydroxypropyl)-4-(3-thienyl)-2H-pyran-6-carboxamide; (2S,3R,4R)—N-[5-[(2-aminophenyl)amino]-5-oxopentyl]-2-ethoxy-3,4-dihydro-3-(3-hydroxypropyl)-4-phenyl-2H-pyran-6-carboxamide; (2R, 4R)—N-(5-(2-aminophenylamino)-5-oxopentyl)-2-(3-hydroxypropoxy)-4-phenyl-3,4-dihydro-2H-pyran-6-carboxamide; (2S,4S)—N-(5-(2-aminophenylamino)-5- oxopentyl)-2-(3-hydroxypropoxy)-4-phenyl-3,4-dihydro-2H-pyran-6-carboxamide; (2S,4S)—N-(5-(2-aminophenylamino)-5-oxopentyl)-2-(3-hydroxypropoxy)-4-(thiophen-3-yl)-3,4-dihydro-2H-pyran-6-carboxamide; (2R,4S)—N-(5-(2-aminophenylamino)-5-oxopentyl)-2-(4-hydroxybutoxy)-4-isopropyl-3,4-dihydro-2H-pyran-6-carboxamide; (2S,4R)—N-(5-(2-aminophenylamino)-5-oxopentyl)-2-(4-hydroxybutoxy)-4-isopropyl-3,4-dihydro-2H-pyran-6-carboxamide; and (2S,4S)—N-(5-(2-aminophenylamino)-5-oxopentyl)-2-(4-hydroxybutoxy)-4-(thiophen-3-yl)-3,4-dihydro-2H-pyran-6-carboxamide.

In some embodiments, it is provided that the compound is not selected from N-(7-(2-aminophenylamino)-7-oxoheptyl)biphenyl-3-carboxamide; N-(7-(2-aminophenylamino)-7-oxoheptyl)biphenyl-4-carboxamide; N-(7-(2-aminophenylamino)-7-oxoheptyl)-6-phenylnicotinamide; N-[5-[(2-aminophenyl)amino]-5-oxopentyl]-2-ethoxy-3,4-dihydro-3-(3-hydroxypropyl)-4-(1-methylethyl)-2H-pyran-6-carboxamide; N-(5-(2-aminophenylamino)-5-oxopentyl)-2-(3-hydroxypropoxy)-4-isopropyl-3,4-dihydro-2H-pyran-6-carboxamide; N-[5-[(2-aminophenyl)amino]-5-oxopentyl]-2-ethoxy-3,4-dihydro-3-(3-hydroxypropyl)-4-(3-thienyl)-2H-pyran-6-carboxamide; N-[5-[(2-aminophenyl)amino]-5-oxopentyl]-2-ethoxy-3,4-dihydro-3-(3-hydroxypropyl)-4-phenyl-2H-pyran-6-carboxamide; N-(5-(2-aminophenylamino)-5-oxopentyl)-2-(3-hydroxypropoxy)-4-phenyl-3,4-dihydro-2H-pyran-6-carboxamide; N-(5-(2-aminophenylamino)-5-oxopentyl)-2-(3-hydroxypropoxy)-4-(thiophen-3-yl)-3,4-dihydro-2H-pyran-6-carboxamide; N-(5-(2-aminophenylamino)-5-oxopentyl)-2-(4-hydroxybutoxy)-4-(thiophen-3-yl)-3,4-dihydro-2H-pyran-6-carboxamide; and N-(5-(2-aminophenylamino)-5-oxopentyl)-2-(4-hydroxybutoxy)-4-isopropyl-3,4-dihydro-2H-pyran-6-carboxamide.

In some embodiments, it is provided that the compound is not selected from N-(7-(2-aminophenylamino)-7-oxoheptyl)biphenyl-3-carboxamide; N-(7-(2-aminophenylamino)-7-oxoheptyl)biphenyl-4-carboxamide; N-(7-(2-aminophenylamino)-7-oxoheptyl)-6-phenylnicotinamide; and one of the following applies:
(i) $Cy^1$ is not optionally substituted 2-dihydropyranyl (e.g., optionally substituted 3,4-dihydro-2H-pyran-6-yl); or
(ii) $Cy^1$ is not substituted 2-dihydropyranyl (e.g., substituted 3,4-dihydro-2H-pyran-6-yl, e.g., substituted with optionally substituted $C_1$-$C_3$ alkyl, such as isopropyl and/or —CH$_2$—CH$_2$—CH$_2$—OH; and/or substituted with $C_1$-$C_6$ heteroaryl, such as thienyl).

In another aspect, this application features compounds of Formula (II):

and pharmaceutically acceptable salts, hydrates, and solvates thereof; wherein:
Su is a surface recognition domain;
Y is selected from C(=O), S(=O), and S(=O)$_2$;
$R^1$ is selected from H, $C_{1-4}$ alkyl, $C_{1-4}$ haloalkyl, $C_{1-4}$alkoxycarbonyl, carbamyl, di-$C_{1-4}$-alkyl-carbamyl, and $C_{1-4}$ alkylcarbamyl;
L is a linker; and
Z is a Zn-binding group.

In one aspect, compositions (e.g., a pharmaceutical composition) are featured, which includes a compound of formula (I) (or II) or a salt (e.g., a pharmaceutically acceptable salt) thereof as defined anywhere herein and a pharmaceutically acceptable carrier. In some embodiments, the composition can include an effective amount of the compound or salt. In some embodiments, the composition can further include an additional therapeutic agent.

The invention relates generally to inhibiting HDAC (e.g., HDAC1, HDAC2, and HDAC3) with a compound of formula (I) (or II) or a salt (e.g., a pharmaceutically acceptable salt) thereof as defined anywhere herein. In some embodiments, the methods can include, e.g., contacting an HDAC (e.g., HDAC1, HDAC2, or HDAC3) in a sample (e.g., a cell or tissue) with a compound of formula (I) (or II) or a salt (e.g., a pharmaceutically acceptable salt) thereof as defined anywhere herein. In other embodiments, the methods can include administering a compound of formula (I) (or II) or a salt (e.g., a pharmaceutically acceptable salt) thereof as defined anywhere herein to a subject (e.g., a mammal, such as a human). Accordingly, in yet another aspect, this invention includes methods of screening for compounds that inhibit (e.g., selectively inhibit) one or more HDACs.

In one aspect, methods of selectively inhibiting HDAC3 are featured, which includes contacting an HDAC3 in a sample (e.g., a cell or tissue) with a compound of formula (I) or a salt (e.g., a pharmaceutically acceptable salt) thereof as defined anywhere herein; or administering a compound of formula (I) (or II) or a salt (e.g., a pharmaceutically acceptable salt) thereof as defined anywhere herein to a subject (e.g., a mammal, such as a human).

In one aspect, a method of selectively inhibiting HDAC1 or HDAC2 (e.g., HDAC1) is featured, which includes contacting HDAC1 or HDAC2 (e.g., HDAC1) in a sample (e.g., a cell or tissue) with a compound of formula (I) or a salt (e.g., a pharmaceutically acceptable salt) thereof as defined anywhere herein; or administering a compound of formula (I) (or II) or a salt (e.g., a pharmaceutically acceptable salt) thereof as defined anywhere herein to a subject (e.g., a mammal, such as a human).

In a further aspect, this application features methods of treating a cancer (e.g., cutaneous T cell lymphoma, B cell lymphomas, and colorectal cancer), an inflammatory disorder (e.g., psoriasis, rheumatoid arthritis, and osteoarthritis), a neurological condition (e.g., Friedreich's ataxia, myotonic dystrophy, Parkinson's disease, spinal muscular atrophy, fragile X syndrome, Huntington's disease, a spinocerebellar ataxia, Kennedy's disease, amyotrophic lateral sclerosis, spinal and bulbar muscular atrophy, or Alzheimer's disease), or a *Plasmodium falciparum* infection (e.g., malaria) that includes administering an HDAC inhibitor described herein to a patient, e.g., a patient having a neurological condition. In particular, an HDAC inhibitor designated R03 in Table 3 herein can be used in methods and kits to treat Friedreich's ataxia.

In another aspect, this application features the use of an HDAC inhibitor described herein in the preparation of a medicament for the treatment or prevention of a cancer, an inflammatory disorder, a *Plasmodium falciparum* infection, or a neurological condition (e.g., as listed herein). In another aspect, this application features the use of an HDAC inhibitor described herein as a medicament, e.g., for the treatment or prevention of a cancer, an inflammatory disorder, a *Plasmodium falciparum* infection, or a neurological condition (e.g., as listed herein).

Some of the formula (I) compounds described herein (e.g., compounds in which $L^2$ contains one or more double bonds) have enhanced (e.g., increased, e.g., increased by a factor of about 2 or more) stabilities in acid. In some embodiments, the formula (I) compounds have enhanced resistances to degradation, e.g., less than about 25% degradation (e.g., less than about 20% degradation, less than about 15% degradation, or less than about 10% degradation)

when exposed to acidic pH, e.g., acidic conditions intended to mimic those in the stomach, e.g., incubation (e.g., as a 10 μM solution) at 50° C. and at a pH of about 2.0 for about four hours. The resistance of compounds to degradation or metabolism at acidic pH can be a useful feature for a pharmaceutical agent (e.g., a drug). Increased stability at low pH can allow, for example, process preparation steps, such as salt formation, to occur without significant degradation of the desired salt. In addition, it is preferable that orally administered pharmaceuticals are stable to the acidic pH of the stomach.

Embodiments can include one or more of the following features.

$Cy^1$ is selected from $C_{2-9}$ heterocycloalkyl, which is substituted with n independently selected $R^y$ groups. $Cy^1$ is selected from $C_{6-10}$ aryl, which is substituted with n independently selected $R^y$ groups.

$Cy^1$ is selected from $C_{2-9}$ heteroaryl, which is substituted with n independently selected $R^y$ groups. $Cy^1$ is indolyl or indazolyl, each of which is substituted with n independently selected $R^y$ groups. $Cy^1$ is indazolyl, which is substituted with n independently selected $R^y$ groups. n is 0. n is an integer selected from 1 and 2, and each occurrence of $R^y$ is independently selected from $C_{1-6}$ alkyl and $C_{1-6}$ alkoxy, wherein said $C_{1-6}$ alkyl and $C_{1-6}$ alkoxy are each optionally substituted by 1, 2, or 3 independently selected $R^{y'}$ groups.

$Cy^1$ is selected from phenyl and $C_{1-6}$ heteroaryl, each of which is optionally substituted with n independently selected $R^y$ groups. $Cy^1$ is phenyl, which is optionally substituted with n independently selected $R^y$ groups. $Cy^1$ is $C_{1-6}$ heteroaryl, which is optionally substituted with n independently selected $R^y$ groups. $Cy^1$ is selected from $C_{2-6}$ heterocycloalkyl; which is optionally substituted with n independently selected $R^y$ groups. $Cy^1$ is not selected from optionally substituted 3,4-dihydro-2H-pyran-6-yl.

$Ar^2$ is selected from phenyl; wherein said phenyl is substituted at one ortho position by one J group and by m independently selected $R^z$ groups.

m is 0.

$R^z$ is independently selected from halogen, cyano, nitro, $C_{1-6}$ alkyl, $C_{1-6}$ haloalkyl, $C_{1-6}$ alkoxy, $C_{1-6}$ haloalkoxy, $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{1-6}$haloalkyl, $C_{1-6}$ alkoxy, and $C_{1-6}$ haloalkoxy are each optionally substituted by 1, 2, or 3 independently selected $R^{z''}$ groups; and wherein said $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$alkyl, phenyl-$C_{1-4}$-alkyl, and $C_{1-6}$ heteroaryl-$C_{1-4}$-alkyl are each optionally substituted by 1 or 2 independently selected $R^z$ groups;

provided that only one $R^z$ is selected from optionally substituted $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl.

Each $R^z$ is independently selected from halogen, cyano, nitro, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{z'}$ groups.

m is 1. $R^z$ is selected from halogen, $C_{1-6}$ alkyl, $C_{1-6}$ haloalkyl, $C_{1-6}$ alkoxy, and $C_{1-6}$ haloalkoxy. $R^z$ is halogen (e.g., fluoro). $R^z$ is selected from phenyl and $C_{1-6}$ heteroaryl, each of which is optionally substituted by 1, 2, or 3 independently selected $R^{z''}$ groups. $Ar^2$ is selected from 5-membered heteroaryl; which is substituted at one ortho position by one J group and by m independently selected $R^z$ groups. $Ar^2$ is selected from 6-membered heteroaryl; which is substituted at one ortho position by one J group and by m independently selected $R^z$ groups.

J is amino.

$L^2$ is selected from straight chain $C_4$ alkylene, straight chain $C_5$ alkylene, and straight chain $C_6$ alkylene; each of which is optionally substituted by 1, 2, or 3 $R^x$ groups.

$L^2$ is straight chain $C_{4-6}$ alkenylene (e.g., $L^2$ is straight chain $C_{4-6}$ alkenylene having one double bond).

$L^2$ is selected from:
∥—$(CH_2)_{1-3}$—$CH_2$—CH=CH-∥ and ∥—$(CH_2)_{1-3}$—CH=CH—$CH_2$-∥.
(e.g., $L^2$ is ∥—$(CH_2)_{1-3}$—$CH_2$—CH=CH-∥).

$R^1$ is hydrogen.

Embodiments can include or further include any one or more of the features set forth in detailed description.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
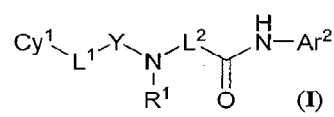
FIG. 1 is a bar graph depicting fold-upregulation of frataxin mRNA expression in human cells after administration of the indicated concentrations of the HDAC3-specific histone deacetylase inhibitor RGFA8.
Figure 1:
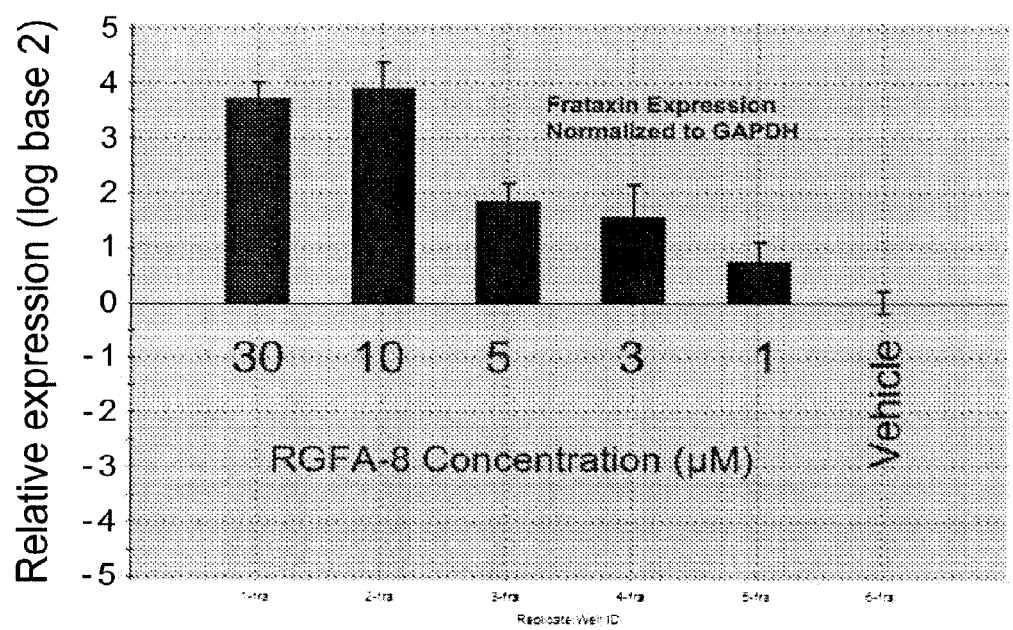

This application features compounds that can be used as HDAC inhibitors and describes their synthesis. These compounds can be used to inhibit class I HDACs for treatment of various disease states, e.g., cancers, inflammatory disorders, neurological conditions, and malaria.

In one aspect, this invention features a compound of Formula (I):

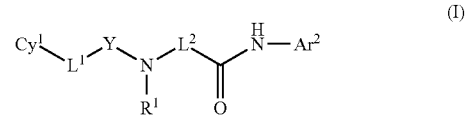

or pharmaceutically acceptable salt thereof; wherein:

Y is selected from C(=O), S(=O), and S(=O)$_2$;

Ar$^2$ is selected from C$_{6-10}$ aryl, 5-membered heteroaryl, 6-membered heteroaryl, and benzo[d][1,3]dioxolyl; wherein said C$_{6-10}$ aryl, 5-membered heteroaryl, 6-membered heteroaryl and benzo[d][1,3]dioxolyl are each substituted at one ortho position by one J group and by m independently selected R$^z$ groups;

L$^2$ is a linking group selected from ‖-A-‖, ‖-a-D-‖, ‖-D-a-‖, and ‖-b-D-b-‖; wherein said linking group is optionally substituted by 1, 2, 3, or 4 R$^x$ groups; ‖-indicates a single bond attaching the linking group to the nitrogen atom of the N(R$^1$)(Y-L$^1$-Cy$^1$) group of Formula (I); and -‖ indicates a single bond attaching the linking group to the carbonyl group of the —C(=O)NH(Ar$^2$) moiety of Formula (I); provided that there are 4, 5, or 6 atoms connecting the shortest path from ‖- to -‖;

A is selected from straight chain C$_{4-6}$ alkylene, straight chain C$_{4-6}$ alkenylene straight chain C$_{4-6}$ alkynylene, 5-membered cycloalkylene, 6-membered cycloalkylene, 7-membered cycloalkylene, 5-membered heterocycloalkylene, 6-membered heterocycloalkylene, 7-membered heterocycloalkylene, phenylene, 5-membered heteroarylene, 6-membered heteroarylene, and 7-membered heteroarylene; wherein 1 or 2 carbon atoms of said straight chain C$_{4-6}$ alkylene, straight chain C$_{4-6}$ alkenylene, and straight chain C$_{4-6}$ alkynylene are each optionally replaced by a group independently selected from —O—, —S—, —S(=O)—, —S(=O)$_2$—, —C(=O)—, and —NR$^a$—;

D is selected from 3-membered cycloalkylene, 4-membered cycloalkylene, 5-membered cycloalkylene, 6-membered cycloalkylene, 7-membered cycloalkylene, 3-membered heterocycloalkylene, 4-membered heterocycloalkylene, 5-membered heterocycloalkylene, 6-membered heterocycloalkylene, 7-membered heterocycloalkylene, phenylene, 3-membered heteroarylene, 4-membered heteroarylene, 5-membered heteroarylene, 6-membered heteroarylene, and 7-membered heteroarylene;

a is selected from straight chain C$_{1-4}$ alkylene, straight chain C$_{1-4}$ alkenylene, and straight chain C$_{1-4}$ alkynylene; wherein 1 or 2 carbons of said straight chain C$_{1-4}$ alkylene, straight chain C$_{1-4}$ alkenylene, straight chain C$_{1-4}$ alkynylene are each optionally replaced by a group independently selected from —O—, —S—, —S(=O)—, —S(=O)$_2$—, —C(=O)—, and —NR$^a$—;

each b is independently selected from straight chain C$_{1-3}$ alkylene, straight chain C$_{1-3}$ alkenylene, and straight chain C$_{1-3}$ alkynylene;

each R$^a$ is independently selected from H and C$_{1-3}$ alkyl;

Cy$^1$ is selected from C$_{2-9}$ heterocycloalkyl, C$_{6-10}$ aryl, and C$_{1-9}$ heteroaryl; each of which is substituted with n independently selected R$^y$ groups;

L$^1$ is selected from a bond and C$_{1-4}$ alkylene; wherein 1 carbon atom of said straight chain C$_{1-4}$ alkylene is optionally replaced by —C(=O)—;

R$^1$ is selected from H, C$_{1-4}$ alkyl, C$_{1-4}$ haloalkyl, C$_{1-4}$alkoxycarbonyl, carbamyl, di-C$_{1-4}$-alkyl-carbamyl, and C$_{1-4}$ alkylcarbamyl;

J is selected from amino and hydroxyl;

each R$^x$ is independently selected from halogen, hydroxyl, cyano, nitro, C$_{1-4}$ alkyl, C$_{1-4}$ alkoxy, C$_{1-4}$ haloalkyl, C$_{1-4}$ haloalkoxy, amino, C$_{1-4}$ alkylamino, and di-C$_{1-4}$-alkylamino;

each R$^y$ is independently selected from halogen, cyano, nitro, hydroxyl, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, C$_{1-6}$ alkoxycarbonyl, C$_{1-6}$alkylcarbonyl, C$_{1-6}$ haloalkylcarbonyl, C$_{6-10}$ arylcarbonyl, C$_{1-6}$ alkylsulfonyl, sulfonamido, C$_{1-6}$ alkylthio, carbamyl, C$_{1-6}$ alkylcarbamyl, di-C$_{1-6}$ alkylcarbamyl, C$_{1-6}$ alkylcarbonylamino, C$_{1-6}$ alkylcarbonyl-(C$_{1-4}$-alkyl)amino, C$_{1-6}$ alkoxycarbonylamino, amino, C$_{1-6}$alkylamino, di-C$_{1-6}$alkylamino, C$_{3-7}$ cycloalkyl, C$_{2-6}$ heterocycloalkyl, phenyl, C$_{1-6}$ heteroaryl, C$_{3-7}$cycloalkyl-C$_{1-4}$-alkyl, C$_{2-6}$ heterocycloalkyl-C$_{1-4}$-alkyl, phenyl-C$_{1-4}$-alkyl, and C$_{1-6}$ heteroaryl-C$_{1-4}$-alkyl; wherein said C$_{1-6}$ alkyl, C$_{2-6}$alkenyl, C$_{2-6}$ alkynyl, C$_{1-6}$ haloalkyl, C$_{1-6}$ alkoxy, C$_{1-6}$ haloalkoxy, C$_{1-6}$ alkoxycarbonyl, C$_{1-6}$alkylcarbonyl, C$_{1-6}$ alkylcarbamyl, di-C$_{1-6}$ alkylcarbamyl, C$_{1-6}$ alkylcarbonylamino, C$_{1-6}$ alkylcarbonyl-(C$_{1-4}$-alkyl)amino, C$_{1-6}$ alkoxycarbonylamino, C$_{1-6}$ alkylamino, di-C$_{1-6}$alkylamino are each optionally substituted by 1, 2, or 3 independently selected R$^{y'}$ groups; and wherein said C$_{3-7}$cycloalkyl, C$_{2-6}$ heterocycloalkyl, phenyl, C$_{1-6}$ heteroaryl, C$_{3-7}$cycloalkyl-C$_{1-4}$-alkyl, C$_{2-6}$ heterocycloalkyl-C$_{1-4}$-alkyl, phenyl-C$_{1-4}$-alkyl, and C$_{1-6}$ heteroaryl-C$_{1-4}$-alkyl are each optionally substituted by 1, 2, or 3 independently selected R$^{y''}$ groups;

provided that only one R$^y$ is selected from optionally substituted C$_{3-7}$ cycloalkyl, C$_{2-6}$ heterocycloalkyl, phenyl, C$_{1-6}$ heteroaryl, C$_{3-7}$ cycloalkyl-C$_{1-4}$-alkyl, C$_{2-6}$ heterocycloalkyl-C$_{1-4}$-alkyl, phenyl-C$_{1-4}$-alkyl, and C$_{1-6}$ heteroaryl-C$_{1-4}$-alkyl;

each R$^z$ is independently selected from halogen, cyano, nitro, hydroxyl, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, C$_{6-10}$ aryloxy, C$_{1-6}$ alkoxycarbonyl, C$_{1-6}$alkylcarbonyl, carbamyl, C$_{1-6}$ alkylcarbamyl, di-C$_{1-6}$ alkylcarbamyl, C$_{1-6}$ alkylcarbonylamino, C$_{1-6}$alkylcarbonyl-(C$_{1-4}$-alkyl)amino, C$_{1-6}$ alkoxycarbonylamino, amino, C$_{1-6}$ alkylamino, di-C$_{1-6}$alkylamino, C$_{3-7}$ cycloalkyl, C$_{2-6}$ heterocycloalkyl, phenyl, C$_{1-6}$ heteroaryl, C$_{3-7}$ cycloalkyl-C$_{1-4}$-alkyl, C$_{2-6}$ heterocycloalkyl-C$_{1-4}$-alkyl, phenyl-C$_{1-4}$-alkyl, and C$_{1-6}$ heteroaryl-C$_{1-4}$-alkyl; wherein said C$_{1-6}$ alkyl, C$_{2-6}$ alkenyl, C$_{2-6}$alkynyl, C$_{1-6}$ haloalkyl, C$_{1-6}$alkoxy, C$_{1-6}$haloalkoxy, C$_{1-6}$ alkoxycarbonyl, C$_{1-6}$alkylcarbonyl, C$_{1-6}$ alkylcarbamyl, di-C$_{1-6}$ alkylcarbamyl, C$_{1-6}$ alkylcarbonylamino, C$_{1-6}$alkylcarbonyl-(C$_{1-4}$-alkyl)amino, C$_{1-6}$ alkoxycarbonylamino, C$_{1-6}$ alkylamino, di-C$_{1-6}$ alkylamino are each optionally substituted by 1, 2, or 3 independently selected R$^{z'}$ groups; and wherein said C$_{3-7}$ cycloalkyl, C$_{2-6}$ heterocycloalkyl, phenyl, C$_{1-6}$ heteroaryl, C$_{3-7}$cycloalkyl-C$_{1-4}$-alkyl, C$_{2-6}$ heterocycloalkyl-C$_{1-4}$-alkyl, phenyl-C$_{1-4}$-alkyl, and C$_{1-6}$ heteroaryl-C$_{1-4}$-alkyl are each optionally substituted by 1, 2, or 3 independently selected R$^{z''}$ groups;

provided that only one R$^z$ is selected from optionally substituted C$_{3-7}$ cycloalkyl, C$_{2-6}$ heterocycloalkyl, phenyl, C$_{1-6}$ heteroaryl, C$_{3-7}$cycloalkyl-C$_{1-4}$-alkyl, C$_{2-6}$ heterocycloalkyl-C$_{1-4}$-alkyl, phenyl-C$_{1-4}$-alkyl, and C$_{1-6}$ heteroaryl-C$_{1-4}$-alkyl;

each R$^{y'}$ and R$^{z'}$ is independently selected from hydroxyl, cyano, nitro, C$_{1-4}$ alkoxy, C$_{1-4}$ haloalkoxy, amino, C$_{1-4}$ alkylamino, and di-C$_{1-4}$-alkylamino;

each R$^{y''}$ and R$^{z''}$ is independently selected from halogen, hydroxyl, cyano, nitro, C$_{1-4}$ alkyl, C$_{1-4}$ haloalkyl, C$_{1-4}$ alkoxy, C$_{1-4}$ haloalkoxy, amino, C$_{1-4}$ alkylamino, and di-C$_{1-4}$-alkylamino;

n is an integer selected from 0, 1, 2, 3, and 4; and m is an integer selected from 0, 1, 2, and 3;

provided that the compound is not selected from N-(7-(2-aminophenylamino)-7-oxoheptyl)biphenyl-3-carboxamide; N-(7-(2-aminophenylamino)-7-oxoheptyl)biphenyl-4-carboxamide; N-(7-(2-aminophenylamino)-7-oxoheptyl)-6-phenylnicotinamide; (2S,3S,4R)—N-[5-[(2-aminophenyl)

amino]-5-oxopentyl]-2-ethoxy-3,4-dihydro-3-(3-hydroxypropyl)-4-(1-methylethyl)-2H-pyran-6-carboxamide; (2R,3S,4S)—N-[5-[(2-aminophenyl)amino]-5-oxopentyl]-2-ethoxy-3,4-dihydro-3-(3-hydroxypropyl)-4-(1-methylethyl)-2H-pyran-6-carboxamide; (2S,3R,4R)—N-[5-[(2-aminophenyl)amino]-5-oxopentyl]-2-ethoxy-3,4-dihydro-3-(3-hydroxypropyl)-4-(1-methylethyl)-2H-pyran-6-carboxamide; (2R,4S)—N-(5-(2-aminophenylamino)-5-oxopentyl)-2-(3-hydroxypropoxy)-4-isopropyl-3,4-dihydro-2H-pyran-6-carboxamide; (2S,4R)—N-(5-(2-aminophenylamino)-5-oxopentyl)-2-(3-hydroxypropoxy)-4-isopropyl-3,4-dihydro-2H-pyran-6-carboxamide; (2R,3R,4S)—N-[5-[(2-aminophenyl)amino]-5-oxopentyl]-2-ethoxy-3,4-dihydro-3-(3-hydroxypropyl)-4-(3-thienyl)-2H-pyran-6-carboxamide; (2S,3R,4R)—N-[5-[(2-aminophenyl)amino]-5-oxopentyl]-2-ethoxy-3,4-dihydro-3-(3-hydroxypropyl)-4-phenyl-2H-pyran-6-carboxamide; (2R,4R)—N-(5-(2-aminophenylamino)-5-oxopentyl)-2-(3-hydroxypropoxy)-4-phenyl-3,4-dihydro-2H-pyran-6-carboxamide; (2S,4S)—N-(5-(2-aminophenylamino)-5-oxopentyl)-2-(3-hydroxypropoxy)-4-phenyl-3,4-dihydro-2H-pyran-6-carboxamide; (2S,4S)—N-(5-(2-aminophenylamino)-5-oxopentyl)-2-(3-hydroxypropoxy)-4-(thiophen-3-yl)-3,4-dihydro-2H-pyran-6-carboxamide; (2R,4S)—N-(5-(2-aminophenylamino)-5-oxopentyl)-2-(4-hydroxybutoxy)-4-isopropyl-3,4-dihydro-2H-pyran-6-carboxamide; (2S,4R)—N-(5-(2-aminophenylamino)-5-oxopentyl)-2-(4-hydroxybutoxy)-4-isopropyl-3,4-dihydro-2H-pyran-6-carboxamide; and (2S,4S)—N-(5-(2-aminophenylamino)-5-oxopentyl)-2-(4-hydroxybutoxy)-4-(thiophen-3-yl)-3,4-dihydro-2H-pyran-6-carboxamide;

or a pharmaceutically acceptable salt thereof.

In one aspect, the invention features compounds of Formula (I):

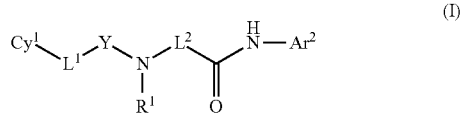

(I)

and pharmaceutically acceptable salts, hydrates, and solvates thereof; wherein:

Y is selected from C(=O), S(=O), and S(=O)$_2$;

$Ar^2$ is selected from phenyl, 5-membered heteroaryl, and 6-membered heteroaryl; wherein said phenyl, 5-membered heteroaryl, and 6-membered heteroaryl are each substituted at one ortho position by one J group and by m independently selected $R^z$ groups;

$L^2$ is a linking group selected from ∥-A-∥, ∥-a-D-∥, ∥-D-a-∥, and ∥-b-D-b-∥; wherein said linking group is optionally substituted by 1, 2, 3, or 4 $R^x$ groups; ∥-indicates a single bond attaching the linking group to the nitrogen atom of the $N(R^1)(Y-L^1-Cy^1)$ group of Formula (I); and -∥ indicates a single bond attaching the linking group to the carbonyl group of the —C(=O)NH($Ar^2$) moiety of Formula (I); provided that there are 4, 5, or 6 atoms connecting the shortest path from ∥- to -∥;

A is selected from straight chain $C_{4-6}$ alkylene, straight chain $C_{4-6}$ alkenylene straight chain $C_{4-6}$ alkynylene, 5-membered cycloalkylene, 6-membered cycloalkylene, 7-membered cycloalkylene, 5-membered heterocycloalkylene, 6-membered heterocycloalkylene, 7-membered heterocycloalkylene, phenylene, 5-membered heteroarylene, 6-membered heteroarylene, and 7-membered heteroarylene; wherein 1 or 2 carbon atoms of said straight chain $C_{4-6}$ alkylene, straight chain $C_{4-6}$ alkenylene, and straight chain $C_{4-6}$ alkynylene are each optionally replaced by a group independently selected from —O—, —S—, —S(=O)—, —S(=O)$_2$—, —C(=O)—, and —NR$^a$—;

D is selected from 3-membered cycloalkylene, 4-membered cycloalkylene, 5-membered cycloalkylene, 6-membered cycloalkylene, 7-membered cycloalkylene, 3-membered heterocycloalkylene, 4-membered heterocycloalkylene, 5-membered heterocycloalkylene, 6-membered heterocycloalkylene, 7-membered heterocycloalkylene, phenylene, 3-membered heteroarylene, 4-membered heteroarylene, 5-membered heteroarylene, 6-membered heteroarylene, and 7-membered heteroarylene;

a is selected from straight chain $C_{1-4}$ alkylene, straight chain $C_{1-4}$ alkenylene, and straight chain $C_{1-4}$ alkynylene; wherein 1 or 2 carbons of said straight chain $C_{1-4}$ alkylene, straight chain $C_{1-4}$ alkenylene, and straight chain $C_{1-4}$ alkynylene are each optionally replaced by a group independently selected from —O—, —S—, —S(=O)—, —S(=O)$_2$—, —C(=O)—, and —NR$^a$—;

each b is independently selected from straight chain $C_{1-3}$ alkylene, straight chain $C_{1-3}$ alkenylene, and straight chain $C_{1-3}$ alkynylene;

each $R^a$ is independently selected from H and $C_{1-3}$ alkyl;

$Cy^1$ is selected from $C_{2-9}$ heterocycloalkyl, $C_{6-10}$ aryl, and $C_{1-9}$ heteroaryl; each of which is substituted with n independently selected $R^y$ groups;

$L^1$ is selected from a bond and $C_{1-4}$ alkylene;

$R^1$ is selected from H, $C_{1-4}$ alkyl, $C_{1-4}$ haloalkyl, $C_{1-4}$alkoxycarbonyl, carbamyl, di-$C_{1-4}$-alkyl-carbamyl, and $C_{1-4}$ alkylcarbamyl;

J is selected from amino and hydroxyl;

each $R^x$ is independently selected from halogen, hydroxyl, cyano, nitro, $C_{1-4}$ alkyl, $C_{1-4}$ alkoxy, $C_{1-4}$ haloalkyl, $C_{1-4}$ haloalkoxy, amino, $C_{1-4}$ alkylamino, and di-$C_{1-4}$-alkylamino;

each $R^y$ is independently selected from halogen, cyano, nitro, hydroxyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$alkylcarbonyl, carbamyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, amino, $C_{1-6}$ alkylamino, di-$C_{1-6}$alkylamino, $C_{3-7}$ cycloalkyl, $C_{2-6}$ heterocycloalkyl, phenyl, $C_{1-6}$ heteroaryl, $C_{3-7}$cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$alkylcarbonyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, $C_{1-6}$ alkylamino, di-$C_{1-6}$alkylamino are each optionally substituted by 1, 2, or 3 independently selected $R^{y'}$ groups; and wherein said $C_{3-7}$ cycloalkyl, $C_{2-6}$ heterocycloalkyl, phenyl, $C_{1-6}$ heteroaryl, $C_{3-7}$cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1, 2, or 3 independently selected $R^{y'}$ groups;

provided that only one $R^y$ is selected from optionally substituted $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;

each $R^z$ is independently selected from halogen, cyano, nitro, hydroxyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$haloalkoxy, $C_{1-6}$ alkoxycarbonyl, $C_{1-6}$alkylcarbonyl, carbamyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, amino, $C_{1-6}$ alkylamino, di-$C_{1-6}$alkylamino, $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$alkylcarbonyl, $C_{1-6}$ alkylcarbamyl, di-$C_{1-6}$ alkylcarbamyl, $C_{1-6}$ alkylcarbonylamino, $C_{1-6}$alkylcarbonyl-($C_{1-4}$-alkyl)amino, $C_{1-6}$alkoxycarbonylamino, $C_{1-6}$ alkylamino, di-$C_{1-6}$ alkylamino are each optionally substituted by 1, 2, or 3 independently selected $R^{z'}$ groups; and wherein said $C_{3-7}$cycloalkyl, $C_{2-6}$ heterocycloalkyl, phenyl, $C_{1-6}$ heteroaryl, $C_{3-7}$cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1, 2, or 3 independently selected $R^{z''}$ groups;

provided that only one $R^z$ is selected from optionally substituted $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;

each $R^{y'}$ and $R^{z'}$ is independently selected from hydroxyl, cyano, nitro, $C_{1-4}$ alkoxy, $C_{1-4}$ haloalkoxy, amino, $C_{1-4}$ alkylamino, and di-$C_{1-4}$-alkylamino;

each $R^{y''}$ and $R^{z''}$ is independently selected from halogen, hydroxyl, cyano, nitro, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

n is an integer selected from 0, 1, 2, 3, and 4; and m is an integer selected from 0, 1, 2, and 3;

provided that the compound is not selected from N-(7-(2-aminophenylamino)-7-oxoheptyl)biphenyl-3-carboxamide, N-(7-(2-aminophenylamino)-7-oxoheptyl)biphenyl-4-carboxamide, and N-(7-(2-aminophenylamino)-7-oxoheptyl)-6-phenylnicotinamide, and pharmaceutically acceptable salts thereof.

In some embodiments, $Cy^1$ is not optionally substituted 3,4-dihydro-2H-pyran-6-yl as defined herein.

In some embodiments, each $R^y$ is independently selected from halogen, cyano, nitro, hydroxyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$alkoxycarbonyl, $C_{1-6}$ alkylcarbonyl, $C_{1-6}$haloalkylcarbonyl, $C_{6-10}$ arylcarbonyl, $C_{1-6}$ alkylsulfonyl; sulfonamido; $C_{1-6}$alkylthio; carbamyl, $C_{1-6}$ alkylcarbamyl, di-$C_{1-6}$ alkylcarbamyl, $C_{1-6}$alkylcarbonylamino, $C_{1-6}$alkylcarbonyl-($C_{1-4}$-alkyl)amino, $C_{1-6}$alkoxycarbonylamino, amino, $C_{1-6}$ alkylamino, di-$C_{1-6}$ alkylamino, $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{2-6}$ alkenyl, $C_{2-6}$ alkynyl, $C_{1-6}$ haloalkyl, $C_{1-6}$ alkoxy, $C_{1-6}$haloalkoxy, $C_{1-6}$ alkoxycarbonyl, $C_{1-6}$alkylcarbonyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, $C_{1-6}$ alkylamino, di-$C_{1-6}$ alkylamino are each optionally substituted by 1, 2, or 3 independently selected $R^{y'}$ groups; and wherein said $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1, 2, or 3 independently selected $R^{y''}$ groups;

provided that only one $R^y$ is selected from optionally substituted $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl.

In some embodiments, each $R^y$ is independently selected from halogen, cyano, nitro, hydroxyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$alkoxycarbonyl, $C_{1-6}$alkylcarbonyl, carbamyl, $C_{1-6}$ alkylcarbamyl, di-$C_{1-6}$ alkylcarbamyl, $C_{1-6}$alkylcarbonylamino, $C_{1-6}$alkylcarbonyl-($C_{1-4}$-alkyl)amino, $C_{1-6}$ alkoxycarbonylamino, amino, $C_{1-6}$ alkylamino, di-$C_{1-6}$alkylamino, $C_{3-7}$ cycloalkyl, $C_{2-6}$ heterocycloalkyl, phenyl, $C_{1-6}$ heteroaryl, $C_{3-7}$cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$alkylcarbonyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$alkoxycarbonylamino, $C_{1-6}$ alkylamino, di-$C_{1-6}$alkylamino are each optionally substituted by 1, 2, or 3 independently selected $R^{y'}$ groups; and wherein said $C_{3-7}$cycloalkyl, $C_{2-6}$ heterocycloalkyl, phenyl, $C_{1-6}$ heteroaryl, $C_{3-7}$cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1, 2, or 3 independently selected $R^{y''}$ groups;

provided that only one $R^y$ is selected from optionally substituted $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;

In some embodiments, each $R^y$ is independently selected from halogen, cyano, nitro, $C_{1-6}$ alkyl, $C_{1-6}$ haloalkyl, $C_{1-6}$ alkoxy, $C_{1-6}$ haloalkoxy, $C_{3-7}$ cycloalkyl, $C_{2-6}$ heterocycloalkyl, phenyl, $C_{1-6}$ heteroaryl, $C_{3-7}$cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{y'}$ groups; and wherein said $C_{3-7}$cycloalkyl, $C_{2-6}$ heterocycloalkyl, phenyl, $C_{1-6}$ heteroaryl, $C_{3-7}$cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1 or 2 independently selected $R^{y''}$ groups;

provided that only one $R^y$ is selected from optionally substituted $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; and provided that the compound is not selected from N-(7-(2-aminophenylamino)-7-oxoheptyl)biphenyl-3-carboxamide, N-(7-(2-aminophenylamino)-7-oxoheptyl)biphenyl-4-carboxamide, N-(7-(2-aminophenylamino)-7-oxoheptyl)-6-phenylnicotinamide, and pharmaceutically acceptable salts thereof.

In some embodiments, $Cy^1$ is not selected from optionally substituted 3,4-dihydro-2H-pyran-6-yl.

In some of the new compounds, each $R^y$ is independently selected from halogen, cyano, $C_{1-6}$ alkyl, $C_{1-6}$ haloalkyl, $C_{1-6}$ alkoxy, $C_{1-6}$ haloalkoxy, $C_{1-6}$alkoxycarbonyl, $C_{1-6}$ alkylcarbonyl, carbamyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, and di-$C_{1-6}$ alkylamino; wherein said $C_{1-6}$ alkyl, $C_{1-6}$ haloalkyl, $C_{1-6}$ alkoxy, $C_{1-6}$ haloalkoxy, $C_{1-6}$alkoxycarbonyl, $C_{1-6}$alkylcarbonyl, carbamyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, and di-$C_{1-6}$alkylamino are each optionally substituted by 1, 2, or 3 independently selected $R^{y'}$ groups.

In some other of the new compounds, each $R^y$ is independently selected from halogen, $C_{1-6}$alkyl, $C_{1-6}$ haloalkyl, $C_{1-6}$ alkoxy, $C_{1-6}$ haloalkoxy, $C_{3-7}$ cycloalkyl, and $C_{2-6}$ heterocycloalkyl; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{y'}$ groups; and wherein said $C_{3-7}$ cycloalkyl and $C_{2-6}$ heterocycloalkyl are each optionally substituted by 1 or 2 independently selected $R^{y''}$ groups.

In certain embodiments, each $R^y$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{y'}$ groups.

In certain embodiments, each $R^y$ is independently selected from $C_{1-6}$ alkyl and $C_{1-6}$ alkoxy, wherein said $C_{1-6}$ alkyl and $C_{1-6}$ alkoxy are each optionally substituted by 1, 2, or 3 independently selected $R^{y'}$ groups.

In certain embodiments, each $R^y$ is independently selected from $C_{1-6}$ haloalkylcarbonyl, $C_{6-10}$ arylcarbonyl, $C_{1-6}$ alkylsulfonyl, sulfonamido, and $C_{1-6}$ alkylthio.

In some embodiments, each $R^z$ is independently selected from halogen, cyano, nitro, hydroxyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{6-10}$ aryloxy, $C_{1-6}$alkoxycarbonyl, $C_{1-6}$alkylcarbonyl, carbamyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$alkoxycarbonylamino, amino, $C_{1-6}$ alkylamino, di-$C_{1-6}$alkylamino, $C_{3-7}$ cycloalkyl, $C_{2-6}$ heterocycloalkyl, phenyl, $C_{1-6}$ heteroaryl, $C_{3-7}$cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_1$-6 alkoxycarbonyl, $C_{1-6}$alkylcarbonyl, $C_{1-6}$ alkylcarbamyl, di-$C_{1-6}$ alkylcarbamyl, $C_{1-6}$ alkylcarbonylamino, $C_{1-6}$alkylcarbonyl-($C_{1-4}$-alkyl)amino, $C_{1-6}$ alkoxycarbonylamino, $C_{1-6}$ alkylamino, di-$C_{1-6}$ alkylamino are each optionally substituted by 1, 2, or 3 independently selected $R^{z'}$ groups; and wherein said $C_{3-7}$cycloalkyl, $C_{2-6}$ heterocycloalkyl, phenyl, $C_{1-6}$ heteroaryl, $C_{3-7}$cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1, 2, or 3 independently selected $R^{z''}$ groups;

provided that only one $R^z$ is selected from optionally substituted $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl.

In some embodiments, each $R^z$ is independently selected from halogen, cyano, nitro, hydroxyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$alkoxycarbonyl, $C_{1-6}$alkylcarbonyl, carbamyl, $C_{1-6}$ alkylcarbamyl, di-$C_{1-6}$ alkylcarbamyl, $C_{1-6}$alkylcarbonylamino, $C_{1-6}$alkylcarbonyl-($C_{1-4}$-alkyl)amino, $C_{1-6}$ alkoxycarbonylamino, amino, $C_{1-6}$ alkylamino, di-$C_{1-6}$alkylamino, $C_{3-7}$cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$ alkylcarbonyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, $C_{1-6}$ alkylamino, di-$C_{1-6}$alkylamino are each optionally substituted by 1, 2, or 3 independently selected $R^{z'}$ groups; and wherein said $C_{3-7}$cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1 or 2 independently selected $R^{z''}$ groups;

provided that only one $R^z$ is selected from optionally substituted $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;

In some of the new compounds, each $R^z$ is independently selected from halogen, cyano, nitro, $C_{1-6}$ alkyl, $C_{1-6}$ haloalkyl, $C_{1-6}$alkoxy, $C_{1-6}$haloalkoxy, $C_{3-7}$cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-6}$-alkyl, phenyl-$C_{1-4}$-alkyl, and $C_{1-6}$ heteroaryl-$C_{1-4}$-alkyl; wherein said $C_{1-6}$ alkyl, $C_{1-6}$ haloalkyl, $C_{1-6}$alkoxy, and $C_{1-6}$ haloalkoxy are each optionally substituted by 1, 2, or 3 independently selected $R^{z'}$ groups; and wherein said $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1 or 2 independently selected $R^{z''}$ groups;

provided that only one $R^z$ is selected from optionally substituted $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl.

In certain of the new compounds, each $R^z$ is independently selected from halogen, cyano, $C_{1-6}$ alkyl, $C_{1-6}$ haloalkyl, $C_{1-6}$ alkoxy, $C_{1-6}$ haloalkoxy, $C_{1-6}$alkoxycarbonyl, $C_{1-6}$ alkylcarbonyl, carbamyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, and di-$C_{1-6}$ alkylamino; wherein said $C_{1-6}$ alkyl, $C_{1-6}$ haloalkyl, $C_{1-6}$ alkoxy, $C_{1-6}$haloalkoxy, $C_{1-6}$alkoxycarbonyl, $C_{1-6}$alkylcarbonyl, carbamyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, and di-$C_{1-6}$ alkylamino are each optionally substituted by 1, 2, or 3 independently selected $R^z$ groups.

In some embodiments, each $R^z$ is independently selected from halogen, cyano, nitro, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^z$ groups.

In certain of the new compounds, each $R^z$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1 or 2 independently selected $R^{z'}$ groups.

In embodiments, each $R^z$ is halogen (e.g., fluoro).

In some embodiments, each $R^z$ is selected from phenyl and $C_{1-6}$ heteroaryl, each of which is optionally substituted by 1, 2, or 3 independently selected $R^{z''}$ groups. In some embodiments, each $R^z$ is selected from phenyl and $C_{1-6}$ heteroaryl. In certain embodiments, each $R^z$ is phenyl or phenyl, which is substituted by 1, 2, or 3 independently selected $R^{z''}$ groups. In certain embodiments, each $R^z$ is $C_{1-6}$ heteroaryl or $C_{1-6}$ heteroaryl, which is optionally substituted by 1, 2, or 3 independently selected $R^{z''}$ groups.

In certain embodiments, m is 1. In embodiments, $R^z$ is selected from halogen, $C_{1-6}$ alkyl, $C_{1-6}$ haloalkyl, $C_{1-6}$ alkoxy, and $C_{1-6}$ haloalkoxy. In embodiments, $R^z$ is halogen (e.g., fluoro). In other embodiments, $R^z$ is selected from phenyl and $C_{1-6}$ heteroaryl, each of which is optionally substituted by 1, 2, or 3 independently selected $R^{z''}$ groups. In some embodiments, $R^z$ is selected from phenyl and $C_{1-6}$ heteroaryl. In certain embodiments, $R^z$ is phenyl or phenyl, which is substituted by 1, 2, or 3 independently selected $R^{z''}$ groups. In certain embodiments, $R^z$ is $C_{1-6}$ heteroaryl or $C_{1-6}$ heteroaryl, which is optionally substituted by 1, 2, or 3 independently selected $R^{z''}$ groups.

In some embodiments, each $R^{y'}$ and $R^{z'}$ group is independently selected from hydroxyl, cyano, nitro, $C_{1-4}$ alkoxy, $C_{1-4}$ haloalkoxy, amino, $C_{1-4}$ alkylamino, and di-$C_{1-4}$-alkylamino. In some embodiments, each $R^{y'}$ and $R^{z'}$ group is independently selected from hydroxyl, $C_{1-4}$ alkoxy, and $C_{1-4}$ haloalkoxy. In some embodiments, each $R^{y''}$ and $R^{z''}$ group is independently selected from hydroxyl, cyano, nitro, $C_{1-4}$ alkoxy, $C_{1-4}$ haloalkoxy, amino, $C_{1-4}$ alkylamino, and di-$C_{1-4}$-alkylamino. In some embodiments, each $R^{y''}$ and $R^{z''}$ group is independently selected from hydroxyl, $C_{1-4}$ alkoxy, and $C_{1-4}$ haloalkoxy.

$R^1$ can also be selected from H, $C_{1-4}$ alkyl, and $C_{1-4}$ haloalkyl, or from H and $C_{1-4}$ alkyl. In some embodiments, $R^1$ is H.

In some embodiments, $L^1$ is selected from a bond or $C_{1-4}$ alkylene.

In some embodiments, $L^1$ is selected from a bond or $C_{1-4}$ alkylene; wherein 1 carbon atom of said straight chain $C_{1-4}$ alkylene is optionally replaced by —C(=O)—.

In some embodiments, $L^1$ is selected from a bond, $C_{1-3}$alkylene and $C_{1-2}$alkylene.

In some embodiments, $L^1$ is a bond. In some embodiments, $L^1$ is a bond, when $Cy^1$ is optionally substituted phenyl or optionally substituted 6-membered heteroaryl.

In some of the new compounds, $L^2$ is selected from straight chain $C_4$ alkylene, straight chain $C_5$ alkylene, and straight chain $C_6$ alkylene; each of which is optionally substituted by 1, 2, or 3 independently selected $R^x$ groups. In some embodiments, $L^2$ is selected from straight chain $C_4$ alkylene, straight chain $C_5$ alkylene, and straight chain $C_6$ alkylene; each of which is optionally substituted by 1 or 2 independently selected $R^x$ groups. In some embodiments, $L^2$ is selected from straight chain $C_4$ alkylene, straight chain $C_5$ alkylene, and straight chain $C_6$ alkylene; each of which is optionally substituted by a $R^x$ group. In some embodiments, $L^2$ is selected from unsubstituted straight chain $C_4$ alkylene, unsubstituted straight chain $C_5$ alkylene, and unsubstituted straight chain $C_6$ alkylene. In some embodiments, $L^2$ is —CH$_2$CH$_2$CH$_2$CH$_2$CH$_2$—. In some embodiments, $L^2$ is selected from:

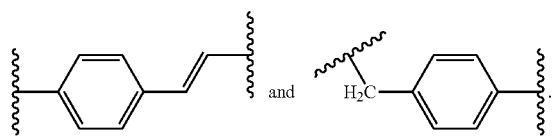 [SMILES: */C=C/c1ccc(*)cc1 ; *Cc1ccc(*)cc1]

In some of the new compounds, $L^2$ is a linking group which is ∥-A-∥; wherein said linking group is optionally substituted by 1, 2, 3, or 4 $R^x$ groups. In some embodiments, $L^2$ is a linking group which is ∥-A-∥; A is selected from straight chain $C_{4-6}$ alkylene, straight chain $C_{4-6}$ alkenylene, and straight chain $C_{4-6}$ alkynylene; wherein 1 or 2 carbon atoms of said straight chain $C_{4-6}$ alkylene, straight chain $C_{4-6}$ alkenylene, and straight chain $C_{4-6}$ alkynylene are each optionally replaced by a group independently selected from —O— and —S—. In some embodiments, $L^2$ is a linking group which is ∥-A-∥; A is selected from unsubstituted straight chain $C_{4-6}$ alkylene, straight chain $C_{4-6}$ alkenylene, and straight chain $C_{4-6}$ alkynylene. In some embodiments, $L^2$ is a linking group which is ∥-A-∥; A is selected from straight chain $C_{4-6}$ alkylene; wherein 1 or 2 carbon atoms of said straight chain $C_{4-6}$ alkylene are each optionally replaced by a group independently selected from —O— and —S—. In some embodiments, $L^2$ is a linking group which is ∥-A-∥; wherein said linking group is optionally substituted by 1 or 2 $R^x$ groups; A is selected from 5-membered cycloalkylene, 6-membered cycloalkylene, 7-membered cycloalkylene, 5-membered heterocycloalkylene, 6-membered heterocycloalkylene, 7-membered heterocycloalkylene, phenylene, 5-membered heteroarylene, 6-membered heteroarylene, and 7-membered heteroarylene. In some embodiments, $L^2$ is a linking group which is ∥-A-∥; A is selected from 5-membered cycloalkylene, 6-membered cycloalkylene, 7-membered cycloalkylene, 5-membered heterocycloalkylene, 6-membered heterocycloalkylene, 7-membered heterocycloalkylene, phenylene, 5-membered heteroarylene, 6-membered heteroarylene, and 7-membered heteroarylene. In some embodiments, $L^2$ is an unsubstituted moiety.

In some embodiments, $L^2$ is straight chain $C_{4-6}$ alkenylene, which is optionally substituted by 1, 2, or 3 independently selected $R^x$ groups. In certain embodiments, $L^2$ is straight chain $C_{4-6}$ alkenylene, which is optionally substituted by 1, 2, or 3 independently selected $R^x$ groups, and which has one double bond.

In some embodiments, $L^2$ is unsubstituted straight chain $C_{4-6}$ alkenylene. In certain embodiments, $L^2$ is unsubstituted straight chain $C_{4-6}$ alkenylene having one double bond. For example, $L^2$ is selected from:

∥—(CH$_2$)$_{1-3}$—CH$_2$—CH=CH-∥ and ∥—(CH$_2$)$_{1-3}$—CH=CH—CH$_2$-∥.

In certain embodiments, $L^2$ is ∥—(CH$_2$)$_{1-3}$—CH$_2$—CH=CH-∥. Examples of such compounds include R112, R113, R114, R115, R116, R117, and R118.

In some embodiments, compounds in which $L^2$ contains one (or more) double bonds have enhanced (e.g., increased, e.g., increased by a factor of about 2 or more relative to the corresponding saturated compounds) stabilities in acid. In certain embodiments, compounds in which $L^2$ contains one or more double bonds have enhanced resistances to degradation, e.g., less than about 25% degradation (e.g., less than about 20% degradation, less than about 15% degradation, or less than about 10% degradation) when exposed to acidic pH, e.g., acidic conditions intended to mimic those in the stomach, e.g., incubation (e.g., as a 10 μM solution) at 50° C. and at a pH of about 2.0 for about four hours.

In certain embodiments, compounds in which $L^2$ is ∥—(CH$_2$)$_{1-3}$—CH$_2$—CH=CH-∥ have enhanced (e.g., increased, e.g., increased by a factor of about 2 or more relative to the corresponding saturated compounds) stabilities in acid. In certain embodiments, compounds in which $L^2$ is ∥—(CH$_2$)$_{1-3}$—CH$_2$—CH=CH-∥ have enhanced resistances to degradation, e.g., less than about 25% degradation (e.g., less than about 20% degradation, less than about 15% degradation, or less than about 10% degradation) when exposed to acidic pH, e.g., acidic conditions intended to mimic those in the stomach, e.g., incubation (e.g., as a 10 μM solution) at 50° C. and at a pH of about 2.0 for about four hours.

In some of the new compounds, $L^2$ is a linking group selected from ∥-a-D-∥ and ∥-D-a-∥; wherein said linking group is optionally substituted by 1, 2, 3, or 4 $R^x$ groups. In some embodiments, $L^2$ is a linking group which is ∥-a-D-∥; wherein said linking group is optionally substituted by 1 or 2 $R^x$ groups. In some embodiments, $L^2$ is a linking group which is ∥-D-a-∥; wherein said linking group is optionally substituted by 1 or 2 $R^x$ groups. In some embodiments, $L^2$ is a linking group which is an unsubstituted ∥-a-D-∥ moiety. In some embodiments, $L^2$ is a linking group which is an unsubstituted ∥-D-a-∥ moiety.

In some embodiments of the embodiments of the preceding paragraph, D is selected from 3-membered cycloalkylene, 4-membered cycloalkylene, 5-membered cycloalkylene, 6-membered cycloalkylene, 7-membered cycloalkylene, 3-membered heterocycloalkylene, 4-membered heterocycloalkylene, 5-membered heterocycloalkylene, 6-membered heterocycloalkylene, 7-membered heterocycloalkylene, phenylene, 3-membered heteroarylene, 4-membered heteroarylene, 5-membered heteroarylene, 6-membered heteroarylene, and 7-membered heteroarylene; and a is selected from straight chain $C_{1-4}$ alkylene, straight chain $C_{1-4}$ alkenylene, and straight chain $C_{1-4}$ alkynylene. In some embodiments of the embodiments of the preceding paragraph, D is selected from phenylene, 5-membered heteroarylene and 6-membered heteroarylene; and a is selected from straight chain $C_{1-2}$ alkylene and straight chain $C_{1-2}$ alkenylene. In some embodiments of the embodiments of the preceding paragraph, D is selected from phenylene; and a is selected from straight chain $C_{1-4}$ alkylene and straight chain $C_{1-2}$ alkenylene. In some embodiments of the embodiments of the preceding paragraph, D is selected from phenylene; and a is selected from straight chain $C_{1-2}$ alkylene and straight chain $C_{1-2}$ alkenylene. In some embodiments of the embodiments of the preceding paragraph, D is selected from phenylene; and a is selected from straight chain $C_{1-2}$ alkylene. In some embodiments of the embodiments of the preceding paragraph, D is selected from phenylene; and a is selected from straight chain $C_{1-2}$ alkenylene.

In some of the new compounds, $L^2$ is a linking group which is ‖-b-D-b-‖; wherein said linking group is optionally substituted by 1, 2, 3, or 4 $R^x$ groups. In some embodiments, $L^2$ is a linking group which is ‖-b-D-b-‖; wherein said linking group is optionally substituted by 1 or 2 $R^x$ groups. In some embodiments, $L^2$ is a linking group which is ‖-b-D-b-‖.

In some embodiments of the embodiments of the preceding paragraph, D is selected from 3-membered cycloalkylene, 4-membered cycloalkylene, 5-membered cycloalkylene, 6-membered cycloalkylene, 7-membered cycloalkylene, 3-membered heterocycloalkylene, 4-membered heterocycloalkylene, 5-membered heterocycloalkylene, 6-membered heterocycloalkylene, 7-membered heterocycloalkylene, phenylene, 3-membered heteroarylene, 4-membered heteroarylene, 5-membered heteroarylene, 6-membered heteroarylene, and 7-membered heteroarylene; and each b is independently selected from straight chain $C_{1-2}$ alkylene, straight chain $C_{1-2}$ alkenylene, and straight chain $C_{1-2}$ alkynylene. In some embodiments of the embodiments of the preceding paragraph, D is selected from phenylene, 5-membered heteroarylene and 6-membered heteroarylene; and each b is independently selected from straight chain $C_{1-2}$ alkylene and straight chain $C_{1-2}$ alkenylene. In some embodiments of the embodiments of the preceding paragraph, D is selected from phenylene; and each b is independently selected from straight chain $C_1$ alkylene and straight chain $C_1$ alkenylene. In some embodiments of the embodiments of the preceding paragraph, D is selected from phenylene; and each b is methylene. In some embodiments of the embodiments of the preceding paragraph, D is selected from phenylene; and each b is methylene.

In some embodiments, each $R^x$ is independently selected from halogen, hydroxyl, $C_{1-4}$ alkyl, $C_{1-4}$ alkoxy, $C_{1-4}$ haloalkyl, and $C_{1-4}$ haloalkoxy. In some embodiments, each $R^x$ is independently selected from hydroxyl, $C_{1-4}$ alkyl, and $C_{1-4}$ alkoxy. In some embodiments, each $R^x$ is independently selected from $C_{1-4}$ alkyl.

In some embodiments, Y can be selected from, or is, $C(=O)$ and/or $S(=O)_2$. In some embodiments, J is amino. In other embodiments, In some embodiments, J is hydroxyl.

In some embodiments, n is an integer selected from 0, 1, 2, and 3. In some embodiments, n is an integer selected from 0, 1, and 2. In some embodiments, n is an integer selected from 0 and 1. In some embodiments, n is an integer selected from 1 and 2. In some embodiments, n is 0.

In some embodiments, m is an integer selected from 0, 1, and 2. In some embodiments, m is an integer selected from 0 and 1. In some embodiments, m is 0. In some embodiments, m is 1.

In some embodiments, $Cy^1$ is selected from $C_{2-9}$ heterocycloalkyl; which is substituted with n independently selected $R^y$ groups.

In certain embodiments, $Cy^1$ is not optionally substituted 2-dihydropyranyl (e.g., optionally substituted 3,4-dihydro-2H-pyran-6-yl).

In certain embodiments, $Cy^1$ is not substituted 2-dihydropyranyl (e.g., substituted 3,4-dihydro-2H-pyran-6-yl, e.g., substituted with optionally substituted $C_1$-$C_3$ alkyl, such as isopropyl and/or —$CH_2$—$CH_2$—$CH_2$—OH; and/or substituted with $C_1$-$C_6$ heteroaryl, such as thienyl).

In some embodiments, $Cy^1$ is other than 2-dihydropyranyl (e.g., 3,4-dihydro-2H-pyran-6-yl) substituted with isopropyl and —$CH_2$—$CH_2$—$CH_2$—OH.

In some embodiments, $Cy^1$ is other than 2-dihydropyranyl (e.g., 3,4-dihydro-2H-pyran-6-yl) substituted with thienyl and —$CH_2$—$CH_2$—$CH_2$—OH.

In some embodiments, the compound is not selected from:

N-[5-[(2-aminophenyl)amino]-5-oxopentyl]-2-ethoxy-3,4-dihydro-3-(3-hydroxypropyl)-4-(1-methylethyl)-2H-pyran-6-carboxamide;

N-(5-(2-aminophenylamino)-5-oxopentyl)-2-(3-hydroxypropoxy)-4-isopropyl-3,4-dihydro-2H-pyran-6-carboxamide;

N-[5-[(2-aminophenyl)amino]-5-oxopentyl]-2-ethoxy-3,4-dihydro-3-(3-hydroxypropyl)-4-(3-thienyl)-2H-pyran-6-carboxamide;

N-[5-[(2-aminophenyl)amino]-5-oxopentyl]-2-ethoxy-3,4-dihydro-3-(3-hydroxypropyl)-4-phenyl-2H-pyran-6-carboxamide;

N-(5-(2-aminophenylamino)-5-oxopentyl)-2-(3-hydroxypropoxy)-4-phenyl-3,4-dihydro-2H-pyran-6-carboxamide;

N-(5-(2-aminophenylamino)-5-oxopentyl)-2-(3-hydroxypropoxy)-4-(thiophen-3-yl)-3,4-dihydro-2H-pyran-6-carboxamide;

N-(5-(2-aminophenylamino)-5-oxopentyl)-2-(4-hydroxybutoxy)-4-(thiophen-3-yl)-3,4-dihydro-2H-pyran-6-carboxamide; and N-(5-(2-aminophenylamino)-5-oxopentyl)-2-(4-hydroxybutoxy)-4-isopropyl-3,4-dihydro-2H-pyran-6-carboxamide; and pharmaceutically acceptable salts thereof.

In some embodiments, the compound is not selected from:

(2S,3S,4R)—N-[5-[(2-aminophenyl)amino]-5-oxopentyl]-2-ethoxy-3,4-dihydro-3-(3-hydroxypropyl)-4-(1-methylethyl)-2H-pyran-6-carboxamide;

(2R,3S,4S)—N-[5-[(2-aminophenyl)amino]-5-oxopentyl]-2-ethoxy-3,4-dihydro-3-(3-hydroxypropyl)-4-(1-methylethyl)-2H-pyran-6-carboxamide;

(2S,3R,4R)—N-[5-[(2-aminophenyl)amino]-5-oxopentyl]-2-ethoxy-3,4-dihydro-3-(3-hydroxypropyl)-4-(1-methylethyl)-2H-pyran-6-carboxamide;

(2R,4S)—N-(5-(2-aminophenylamino)-5-oxopentyl)-2-(3-hydroxypropoxy)-4-isopropyl-3,4-dihydro-2H-pyran-6-carboxamide;
(2S,4R)—N-(5-(2-aminophenylamino)-5-oxopentyl)-2-(3-hydroxypropoxy)-4-isopropyl-3,4-dihydro-2H-pyran-6-carboxamide;
(2R,3R,4S)—N-[5-[(2-aminophenyl)amino]-5-oxopentyl]-2-ethoxy-3,4-dihydro-3-(3-hydroxypropyl)-4-(3-thienyl)-2H-pyran-6-carboxamide;
(2S,3R,4R)—N-[5-[(2-aminophenyl)amino]-5-oxopentyl]-2-ethoxy-3,4-dihydro-3-(3-hydroxypropyl)-4-phenyl-2H-pyran-6-carboxamide;
(2R,4R)—N-(5-(2-aminophenylamino)-5-oxopentyl)-2-(3-hydroxypropoxy)-4-phenyl-3,4-dihydro-2H-pyran-6-carboxamide;
(2S,4S)—N-(5-(2-aminophenylamino)-5-oxopentyl)-2-(3-hydroxypropoxy)-4-phenyl-3,4-dihydro-2H-pyran-6-carboxamide;
(2S,4S)—N-(5-(2-aminophenylamino)-5-oxopentyl)-2-(3-hydroxypropoxy)-4-(thiophen-3-yl)-3,4-dihydro-2H-pyran-6-carboxamide;
(2R,4S)—N-(5-(2-aminophenylamino)-5-oxopentyl)-2-(4-hydroxybutoxy)-4-isopropyl-3,4-dihydro-2H-pyran-6-carboxamide;
(2S,4R)—N-(5-(2-aminophenylamino)-5-oxopentyl)-2-(4-hydroxybutoxy)-4-isopropyl-3,4-dihydro-2H-pyran-6-carboxamide; and
(2S,4S)—N-(5-(2-aminophenylamino)-5-oxopentyl)-2-(4-hydroxybutoxy)-4-(thiophen-3-yl)-3,4-dihydro-2H-pyran-6-carboxamide.

In some embodiments, $Cy^1$ is selected from $C_{6-10}$ aryl; which is substituted with n independently selected $R^y$ groups.

In some embodiments, $Cy^1$ is selected from $C_{2-9}$ heteroaryl; which is substituted with n independently selected $R^y$ groups. In certain embodiments, $Cy^1$ is indolyl or indazolyl, each of which is substituted with n independently selected $R^y$ groups. In certain embodiments, $Cy^1$ is indazolyl, which is substituted with n independently selected $R^y$ groups.

In embodiments, n is 0.

In other embodiments, n is an integer selected from 1 and 2. In certain embodiments, each occurrence of $R^y$ is independently selected from $C_{1-6}$ alkyl and $C_{1-6}$ alkoxy, wherein said $C_{1-6}$ alkyl and $C_{1-6}$ alkoxy are each optionally substituted by 1, 2, or 3 independently selected $R^1$ groups.

In some embodiments, $Cy^1$ is selected from phenyl and $C_{1-6}$ heteroaryl; each of which is optionally substituted with n independently selected $R^y$ groups. In some embodiments, $Cy^1$ is selected from phenyl; which is optionally substituted with n independently selected $R^y$ groups. In some embodiments, $Cy^1$ is selected from $C_{1-6}$ heteroaryl; which is optionally substituted with n independently selected $R^y$ groups. In some embodiments, $Cy^1$ is selected from $C_{2-6}$ heterocycloalkyl; which is optionally substituted with n independently selected $R^y$ groups.

In some embodiments, $Ar^2$ is selected from phenyl, 5-membered heteroaryl, and 6-membered heteroaryl; wherein said phenyl, 5-membered heteroaryl, and 6-membered heteroaryl are each substituted at one ortho position by one J group and by m independently selected $R^z$ groups;

In some embodiments, $Ar^2$ is selected from $C_6$-10 aryl, 5-membered heteroaryl, 6-membered heteroaryl, and benzo[d][1,3]dioxolyl; wherein said $C_{6-10}$ aryl, 5-membered heteroaryl, 6-membered heteroaryl and benzo[d][1,3]dioxolyl are each substituted at one ortho position by one J group and by m independently selected $R^z$ groups.

In some embodiments, $Ar^2$ is selected from phenyl; wherein said phenyl; which is substituted at one ortho position by one J group and by m independently selected $R^z$ groups. In some embodiments, $Ar^2$ is selected from 5-membered heteroaryl; which is substituted at one ortho position by one J group and by m independently selected $R^z$ groups. In some embodiments, $Ar^2$ is selected from 6-membered heteroaryl; which is substituted at one ortho position by one J group and by m independently selected $R^z$ groups. In some embodiments, $Ar^2$ is substituted at the para (i.e., the 4-position) position by halogen, $C_{1-6}$ alkyl or $C_{1-6}$ alkoxy. In some embodiments, $Ar^2$ is substituted at the meta (i.e., the 5-position) position by $C_{1-6}$ alkyl or $C_{1-6}$ alkoxy. In some embodiments, $Ar^2$ is substituted at the meta (i.e., the 5-position) position by phenyl and $C_{1-6}$ heteroaryl, each of which is optionally substituted by 1, 2, or 3 independently selected $R^{z''}$ groups.

In some embodiments, the new compounds have Formula (Ia):

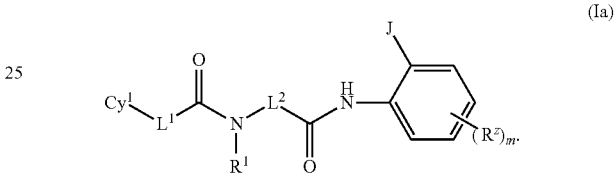

In some embodiments, the compounds have Formula (Ib):

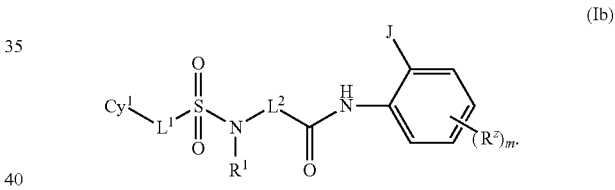

In some of these compounds:
Y is selected from C(═O) and S(═O)$_2$;
$Cy^1$ is selected from $C_{2-9}$ heterocycloalkyl; which is substituted with n independently selected $R^y$ groups;
$Ar^2$ is selected from phenyl, 5-membered heteroaryl, and 6-membered heteroaryl; which is substituted at one ortho position by one J group and by m independently selected $R^z$ groups;
$L^1$ is selected from a bond and $C_{1-4}$ alkylene;
$L^2$ is selected from straight chain $C_4$ alkylene, straight chain $C_5$ alkylene, and straight chain $C_6$ alkylene; each of which is optionally substituted by 1, 2, or 3 $R^x$ groups;
$R^1$ is selected from H, $C_{1-4}$ alkyl, and $C_{1-4}$ haloalkyl;
J is selected from amino and hydroxyl;
each $R^x$ is independently selected from halogen, hydroxyl, cyano, nitro, $C_{1-4}$ alkyl, $C_{1-4}$ alkoxy, $C_{1-4}$ haloalkyl, and $C_{1-4}$ haloalkoxy;
each $R^y$ is independently selected from halogen, cyano, nitro, $C_{1-6}$ alkyl, $C_{1-6}$ haloalkyl, $C_{1-6}$ alkoxy, $C_{1-6}$ haloalkoxy, $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$alkyl, $C_{1-6}$ haloalkyl, $C_{1-6}$ alkoxy, and $C_{1-6}$ haloalkoxy are each optionally substituted by 1, 2, or 3 independently selected $R^{y'}$ groups; and wherein said $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1 or 2 independently selected $R^{y''}$ groups;

provided that only one $R^y$ is selected from optionally substituted $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;

each $R^z$ is independently selected from halogen, cyano, nitro, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{z'}$ groups;

each $R^{y'}$ and $R^{z'}$ is independently selected from hydroxyl, cyano, nitro, $C_{1-4}$ alkoxy, and $C_{1-4}$ haloalkoxy;

each $R^{y''}$ is independently selected from halogen, hydroxyl, cyano, nitro, $C_{1-4}$ alkyl, $C_{1-4}$ haloalkyl, $C_{1-4}$ alkoxy, and $C_{1-4}$ haloalkoxy;

n is an integer selected from 0, 1, 2, and 3; and m is an integer selected from 0, 1, and 2.

In other of these new compounds:

Y is selected from $C(=O)$ and $S(=O)_2$;

$Cy^1$ is selected from $C_{6-10}$ aryl; which is substituted with n independently selected $R^y$ groups;

$Ar^2$ is selected from phenyl; which is substituted at one ortho position by one J group and by m independently selected $R^z$ groups;

$L^1$ is selected from a bond and $C_{1-4}$ alkylene;

$L^2$ is selected from straight chain $C_4$ alkylene, straight chain $C_5$ alkylene, and straight chain $C_6$ alkylene; each of which is optionally substituted by 1, 2, or 3 $R^x$ groups;

$R^1$ is selected from H, $C_{1-4}$ alkyl, and $C_{1-4}$ haloalkyl;

J is selected from amino and hydroxyl;

each $R^x$ is independently selected from halogen, hydroxyl, cyano, nitro, $C_{1-4}$ alkyl, $C_{1-4}$ alkoxy, $C_{1-4}$ haloalkyl, and $C_{1-4}$ haloalkoxy;

each $R^y$ is independently selected from halogen, cyano, nitro, $C_{1-6}$ alkyl, $C_{1-6}$ haloalkyl, $C_{1-6}$ alkoxy, $C_{1-6}$ haloalkoxy, $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{y''}$ groups; and wherein said $C_{3-7}$ cycloalkyl, $C_{2-6}$ heterocycloalkyl, phenyl, $C_{1-6}$ heteroaryl, $C_{3-7}$cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1 or 2 independently selected $R^y$ groups;

provided that only one $R^y$ is selected from optionally substituted $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;

each $R^z$ is independently selected from halogen, cyano, nitro, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{z'}$ groups;

each $R^{y'}$ and $R^{z'}$ is independently selected from hydroxyl, cyano, nitro, $C_{1-4}$ alkoxy, and $C_{1-4}$ haloalkoxy;

each $R^{y''}$ is independently selected from halogen, hydroxyl, cyano, nitro, $C_{1-4}$ alkyl, $C_{1-4}$ haloalkyl, $C_{1-4}$ alkoxy, and $C_{1-4}$ haloalkoxy;

n is an integer selected from 0, 1, 2, and 3; and m is an integer selected from 0, 1, and 2.

In other of the new compounds:

Y is selected from $C(=O)$ and $S(=O)_2$;

$Cy^1$ is selected from $C_{6-10}$ aryl; which is substituted with n independently selected $R^y$ groups;

$Ar^2$ is 5-membered heteroaryl or 6-membered heteroaryl; each of which is substituted at one ortho position by one J group and by m independently selected $R^z$ groups;

$L^1$ is selected from a bond and $C_{1-4}$ alkylene;

$L^2$ is selected from straight chain $C_4$ alkylene, straight chain $C_5$ alkylene, and straight chain $C_6$ alkylene; each of which is optionally substituted by 1, 2, or 3 $R^x$ groups;

$R^1$ is selected from H, $C_{1-4}$ alkyl, and $C_{1-4}$ haloalkyl;

J is selected from amino and hydroxyl;

each $R^x$ is independently selected from halogen, hydroxyl, cyano, nitro, $C_{1-4}$ alkyl, $C_{1-4}$ alkoxy, $C_{1-4}$ haloalkyl, and $C_{1-4}$ haloalkoxy;

each $R^y$ is independently selected from halogen, cyano, nitro, $C_{1-6}$ alkyl, $C_{1-6}$ haloalkyl, $C_{1-6}$ alkoxy, $C_{1-6}$ haloalkoxy, $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^y$ groups; and wherein said $C_{3-7}$ cycloalkyl, $C_{2-6}$ heterocycloalkyl, phenyl, $C_{1-6}$ heteroaryl, $C_{3-7}$cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1 or 2 independently selected $R^{y''}$ groups;

provided that only one $R^y$ is selected from optionally substituted $C_{3-7}$cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;

each $R^z$ is independently selected from halogen, cyano, nitro, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{z'}$ groups;

each $R^{y'}$ and $R^{z'}$ is independently selected from hydroxyl, cyano, nitro, $C_{1-4}$ alkoxy, and $C_{1-4}$ haloalkoxy;

each $R^{y''}$ is independently selected from halogen, hydroxyl, cyano, nitro, $C_{1-4}$ alkyl, $C_{1-4}$ haloalkyl, $C_{1-4}$ alkoxy, and $C_{1-4}$ haloalkoxy;

n is an integer selected from 0, 1, 2, and 3; and m is an integer selected from 0, 1, and 2.

In some embodiments:

Y is selected from $C(=O)$ and $S(=O)_2$;

$Cy^1$ is selected from $C_{1-9}$ heteroaryl; which is substituted with n independently selected $R^y$ groups;

$Ar^2$ is selected from phenyl; which is substituted at one ortho position by one J group and by m independently selected $R^z$ groups;

$L^1$ is selected from a bond and $C_{1-4}$ alkylene;

$L^2$ is selected from straight chain $C_4$ alkylene, straight chain $C_5$ alkylene, and straight chain $C_6$ alkylene; each of which is optionally substituted by 1, 2, or 3 $R^x$ groups;

$R^1$ is selected from H, $C_{1-4}$ alkyl, and $C_{1-4}$ haloalkyl;

J is selected from amino and hydroxyl;

each $R^x$ is independently selected from halogen, hydroxyl, cyano, nitro, $C_{1-4}$ alkyl, $C_{1-4}$ alkoxy, $C_{1-4}$ haloalkyl, and $C_{1-4}$ haloalkoxy;

each $R^y$ is independently selected from halogen, cyano, nitro, $C_{1-6}$ alkyl, $C_{1-6}$ haloalkyl, $C_{1-6}$ alkoxy, $C_{1-6}$ haloalkoxy, $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl- $C_{1-4}$-alkyl; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{y'}$ groups; and wherein said $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1 or 2 independently selected $R^{y''}$ groups;

provided that only one $R^y$ is selected from optionally substituted $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;

each $R^z$ is independently selected from halogen, cyano, nitro, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{z'}$ groups;

each $R^{y'}$ and $R^{z'}$ is independently selected from hydroxyl, cyano, nitro, $C_{1-4}$ alkoxy, and $C_{1-4}$ haloalkoxy;

each $R^{y''}$ is independently selected from halogen, hydroxyl, cyano, nitro, $C_{1-4}$ alkyl, $C_{1-4}$ haloalkyl, $C_{1-4}$ alkoxy, and $C_{1-4}$ haloalkoxy;

n is an integer selected from 0, 1, 2, and 3; and m is an integer selected from 0, 1, and 2.

In some embodiments:

Y is selected from C(=O) and S(=O)$_2$;

$Cy^1$ is selected from $C_{1-9}$ heteroaryl; which is substituted with n independently selected $R^y$ groups;

$Ar^2$ is 5-membered heteroaryl or 6-membered heteroaryl; each of which is substituted at one ortho position by one J group and by m independently selected $R^z$ groups;

L is selected from a bond and $C_{1-4}$ alkylene;

$L^2$ is selected from straight chain $C_4$ alkylene, straight chain $C_5$ alkylene, and straight chain $C_6$ alkylene; each of which is optionally substituted by 1, 2, or 3 $R^x$ groups;

$R^1$ is selected from H, $C_{1-4}$ alkyl, and $C_{1-4}$ haloalkyl;

J is selected from amino and hydroxyl;

each $R^x$ is independently selected from halogen, hydroxyl, cyano, nitro, $C_{1-4}$ alkyl, $C_{1-4}$ alkoxy, $C_{1-4}$ haloalkyl, and $C_{1-4}$ haloalkoxy;

each $R^y$ is independently selected from halogen, cyano, nitro, $C_{1-6}$ alkyl, $C_{1-6}$ haloalkyl, $C_{1-6}$ alkoxy, $C_{1-6}$ haloalkoxy, $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{y'}$ groups; and wherein said $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1 or 2 independently selected $R^{y''}$ groups;

provided that only one $R^y$ is selected from optionally substituted $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;

each $R^z$ is independently selected from halogen, cyano, nitro, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{z'}$ groups;

each $R^{y'}$ and $R^{z'}$ is independently selected from hydroxyl, cyano, nitro, $C_{1-4}$ alkoxy, and $C_{1-4}$ haloalkoxy;

each $R^{y''}$ is independently selected from halogen, hydroxyl, cyano, nitro, $C_{1-4}$ alkyl, $C_{1-4}$ haloalkyl, $C_{1-4}$ alkoxy, and $C_{1-4}$ haloalkoxy;

n is an integer selected from 0, 1, 2, and 3; and m is an integer selected from 0, 1, and 2.

In some embodiments:

Y is selected from C(=O) and S(=O)$_2$;

$Cy^1$ is selected from $C_{2-9}$ heterocycloalkyl; which is substituted with n independently selected $R^y$ groups;

$Ar^2$ is selected from phenyl, 5-membered heteroaryl, and 6-membered heteroaryl; which is substituted at one ortho position by one J group and by m independently selected $R^z$ groups;

$L^1$ is selected from a bond and $C_{1-4}$ alkylene;

$L^2$ is selected from straight chain $C_4$ alkylene, straight chain $C_5$ alkylene, and straight chain $C_6$ alkylene; each of which is optionally substituted by 1, 2, or 3 $R^x$ groups;

$R^1$ is selected from H, $C_{1-4}$ alkyl, and $C_{1-4}$ haloalkyl;

J is selected from amino and hydroxyl;

each $R^x$ is independently selected from halogen, hydroxyl, $C_{1-4}$ alkyl, and $C_{1-4}$ alkoxy;

each $R^y$ is independently selected from halogen, $C_{1-6}$ alkyl, $C_{1-6}$ haloalkyl, $C_{1-6}$ alkoxy, $C_{1-6}$ haloalkoxy, $C_{3-7}$ cycloalkyl, and $C_{2-6}$ heterocycloalkyl; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{y'}$ groups; and wherein said $C_{3-7}$ cycloalkyl and $C_{2-6}$ heterocycloalkyl are each optionally substituted by 1 or 2 independently selected $R^{y''}$ groups;

provided that only one $R^y$ is selected from optionally substituted $C_{3-7}$ cycloalkyl and $C_{2-6}$ heterocycloalkyl;

each $R^z$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1 or 2 independently selected $R^{z'}$ groups;

each $R^{y'}$ and $R^{z'}$ is independently selected from hydroxyl, $C_{1-4}$ alkoxy, and $C_{1-4}$ haloalkoxy;

each $R^{y''}$ is independently selected from halogen, hydroxyl, $C_{1-4}$ alkyl, $C_{1-4}$ haloalkyl, $C_{1-4}$ alkoxy, and $C_{1-4}$ haloalkoxy;

n is an integer selected from 0, 1, and 2.

m is an integer selected from 0, 1 and 2.

In some embodiments:

Y is selected from C(=O) and S(=O)$_2$;

$Cy^1$ is selected from $C_{6-10}$ aryl; which is substituted with n independently selected $R^y$ groups;

$Ar^2$ is selected from phenyl; which is substituted at one ortho position by one J group and by m independently selected $R^z$ groups;

$L^1$ is selected from a bond and $C_{1-4}$ alkylene;

$L^2$ is selected from straight chain $C_4$ alkylene, straight chain $C_5$ alkylene, and straight chain $C_6$ alkylene; each of which is optionally substituted by 1, 2, or 3 $R^x$ groups;

$R^1$ is selected from H, $C_{1-4}$ alkyl, and $C_{1-4}$ haloalkyl;

J is selected from amino and hydroxyl;

each $R^x$ is independently selected from halogen, hydroxyl, $C_{1-4}$ alkyl, and $C_{1-4}$ alkoxy;

each $R^y$ is independently selected from halogen, $C_{1-6}$ alkyl, $C_{1-6}$ haloalkyl, $C_{1-6}$ alkoxy, $C_{1-6}$ haloalkoxy, $C_{3-7}$ cycloalkyl, and $C_{2-6}$ heterocycloalkyl; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{y'}$ groups; and wherein said $C_{3-7}$ cycloalkyl and $C_{2-6}$ heterocycloalkyl are each optionally substituted by 1 or 2 independently selected $R^{y''}$ groups;

provided that only one $R^y$ is selected from optionally substituted $C_{3-7}$ cycloalkyl and $C_{2-6}$ heterocycloalkyl;

each $R^z$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1 or 2 independently selected $R^{z'}$ groups;

each $R^{y'}$ and $R^{z'}$ is independently selected from hydroxyl, $C_{1-4}$ alkoxy, and $C_{1-4}$ haloalkoxy;

each $R^{y''}$ is independently selected from halogen, hydroxyl, $C_{1-4}$ alkyl, $C_{1-4}$ haloalkyl, $C_{1-4}$ alkoxy, and $C_{1-4}$ haloalkoxy.

n is an integer selected from 0, 1, and 2.

m is an integer selected from 0, 1 and 2.

In some embodiments:

Y is selected from C(=O) and S(=O)$_2$;

$Cy^1$ is selected from $C_{6-10}$ aryl; which is substituted with n independently selected $R^y$ groups;

$Ar^2$ is selected from 5-membered heteroaryl and 6-heteroaryl; each of which is substituted at one ortho position by one J group and by m independently selected $R^z$ groups;

$L^1$ is selected from a bond and $C_{1-4}$ alkylene;

$L^2$ is selected from straight chain $C_4$ alkylene, straight chain $C_5$ alkylene, and straight chain $C_6$ alkylene; each of which is optionally substituted by 1, 2, or 3 $R^x$ groups;

$R^1$ is selected from H, $C_{1-4}$ alkyl, and $C_{1-4}$ haloalkyl;

J is selected from amino and hydroxyl;

each $R^x$ is independently selected from halogen, hydroxyl, $C_{1-4}$ alkyl, and $C_{1-4}$ alkoxy;

each $R^y$ is independently selected from halogen, $C_{1-6}$ alkyl, $C_{1-6}$ haloalkyl, $C_{1-6}$ alkoxy, $C_{1-6}$ haloalkoxy, $C_{3-7}$ cycloalkyl, and $C_{2-6}$ heterocycloalkyl; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{y'}$ groups; and wherein said $C_{3-7}$ cycloalkyl and $C_{2-6}$ heterocycloalkyl are each optionally substituted by 1 or 2 independently selected $R^{y''}$ groups;

provided that only one $R^y$ is selected from optionally substituted $C_{3-7}$ cycloalkyl and $C_{2-6}$ heterocycloalkyl;

each $R^z$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1 or 2 independently selected $R^{z'}$ groups;

each $R^{y'}$ and $R^{z'}$ is independently selected from hydroxyl, $C_{1-4}$ alkoxy, and $C_{1-4}$ haloalkoxy;

each $R^{y''}$ is independently selected from halogen, hydroxyl, $C_{1-4}$ alkyl, $C_{1-4}$ haloalkyl, $C_{1-4}$ alkoxy, and $C_{1-4}$ haloalkoxy;

n is an integer selected from 0, 1, and 2.

m is an integer selected from 0, 1 and 2.

In some embodiments:

Y is selected from C(=O) and S(=O)$_2$;

$Cy^1$ is selected from $C_{1-9}$ heteroaryl; which is substituted with n independently selected $R^y$ groups;

$Ar^2$ is selected from phenyl; which is substituted at one ortho position by one J group and by m independently selected $R^z$ groups;

$L^1$ is selected from a bond and $C_{1-4}$ alkylene;

$L^2$ is selected from straight chain $C_4$ alkylene, straight chain $C_5$ alkylene, and straight chain $C_6$ alkylene; each of which is optionally substituted by 1, 2, or 3 $R^x$ groups;

$R^1$ is selected from H, $C_{1-4}$ alkyl, and $C_{1-4}$ haloalkyl;

J is selected from amino and hydroxyl;

each $R^x$ is independently selected from halogen, hydroxyl, $C_{1-4}$ alkyl, and $C_{1-4}$ alkoxy;

each $R^y$ is independently selected from halogen, $C_{1-6}$ alkyl, $C_{1-6}$ haloalkyl, $C_{1-6}$ alkoxy, $C_{1-6}$ haloalkoxy, $C_{3-7}$ cycloalkyl, and $C_{2-6}$ heterocycloalkyl; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{y'}$ groups; and wherein said $C_{3-7}$ cycloalkyl and $C_{2-6}$ heterocycloalkyl are each optionally substituted by 1 or 2 independently selected $R^{y''}$ groups;

provided that only one $R^y$ is selected from optionally substituted $C_{3-7}$ cycloalkyl and $C_{2-6}$ heterocycloalkyl;

each $R^z$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1 or 2 independently selected $R^{z'}$ groups;

each $R^{y'}$ and $R^{z'}$ is independently selected from hydroxyl, $C_{1-4}$ alkoxy, and $C_{1-4}$ haloalkoxy;

each $R^{y''}$ is independently selected from halogen, hydroxyl, $C_{1-4}$ alkyl, $C_{1-4}$ haloalkyl, $C_{1-4}$ alkoxy, and $C_{1-4}$ haloalkoxy;

n is an integer selected from 0, 1, and 2.

m is an integer selected from 0, 1 and 2.

In some embodiments:

Y is selected from C(=O) and S(=O)$_2$;

$Cy^1$ is selected from $C_{1-9}$ heteroaryl; which is substituted with n independently selected $R^y$ groups;

$Ar^2$ is selected from 5-membered heteroaryl and 6-heteroaryl; each of which is substituted at one ortho position by one J group and by m independently selected $R^z$ groups;

$L^1$ is selected from a bond and $C_{1-4}$ alkylene;

$L^2$ is selected from straight chain $C_4$ alkylene, straight chain $C_5$ alkylene, and straight chain $C_6$ alkylene; each of which is optionally substituted by 1, 2, or 3 $R^x$ groups;

$R^1$ is selected from H, $C_{1-4}$ alkyl, and $C_{1-4}$ haloalkyl;

J is selected from amino and hydroxyl;

each $R^x$ is independently selected from halogen, hydroxyl, $C_{1-4}$ alkyl, and $C_{1-4}$ alkoxy;

each $R^y$ is independently selected from halogen, $C_{1-6}$ alkyl, $C_{1-6}$ haloalkyl, $C_{1-6}$ alkoxy, $C_{1-6}$ haloalkoxy, $C_{3-7}$ cycloalkyl, and $C_{2-6}$ heterocycloalkyl; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{y'}$ groups; and wherein said $C_{3-7}$ cycloalkyl and $C_{2-6}$ heterocycloalkyl are each optionally substituted by 1 or 2 independently selected $R^{y''}$ groups; provided that only one $R^y$ is selected from optionally substituted $C_{3-7}$ cycloalkyl and $C_{2-6}$ heterocycloalkyl;

each $R^z$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1 or 2 independently selected $R^{z'}$ groups;

each $R^{y'}$ and $R^{z'}$ is independently selected from hydroxyl, $C_{1-4}$ alkoxy, and $C_{1-4}$ haloalkoxy;

each $R^{y''}$ is independently selected from halogen, hydroxyl, $C_{1-4}$ alkyl, $C_{1-4}$ haloalkyl, $C_{1-4}$ alkoxy, and $C_{1-4}$ haloalkoxy;

n is an integer selected from 0, 1, and 2.

m is an integer selected from 0, 1 and 2.

In some embodiments:

Y is selected from C(=O) and S(=O)$_2$;

$Cy^1$ is selected from $C_{2-6}$ heterocycloalkyl; which is optionally substituted with 1, 2, or 3 independently selected $R^y$ groups;

$Ar^2$ is selected from phenyl, 5-membered heteroaryl, and 6-membered heteroaryl; wherein said phenyl, 5-membered heteroaryl, and 6-membered heteroaryl are each substituted at one ortho position by one J group and by m independently selected $R^z$ groups;

$L^1$ is selected from a bond and $C_{1-4}$ alkylene;

$L^2$ is selected from unsubstituted straight chain $C_4$ alkylene, unsubstituted straight chain $C_5$ alkylene, and unsubstituted straight chain $C_6$ alkylene;

$R^1$ is selected from H and $C_{1-4}$ alkyl;

J is selected from amino and hydroxyl;

each $R^y$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{y'}$ groups;

each $R^z$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1 or 2 independently selected $R^{z'}$ groups;

each $R^{y'}$ and $R^{z'}$ is independently selected from hydroxyl, $C_{1-4}$ alkoxy, and $C_{1-4}$ haloalkoxy;

each $R^{y''}$ is independently selected from halogen, hydroxyl, $C_{1-4}$ alkyl, $C_{1-4}$ haloalkyl, $C_{1-4}$ alkoxy, and $C_{1-4}$ haloalkoxy;

n is an integer selected from 0, 1, and 2.

m is an integer selected from 0, 1 and 2.

In some embodiments:

Y is selected from C(=O) and S(=O)$_2$;

$Cy^1$ is phenyl; which is optionally substituted with 1, 2, or 3 independently selected $R^y$ groups;

$Ar^2$ is selected from phenyl; which is substituted at one ortho position by one J group and by m independently selected $R^z$ groups;

$L^1$ is selected from a bond and $C_{1-4}$ alkylene;

$L^2$ is selected from unsubstituted straight chain $C_4$ alkylene, unsubstituted straight chain $C_5$ alkylene, and unsubstituted straight chain $C_6$ alkylene;

$R^1$ is selected from H and $C_{1-4}$ alkyl;

J is selected from amino and hydroxyl;

each $R^y$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{y'}$ groups;

each $R^z$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1 or 2 independently selected $R^{z'}$ groups;

each $R^{y'}$ and $R^{z'}$ is independently selected from hydroxyl, $C_{1-4}$ alkoxy, and $C_{1-4}$ haloalkoxy;

each $R^{y''}$ is independently selected from halogen, hydroxyl, $C_{1-4}$ alkyl, $C_{1-4}$ haloalkyl, $C_{1-4}$ alkoxy, and $C_{1-4}$ haloalkoxy;

n is an integer selected from 0, 1, and 2.

m is an integer selected from 0, 1 and 2.

In some embodiments:

Y is selected from C(=O) and S(=O)$_2$;

$Cy^1$ is phenyl; which is optionally substituted with 1, 2, or 3 independently selected $R^y$ groups;

$Ar^2$ is selected from 5-membered heteroaryl and 6-membered heteroaryl; each of which is substituted at one ortho position by one J group and by m independently selected $R^z$ groups;

$L^1$ is selected from a bond and $C_{1-4}$ alkylene;

$L^2$ is selected from unsubstituted straight chain $C_4$ alkylene, unsubstituted straight chain $C_5$ alkylene, and unsubstituted straight chain $C_6$ alkylene;

$R^1$ is selected from H and $C_{1-4}$ alkyl;

J is selected from amino and hydroxyl;

each $R^y$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{y'}$ groups;

each $R^z$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1 or 2 independently selected $R^{z'}$ groups;

each $R^{y'}$ and $R^{z'}$ is independently selected from hydroxyl, $C_{1-4}$ alkoxy, and $C_{1-4}$ haloalkoxy;

each $R^{y''}$ is independently selected from halogen, hydroxyl, $C_{1-4}$ alkyl, $C_{1-4}$ haloalkyl, $C_{1-4}$ alkoxy, and $C_{1-4}$ haloalkoxy;

n is an integer selected from 0, 1, and 2.

m is an integer selected from 0, 1 and 2.

In some embodiments:

Y is selected from C(=O) and S(=O)$_2$;

$Cy^1$ is $C_{1-6}$ heteroaryl; which is optionally substituted with 1, 2, or 3 independently selected $R^y$ groups;

$Ar^2$ is selected from phenyl; which is substituted at one ortho position by one J group and by m independently selected $R^z$ groups;

$L^1$ is selected from a bond and $C_{1-4}$ alkylene;

$L^2$ is selected from unsubstituted straight chain $C_4$ alkylene, unsubstituted straight chain $C_5$ alkylene, and unsubstituted straight chain $C_6$ alkylene;

$R^1$ is selected from H and $C_{1-4}$ alkyl;

J is selected from amino and hydroxyl;

each $R^y$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{y'}$ groups;

each $R^z$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1 or 2 independently selected $R^{z'}$ groups;

each $R^{y'}$ and $R^{z'}$ is independently selected from hydroxyl, $C_{1-4}$ alkoxy, and $C_{1-4}$ haloalkoxy;

each $R^{y''}$ is independently selected from halogen, hydroxyl, $C_{1-4}$ alkyl, $C_{1-4}$ haloalkyl, $C_{1-4}$ alkoxy, and $C_{1-4}$ haloalkoxy;

n is an integer selected from 0, 1, and 2.

m is an integer selected from 0, 1 and 2.

In some embodiments:

Y is selected from C(=O) and S(=O)$_2$;

$Cy^1$ is $C_{1-6}$ heteroaryl; which is optionally substituted with 1, 2, or 3 independently selected $R^y$ groups;

$Ar^2$ is selected from 5-membered heteroaryl and 6-membered heteroaryl; each of which is substituted at one ortho position by one J group and by m independently selected $R^z$ groups;

$L^1$ is selected from a bond and $C_{1-4}$ alkylene;

$L^2$ is selected from unsubstituted straight chain $C_4$ alkylene, unsubstituted straight chain $C_5$ alkylene, and unsubstituted straight chain $C_6$ alkylene;

$R^1$ is selected from H and $C_{1-4}$ alkyl;

J is selected from amino and hydroxyl;

each $R^y$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_1$—. haloalkoxy are each optionally substituted by 1, 2, or 3 independently selected $R^{y'}$ groups;

each $R^z$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1 or 2 independently selected $R^{z'}$ groups;

each $R^{y'}$ and $R^{z'}$ is independently selected from hydroxyl, $C_{1-4}$ alkoxy, and $C_{1-4}$ haloalkoxy;

each $R^{y''}$ is independently selected from halogen, hydroxyl, $C_{1-4}$ alkyl, $C_{1-4}$ haloalkyl, $C_{1-4}$ alkoxy, and $C_{1-4}$ haloalkoxy;

n is an integer selected from 0, 1, and 2.

m is an integer selected from 0, 1 and 2.

In some embodiments:

Y is $C(=O)$;

$Cy^1$ is selected from phenyl; which is substituted with n independently selected $R^y$ groups;

$Ar^2$ is selected from phenyl; wherein said phenyl is substituted at one ortho position by one J group and by m independently selected $R^z$ groups;

$L^1$ is selected from a bond;

$L^2$ is —$CH_2CH_2CH_2CH_2CH_2$—;

$R^1$ is selected from H;

J is selected from amino;

each $R^y$ is independently selected from halogen and $C_{1-6}$ alkyl;

each $R^z$ is independently selected from halogen;

n is an integer selected from 0 and 1; and m is an integer selected from 0 and 1.

In some embodiments:

Y is $S(=O)_2$;

$Cy^1$ is selected from phenyl; which is substituted with n independently selected $R^y$ groups;

$Ar^2$ is selected from phenyl; wherein said phenyl is substituted at one ortho position by one J group and by m independently selected $R^z$ groups;

$L^1$ is selected from a bond;

$L^2$ is —$CH_2CH_2CH_2CH_2CH_2$—;

$R^1$ is selected from H;

J is selected from amino;

each $R^y$ is independently selected from halogen and $C_{1-6}$ alkyl;

each $R^z$ is independently selected from halogen;

n is an integer selected from 0 and 1; and m is an integer selected from 0 and 1.

In some embodiments:

Y is $C(=O)$;

$Cy^1$ is selected from $C_{1-6}$ heteroaryl; which is substituted with n independently selected $R^y$ groups;

$Ar^2$ is selected from phenyl; wherein said phenyl is substituted at one ortho position by one J group and by m independently selected $R^z$ groups;

$L^1$ is a bond;

$L^2$ is —$CH_2CH_2CH_2CH_2CH_2$—;

$R^1$ is selected from H;

J is selected from amino;

each $R^y$ is independently selected from halogen and $C_{1-6}$ alkyl;

each $R^z$ is independently selected from halogen;

n is an integer selected from 0 and 1; and m is an integer selected from 0 and 1.

In some embodiments:

Y is $C(=O)$;

$Cy^1$ is selected from $C_{2-6}$ heterocycloalkyl; which is substituted with n independently selected $R^y$ groups;

$Ar^2$ is selected from phenyl; wherein said phenyl is substituted at one ortho position by one J group and by m independently selected $R^z$ groups;

$L^1$ is selected from methylene;

$L^2$ is —$CH_2CH_2CH_2CH_2CH_2$—;

$R^1$ is selected from H;

J is selected from amino;

each $R^y$ is independently selected from halogen and $C_{1-6}$ alkyl;

each $R^z$ is independently selected from halogen;

n is an integer selected from 0 and 1; and m is an integer selected from 0 and 1.

In some embodiments:

Y is $C(=O)$;

$Ar^2$ is selected from phenyl; which is substituted at one ortho position by one J group and by m independently selected $R^z$ groups;

$L^1$ is selected from a bond and $C_{1-4}$ alkylene;

$L^2$ is:

(i) straight chain $C_4$ alkylene, straight chain $C_5$ alkylene, or straight chain $C_6$ alkylene; each of which is optionally substituted by 1, 2, or 3 $R^x$ groups; or (ii) straight chain $C_{4-6}$ alkenylene $Cy^1$ is selected from $C_{1-9}$ heteroaryl; which is substituted with n independently selected $R^y$ groups;

$R^1$ is selected from H, $C_{1-4}$ alkyl, and $C_{1-4}$haloalkyl;

J is amino;

each $R^x$ is independently selected from halogen, hydroxyl, cyano, nitro, $C_{1-4}$ alkyl, $C_{1-4}$ alkoxy, $C_{1-4}$ haloalkyl, and $C_{1-4}$ haloalkoxy;

each $R^y$ is independently selected from halogen, cyano, nitro, $C_{1-6}$ alkyl, $C_{1-6}$ haloalkyl, $C_{1-6}$ alkoxy, $C_{1-6}$ haloalkoxy, $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{1-6}$ haloalkyl, $C_{1-6}$ alkoxy, and $C_{1-6}$haloalkoxy are each optionally substituted by 1, 2, or 3 independently selected $R^{y'}$ groups; and wherein said $C_{3-7}$cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{7-4}$-alkyl, and $C_{1-6}$ heteroaryl-$C_{1-4}$-alkyl are each optionally substituted by 1 or 2 independently selected $R^{y''}$ groups;

provided that only one $R^y$ is selected from optionally substituted $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;

each $R^z$ is independently selected from halogen, cyano, nitro, $C_{1-6}$ alkyl, $C_{1-6}$ haloalkyl, $C_{1-6}$ alkoxy, $C_{1-6}$ haloalkoxy, $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{1-6}$ haloalkyl, $C_{1-6}$alkoxy, and $C_{1-6}$ haloalkoxy are each optionally substituted by 1, 2, or 3 independently selected $R^{z'}$ groups; and wherein said $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1 or 2 independently selected $R^{z''}$ groups;

each $R^{y'}$ and $R^{z'}$ is independently selected from hydroxyl, cyano, nitro, $C_{1-4}$ alkoxy, and $C_{1-4}$ haloalkoxy;

each $R^{y''}$ is independently selected from halogen, hydroxyl, cyano, nitro, $C_{1-4}$ alkyl, $C_{1-4}$ haloalkyl, $C_{1-4}$ alkoxy, and $C_{1-4}$ haloalkoxy;

n is an integer selected from 0, 1, 2, and 3; and m is an integer selected from 0, 1, and 2.

In some embodiments:

Y is C(=O);

$Ar^2$ is selected from phenyl; which is substituted at one ortho position by one J group and by m independently selected $R^z$ groups;

$L^2$ is:

(i) straight chain $C_4$ alkylene, straight chain $C_5$ alkylene, or straight chain $C_6$ alkylene; each of which is optionally substituted by 1, 2, or 3 $R^x$ groups; or (ii) straight chain $C_{4-6}$ alkenylene J is amino;

$R^z$ or one $R^z$ is selected from phenyl and $C_{1-6}$ heteroaryl, each of which is optionally substituted by 1, 2, or 3 independently selected $R^{z''}$ groups, and attached to the meta position (i.e., para to J); and m is 1 and 2.

In certain embodiments:

Y is C(=O);

$Ar^2$ is selected from phenyl; which is substituted at one ortho position by one J group and by m independently selected $R^z$ groups;

$L^2$ is straight chain $C_4$ alkylene, straight chain $C_5$ alkylene, or straight chain $C_6$ alkylene; each of which is optionally substituted by 1, 2, or 3 $R^x$ groups;

J is amino;

$R^z$ or one $R^z$ is selected from phenyl and $C_{1-6}$ heteroaryl, each of which is optionally substituted by 1, 2, or 3 independently selected $R^{z''}$ groups, and attached to the meta position (i.e., para to J); and m is 1 and 2.

In embodiments, $R^z$ or one $R^z$ is selected from phenyl optionally substituted by 1, 2, or 3 independently selected $R^{z''}$ groups, and attached to the meta position (i.e., para to J).

In embodiments, $R^z$ or one $R^z$ is $C_{1-6}$ heteroaryl, each of which is optionally substituted by 1, 2, or 3 independently selected $R^{z''}$ groups, and attached to the meta position (i.e., para to J).

For example, the compound of formula (I) can be:

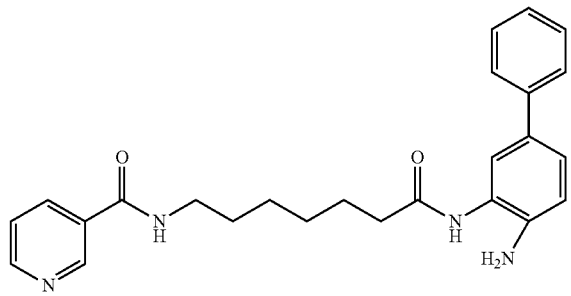 [SMILES: Nc1ccc(-c2ccccc2)cc1NC(=O)CCCCCCNC(=O)c1cccnc1]

In certain embodiments:

Y is C(=O);

$Ar^2$ is selected from phenyl; which is substituted at one ortho position by one J group and by m independently selected $R^z$ groups;

$L^2$ is straight chain $C_{4-6}$ alkenylene (e.g., having one double bond, e.g., $L^2$ is ∥—$(CH_2)_{1-3}$—$CH_2$—CH=CH-∥);

J is amino;

$R^z$ or one $R^z$ is selected from phenyl and $C_{1-6}$ heteroaryl, each of which is optionally substituted by 1, 2, or 3 independently selected $R^{z''}$ groups, and attached to the meta position (i.e., para to J); and m is 1 and 2.

In embodiments, $R^z$ or one $R^z$ is selected from phenyl optionally substituted by 1, 2, or 3 independently selected $R^{z''}$ groups, and attached to the meta position (i.e., para to J).

In embodiments, $R^z$ or one $R^z$ is $C_1$ is heteroaryl, each of which is optionally substituted by 1, 2, or 3 independently selected $R^{z''}$ groups, and attached to the meta position (i.e., para to J).

For example, the compound of formula (D) can be:

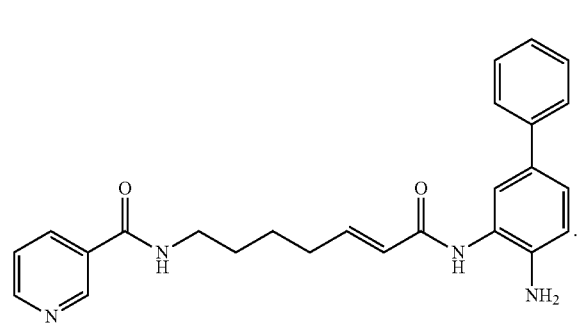 [SMILES: Nc1ccc(-c2ccccc2)cc1NC(=O)/C=C/CCCCNC(=O)c1cccnc1]

In some embodiments, the compound is:

N-(6-(2-aminophenylamino)-6-oxohexyl)-4-methylbenzamide;

N-(2-amino-4-fluorophenyl)-6-(thiazol-2-ylcarbonylamino)hexanamide;

N-(6-(2-amino-4-fluorophenylamino)-6-oxohexyl)-4-methylbenzamide;

N-(2-amino-4-fluorophenyl)-6-[2-(4-morpholinyl)acetamido]hexanamide;

N-(6-(2-amino-5-fluorophenylamino)-6-oxohexyl)-4-fluorobenzamide

N-(6-(2-amino-4-fluorophenylamino)-6-oxohexyl)-4-fluorobenzamide;

N-(2-aminophenyl)-6-(4-fluorophenylsulfonamido)hexanamide;

N-(2-amino-4-fluorophenyl)-6-(4-fluorophenylsulfonamido)hexanamide;

N-(2-amino-5-fluorophenyl)-6-(thiazol-2-ylcarbonylamino)hexanamide;

N-(6-(2-amino-5-fluorophenylamino)-6-oxohexyl)-4-methylbenzamide;

(E)-N-(3-(3-(2-amino-4-fluorophenylamino)-3-oxoprop-1-enyl)phenyl)-4-methylbenzamide;

N-(6-(2-amino-4-fluorophenylamino)-6-oxohexyl)-4-fluoro-N-methylbenzamide;

N-(5-(2-aminophenylamino)-5-oxopentyl)-4-methylbenzamide;

N-(7-(2-aminophenylamino)-7-oxoheptyl)-4-methylbenzamide;

N-(6-(2-amino-4-fluorophenylamino)-6-oxohexyl)benzofuran-2-carboxamide;

N-(6-(4-fluoro-2-hydroxyphenylamino)-6-oxohexyl)-4-methylbenzamide;

N-(6-(2-amino-4-fluorophenylamino)-6-oxohexyl)picolinamide;

N-(6-(2-amino-4-fluorophenylamino)-6-oxohexyl)nicotinamide;

N-(6-(3-aminopyridin-2-ylamino)-6-oxohexyl)-4-methylbenzamide;

N-(6-(2-amino-5-methoxyphenylamino)-6-oxohexyl)-4-methylbenzamide;
N-(2-(3-(2-aminophenylamino)-3-oxopropoxy)ethyl)-4-methylbenzamide;
N-(6-(2-amino-4-fluoro-5-(piperidin-1-yl)phenylamino)-6-oxohexyl)-4-methylbenzamide;
N-(6-(2-amino-5-phenoxyphenylamino)-6-oxohexyl)nicotinamide;
N-(7-(4-aminobiphenyl-3-yl amino)-7-oxoheptyl)nicotinamide;
N-(7-(4-aminobiphenyl-3-ylamino)-7-oxoheptyl)nicotinamide;
N-(7-(2-amino-5-(thiophen-2-yl)phenylamino)-7-oxoheptyl)nicotinamide;
N-(6-(2-aminophenylamino)-6-oxohexyl)-4-fluorobenzamide;
N-(6-(2-aminophenylamino)-6-oxohexyl)-4-chlorobenzamide;
N-(6-(2-aminophenylamino)-6-oxohexyl)-3,4-dichlorobenzamide;
N-(6-(2-aminophenylamino)-6-oxohexyl)-4-methoxybenzamide;
N-(6-(2-aminophenylamino)-6-oxohexyl)-3-chlorobenzamide;
N-(6-(2-aminophenylamino)-6-oxohexyl)-4-(dimethylamino)benzamide;
N-(6-(2-aminophenylamino)-6-oxohexyl)-4-tert-butylbenzamide;
N-(6-(2-aminophenylamino)-6-oxohexyl)-4-(trifluoromethyl)benzamide;
N-(6-(2-aminophenylamino)-6-oxohexyl)-4-nitrobenzamide;
N-(6-(2-aminophenylamino)-6-oxohexyl)-3-nitrobenzamide;
N-(6-(2-aminophenylamino)-6-oxohexyl)-3-(trifluoromethyl)benzamide;
N-(6-(2-aminophenylamino)-6-oxohexyl)-4-cyanobenzamide;
N-(6-(2-aminophenylamino)-6-oxohexyl)-3,5-dichlorobenzamide;
N-(6-(2-aminophenylamino)-6-oxohexyl)thiophene-2-carboxamide;
N-(6-(2-amino-5-fluoro-4-(piperidin-1-yl)phenylamino)-6-oxohexyl)-4-methylbenzamide;
N-(6-(2-amino-4-hydroxyphenylamino)-6-oxohexyl)-4-methylbenzamide;
N-(6-(2,4-diaminophenylamino)-6-oxohexyl)-4-methylbenzamide;
N-(6-(2-amino-4,5-dimethylphenylamino)-6-oxohexyl)-4-methylbenzamide;
N-(6-(2-amino-4-chlorophenylamino)-6-oxohexyl)-4-methylbenzamide;
N-(6-(2-amino-4-fluoro-5-(1H-pyrazol-1-yl)phenylamino)-6-oxohexyl)-4-methylbenzamide;
N-(6-(2-amino-4-bromophenylamino)-6-oxohexyl)-4-methylbenzamide;
N-(6-(4-aminobenzo[d][1,3]dioxol-5-ylamino)-6-oxohexyl)-4-methylbenzamide;
N-(6-(2-amino-4-fluoro-5-morpholinophenylamino)-6-oxohexyl)-4-methylbenzamide;
N-(6-(3-aminonaphthalen-2-ylamino)-6-oxohexyl)-4-methylbenzamide;
N-(6-(3-aminopyridin-4-ylamino)-6-oxohexyl)-4-methylbenzamide;
N-(6-(2-aminophenylamino)-6-oxohexyl)thiazole-2-carboxamide;
N-(6-(2-aminophenylamino)-6-oxohexyl)-4-methylthiazole-2-carboxamide;
N-(6-(2-aminophenylamino)-6-oxohexyl)-5-methylthiazole-2-carboxamide;
N-(2-(3-(2-aminophenylamino)-3-oxopropylamino)ethyl)-4-methylbenzamide;
N-(6-(2-aminophenylamino)-6-oxohexyl)-2,4-dichlorobenzamide;
N-(6-(2-aminophenylamino)-6-oxohexyl)-4-(methylsulfonyl)benzamide;
N-(6-(2-aminophenylamino)-6-oxohexyl)-4-sulfamoylbenzamide;
N-(6-(2-aminophenylamino)-6-oxohexyl)isonicotinamide;
N-(6-(2-aminophenylamino)-6-oxohexyl)pyrazine-2-carboxamide;
N-(6-(2-aminophenylamino)-6-oxohexyl)pyridazine-4-carboxamide;
N-(6-(2-aminophenylamino)-6-oxohexyl)furan-2-carboxamide;
N-(6-(2-aminophenylamino)-6-oxohexyl)furan-3-carboxamide;
N-(6-(2-aminophenylamino)-6-oxohexyl)thiophene-2-carboxamide;
N-(6-(2-aminophenylamino)-6-oxohexyl)thiophene-3-carboxamide;
N-(6-(2-aminophenylamino)-6-oxohexyl)-1H-pyrrole-2-carboxamide;
N-(6-(2-aminophenylamino)-6-oxohexyl)-4H-1,2,4-triazole-3-carboxamide;
N-(6-(2-aminophenylamino)-6-oxohexyl)isoxazole-5-carboxamide;
N-(6-(2-aminophenylamino)-6-oxohexyl)thiazole-4-carboxamide;
N-(6-(2-aminophenylamino)-6-oxohexyl)-2-(piperidin-1-yl)isonicotinamide;
N-(6-(2-aminophenylamino)-6-oxohexyl)-3-phenyl-1H-pyrazole-5-carboxamide;
N-(6-(2-aminophenylamino)-6-oxohexyl)-2,3-dihydrobenzo[b][1,4]dioxine-6-carboxamide;
N-(6-(2-aminophenylamino)-6-oxohexyl)benzofuran-2-carboxamide;
N-(6-(2-aminophenylamino)-6-oxohexyl)benzo[d]thiazole-6-carboxamide;
N-(2-aminophenyl)-6-(4-oxo-4-(thiophen-2-yl)butanamido)hexanamide;
N-(6-(2-aminophenylamino)-6-oxohexyl)benzo[c][1,2,5]oxadiazole-5-carboxamide;
N-(6-(2-aminophenylamino)-6-oxohexyl)quinoxaline-6-carboxamide;
N-(6-(2-aminophenylamino)-6-oxohexyl)quinoline-7-carboxamide;
N-(6-(2-aminophenylamino)-6-oxohexyl)-2-naphthamide;
N-(6-(2-aminophenylamino)-6-oxohexyl)-2-oxoindoline-6-carboxamide;
N-(6-(2-aminophenylamino)-6-oxohexyl)-3-(1H-tetrazol-5-yl)benzamide;
N-(6-(2-aminophenylamino)-6-oxohexyl)-4-(1H-tetrazol-5-yl)benzamide;
N-(2-aminophenyl)-6-(3-(5-phenyloxazol-2-yl)propanamido)hexanamide;
N-(6-(2-aminophenylamino)-6-oxohexyl)-5-(thiophen-3-yl)isoxazole-3-carboxamide;
N-(6-(2-aminophenylamino)-6-oxohexyl)-1H-indole-2-carboxamide;
N-(6-(2-aminophenylamino)-6-oxohexyl)-1H-indole-5-carboxamide;

N-(6-(2-aminophenylamino)-6-oxohexyl)-5-methoxy-1H-indole-2-carboxamide;
N-(6-(2-aminophenylamino)-6-oxohexyl)-5-cyclopropylisoxazole-3-carboxamide;
N-(6-(2-aminophenylamino)-6-oxohexyl)-1H-indazole-3-carboxamide;
N-(6-(2-aminophenylamino)-6-oxohexyl)isoquinoline-3-carboxamide;
N-(6-(2-aminophenylamino)-6-oxohexyl)quinoline-3-carboxamide;
N-(6-(2-aminophenylamino)-6-oxohexyl)cinnoline-4-carboxamide;
N-(6-(2-aminophenylamino)-6-oxohexyl)quinoxaline-2-carboxamide;
N-(6-(2-aminophenylamino)-6-oxohexyl)-2-(pyridin-4-yl)thiazole-4-carboxamide;
N-(6-(2-aminophenylamino)-6-oxohexyl)-4-methyl-2-(pyridin-3-yl)thiazole-5-carboxamide;
N-(6-(2-aminophenylamino)-6-oxohexyl)-4-(1H-pyrrol-1-yl)benzamide;
N-(6-(2-aminophenylamino)-6-oxohexyl)-1-(pyridin-4-yl)piperidine-4-carboxamide;
N-(6-(2-aminophenylamino)-6-oxohexyl)-4-methyl-2-(pyridin-2-yl)thiazole-5-carboxamide;
N-(5-(2-aminophenylamino)-5-oxopentyl)-5-methylthiazole-2-carboxamide;
N-(5-(2-aminophenylamino)-5-oxopentyl)-2,6-dimethoxynicotinamide;
N-(5-(2-aminophenylamino)-5-oxopentyl)-4-(methylsulfonyl)benzamide;
N-(5-(2-aminophenylamino)-5-oxopentyl)-5-methoxy-1H-indole-2-carboxamide;
N-(5-(2-aminophenylamino)-5-oxopentyl)benzo[d]thiazole-6-carboxamide;
N-(5-(2-aminophenylamino)-5-oxopentyl)-2-(pyridin-4-yl)thiazole-4-carboxamide;
N-(5-(2-aminophenylamino)-5-oxopentyl)-2-(piperidin-1-yl)isonicotinamide;
N-(5-(2-aminophenylamino)-5-oxopentyl)-2,3-dihydrobenzo[b][1,4]dioxine-6-carboxamide;
N-(5-(2-aminophenylamino)-5-oxopentyl)isoxazole-5-carboxamide;
N-(5-(2-aminophenylamino)-5-oxopentyl)-5-phenyl-4H-pyrazole-3-carboxamide;
N-(5-(2-aminophenylamino)-5-oxopentyl)-3-(1-methyl-1H-pyrazol-4-yl)isoxazole-5-carboxamide;
N-(6-(2-aminophenylamino)-6-oxohexyl)-2-methylbenzamide;
N-(6-(2-aminophenylamino)-6-oxohexyl)-3-ethylbenzamide;
N-(6-(2-aminophenylamino)-6-oxohexyl)-4-ethylbenzamide;
N-(6-(2-aminophenylamino)-6-oxohexyl)-3,4-dimethylbenzamide;
N-(6-(2-aminophenylamino)-6-oxohexyl)-4-propylbenzamide;
N-(6-(2-aminophenylamino)-6-oxohexyl)-4-isopropylbenzamide;
N-(6-(2-aminophenylamino)-6-oxohexyl)-4-cyclopropylbenzamide;
N-(6-(2-aminophenylamino)-6-oxohexyl)-4-(hydroxymethyl)benzamide;
N-(6-(2-aminophenylamino)-6-oxohexyl)-2-(dimethylamino)benzamide;
N-(6-(2-aminophenylamino)-6-oxohexyl)-2,4-difluorobenzamide;
N-(6-(2-aminophenylamino)-6-oxohexyl)-3-methyl-1H-indole-2-carboxamide;
N-(6-(2-aminophenylamino)-6-oxohexyl)-4-methoxy-1H-indole-2-carboxamide;
N-(6-(2-aminophenylamino)-6-oxohexyl)-4-ethoxy-1H-indole-2-carboxamide;
N-(6-(2-aminophenylamino)-6-oxohexyl)-4-fluoro-1H-indole-2-carboxamide;
N-(6-(2-aminophenylamino)-6-oxohexyl)-4-chloro-1H-indole-2-carboxamide;
N-(6-(2-aminophenylamino)-6-oxohexyl)-5-(trifluoromethoxy)-1H-indole-2-carboxamide;
N-(6-(2-aminophenylamino)-6-oxohexyl)-5-methyl-1H-indole-2-carboxamide;
N-(6-(2-aminophenylamino)-6-oxohexyl)-5-fluoro-1H-indole-2-carboxamide;
N-(6-(2-aminophenylamino)-6-oxohexyl)-5-chloro-1H-indole-2-carboxamide;
N-(6-(2-aminophenylamino)-6-oxohexyl)-7-methoxy-1H-indole-2-carboxamide;
N-(6-(2-aminophenylamino)-6-oxohexyl)-7-methyl-1H-indole-2-carboxamide;
N-(6-(2-aminophenylamino)-6-oxohexyl)-7-fluoro-1H-indole-2-carboxamide;
N-(6-(2-aminophenylamino)-6-oxohexyl)-6-(dimethylamino)-1H-indole-2-carboxamide;
N-(6-(2-aminophenylamino)-6-oxohexyl)-4-(difluoromethoxy)-1H-indole-2-carboxamide;
N-(6-(2-aminophenylamino)-6-oxohexyl)-1-methyl-1H-indole-2-carboxamide;
N-(6-(2-aminophenylamino)-6-oxohexyl)-5-methoxy-1-methyl-1H-indole-2-carboxamide;
N-(6-(2-aminophenylamino)-6-oxohexyl)-5-fluoro-1-methyl-1H-indole-2-carboxamide;
N-(6-(2-aminophenylamino)-6-oxohexyl)-5-chloro-1-methyl-1H-indole-2-carboxamide;
N-(6-(2-aminophenylamino)-6-oxohexyl)-1,5-dimethyl-1H-indole-2-carboxamide;
N-(6-(2-aminophenylamino)-6-oxohexyl)-1-(2-methoxyethyl)-1H-indole-2-carboxamide;
N-(6-(2-aminophenylamino)-6-oxohexyl)-2-ethylbenzamide;
N-(6-(2-aminophenylamino)-6-oxohexyl)-3-(dimethylamino)benzamide;
N-(6-(2-aminophenylamino)-6-oxohexyl)-7-methoxy-1H-indole-3-carboxamide;
N-(6-(2-aminophenylamino)-6-oxohexyl)-1-methyl-1H-indole-6-carboxamide;
N-(6-(2-aminophenylamino)-6-oxohexyl)-2,3-dimethyl-1H-indole-7-carboxamide;
N-(6-(2-aminophenylamino)-6-oxohexyl)-3-(trifluoromethoxy)benzamide;
N-(6-(2-aminophenylamino)-6-oxohexyl)-4-(trifluoromethoxy)benzamide;
N-(6-(2-aminophenylamino)-6-oxohexyl)-1-methyl-1H-indole-3-carboxamide;
N-(6-(2-aminophenylamino)-6-oxohexyl)-5-ethoxy-1H-indole-2-carboxamide;
N-(6-(2-aminophenylamino)-6-oxohexyl)-4-(ethylamino)benzamide;
N-(6-(2-aminophenylamino)-6-oxohexyl)-2,3-dimethyl-1H-indole-5-carboxamide;
N-(6-(2-aminophenylamino)-6-oxohexyl)-7-chloro-1H-indole-3-carboxamide;
N-(6-(2-hydroxyphenylamino)-6-oxohexyl)-4-methylbenzamide;
2-(6-(4-methylbenzamido)hexanamido)pyridine 1-oxide;

N-(6-(2-aminophenylamino)-6-oxohexyl)-3-methylbenzamide;
N-(6-(2-aminophenylamino)-6-oxohexyl)-2,4-dimethylbenzamide;
N-(6-(2-aminophenylamino)-6-oxohexyl)-4-(difluoromethyl)benzamide;
N-(6-(2-aminophenylamino)-6-oxohexyl)-4-(2-hydroxypropan-2-yl)benzamide;
N-(6-(2-aminophenylamino)-6-oxohexyl)-4-(azetidin-1-yl)benzamide;
N-(6-(2-aminophenylamino)-6-oxohexyl)-3-(4-methylpiperazin-1-yl)benzamide;
N-(6-(2-aminophenylamino)-6-oxohexyl)-2-(4-methylpiperazin-1-yl)benzamide;
N-(6-(2-aminophenylamino)-6-oxohexyl)-4-morpholinobenzamide;
N-(6-(2-aminophenylamino)-6-oxohexyl)-2-chlorobenzamide;
N-(6-(2-aminophenylamino)-6-oxohexyl)-3,4-difluorobenzamide;
N-(6-(2-aminophenylamino)-6-oxohexyl)-1H-indole-3-carboxamide;
N-(6-(2-aminophenylamino)-6-oxohexyl)-5-methoxy-1H-indole-3-carboxamide;
N-(6-(2-aminophenylamino)-6-oxohexyl)-2-cyclohexylbenzamide;
N-(6-(2-aminophenylamino)-6-oxohexyl)-2-(methoxymethyl)benzamide;
N-(6-(2-aminophenylamino)-6-oxohexyl)-6-methoxy-1H-indole-3-carboxamide;
N-(6-(2-aminophenylamino)-6-oxohexyl)-1H-indole-4-carboxamide;
N-(6-(2-aminophenylamino)-6-oxohexyl)-1-methyl-1H-indole-4-carboxamide;
N-(6-(2-aminophenylamino)-6-oxohexyl)-1H-indole-5-carboxamide;
N-(6-(2-aminophenylamino)-6-oxohexyl)-1-methyl-1H-indole-5-carboxamide;
N-(6-(2-aminophenylamino)-6-oxohexyl)-1-methyl-1H-indazole-3-carboxamide;
N-(6-(2-aminophenylamino)-6-oxohexyl)-1H-indazole-7-carboxamide;
2-allyl-N-(6-(2-aminophenylamino)-6-oxohexyl)benzamide;
N-(6-(2-aminophenylamino)-6-oxohexyl)-2-(2,2,2-trifluoroacetyl)benzamide;
N-(6-(2-aminophenylamino)-6-oxohexyl)-2-ethoxybenzamide;
N-(6-(2-aminophenylamino)-6-oxohexyl)-2-propoxybenzamide;
N-(6-(2-aminophenylamino)-6-oxohexyl)-2-(ethylthio)benzamide;
N-(6-(2-aminophenylamino)-6-oxohexyl)-2-(methyl sulfonyl)benzamide;
N-(6-(2-aminophenylamino)-6-oxohexyl)-2-cyanobenzamide;
2-acetyl-N-(6-(2-aminophenylamino)-6-oxohexyl)benzamide;
N-(6-(2-aminophenylamino)-6-oxohexyl)-2-benzoylbenzamide;
N-(6-(2-aminophenylamino)-6-oxohexyl)biphenyl-2-carboxamide;
N-(6-(2-aminophenylamino)-6-oxohexyl)-2-(difluoromethoxy)benzamide;
N-(6-(2-aminophenylamino)-6-oxohexyl)-2-(2-methoxyethoxy)benzamide;
N-(6-(2-aminophenylamino)-6-oxohexyl)-2-(trifluoromethyl)benzamide;
N-(6-(2-aminophenylamino)-6-oxohexyl)-2-fluorobenzamide;
N-(6-(2-aminophenylamino)-6-oxohexyl)-2-methoxybenzamide;
N-(6-(2-aminophenylamino)-6-oxohexyl)-2-bromobenzamide;
N-(6-(2-aminophenylamino)-6-oxohexyl)-4-methoxy-1H-indole-3-carboxamide;
N-(6-(2-aminophenylamino)-6-oxohexyl)-1H-indole-7-carboxamide;
N-(6-(2-aminophenylamino)-6-oxohexyl)-1H-indazole-6-carboxamide;
N-(6-(2-aminophenylamino)-6-oxohexyl)-6-methoxy-1H-indole-2-carboxamide;
N-(6-(2-aminophenylamino)-6-oxohexyl)-4-(methylamino)benzamide;
N-(6-(2-aminophenyl amino)-6-oxohexyl)-4-(cyclopropylamino)benzamide;
N-(6-(2-aminophenylamino)-6-oxohexyl)-4-(4-methylpiperazin-1-yl)benzamide;
N-(6-(2-aminophenylamino)-6-oxohexyl)-6-methyl-1 Hz-indole-2-carboxamide;
N-(6-(2-aminophenylamino)-6-oxohexyl)-5-ethoxy-1-methyl-1H-indole-2-carboxamide;
N-(6-(2-aminophenylamino)-6-oxohexyl)-2,3-dimethyl-1H-indole-6-carboxamide;
N-(6-(2-aminophenylamino)-6-oxohexyl)-5-methyl-1H-indazole-3-carboxamide;
N-(6-(2-aminophenylamino)-6-oxohexyl)-5-chloro-1H-indole-3-carboxamide;
N-(6-(2-aminophenylamino)-6-oxohexyl)-1H-indole-6-carboxamide;
(E)-N-(6-(2-aminophenylamino)-6-oxohex-3-enyl)-4-methylbenzamide;
(E)-N-(6-(2-aminophenylamino)-6-oxohex-3-enyl)-4-methoxybenzamide;
(E)-N-(6-(2-aminophenylamino)-6-oxohex-3-enyl)benzamide;
(E)-N-(6-(2-aminophenylamino)-6-oxohex-3-enyl)-4-fluorobenzamide;
(E)-N-(6-(2-aminophenylamino)-6-oxohex-3-enyl)-3-chlorobenzamide;
(E)-N-(6-(2-aminophenylamino)-6-oxohex-4-enyl)-4-morpholinobenzamide;
(E)-N-(6-(2-aminophenylamino)-6-oxohex-4-enyl)-4-(dimethylamino)benzamide;
(E)-N-(6-(2-aminophenylamino)-6-oxohex-4-enyl)-4-methoxybenzamide;
(E)-N-(6-(2-aminophenylamino)-6-oxohex-4-enyl)-3-chlorobenzamide;
(E)-N-(6-(2-aminophenylamino)-6-oxohex-4-enyl)-4-fluorobenzamide;
(E)-N-(6-(2-aminophenyl amino)-6-oxohex-4-enyl)-4-methylbenzamide;
(E)-N-(6-(2-aminophenylamino)-6-oxohex-4-enyl)benzamide;
N-(6-(2-aminophenylamino)-6-oxohexyl)-3-(difluoromethoxy)benzamide;
N-(6-(2-aminophenylamino)-6-oxohexyl)-3-cyanobenzamide;
N-(6-(2-aminophenylamino)-6-oxohexyl)-3-morpholinobenzamide;
N-(6-(2-aminophenylamino)-6-oxohexyl)-3-ethoxybenzamide;

N-(6-(2-aminophenylamino)-6-oxohexyl)-3-nitrobenzamide; and

N-(2-aminophenyl)-6-(phenylsulfonamido)hexanamide;

or a pharmaceutically acceptable salt, hydrate, or solvate thereof.

In another aspect, compounds having Formula (Ic) and Formula (Id) are featured:

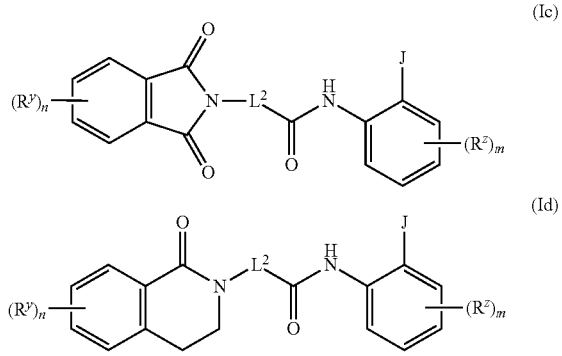

or a pharmaceutically acceptable salt thereof; wherein:

$L^2$ is selected from a straight chain $C_{4-5}$ alkylene and a $C_{4-6}$ alkenylene;

J is selected from amino and hydroxyl;

each $R^y$ is independently selected from halogen, cyano, nitro, hydroxyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy;

each $R^z$ is independently selected from halogen, cyano, nitro, hydroxyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy;

n is an integer selected from 0, 1, 2, 3, and 4; and m is an integer selected from 0, 1, 2, and 3.

In some embodiments, the compound is a compound of Formula (Ic), or a pharmaceutically acceptable salt thereof; wherein:

$L^2$ is $C_{4-6}$ alkenylene;

J is amino;

$R^z$ is halogen;

n is 0; and m is an integer selected from 0 and 1.

In some embodiments, the compound is a compound of Formula (Id), or a pharmaceutically acceptable salt thereof, wherein:

$L^2$ is straight chain $C_{4-6}$ alkenylene;

J is amino;

$R^y$ is halogen;

$R^z$ is halogen;

n is an integer selected from 0 and 1; and m is an integer selected from 0 and 1.

In some embodiments, the compound is:

N-(2-amino-4-fluorophenyl)-6-(1,3-dioxoisoindolin-2-yl)hexanamide;

N-(2-aminophenyl)-5-(6-fluoro-1-oxo-3,4-dihydroisoquinolin-2(1H)-yl)pentanamide;

(E)-N-(2-aminophenyl)-6-(1,3-dioxoisoindolin-2-yl)hex-3-enamide;

(E)-N-(2-aminophenyl)-6-(1,3-dioxoisoindolin-2-yl)hex-2-enamide; and

N-(2-amino-4-fluorophenyl)-6-(6-fluoro-1-oxo-3,4-dihydroisoquinolin-2(1H)-yl)hexanamide;

or a pharmaceutically acceptable salt, hydrate, or solvate thereof.

In another aspect, this application features compounds of Formula (II):

and pharmaceutically acceptable salts, hydrates, and solvates thereof; wherein:

Su is a surface recognition domain;

Y is selected from C(=O), S(=O), and S(=O)2;

R1 is selected from H, $C_{1-4}$ alkyl, $C_{1-4}$ haloalkyl, $C_{1-4}$ alkoxycarbonyl, carbamyl, di-$C_{1-4}$-alkyl-carbamyl, and $C_{1-4}$ alkylcarbamyl;

L is a linker; and

Z is a Zn-binding group.

The surface recognition domain is a portion of the molecule that makes contact with the rim of active site channel of the HDAC (Chen et al., 2008, Bioorg. Med. Chem., 16:4839-53; Vannini et al., 2004, Proc. Natl. Acad. Sci. USA, 101:15064-69; Paris et al., 2008, J. Med. Chem., 51:1505-29). Exemplary surface recognition domains include heterocycloalkyls, aryls, and heteroaryls, with optional substitutions.

The linker region makes contact with the interior of the channel of the HDAC active site (Paris et al., 2008, J. Med. Chem., 51:1505-29). Exemplary linkers include alkanes, alkenes, cyclics, aromatics, and heterocyclics, and heteroaromatics (all with optional substitutions), such that the number of atoms between the N and O is between 4 and 6, inclusive.

The Zn-binding group bind to the zinc molecule in the HDAC (Paris et al., 2008, J. Med. Chem., 51:1505-29). This zinc is required for catalysis. The most common Zn-binding groups are hydroxamic acids and 2-aminobenzanilides and examples of each are currently in human clinical trials.

The compounds in this invention may contain one or more asymmetric centers, which can thus give rise to optical isomers (enantiomers) and diastereomers. While shown without respect to the stereochemistry in Formula I, the present invention includes such optical isomers (enantiomers) and diastereomers (geometric isomers); as well as the racemic and resolved, enantiomerically pure R and S stereoisomers; as well as other mixtures of the R and S stereoisomers and pharmaceutically acceptable salts thereof. The use of these compounds is intended to cover the racemic mixture or either of the chiral enantiomers.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

One skilled in the art will also recognize that it is possible for tautomers to exist for the compounds described herein. The present invention includes all such tautomers even though not shown in the formulas herein.

The present invention also includes various hydrate and solvate forms of the compounds.

Compounds described herein can also include all isotopes of atoms occurring in the intermediates or final compounds. Isotopes include those atoms having the same atomic number but different mass numbers. For example, isotopes of hydrogen include tritium and deuterium.

The compounds described herein also include pharmaceutically acceptable salts of the compounds disclosed herein. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

In some embodiments, the compounds are prodrugs. As used herein, "prodrug" refers to a moiety that releases a compound described herein when administered to a patient. Prodrugs can be prepared by modifying functional groups present in the compounds in such a way that the modifications are cleaved, either in routine manipulation or in vivo, to the parent compounds. Examples of prodrugs include compounds as described herein that contain one or more molecular moieties appended to a hydroxyl, amino, sulfhydryl, or carboxyl group of the compound, and that when administered to a patient, cleave in vivo to form the free hydroxyl, amino, sulfhydryl, or carboxyl group, respectively. Examples of prodrugs include, but are not limited to, acetate, formate and benzoate derivatives of alcohol and amine functional groups in the compounds described herein. Preparation and use of prodrugs is discussed in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference in their entireties.

The following definitions are used, unless otherwise described. Specific and general values listed below for radicals, substituents, and ranges, are for illustration only; they do not exclude other defined values or other values within defined ranges for the radicals and substituents. Alkyl, alkoxy, alkenyl, and the like denote both straight and branched groups.

As used herein, the term "alkyl," employed alone or in combination with other terms, refers to a saturated hydrocarbon group that may be straight-chain or branched. In some embodiments, the alkyl group contains 1 to 12, 1 to 8, or 1 to 6 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, n-heptyl, n-octyl, and the like. In some embodiments, the alkyl moiety is methyl, ethyl, n-propyl, isopropyl, n-butyl, isobutyl, tert-butyl, n-pentyl, isopentyl, neopentyl, n-hexyl, or 2,4,4-trimethylpentyl.

As used herein, the term "$C_{n-m}$ alkylene," employed alone or in combination with other terms, refers to a divalent alkyl linking group having n to m carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

As used herein, the term "$C_{n-m}$ alkylene," employed alone or in combination with other terms, refers to a divalent alkyl linking group having n to m carbon atoms.

Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

As used herein, the term "straight chain $C_{n-m}$ alkylene," employed alone or in combination with other terms, refers to a non-branched alkylene group of n to m carbon atoms.

As referred to herein, the term "alkoxy group" refers to a group of formula —O(alkyl). Alkoxy can be, for example, methoxy, ethoxy, propoxy, isopropoxy, butoxy, iso-butoxy, sec-butoxy, pentoxy, 2-pentoxy, 3-pentoxy, or hexyloxy.

As used herein, the term "aryl," employed alone or in combination with other terms, refers to a monocyclic or polycyclic (e.g., having 2, 3 or 4 fused or covalently linked rings) aromatic hydrocarbon moiety, such as, but not limited to, phenyl, 1-naphthyl, 2-naphthyl, anthracenyl, phenanthrenyl, and the like. In some embodiments, aryl groups have from 6 to 20 carbon atoms, about 6 to 10 carbon atoms, or about 6 to 8 carbons atoms.

As referred to herein, "heteroaryl" refers to a monocyclic, bicyclic, or tricyclic ring system containing one, two, or three aromatic rings and containing at least one (typically one to about three) nitrogen, oxygen, or sulfur atoms in an aromatic ring. Heteroaryl groups can possess optional substituents as described herein.

Examples of heteroaryl groups include, but are not limited to, 2H-pyrrolyl, 3H-indolyl, 4H-quinolizinyl, acridinyl, benzo[b]thienyl, benzothiazolyl, (3-carbolinyl, carbazolyl, chromenyl, cinnolinyl, dibenzo[b,d]furanyl, furyl, imidazolyl, indazolyl, indolyl, isobenzofuranyl, isoindolyl, isoquinolyl, isothiazolyl, isoxazolyl, naphthyridinyl, oxazolyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, and xanthenyl.

Within the above definition, the term "heteroaryl" can include a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, phenyl or benzyl. The term heteroaryl can also include an ortho-fused bicyclic heterocycle of about eight to ten ring atoms derived therefrom, particularly a benz-derivative or one derived by fusing a propylene, trimethylene, or tetramethylene diradical thereto.

As referred to herein, "optionally" substituted group refers to the substitution of a group in which one or more hydrogen atoms may be independently replaced with a non-hydrogen substituent. Groups that are optionally substituted are typically substituted with one to five substituents. In other embodiments, optionally substituted groups are substituted with one to three substituents. Typical substituents include, but are not limited to, —X, —R, —O⁻, =O, —OR, —S⁻, —SR, —S(=O)R, —S(=O)₂R, —S(=O)₂O⁻, —S(=O)₂OH, —OS(=O)₂OR, —S(=O)₂NR, —NR₂, —N⁺R₃, =NR, —N=C=O, —NCS, —NO, —NO₂, =N₂, —N₃, —NC(=O)R, —CX₃, —C(O)O⁻, —C(=O)R, —C(=O)OR, —C(=O)X, —C(=O)NRR, —C(S)R, —C(S)OR, —C(O)SR, —C(S)SR, —C(S)NRR, —C(NR)NRR, —CN, —OCN, —SCN, —OP(=O)(OR)₂, —P(=O)(OR)₂, —P(=O)(O⁻)₂, —P(=O)(OH)₂, where each X is independently a halogen (F, Cl, Br, or I); and each R is independently H, alkyl, aryl, a heterocycle, or a protecting group. When the substituent is attached to a group by two bonds (e.g., by a "double bond"), two hydrogen atoms are replaced by the substituent.

As used herein, the phrase "optionally substituted" means unsubstituted (e.g., substituted with a H) or substituted. As used herein, the term "substituted" means that a hydrogen atom is removed and replaced by a substituent. It is understood that substitution at a given atom is limited by valency.

As used herein, when a first ring is "optionally fused" to a second ring, the first ring may be unfused, or may be fused to the second ring. For example, a phenyl ring optionally fused to a phenyl ring refers to either an unfused phenyl ring or a naphthalene ring. As used herein, a ring "substituted at one ortho position" refers to a ring substituted at the position of the ring directly adjacent to the point of attachment of the ring to the core moiety (e.g. the core moiety of Formula (I)).

At various places in the present specification, substituents of compounds described herein are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

As used herein, the term "$C_{n-m}$ alkylene," employed alone or in combination with other terms, refers to a divalent alkyl group having n to m carbon atoms.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring and 1,2,3,4-tetrahydro-naphthalene is an example of a 10-membered cycloalkyl group.

For compounds described herein in which a variable appears more than once, each variable can be a different moiety independently selected from the group defining the variable. For example, where a structure is described as having two R groups that are simultaneously present on the same compound, the two R groups can represent different moieties independently selected from the group defined for R. In another example, when an optionally multiple substituent is designated in the form:

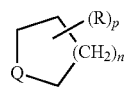

then it is understood that substituent R can occur p number of times on the ring, and R can be a different moiety at each occurrence. It is understood that each R group may replace any hydrogen atom attached to a ring atom, including one or both of the (CH₂)ₙ hydrogen atoms. Further, in the above example, should the variable Q be defined to include hydrogens, such as when Q is said to be CH₂, NH, etc., any floating substituent such as R in the above example, can replace a hydrogen of the Q variable as well as a hydrogen in any other non-variable component of the ring.

Throughout the definitions, the term "$C_{n-m}$" (e.g., $C_{1-4}$, $C_{1-6}$, and the like) is used, wherein n and m are integers and indicate the number of carbons, wherein n-m indicates a range which includes the endpoints.

Unless indicated otherwise, the nomenclature of substituents that are not explicitly defined herein are arrived at by naming the terminal portion of the functionality followed by the adjacent functionality toward the point of attachment. In generally, the point of attachment for a substituent is indicated by the last term in the group. For example, $C_{1-6}$ heteroaryl-$C_{1-4}$ alkyl refers to a moiety of heteroaryl-alkylene-, wherein the heteroaryl group has 1 to 6 carbon atoms, the alkylene linker has 1 to 4 carbons, and the substituent is attached through the alkylene linker.

As used herein, "$C_{n-m}$ alkynyl," employed alone or in combination with other terms, refers to an alkyl group having one or more triple carbon-carbon bonds with n to m carbon atoms. Example alkynyl groups include, but are not limited to, ethynyl, propyn-1-yl, propyn-2-yl, and the like. In some embodiments, the alkynyl moiety contains 2 to 10 or 2 to 6 carbon atoms.

As used herein, the term "$C_{n-m}$ alkynylene," employed alone or in combination with other terms, refers to a divalent alkynyl group having n to m carbon atoms. In some embodiments, the alkynylene moiety contains 2 to 12 carbon atoms. In some embodiments, the alkynylene moiety contains 2 to 6 carbon atoms. Example alkynylene groups include, but are not limited to, ethyn-1,2-diyl, propyn-1,3,-diyl, 1-butyn-1,4-diyl, 1-butyn-1,3-diyl, 2-butyn-1,4-diyl, and the like.

As used herein, "$C_{n-m}$ alkenyl," employed alone or in combination with other terms, refers to an alkyl group having one or more double carbon-carbon bonds, with n to m carbon atoms. In some embodiments, the alkenyl moiety contains 2 to 10 or 2 to 6 carbon atoms. Example alkenyl groups include, but are not limited to, ethenyl, n-propenyl, isopropenyl, n-butenyl, sec-butenyl, and the like.

As used herein, the term "alkenylene," employed alone or in combination with other terms, refers to a divalent alkenyl group. In some embodiments, the alkenylene moiety contains 2 to 12 carbon atoms. In some embodiments, the alkenylene moiety contains 2 to 6 carbon atoms. Example alkenylene groups include, but are not limited to, ethen-1,2-diyl, propen-1,3-diyl, propen-1,2-diyl, buten-1,4-diyl, buten-1,3-diyl, buten-1,2-diyl, 2-methyl-propen-1,3-diyl, and the like.

As used herein, the term "amino," employed alone or in combination with other terms, refers to a group of formula —NH₂.

As used herein, the term "$C_{n-m}$ alkylamino," employed alone or in combination with other terms, refers to a group of formula —NH(alkyl), wherein the alkyl group has n to m carbon atoms.

As used herein, the term "di-$C_{n-m}$-alkylamino," employed alone or in combination with other terms, refers to a group of formula —N(alkyl)₂, wherein the alkylene group and two alkyl groups each has, independently, n to m carbon atoms.

As used herein, the term "carbamyl," employed alone or in combination with other terms, refers to a group of formula —C(O)NH$_2$.

As used herein, the term "C$_{n-m}$ alkylcarbamyl," employed alone or in combination with other terms, refers to a group of formula —C(O)—NH(alkyl), wherein the alkyl group has n to m carbon atoms.

As used herein, the term "di-C$_{n-m}$ alkylcarbamyl," employed alone or in combination with other terms, refers to a group of formula —C(O)N(alkyl)$_2$, wherein the alkyl group has n to m carbon atoms.

As used herein, the term "C$_{n-m}$ alkoxycarbonyl," employed alone or in combination with other terms, refers to a group of formula —C(O)O-alkyl, wherein the alkyl group has n to m carbon atoms.

As used herein, the term "C$_{n-m}$ alkylcarbonyl," employed alone or in combination with other terms, refers to a group of formula —C(O)-alkyl, wherein the alkyl group has n to m carbon atoms.

As used herein, the term "C$_{n-m}$ alkylcarbonylamino," employed alone or in combination with other terms, refers to a group of formula —NHC(O)-alkyl, wherein the alkyl group has n to m carbon atoms.

As used herein, the term "C$_{n-m}$ alkylcarbonyl-(C$_{n-m}$ alkyl)amino," employed alone or in combination with other terms, refers to a group of formula —N(alkyl)C(O)-alkyl, wherein each alkyl group, independently, has n to m carbon atoms.

As used herein, the term "C$_{n-m}$ alkoxycarbonylamino," employed alone or in combination with other terms, refers to a group of formula —NHC(O)O-alkyl, wherein the alkyl group has n to m carbon atoms.

As used herein, the term "C$_{o-p}$ heteroaryl-C$_{n-m}$-alkyl," employed alone or in combination with other terms, refers to a group of formula-alkylene-heteroaryl, wherein the alkylene linker has n to m carbon atoms.

As used herein, the term "carbonyl," employed alone or in combination with other terms, refers to a —C(O)— group, which is a divalent one-carbon moiety further bonded to an oxygen atom with a double bond.

As used herein, the term "carboxy," employed alone or in combination with other terms, refers to a group of formula —C(O)OH.

As used herein, the term "sulfonyl", employed alone or in combination with other terms, refers to a group of formula —S(=O)$_2$—.

As used herein, the term "sulfonamido", employed alone or in combination with other terms, refers to a group of formula —S(=O)$_2$NH$_2$.

As used herein, the term "cycloalkyl," employed alone or in combination with other terms, refers to a non-aromatic cyclic hydrocarbon moiety, which may optionally contain one or more alkenylene or alkynylene groups as part of the ring structure. Cycloalkyl groups can include mono- or polycyclic (e.g., having 2, 3 or 4 fused or covalently linked rings) ring systems. Also included in the definition of cycloalkyl are moieties that have one or more aromatic rings fused (i.e., having a bond in common with) to the cycloalkyl ring, for example, benzo derivatives of pentane, pentene, hexane, and the like. The term "cycloalkyl" also includes bridgehead cycloalkyl groups and spirocycloalkyl groups. As used herein, "bridgehead cycloalkyl groups" refers to non-aromatic cyclic hydrocarbon moieties containing at least one bridgehead carbon, such as adamantazn-1-yl. As used herein, "spirocycloalkyl groups" refers to non-aromatic hydrocarbon moieties containing at least two rings fused at a single carbon atom, such as spiro[2.5]octane and the like. In some embodiments, the cycloalkyl group has 3 to 14 ring members, 3 to 10 ring members, or 3 to 8 ring members. One or more ring-forming carbon atoms of a cycloalkyl group can be oxidized to form carbonyl linkages. Exemplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, the cycloalkyl group is admanatan-1-yl.

As used herein, the term "cyano," employed alone or in combination with other terms, refers to a group of formula —CN, wherein the carbon and nitrogen atoms are bound together by a triple bond.

As used herein, the term "haloalkyl," employed alone or in combination with other terms, refers to an alkyl group having from one halogen atom to 2 n+1 halogen atoms which may be the same or different, where "n" is the number of carbon atoms in the alkyl group. In some embodiments, the halogen atoms are fluoro atoms.

As used herein, "haloalkoxy," employed alone or in combination with other terms, refers to a group of formula —O-haloalkyl. An example haloalkoxy group is OCF$_3$. In some embodiments, the halogen atoms are fluoro atoms.

As used herein, the terms "halo" and "halogen," employed alone or in combination with other terms, refer to fluoro, chloro, bromo, and iodo.

As used herein, the term "C$_{o-p}$ heteroaryl-C$_{n-m}$-alkyl," employed alone or in combination with other terms, refers to a group of formula-alkylene-heteroaryl, the alkylene linker has n to m carbon atoms and the heteroaryl group has o to p carbon atoms. In some embodiments, the alkylene portion has 1 to 4 carbon atoms.

As used herein, the term "C$_{o-p}$ cycloalkyl-C$_{n-m}$-alkyl," employed alone or in combination with other terms, refers to a group of formula-alkylene-cycloalkyl, the alkylene linker has n to m carbon atoms and the cycloalkyl group has o to p carbon atoms. In some embodiments, the alkylene portion has 1 to 4 carbon atoms.

As used herein, the term "C$_{o-p}$ aryl-C$_{n-m}$-alkyl," employed alone or in combination with other terms, refers to a group of formula-alkylene-aryl, the alkylene linker has n to m carbon atoms and the aryl group has o to p carbon atoms. In some embodiments, the alkylene portion has 1 to 4 carbon atoms.

As used herein, the term "phenyl-C$_{n-m}$-alkyl," employed alone or in combination with other terms, refers to a group of formula-alkylene-phenyl, the alkylene linker has n to m carbon atoms. In some embodiments, the alkylene portion has 1 to 4 carbon atoms.

As used herein, the term "C$_{o-p}$ heterocycloalkyl-C$_{n-m}$-alkyl," employed alone or in combination with other terms, refers to a group of formula-alkylene-heterocycloalkyl, the alkylene linker has n to m carbon atoms and the heterocycloalkyl group has o to p carbon atoms. In some embodiments, the alkylene portion has 1 to 4 carbon atoms.

As used herein, the term "heterocycloalkyl," "heterocycloalkyl ring," or "heterocycloalkyl group," employed alone or in combination with other terms, refers to a non-aromatic ring system, which may optionally contain one or more alkenylene or alkynylene groups as part of the ring structure, and which has at least one heteroatom ring member selected from nitrogen, sulfur, and oxygen. When the heterocycloalkyl groups contains more than one heteroatom, the heteroatoms may be the same or different. Heterocycloalkyl groups can include mono- or polycyclic (e.g., having 2, 3, or 4 fused or covalently bonded rings) ring systems. Also included in the definition of heterocycloalkyl are moieties that have one or more aromatic rings fused (i.e., having a bond in common with) to the non-aromatic ring, for example, 1,2,3,4-tetrahydro-quinoline and the like. Heterocycloalkyl groups can also include bridgehead heterocycloalkyl groups and spiroheterocycloalkyl groups. As used herein, "bridgehead heterocycloalkyl group" refers to a heterocycloalkyl moiety containing at least one bridgehead atom, such as azaadamantan-1-yl and the like. As used herein, "spiroheterocycloalkyl group" refers to a heterocycloalkyl moiety containing at least two rings fused at a single atom, such as [1,4-dioxa-8-aza-spiro[4.5]decan-N-yl] and the like. In some embodiments, the heterocycloalkyl group has 3 to 20 ring-forming atoms, 3 to 10 ring-forming atoms, or about 3 to 8 ring forming atoms. The carbon atoms or hetereoatoms in the ring(s) of the heterocycloalkyl group can be oxidized to form a carbonyl, or sulfonyl group (or other oxidized linkage) or a nitrogen atom can be quaternized.

Where a particular heteroaryl or heterocycloalkyl group appears in the embodiments, such as "a pyrazole ring," the term is intended to refer to a pyrazole ring attached at any atom of the ring, as permitted by valency rules, and is intended to include various tautomeric forms of the ring. Conversely, in some embodiments, the point of attachment is indicated by the name, e.g., pyrazol-1-yl refers to a pyrazole ring attached at the 1-position of the ring.

As used herein, the term "hydroxyl," employed alone or in combination with other terms, refers to a group of formula —OH.

As used herein, the term "linking group" refers to a divalent group connecting two positions in Formula (I).

As used herein, the term "n-membered cycloalkylene" refers to a divalent monocyclic cycloalkyl group having n ring atoms.

As used herein, the term "n-membered heterocycloalkylene" refers to a divalent monocyclic heterocycloalkyl linking group having n ring atoms.

As used herein, the term "phenylene" refers to a divalent phenyl ring linking group.

As used herein, the term "n-membered heteroarylene" refers to a divalent monocyclic heteroaryl linking group having n ring atoms.

As to any of the above groups that contain one or more substituents, it is understood, of course, that such groups do not contain any substitution or substitution patterns that are sterically impractical and/or synthetically un-feasible. In addition, the compounds of this invention include all stereochemical isomers arising from the substitution of these compounds.

As used herein, a "base" refers to any molecule, ion, or other entity that acts as a proton acceptor. A base can be an organic compound or ion with an unshared electron pair. Typical bases include mono-, di-, and tri-alkyl substituted amines. A base can also be an inorganic compound or ion, such as a metal oxide or metal hydroxide. Bases used in organic synthesis are well known to those of skill in the art. Many bases are disclosed in, for example, the Aldrich Handbook of Fine Chemicals, 2003-2004 (Milwaukee, Wis.).

As used herein, "solvent" refers to a substance, usually a liquid, capable of dissolving another substance, e.g., a solid substance, semi-solid substance, or a liquid. Typical solvents include water and organic solvents. It is appreciated by those of skill in the art that the solvent should not chemically react with any of the starting materials or reagents present in the reaction mixture, to any significant degree, under the reaction conditions employed. As used herein, "solvent system" refers to a medium that includes one or more solvents. A solvent system can be homogeneous (miscible solvents) or heterogeneous (e.g., an organic/aqueous system).

As used herein, "reflux" refers to the process of boiling a liquid solvent system in a vessel, for example, a vessel attached to a condenser, so that the vapors of the solvent system continuously condense for reboiling.

As used herein, "purifying" refers to the process of ridding a substrate (e.g., crystals, an amorphous solid, a liquid, or an oil) of impurities. Suitable methods of purifying include, for example, filtering, washing, recrystallizing and drying, distilling, and chromatography. As used herein, the terms "isolated" and "purified" refer to substances that are at least about 90% free of other agents, for example, at least about 95%, at least about 98%, or at least about 99% pure by weight.

As used herein, "anhydrous" refers to a substance that contains less than 10 wt. % water, less than about 1 wt. % water, less than about 0.5 wt. % water, less than about 0.1 wt. % water, e.g., or less than about 0.01 wt. % water. "Anhydrous conditions" refer to reaction conditions that have less than 2 wt. % water, e.g. less than about 1 wt. % water, less than about 0.5 wt. % water, less than about 0.1 wt. % water, or less than about 0.01 wt. % water present.

As used herein, "contacting" refers to the act of touching, making contact, or of bringing into immediate proximity. Compounds are typically contacted by forming a solution in a suitable solvent system.

When describing the details of the compounds, compositions, and other limitations, the numerical ranges given herein are those amounts that provide functional results in the composition. Thus, ranges are generally introduced with the term "about" to indicate a certain flexibility in the range. For example, the term "about" can refer to +/− one integer from a given number or the upper or lower limit of range. In other embodiments, the term "about" can refer to +/− two integers from a given number or the upper or lower limit of range. The term "about" can also refer to +/−20% of a given number or numerical range. In other embodiments, the term "about" can refer to +/−10%, or +/−5% of a given number or numerical range. In yet other embodiments, the term "about" refers to +/−1%. In still other embodiments, the term "about" refers to exactly the given number or numerical range.

The compounds described herein can be prepared in a variety of ways known to one skilled in the art of organic synthesis. The compounds described herein can be synthesized using the methods as hereinafter described below, together with synthetic methods known in the art of synthetic organic chemistry or variations thereon as appreciated by those skilled in the art.

The compounds of present invention can be conveniently prepared in accordance with the procedures outlined in the schemes below, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Those skilled in the art of organic synthesis will recognize that the nature and order of the synthetic steps presented may be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C NMR) infrared spectroscopy, spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 4 d. Ed., Wiley & Sons, 2007, which is incorporated herein by reference in its entirety. Adjustments to the protecting groups and formation and cleavage methods described herein may be adjusted as necessary in light of the various substituents.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

For example, compounds of Formula (I) may be prepared by procedures analogous to that described in General Scheme I. An amino acid or amino ester of formula (iii) (R is H or alkyl) may first be reacted with a compound of formula (i), wherein LG is a leaving group such as a halide (e.g., chloro) in the presence of a base such as a tertiary amine (e.g., dimethylaminopyridine (DMAP), diisopropylethylamine (DIEA or DIPEA), or triethylamine (TEA)) to form a compound of formula (iv). Alternatively, a carboxylic acid of formula (ii), wherein Y is C(=O), may be reacted with the amino acid or amino ester of formula (iii) in the presence of a coupling agent such as 1-ethyl-3-(3'-dimethylaminopropyl)carbodiimide (EDCI) and 1-hydroxybenzotriazole (HOBt), or O-benzotriazole-N,N,N',N'-tetramethyluronium-hexafluorophosphate (HBTU), in the presence of a base such as a tertiary amine (e.g., DMAP, DIPEA, or TEA) to produce the compound of formula (iv). Where R is alkyl, the ester of formula (iv) may be hydrolyzed in the next step to produce the carboxylic acid of formula (v). The carboxylic acid of the compound of formula (v) (or carboxylic acid of formula (iv) wherein R is H) may then be reacted with an aromatic amine compound of formula (vi) in the presence of a coupling agent(s) such as EDCI and HOBT, or HBTU, in the presence of a base such as a tertiary amine (e.g., DMAP, DIPEA, or TEA) to form a compound of formula (vii).

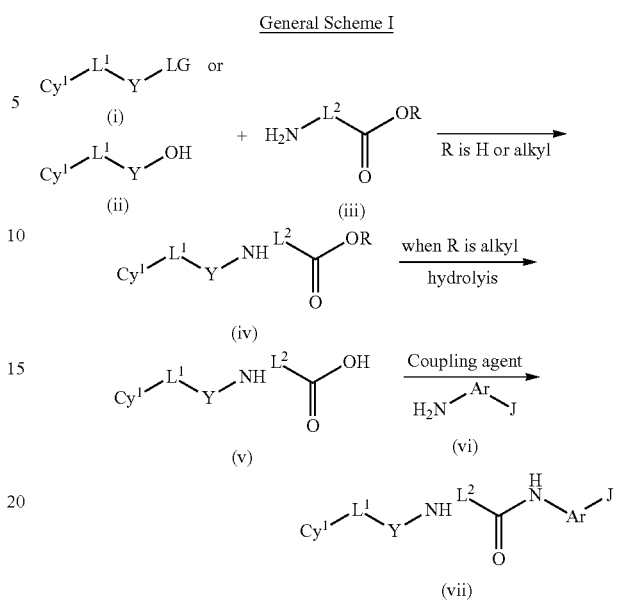

General Scheme I

Alternatively, compounds of Formula (I) may be prepared by procedures analogous to that described in General Scheme II. The amino acid of formula (a) may first be protected using an appropriate protecting group such as 9H-fluoren-9-ylmethoxycarbonyl (Fmoc) to give the protected amine of formula (b). The carboxylic acid of the protected amine can then be converted to an acid chloride of formula (c) by use of an appropriate reagent, such as thionyl chloride. The acid chloride of formula (c) may then be reacted with an aromatic amine of formula (d) in the presence of a base such as a tertiary amine (e.g., triethylamine) to form a compound of formula (e). The protecting group may then be removed by appropriate means (e.g., piperidine for Fmoc protected amines) to produce the amino compound of formula (f). Finally, the amine of formula (f) can be reacted with a carboxylic acid of formula (g) to form the desired compound of formula (h).

One of skill in the art will recognize that there are additional methods of producing the compounds of Formula I in addition to those described in General Schemes I and II and the surrounding text.

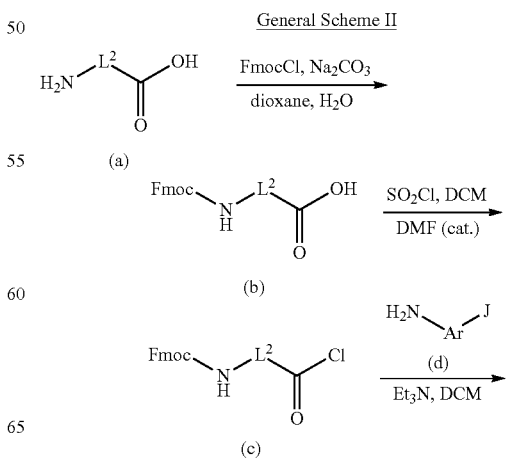

General Scheme II

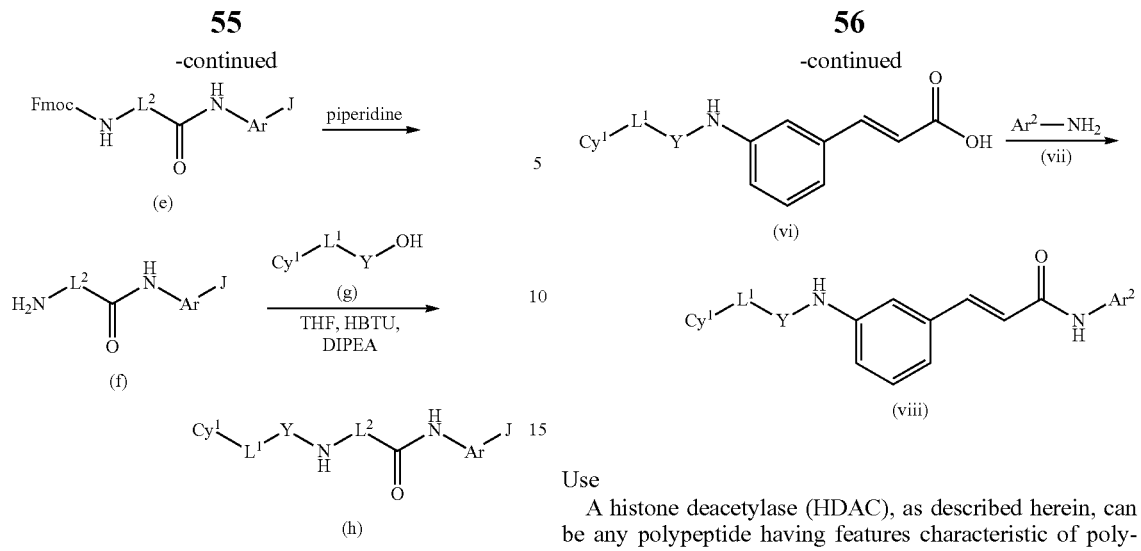

Other compounds of Formula (I) can be synthesized by processes similar to that shown in General Scheme III. First, a cinnamate ester is formed by reaction of the nitrobenzaldehyde (i) with a Wittig reagent. It is recognized that nitrobenzaldehyde with different substitution patterns can be used to form different types of cinnamate esters. The nitro group of the ester (ii) can be reduced to the amine (iii), followed by reaction with an acid chloride (iv) (or sulfonic or sulfonic chloride, or sulfinate or sulfonate ester) to form the amide (v). The ester group of (v) can then be hydrolyzed to give the carboxylic acid (vi). The carboxylic acid (vi) can then be reacted to with an aromatic amine to give the desired compound of Formula I. Compounds with other linking groups can be formed starting from amine-ester compounds similar to compound (iii) of General Scheme III.

General Scheme III

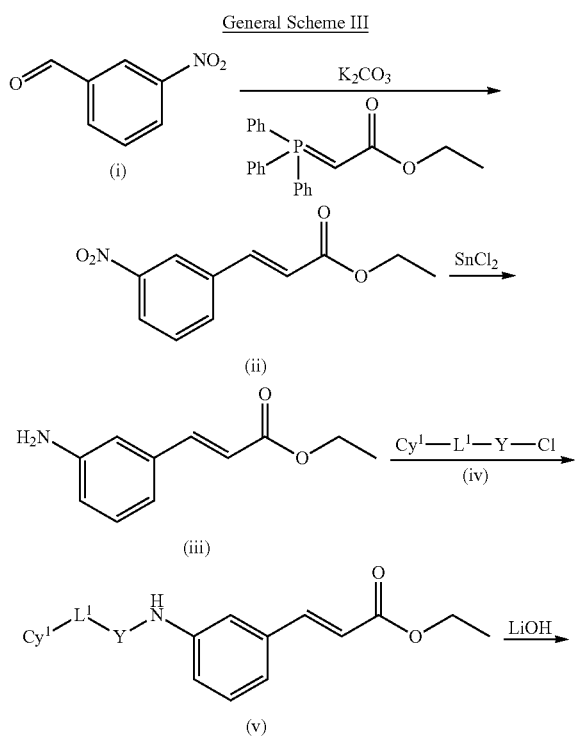

Use

A histone deacetylase (HDAC), as described herein, can be any polypeptide having features characteristic of polypeptides that catalyze the removal of the acetyl group (deacetylation) from acetylated target proteins. Features characteristic of HDACs are known in the art, see, for example, Finnin et al., 1999, Nature, 401:188. Thus, an HDAC can be a polypeptide that represses gene transcription by deacetylating the ϵ-amino groups of conserved lysine residues located at the N-termini of histones, e.g., H3, H4, H2A, and H2B, that form the nucleosome. HDACs also deacetylate other proteins such as p53, E2F, α-tubulin, and MyoD. See Annemieke et al., 2003, Biochem. J., 370:737. HDACs can also be localized to the nucleus and certain HDACs can be found in both the nucleus and also the cytoplasm.

HDAC inhibitors described herein may interact with any HDAC. However, the HDAC inhibitors will have at least about 2-fold (e.g., at least about 5-fold, 10-fold, 15-fold, or 20-fold) greater activity to inhibit one or more class I HDACS (e.g., HDAC3) as compared to one or more other HDACs (e.g., one or more HDACs of class I or class II). Class I HDACs are those that most closely resemble the yeast transcriptional regulator RPD3. Examples of class I HDACs include HDACs 1, 2, 3 and 8, as well as any HDAC that has a deacetylase domain exhibiting from 45% to 93% identity in amino acid sequence to HDACs 1, 2, 3 and 8. Class II HDACs are those that most closely resemble the yeast HDAC1 enzyme. Examples of class II HDACs include HDACs 4, 5, 6, 7, 9 and 10.

The present invention provides a method of treating a cancer in patient in need thereof, comprising administering a therapeutically effective amount of an HDAC inhibitor as described herein, or pharmaceutically acceptable salt thereof. In some embodiments, the cancer is a solid tumor, neoplasm, carcinoma, sarcoma, leukemia, or lymphoma. In some embodiments, leukemias include acute leukemias and chronicleukemias such as acute lymphocytic leukemia (ALL), acute myeloid leukemia chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-celllymphotrophic virus (fITLV) such as adult T-cell leukemia/lymphoma (ATLL), Hodgkin's disease and non-Hodgkin's lymphomas, large-cell lymphomas, diffuse large B-celllymphoma (DLBCL); Burkitt's lymphoma; primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genitourinary cancers (e.g., prostate, bladder, renal, uterine, ovarian, testicular, rectal and colon), lung cancer, breast cancer.

In some embodiments, the cancer is (a) Cardiac: sarcoma (angiosarcoma, fibrosarcoma, rhabdomyosarcoma, liposarcoma), myxoma, rhabdomyoma, fibroma, lipoma and teratoma; (b) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, .non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma conditions.

In another aspect, the present invention provides a method of treating a inflammatory disorder in patient in need thereof, comprising administering a therapeutically effective amount of an HDAC inhibitor as described herein, or pharmaceutically acceptable salt thereof. In some embodiments, the inflammatory disorder is an acute and chronic inflammatory disease, autoimmune disease, allergic disease, disease associated with oxidative stress, and diseases characterized by cellular hyperproliferation. Non-limiting examples are inflammatory conditions of a joint including rheumatoid arthritis (RA) and psoriatic arthritis; inflammatory bowel diseases such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs, ischemic injury, including cerebral ischemia (e.g., brain injury as a result of trauma, epilepsy, hemorrhage or stroke, each of which may lead to neurodegeneration); HIV, heart failure, chronic, acute or malignant liver disease, autoimmune thyroiditis; systemic lupus erythematosus, Sjorgren's syndrome, lung diseases (e.g., ARDS); acute pancreatitis; amyotrophic lateral sclerosis (ALS); Alzheimer's disease; cachexia/anorexia; asthma; atherosclerosis; chronic fatigue syndrome, fever; diabetes (e.g., insulin diabetes or juvenile onset diabetes); glomerulonephritis; graft versus host rejection (e.g., in transplantation); hemohorragic shock; hyperalgesia: inflammatory bowel disease; multiple sclerosis; myopathies (e.g., muscle protein metabolism, esp. in sepsis); osteoarthritis; osteoporosis; Parkinson's disease; pain; pre-term labor; psoriasis; reperfusion injury; cytokine-induced toxicity (e.g., septic shock, endotoxic shock); side effects from radiation therapy, temporal mandibular joint disease, tumor metastasis; or an inflammatory condition resulting from strain, sprain, cartilage damage, trauma such as burn, orthopedic surgery, infection or other disease processes.

Allergic diseases and conditions, include but are not limited to respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies, and the like.

In a further aspect, this application features methods of treating a neurological condition (e.g., Friedreich's ataxia (FRDA), myotonic dystrophy, spinal muscular atrophy, fragile X syndrome, Huntington's disease, a spinocerebellar ataxia, Kennedy's disease, amyotrophic lateral sclerosis, spinal and bulbar muscular atrophy, Alzheimer's disease or schizophrenia, bipolar disorder, and related diseases) that include administering an HDAC inhibitor described herein to a patient having a neurological condition.

In another aspect, this application features the use of an HDAC inhibitor described herein in the preparation of a medicament for the treatment or prevention of a neurological condition (e.g., Friedreich's ataxia, myotonic dystrophy, spinal muscular atrophy, fragile X syndrome, Huntington's disease, a spinocerebellar ataxia, Kennedy's disease, amyotrophic lateral sclerosis, spinal and bulbar muscular atrophy, or Alzheimer's disease); a cancer; or an inflammatory disorder.

In another aspect, this application features an HDAC inhibitor described herein for use in a method of treatment or prevention of a neurological condition (e.g., Friedreich's ataxia, myotonic dystrophy, spinal muscular atrophy, fragile X syndrome, Huntington's disease, a spinocerebellar ataxia, Kennedy's disease, amyotrophic lateral sclerosis, spinal and bulbar muscular atrophy, or Alzheimer's disease); a cancer; an inflammatory disorder; or a *Plasmodium falciparum* infection (e.g., malaria).

In further aspect, the application provides a kit for the treatment or prevention of a disorder selected from a neurological disorder (e.g., Friedreich's ataxia, myotonic dystrophy, spinal muscular atrophy, fragile X syndrome, Huntington's disease, a spinocerebellar ataxia, Kennedy's disease, amyotrophic lateral sclerosis, spinal and bulbar muscular atrophy, or Alzheimer's disease), a cancer, an inflammatory disorder, or a *Plasmodium falciparum* infection (e.g., malaria) in a patient in need thereof, comprising (i) a compound according to any one of claims 1 to 46, or a pharmaceutically acceptable salt thereof; and (ii) instructions comprising a direction to administer said compound to said patient.

The invention further relates to the discovery that specific histone deacetylase 3 (HDAC3) inhibitors also increase expression of frataxin, and could therefore be useful in the treatment of neurological conditions (e.g., neurological conditions associated with reduced frataxin expression). Accordingly, the invention provides HDAC3 inhibitors, methods of treating various chronic and/or acute neurological conditions such as, for example, Friedreich's ataxia, and methods of identifying compounds that could be used as therapeutics for various chronic and/or acute neurological conditions such as, for example, Friedreich's ataxia.

The DNA abnormality found in 98% of FRDA patients is an unstable hyper-expansion of a GAA triplet repeat in the first intron of the frataxin gene that results in a defect in transcription of the frataxin gene (see Campuzano et al., 1996, Science, 271:1423-27). FRDA patients have a marked deficiency of frataxin mRNA, and the longer the GAA triplet repeats, the more profound the frataxin deficiency. FRDA is typical of triplet repeat diseases: normal alleles have 6-34 repeats while FRDA patient alleles have 66 1700 repeats. Longer GAA triplet repeats are associated with earlier onset and increased severity of the disease. The invention provides for methods of identifying specific HDAC3 inhibitors that can restore gene function in a neurological disease that is associated with expansion of a triplet repeat, such as FRDA or Huntington's disease. For example, HDAC3 inhibitors identified by the methods described herein increase frataxin mRNA and protein in lymphocytes from FRDA patients. A "histone deacetylase 3 (HDAC3) inhibitor" is a small molecule that binds to HDAC3 to modulate the levels of acetylation of histones, non-histone chromosomal proteins, and other cellular proteins. An HDAC3 inhibitor described herein may interact with a HDAC3 to modulate the level of acetylation of cellular targets.

In one aspect, the invention features methods of identifying a candidate compound for treatment of a neurological condition by obtaining a test compound; assaying a first activity of the test compound to inhibit histone deacetylase activity of a histone deacetylase 3 (HDAC3); assaying a second activity of the test compound to inhibit histone deacetylase activity of a class I histone deacetylase other than the HDAC3 (e.g., HDAC1, HDAC2, or HDAC8); and identifying the test compound as a candidate compound for treatment of a neurological condition associated with a frataxin deficiency if the first activity of the test compound is greater than the second activity of the test compound.

In another aspect, the invention features methods of identifying a candidate compound for treatment of a neurological condition by obtaining a test compound; assaying a first activity of the test compound to inhibit histone deacetylase activity of a HDAC3; assaying a second activity of the test compound to inhibit histone deacetylase activity of a HDAC1; assaying a third activity of the test compound to inhibit histone deacetylase activity of a HDAC2; assaying a fourth activity of the test compound to inhibit histone deacetylase activity of a HDAC8; and identifying the test compound as a candidate compound for treatment of a neurological condition if the first activity of the test compound is greater than each of the second, third, and fourth activities of the test compound.

In a further aspect, the invention features methods of identifying a candidate compound for treatment of a neurological condition by obtaining a test compound; assaying a first activity of the test compound to inhibit histone deacetylase activity of a HDAC3; assaying a second activity of the test compound to inhibit histone deacetylase activity of a class I or class II histone deacetylase other than the HDAC3 (e.g., HDAC1, HDAC2, HDAC4, HDAC5, HDAC6, HDAC7, HDAC8, HDAC9, or HDAC10); and identifying the test compound as a candidate compound for treatment of a neurological condition associated with a frataxin deficiency if the first activity of the test compound is greater than the second activity of the test compound.

In another aspect, this application features methods of identifying a candidate compound for treatment of a neurological condition by obtaining a test compound; assaying a first activity of the test compound to inhibit histone deacetylase activity of a HDAC3; assaying a set of activities of the test compound to inhibit histone deacetylase activity of each of histone deacetylases 1, 2, 4, 5, 6, 7, 8, 9, and 10; and identifying the test compound as a candidate compound for treatment of a neurological condition if the first activity of the test compound is greater than each activity of the set of activities of the test compound.

In some embodiments of the above methods, one or more of the HDACs (e.g., HDAC3) is a human HDAC (e.g., a human HDAC3).

In some embodiments of the above methods, the test compound is identified as a candidate compound for treatment of a neurological condition if the first activity is at least about 1.5-fold greater (e.g., at least about 2-fold, 3-fold, 4-fold, 5-fold, 10-fold, 15-fold, or 20-fold greater) than another activity (e.g., the second, third, or fourth activity, or each activity of the set of activities).

In some embodiments of the above methods, the neurological condition is Friedreich's ataxia, myotonic dystrophy, spinal muscular atrophy, fragile X syndrome, Huntington's disease, a spinocerebellar ataxia, Kennedy's disease, amyotrophic lateral sclerosis, spinal and bulbar muscular atrophy, or Alzheimer's disease. In some embodiments of the above methods, the neurological condition is associated with expansion of a triplet repeat (e.g., Friedreich's ataxia, myotonic dystrophy, spinal muscular atrophy, fragile X syndrome, Huntington's disease, spinocerebellar ataxias, or Kennedy's disease).

In some embodiments of the above methods, the methods further include assaying the activity of the candidate compound to increase expression of one or more genes whose expression is decreased in the neurological condition (e.g., frataxin, huntingtin, brain derived neurotrophic factor (BDNF), peroxisome proliferator-activated receptor-gamma, coactivator 1, alpha (PGC1A), ataxin, fragile X mental retardation (FMR1), dystrophia myotonica protein kinase (DMPK), or androgen receptor). In some embodiments, the activity of the candidate compound to increase expression of one or more genes whose expression is decreased in the neurological condition is measured in an animal, e.g., an animal model of the neurological condition.

In some embodiments of the above methods, the method is repeated for a plurality of test compounds (e.g., at least 10, 20, 50, 100, 200, 500, or 1000 test compounds).

In another aspect, this application features methods of treating a neurological condition (e.g., Friedreich's ataxia, myotonic dystrophy, spinal muscular atrophy, fragile X syndrome, Huntington's disease, spinocerebellar ataxias, Kennedy's disease, amyotrophic lateral sclerosis, spinal and bulbar muscular atrophy, or Alzheimer's disease) that include performing any of the above methods, formulating the candidate compound in a pharmaceutical composition, and administering the pharmaceutical composition to a patient having a neurological condition.

Specific inhibitors of HDAC3 provide advantages for treatment of neurological conditions over the use of broad-spectrum HDAC inhibitors by reducing toxicities associated with inhibition of other HDACs. Such specific HDAC3 inhibitors provide a higher therapeutic index, resulting in better tolerance by patients during chronic or long-term treatment.

HDAC inhibitors have been shown to have antimalarial activity (Andrews et al., 2000, Int. J. Parasitol., 30:761-768; Andrews et al., Antimicrob. Agents Chemother., 52:1454-61). The present invention provides methods of treating a *Plasmodium falciparum* infection (e.g., malaria) in a patient in need thereof.

Assaying Test Compounds

In certain aspects, inhibitors of specific HDACs are found by identifying test compounds (e.g., from a group of test compounds) that inhibit the activity of a specific HDAC (e.g., HDAC3) more, e.g., 2, 3, 4, 5, 10, or more times, than they inhibit the activity of one or more other HDACs. HDAC inhibitory activity of test compounds can be assayed by standard means. Briefly, an assay typically involves incubating an acetylated HDAC substrate with a HDAC enzyme in the presence or absence of a test compound and detecting the removal of acetyl groups from the substrate. HDAC inhibition assays can be performed, e.g., in a cell, in a cell extract, or in a cell-free mixture. Exemplary HDAC inhibition assays are described in Pérez-Balado et al., 2007, J. Med. Chem., 50:2497-2505; Herman et al., 2006, Nat. Chem. Biol., 2:551-558; and Beckers et al., 2007, Int. J. Cancer, 121:1138-48. HDAC assay kits are commercially available from BIOMOL (Plymouth Meeting, Pa.) and Upstate (Charlottesville, Va.). A small molecule microarray method for screening for HDAC inhibitors is described in Vegas et al., 2007, Angew. Chem. Int. Ed. Engl., 46:7960-64.

HDAC enzymes can be provided, e.g., as purified proteins, partially purified proteins, purified recombinant proteins, in cells, or cell extracts. Purification or partial purification of HDAC3 and other HDAC enzymes can be performed by standard means, including affinity chromatography and immunoprecipitation.

The HDAC substrate can be a commercially available substrate (e.g., Fluor de Lys™, BIOMOL) or an acetylated cellular HDAC substrate, e.g., histone H2A, histone H2B, histone H3, histone H4, α-tubulin, NFκB-3, or p53. Exemplary substrates further include acetylated peptides of the preceding proteins, e.g., residues 2-24 or 1-18 of Histone H4.

The deacetylation of the HDAC substrate can be detected by standard means. Commercially available substrates are provided with fluorimetric or colorimetric reagents that detect deacetylated lysines. In other aspects, the substrate can be $^3$H-acetylated, and deacetylation is detected by measuring the release of $^3$H from the substrate. In further aspects, antibodies can be used to distinguish acetylated substrates from deacetylated substrates. For example, antibodies specific for acetylated α-tubulin are available from Sigma, and antibodies specific for acetylated histone H3 are available from Upstate.

Compounds identified as HDAC3 inhibitors can be further tested for induction of expression of one or more genes that are underexpressed in a neurological disorder, e.g., frataxin (GenBank Accession No. NM_000144.3), huntingtin (GenBank Accession No. NM_002111.6), brain derived neurotrophic factor (BDNF; GenBank Accession No. NM_170735.4), peroxisome proliferator-activated receptor-gamma, coactivator 1, alpha (PGC1A; GenBank Accession No. NM_013261.3), ataxins (e.g., ataxin 1 (GenBank Accession No. NM_000332.2), fragile X mental retardation (FMR1; GenBank Accession No. NM_002024.3), dystrophia myotonica protein kinase (DMPK; GenBank Accession No. NM_004409.3), or androgen receptor (GenBank Accession No. NM_000044.2). Listed GenBank accession numbers indicate exemplary human cDNA sequences and are not meant to be limiting. Sequences of other alleles or alternatively spliced versions can also be used.

Typically, the inhibitor is administered to a cell or cell-free extract that expresses a nucleic acid or protein product of the gene, and the expression of the gene product is compared to its expression in the absence of the inhibitor. Any cells can be used, including primary cells obtained from a subject (e.g., a subject having a neurological disorder) or cells of a cell line. Exemplary cells include neural cells, neuronal cells, and lymphocytes. The cells can be isolated and stored frozen in aliquots to provide ease in scaling the assay to allow multiple samples or multiple assays to be done with the same cell source. In one embodiment, the cells are lymphocytes (e.g., derived from Friedreich's ataxia patients), which are primary cells or cells of a lymphoblastoid cell line.

Determination of the expression of nucleic acid and protein gene products can be accomplished by any of several standard methods. Nucleic acid expression can be determined, e.g., by hybridization (e.g., Northern blotting), nucleic acid microarrays, PCR (e.g., reverse transcription-PCR (RT-PCR) or quantitative RT-PCR), primer extension, serial analysis of gene expression, nuclease protection assays, or reporter gene constructs. Protein expression can be determined, e.g., by immunoblotting (e.g., Western blotting), immunoprecipitation, immunosorbent assay (e.g., ELISA or RIA), peptide microarrays, or fusion proteins (e.g., GFP fusions).

Useful compounds for chronic treatment include those that inhibit HDAC3 at concentrations that do not show significant cytotoxic activity. Cytotoxic activity can be measured by incubating compounds with an indicator cell line (e.g., the human transformed liver cell HepG2). Viable cell number is determined after an incubation period, typically between 24-72 hours following administration of the compound. Viable cells can be determined by many methods including but not limited to cell counting or using a substrate converted to a colored product by live cells such as MTS. The ratio of HDAC3 activity to cytotoxicity can identify molecules that increase expression of gene products reduced by disease and are tolerable to administration over long periods of time.

Methods of Administering HDAC Inhibitors

HDAC inhibitors, e.g., those inhibitors described herein, can be used prophylactically or as a treatment for various conditions described herein, including neurological conditions (e.g., neurological conditions associated with frataxin deficiency). More specifically, HDAC inhibitors (e.g., those identified by the methods described herein) can be used to delay or prevent the onset of one or more symptoms of a neurodegenerative or neuromuscular condition, as well as to treat a mammal, such as a human subject, suffering from a neurological condition (e.g., a neurodegenerative or neuromuscular condition). Non-limiting examples of neurodegenerative conditions include, without limitation, fragile X syndrome, Friedreich's ataxia, Huntington's disease, spinocerebellar ataxias, amyotrophic lateral sclerosis, Kennedy's disease, spinal and bulbar muscular atrophy and Alzheimer's disease. Non-limiting examples of neuromuscular conditions include spinal muscular atrophy and myotonic dystrophy.

Mammals, e.g. humans, to which HDAC inhibitors can be administered include those suffering from, or diagnosed as having, the conditions discussed herein as well as those who are at risk for developing the above conditions. A mammal at risk for developing a neurodegenerative condition can be identified in numerous ways, including, for example, first determining (1) the length, extent, and/or number of repeats of particular nucleic acid sequences (e.g., a frataxin gene sequence, a huntingtin gene sequence, an ataxin gene sequence, a fragile X mental retardation (FMR1) gene sequence, a dystrophia myotonica protein kinase (DMPK) gene sequence, or an androgen receptor gene sequence) in the individual's genome; the degree of acetylation of core histones; or the expression level of a particular mRNA or protein (e.g., frataxin, huntingtin, brain derived neurotrophic factor (BDNF), peroxisome proliferator-activated receptor-gamma, coactivator 1, alpha (PGC1A), ataxin, fragile X mental retardation (FMR1), dystrophia myotonica protein kinase (DMPK), or androgen receptor), and then (2) comparing it with that of a normal individual (see Riley et al., 2006, Genes Dev., 20:2183-92; Tan et al., 2005, Expert Rev. Mol. Diagn., 5:101-109; Everett et al., 2004, Brain, 127: 2385-2405; Monckton et al., 1995, Circulation, 91:513-520; and Caskey et al., 1992, Science, 256:784-789). An individual at risk for developing a neurodegenerative or neuromuscular condition is one who has an aberrant number of repeats of a particular nucleic aid sequence, degree of acetylation of core histones or expression of a particular gene. For example, an animal or person at risk for developing Friedreich's ataxia can be identified by determining the length, extent, or number of repeats of a GAA triplet in the first intron of the frataxin gene. A person would be at risk for Friedreich's ataxia if the above analysis indicates that there are more than 34 repeats of the GAA triplet, for example, if the person has more than 66 repeats of the GAA triplet. A person at risk for Friedreich's ataxia could also be identified by determining the levels of frataxin mRNA or protein expressed in the person. A person would be at risk for Friedreich's ataxia if the levels of frataxin mRNA or protein is lower than the level normally observed in a healthy individual such as for example, an unaffected sibling.

For test purposes, a HDAC inhibitor can be administered to an animal or cellular model of a neurological condition. In some embodiments, an HDAC inhibitor is administered to an animal model with a naturally occurring or genetically engineered triplet repeat expansion. Exemplary animal models are described in Al-Mahdawi et al., 2006, Genomics, 88:580-590; Rai et al., 2008, PLoS ONE 3:e1958 doi: 10.1371/journal.pone.0001958; Wang et al., 2006, Acta Pharmacol. Sin. 27:1287-1302; Butler et al., 2006, Nat. Rev. Neurosci., 7:784-796; Bates and Gonitel, 2006, Mol. Biotechnol., 32:147-158; Puccio, 2007, Handb. Exp. Pharmacol., 178:365-375; Bates and Hay, 2004, Methods Mol. Biol., 277:3-15; Wansink and Wieringa, 2003, Cytogenet. Genome Res., 100:230-421; Merry et al., 2005, NeuroRx, 2:471-479; Gu and Nelson, 2003, Cytogenet. Genome Res., 100:129-139; Hoogeveen et al., 2002, Microsc. Res. Tech., 57:148-155; Gardian, 2006, Ideggyogy Sz., 59:396-399; Li et al., 2005, NeuroRx, 2:447-464; Levine et al., 2004, Trends Neurosci., 27:691-697; Everett and Wood, 2004, Brain, 127:2385-2405; Outeiro and Muchowski, 2004, J. Mol. Neurosci., 23:49-60; Beal and Ferrante, Nat. Rev. Neurosci., 5:373-384; Link, 2001, Mech. Ageing Dev., 122:1639-49; Heintz and Zoghbi, 2000, Annu. Rev. Physiol., 62:779-802; Martin, 2007, Rev. Neurosci., 18:115-136; Cauchi and van den Heuvel, 2006, Neurodegener. Dis., 3:338-356; Grieb, 2004, Folia Neuropathol., 42:239-248; Robertson et al., 2002, Biochimie, 84:1151-60; Newman et al., 2007, Biochim. Biophys. Acta, 1772:285-297; Van Dam and De Deyn, 2006, Nat. Rev. Drug Discov., 5:956-970; and Shaughnessy et al., J. Mol. Neurosci., 24:23-32.

For therapy or prophylaxis, the amount of HDAC inhibitor to be administered to the individual can be any amount appropriate to restore the level of histone acetylation, or the level of mRNA or protein expression, in the afflicted individual to that typical of a healthy individual such as an unaffected sibling. The amount of the HDAC inhibitor to be administered can be an effective dose or an appropriate fraction thereof, if administration is performed serially. Such amounts will depend on individual patient parameters including age, physical condition, size, weight, the condition being treated, the severity of the condition, and any concurrent treatment. For example, the effective dose range that is necessary to prevent or delay the onset of the neurodegenerative condition, can be lower than the effective dose range for inhibiting the progression of the condition being treated. Factors that determine appropriate dosages are well known to those of ordinary skill in the art and can be addressed with routine experimentation. For example, determination of the physicochemical, toxicological and pharmacokinetic properties can be made using standard chemical and biological assays and through the use of mathematical modeling techniques known in the chemical, pharmacological and toxicological arts. The therapeutic utility and dosing regimen can be extrapolated from the results of such techniques and through the use of appropriate pharmacokinetic and/or pharmacodynamic models. The precise amount of HDAC inhibitor administered to a patient will be the responsibility of the attendant physician.

In particular, HDAC inhibitors can be administered orally or by injection at a dose of from 0.1 to 30 mg per kg weight of the mammal, typically 2 to 15 mg/kg weight of the mammal. The dose range for adult humans is generally from 8 to 2,400 mg/day, e.g., from 35 to 1,050 mg/day. If the salt of the compound is administered, then the amount of salt administered is calculated in terms of the base.

HDAC inhibitors can be administered in numerous ways. For example, the HDAC inhibitors can be administered orally, rectally, topically, or by intramuscular, intraperitoneal subcutaneous or intravenous injection. Preferably, the inhibitors are administered orally or by injection. Other routes include intrathecal administration directly into spinal fluid and direct introduction onto, in the vicinity of, or within the target cells. The route of administration will depend on the condition being treated and its severity.

Toxicity and therapeutic efficacy of HDAC inhibitors can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. In another embodiment, the therapeutic index can be estimated by assaying the HDAC3 specific inhibitory activity of a HDAC3 inhibitor (the HDAC3 $IC_{50}$) as compared to the growth inhibitory activity of the HDAC3 inhibitor on a cell in vitro, e.g., a HepG2 cell or other cell line (the growth $IC_{50}$). The ratio between the growth inhibitory (e.g., cytotoxic or cytostatic) effect and the HDAC3 specific inhibitory effect provides an estimate of the therapeutic index.

Pharmaceutical Compositions

HDAC inhibitors can be administered neat or formulated as pharmaceutical compositions. Pharmaceutical compositions include an appropriate amount of the HDAC inhibitor in combination with an appropriate carrier and optionally as other useful ingredients.

Acceptable salts of HDAC inhibitors include, but are not limited to, those prepared from the following acids: alkyl, alkenyl, aryl, alkylaryl and alkenylaryl mono-, di- and tricarboxylic acids of 1 to 20 carbon atoms, optionally substituted by 1 to 4 hydroxyls; alkyl, alkenyl, aryl, alkylaryl and alkenylaryl mono-, di- and trisulfonic acids of 1 to 20 carbon atoms, optionally substituted by 1 to 4 hydroxyls; dibasic acids and mineral acids. Examples include hydrochloric; hydrobromic; sulfuric; nitric; phosphoric; lactic (including (+)-L-lactic, (+/−)-DL-lactic); fumaric; glutaric; maleic; acetic; salicyclic; p-toluenesulfonic; tartaric (including (+)-L-tartaric); citric; methanesulfonic; formic; malonic; succinic; naphthalene-2-sulfonic; and benzenesulfonic acid. Also, pharmaceutically-acceptable salts can be prepared as amine salts, ammonium salts, or alkaline metal or alkaline earth salts, such as sodium, potassium or calcium salts of the carboxylic acid group. These are formed from alkaline metal or alkaline earth metal bases or from amine compounds.

Pharmaceutical compositions of HDAC inhibitors suitable for oral administration can be in the form of (1) discrete units such as capsules, sachets, tablets, or lozenges each containing a predetermined amount of the HDAC inhibitor; (2) a powder or granules; (3) a bolus, electuary, or paste; (4) a solution or a suspension in an aqueous liquid or a non-aqueous liquid; or (5) an oil-in-water liquid emulsion or a water-in-oil liquid emulsion. Compositions suitable for topical administration in the mouth, for example buccally or sublingually, include lozenges. Compositions suitable for parenteral administration include aqueous and non-aqueous sterile suspensions or injection solutions. Compositions suitable for rectal administration can be presented as a suppository.

Pharmaceutical compositions of HDAC inhibitors can be formulated using a solid or liquid carrier. The solid or liquid carrier should be compatible with the other ingredients of the formulation and not deleterious to the recipient. If the pharmaceutical composition is in tablet form, then the HDAC inhibitor is mixed with a carrier having the necessary compression properties in suitable proportions and compacted in the shape and size desired. If the composition is in powder form, the carrier is a finely divided solid in admixture with the finely divided active ingredient. The powders and tablets can contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. A solid carrier can include one or more substances that can act as flavoring agents, lubricants, solubilizers, suspending agents, fillers, glidants, compression aids, binders or tablet-disintegrating agents. A suitable carrier can also be an encapsulating material.

If the composition is a solution, suspension, emulsion, syrup, elixir, or pressurized composition, then liquid carriers can be used. In this case, the HDAC inhibitor is dissolved or suspended in a pharmaceutically acceptable liquid carrier. Suitable examples of liquid carriers for oral and parenteral administration include (1) water; (2) alcohols, e.g. monohydric alcohols and polyhydric alcohols such as glycols, and their derivatives; and (3) oils, e.g. fractionated coconut oil and *arachis* oil. For parenteral administration, the carrier can also be an oily ester such as ethyl oleate and isopropyl myristate. Liquid carriers for pressurized compositions include halogenated hydrocarbon or other pharmaceutically acceptable propellant. The liquid carrier can contain other suitable pharmaceutical additives such as solubilizers; emulsifiers; buffers; preservatives; sweeteners; flavoring agents; suspending agents; thickening agents; colors; viscosity regulators; stabilizers; osmo-regulators; cellulose derivatives such as sodium carboxymethyl cellulose; antioxidants; and bacteriostatics. Other carriers include those used for formulating lozenges such as sucrose, acacia, tragacanth, gelatin and glycerin as well as those used in formulating suppositories such as cocoa butter or polyethylene glycol.

If the composition is to be administered intravenously or intraperitoneally by infusion or injection, solutions of the HDAC inhibitor can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. The composition suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium as described above. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin. Sterile injectable solutions are prepared by incorporating the HDAC inhibitor in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the HDAC inhibitor, plus any additional desired ingredient present in the previously sterile-filtered solutions.

Pharmaceutical compositions can be in unit-dose or multi-dose form or in a form that allows for slow or controlled release of the HDAC inhibitor. Each unit-dose can be in the form of a tablet, capsule or packaged composition such as, for example, a packeted powder, vial, ampoule, prefilled syringe or sachet containing liquids. The unit-dose form also can be the appropriate number of any such compositions in package form. Pharmaceutical compositions in multi-dose form can be in packaged in containers such as sealed ampoules and vials. In this case, the HDAC inhibitor can be stored in a freeze-dried (lyophilized) condition requiring only the addition of a sterile liquid carrier immediately prior to use. In addition, extemporaneous injection solutions and suspensions can be prepared from sterile powders, granules and tablets of the kind previously described.

EXAMPLES

Example 1. RGFA8 Increases Expression of Frataxin

To determine whether RGFA8 ($N^1$-(2-aminophenyl)-$N^7$-p-tolylheptanedioic acid diamide; WO 2007/058927) or other compounds could increase expression of frataxin, human lymphocytes isolated from peripheral blood from normal donors were incubated with 1-30 µM RGFA8. Frataxin mRNA levels were measured with quantitative RT-PCR and normalized to expression levels of the housekeeping gene GADPH (Herman et al., Nat. Chem. Biol., 2:551-558, 2006).

RGFA8 increased expression of frataxin in normal lymphocytes or patient lymphocytes at all concentrations tested, with a maximum observed increase of about 16-fold compared to vehicle control (FIG. 1, normal lymphocytes). This example indicates that RGFA8 could be used to treat patients with Friedreich's ataxia by increasing frataxin expression.

Example 2. RGFA8 is a Specific Inhibitor of HDAC3

To determine whether RGFA8 was specific for any particular HDAC or subset of HDACs, the activities of RGFA8 and known HDAC inhibitor trichostatin A (TSA) were tested on a panel of individual purified HDAC enzymes and a nuclear extract, which contained a mixture of HDACs. HDAC enzyme inhibition assays were performed using purified HDACs 1-10 essentially as described in Beckers et al., 2007, Int. J. Cancer., 121:1138-48 and Pérez-Balado et al., 2007, J. Med. Chem., 50:2497-2505. Inhibition assays using nuclear extract were performed essentially as described in Herman et al., 2006, Nat. Chem. Biol., 2:551-558. Briefly, the purified HDACs or nuclear extract were incubated with an acetylated substrate in the absence of the compound to be assayed and with increasing concentrations of the compound. The rate of substrate deacetylation was measured under each condition, and half-maximal inhibitory concentration with regard to each HDAC was determined by standard means.

RGFA8 was most active on HDAC3, with a half-maximal inhibitory concentration ($IC_{50}$) of 0.7 µM (Table 1). At least 10-fold lesser activity was observed by RGFA8 on other HDACs or on nuclear extract. Although TSA was found to be a more potent inhibitor of HDAC3 than RGF8, TSA had greater inhibitory activity on HDAC6 ($IC_{50}$ of 0.0014±0.0006) and HDAC1 ($IC_{50}$ of 0.0067 µM) as compared to HDAC3 ($IC_{50}$ of 0.0096 µM). Sub-micromolar inhibition by TSA was observed for all HDACs tested.

TABLE 1

Inhibition of HDAC Activity by RGFA8 and TSA

| Enzyme or Extract | $IC_{50}$ (µM) RGFA8 | $IC_{50}$ (µM) TSA |
|---|---|---|
| HDAC1 | 3.05 | 0.0067 |
| HDAC2 | 3.73 | 0.0148 |
| HDAC3 | 0.74 | 0.0096 |
| HDAC4 | >100 | 0.0348 |
| HDAC5 | >100 | 0.0125 |
| HDAC6 | >80 | 0.0014 |
| HDAC7 | >100 | 0.197 |
| HDAC8 | >100 | 0.165 |
| HDAC9 | >100 | 0.0701 |
| HDAC10 | >66.2 | 0.0228 |
| Nuclear Extract | 6.00 | 0.0012 |

This example demonstrates that RGFA8 specifically inhibits HDAC3 as compared to other human HDACs. HDAC inhibitors that are specific for HDAC3 can be used to treat neurological conditions (e.g., Friedreich's ataxia).

Example 3. Screen for HDAC3 Inhibitors

A chemical library was screened to identify compounds that specifically inhibited HDAC3, relative to other HDACs. Briefly, a chemical library of test compounds was created by standard organic chemistry methods, and the inhibitory activity of the compounds on purified HDACs 1-10 was determined (see Example 2). Fourteen compounds were identified that had stronger inhibitory activity for HDAC3 as compared to one or more other HDACs. These compounds, their structures, and inhibitory activities for HDAC1, HDAC2, HDAC3, HDAC5, are presented in Table 2, along with growth inhibitory activity on HepG2 cells. HDAC inhibitory activities were measured essentially as described in Example 2. Growth inhibition of HepG2 cells was measured by adding serial dilutions of the compounds to HepG2 cells at a density of $5 \times 10^4$ cells/ml, and incubating the mixture for 72 hours at 37° C., 5% $CO_2$. The viable cells were then measured using a CellTiter 96™ AQueous One Solution cell proliferation assay (Promega, Madison, Wis.). The activities of RGFA8 and the known HDAC inhibitor MS 275 are also presented.

TABLE 2

Activity of Identified HDAC3 Inhibitors

| Compound | Structure | $IC_{50}$ (µM) HDAC1 | $IC_{50}$ (µM) HDAC2 | $IC_{50}$ (µM) HDAC3 | HepG2 Growth $IC_{50}$ (µM) |
|---|---|---|---|---|---|
| MS-275 | 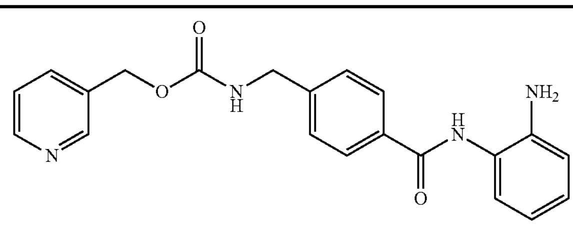 | 3.2 | 0.72 | 0.59 | 4.00 |

TABLE 2-continued

Activity of Identified HDAC3 Inhibitors

| Compound | Structure | IC$_{50}$ (μM) HDAC1 | HDAC2 | HDAC3 | HepG2 Growth IC$_{50}$ (μM) |
|---|---|---|---|---|---|
| RGFA8 | *p-tolyl-NH-CO-(CH$_2$)$_4$-CO-NH-(2-aminophenyl)* | 2.0 | 3.73 | 0.7 | 10.00 |
| R01 | *p-tolyl-CO-NH-(CH$_2$)$_5$-CO-NH-(2-aminophenyl)* | 2.4 | 1.98 | 0.3 | 12.00 |

Example 4. Additional HDAC3 Inhibitors

Additional HDAC3 inhibitors were identified as above. The activities of the compounds to inhibit HDAC1 and HDAC3 are listed in Table 3.

TABLE 3

Activity of Additional HDAC3 Inhibitors

| Compound | Structure | Mw | HDAC1 IC$_{50}$ (μM) | HDAC3 IC$_{50}$ (μM) |
|---|---|---|---|---|
| RGFA8 | *p-tolyl-NH-CO-(CH$_2$)$_4$-CO-NH-(2-aminophenyl)* | 339.4 | 2.0 | 0.7 |
| R02 | *thiazole-2-CO-NH-(CH$_2$)$_4$-CO-NH-(4-fluoro-2-aminophenyl)* | 350.4 | 18.0 | 2.3 |
| R03 | *p-tolyl-CO-NH-(CH$_2$)$_4$-CO-NH-(2-amino-4-fluorophenyl)* | 357.4 | 8.2 | 0.8 |
| R04 | *morpholino-CH$_2$-CO-NH-(CH$_2$)$_4$-CO-NH-(2-amino-4-fluorophenyl)* | 366.2 | >30 | 14.0 |

TABLE 3-continued

Activity of Additional HDAC3 Inhibitors

| Compound | Structure | Mw | HDAC1 IC$_{50}$ (µM) | HDAC3 IC$_{50}$ (µM) |
|---|---|---|---|---|
| R05 | 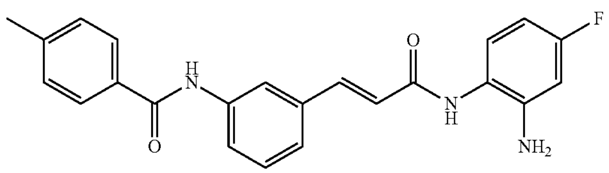 | 389.42 | 30.0 | 1.4 |
| R06 | 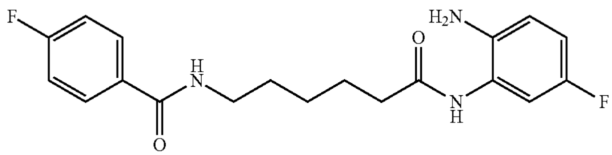 | 361.2 | 5.7 | 1.8 |
| R07 | 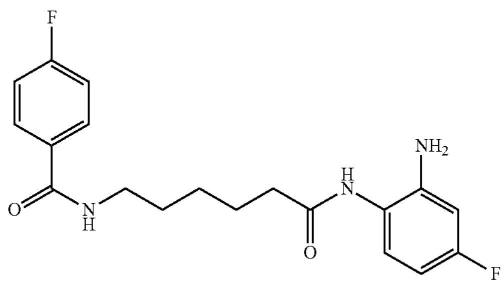 | 361.2 | 18.0 | 1.6 |
| R08 | 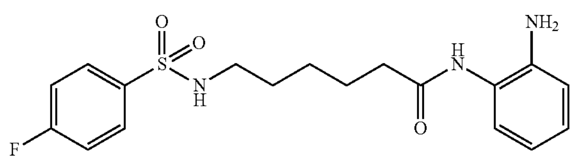 | 379.1 | 24.0 | 3.6 |
| R09 | 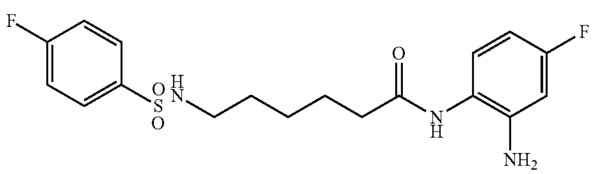 | 397.1 | >30 | 7.3 |

The additional compounds were also tested for growth inhibitory activity as described above using both HepG2 cells and HCT116 cells. The results of growth inhibition and relative inhibitory activity on HDAC1 as compared to HDAC3 is presented in Table 4.

TABLE 4

Relative Inhibition and Proliferation Inhibition of HDAC3 Inhibitors

| Compound | Relative Inhibitory Activity HDAC1/ HDAC3 | Proliferation Inhibition IC$_{50}$, µM | |
|---|---|---|---|
| | | HCT116 | HepG2 |
| RGFA8 | 2.86 | 8.00 | 10 |
| R01 | 8.54 | 6.50 | 12 |
| R02 | 8.00 | 110.00 | 150 |
| R03 | 10.87 | 40.00 | 32 |
| R04 | >2.14 | N.D. | >120 |
| R06 | 3.22 | 20.00 | 16 |
| R07 | 11.08 | 70.00 | 82 |
| R08 | 6.76 | N.D. | >100 |
| R09 | >4.17 | N.D. | N.D. |

N.D.: Not determined.

Example 5. HDAC Inhibitors Increase Frataxin Expression

Selected compounds were assayed by quantitative RT-PCR for their activity to increase expression of frataxin (FXN1) mRNA in human lymphocytes isolated from peripheral blood of normal donors (see Example 1). Briefly, the identified compounds were added to lymphocytes at a concentration of 10 μM, and increase in expression of FXN1 mRNA was determined compared to vehicle control. The majority of the identified compounds increased frataxin mRNA expression at a concentration of 10 μM (Table 5), indicating that these compounds can be useful in treatment of Friedrich's ataxia and other neurological disorders described herein.

TABLE 5

Relative HDAC Inhibition Activities and Effect on FXN1 Expression

| Compound | IC50 (μM) HDAC1 | IC50 (μM) HDAC3 | Frataxin mRNA increase at 10 μM in patient PBMC (fold) |
|---|---|---|---|
| R01 | 1.76 | 0.19 | 8.5 |
| R03 | 8.80 | 0.40 | 2.5 |
| R07 | 20.00 | 0.67 | 1.9 |

Example 6. HDAC Inhibitors Increase Frataxin Expression In Vivo

Compound R01 is administered to knock-in mice homozygous for a $(GAA)_{230}$ repeat in the first intron of the endogenous frataxin gene (Miranda et al., 2002, FEBS Lett., 512:291-297). The mice are treated by subcutaneous daily injections with 150 mg/kg of compound or its equivalent of vehicle, for 3 consecutive days. Brain, heart, and skeletal muscle are recovered 24 hours after the last injection. Total RNA from brain stem, heart, and/or cerebellum is extracted. Frataxin mRNA expression is determined by one step quantitative real-time PCR using the primers 5'-CCTGGC-CGAGTTCTTTGAAG-3' (SEQ ID NO:1) and 5'-GCCA-GATTTGCTTGTTTGG-3' (SEQ ID NO:2). Frataxin mRNA is significantly lower in the brain, cerebellum and heart of vehicle-treated knock-in mice than in similarly treated wild-type animals. Treatment with compound R01 increases knock-in frataxin mRNA to levels that do not significantly differ from wild-type, thus demonstrating correction of fxn deficiency in these animals. Western blotting confirms that increased fxn mRNA levels result in higher frataxin protein level. Treatment with compound R01 does not result in increased frataxin mRNA levels in wild-type animals, indicating that its effect is due to removal of the inhibition caused by the GAA expansion.

Example 7. Synthesis of R01

N-[6-(2-aminophenylamino)-6-oxohexyl]-4-methyl-benzamide

This compound was made the procedure shown below.

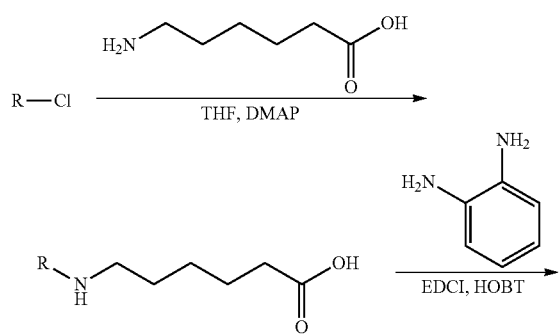
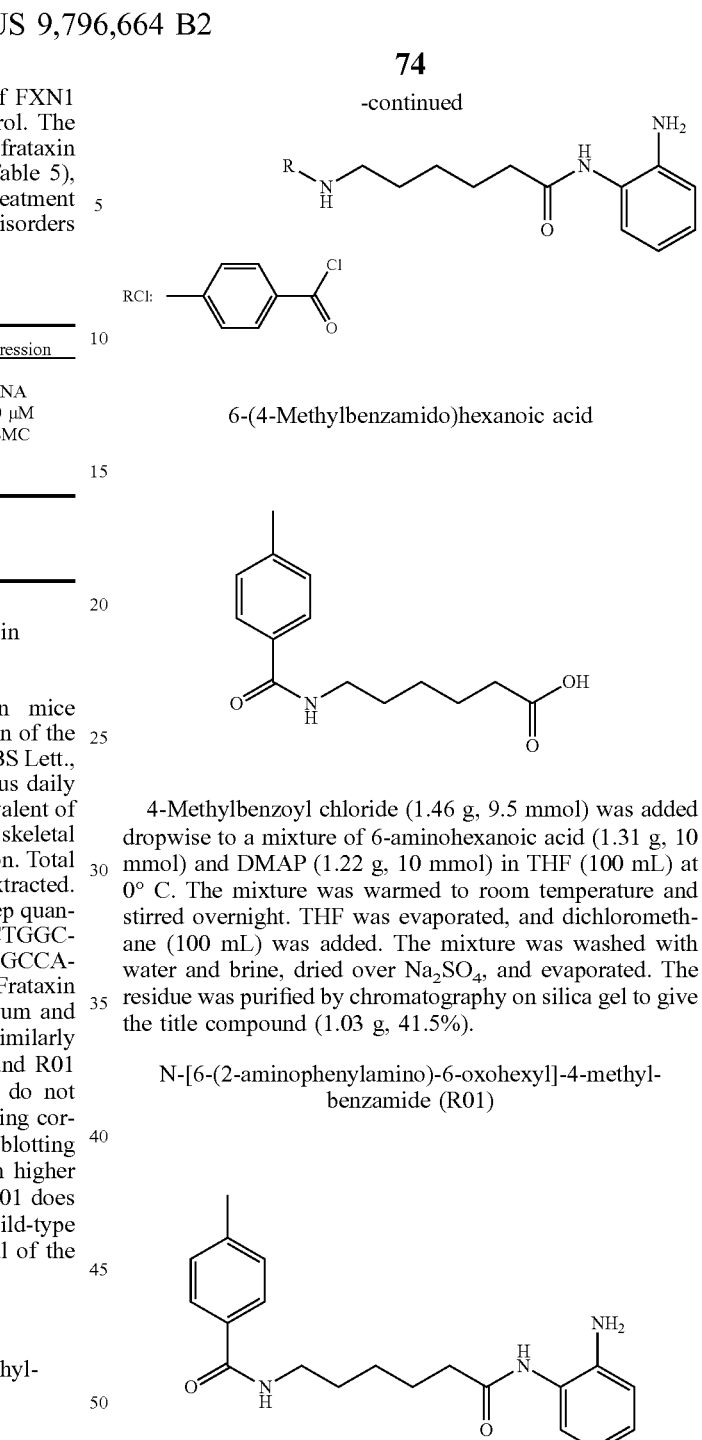

6-(4-Methylbenzamido)hexanoic acid

4-Methylbenzoyl chloride (1.46 g, 9.5 mmol) was added dropwise to a mixture of 6-aminohexanoic acid (1.31 g, 10 mmol) and DMAP (1.22 g, 10 mmol) in THF (100 mL) at 0° C. The mixture was warmed to room temperature and stirred overnight. THF was evaporated, and dichloromethane (100 mL) was added. The mixture was washed with water and brine, dried over $Na_2SO_4$, and evaporated. The residue was purified by chromatography on silica gel to give the title compound (1.03 g, 41.5%).

N-[6-(2-aminophenylamino)-6-oxohexyl]-4-methyl-benzamide (R01)

A mixture of 6-(4-methylbenzamido)hexanoic acid (498 mg, 2 mmol), o-phenylenediamine (216 mg, 2 mmol), EDCI (383 mg, 2 mmol), HOBt (405 mg, 3 mmol), and triethylamine (404 mg, 4 mmol) in dichloromethane (30 mL) was stirred at room temperature under nitrogen overnight. The reaction mixture was washed with water and brine, dried over $Na_2SO_4$, and evaporated. The residue was purified by chromatography on silica gel to give the title compound (227 mg, 33.9%) as a white solid. $^1$H NMR (DMSO): δ 9.06 (s, 1H), 8.35 (s, 1H), 7.73 (d, J=3.0 Hz, 2H), 7.24 (d, J=3.0 Hz, 2H), 7.14 (1H, J=3.0, d), 6.86-6.89 (m, 1H), 6.70 (d, J=3.0 Hz, 1H), 6.50 (M, 1H), 4.80 (s, 2H), 3.22-3.26 (m, 2H), 2.30-2.35 (m, 5H), 1.53-1.65 (m, 4H), 1.36-1.38 (m, 2H). LC-MS: 340 (MH)$^+$. purity >95%.

Example 8. Synthesis of R02
N-(2-amino-4-fluorophenyl)-6-(thiazol-2-ylcarbonylamino)hexanamide
This compound was made by the procedure shown below.
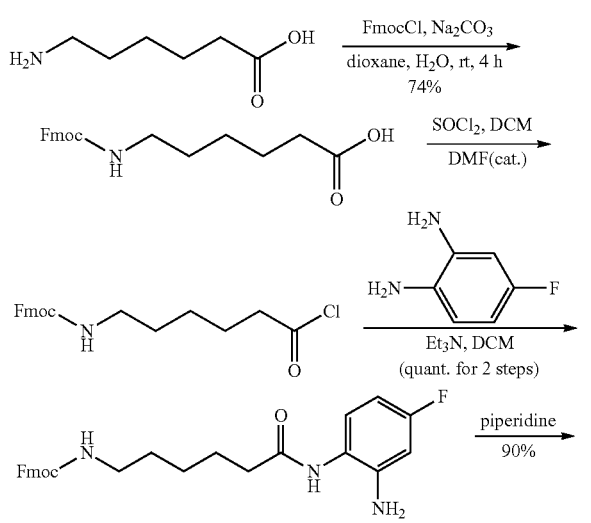
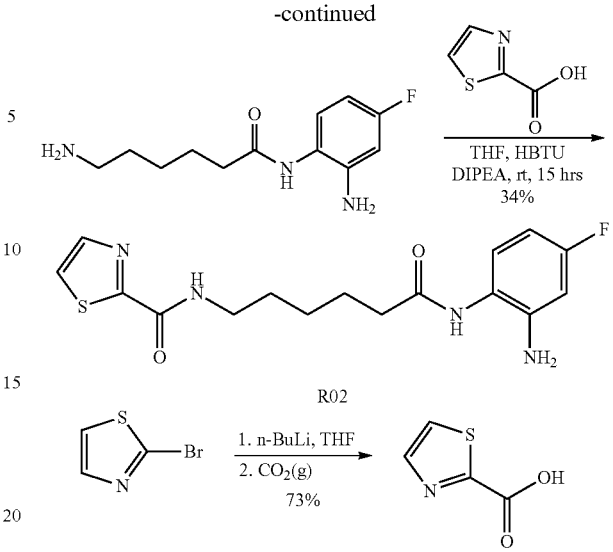
Example 9. Synthesis of R03
N-(6-(2-amino-4-fluorophenylamino)-6-oxohexyl)-4-methylbenzamide
This compound was made by the procedure shown below.
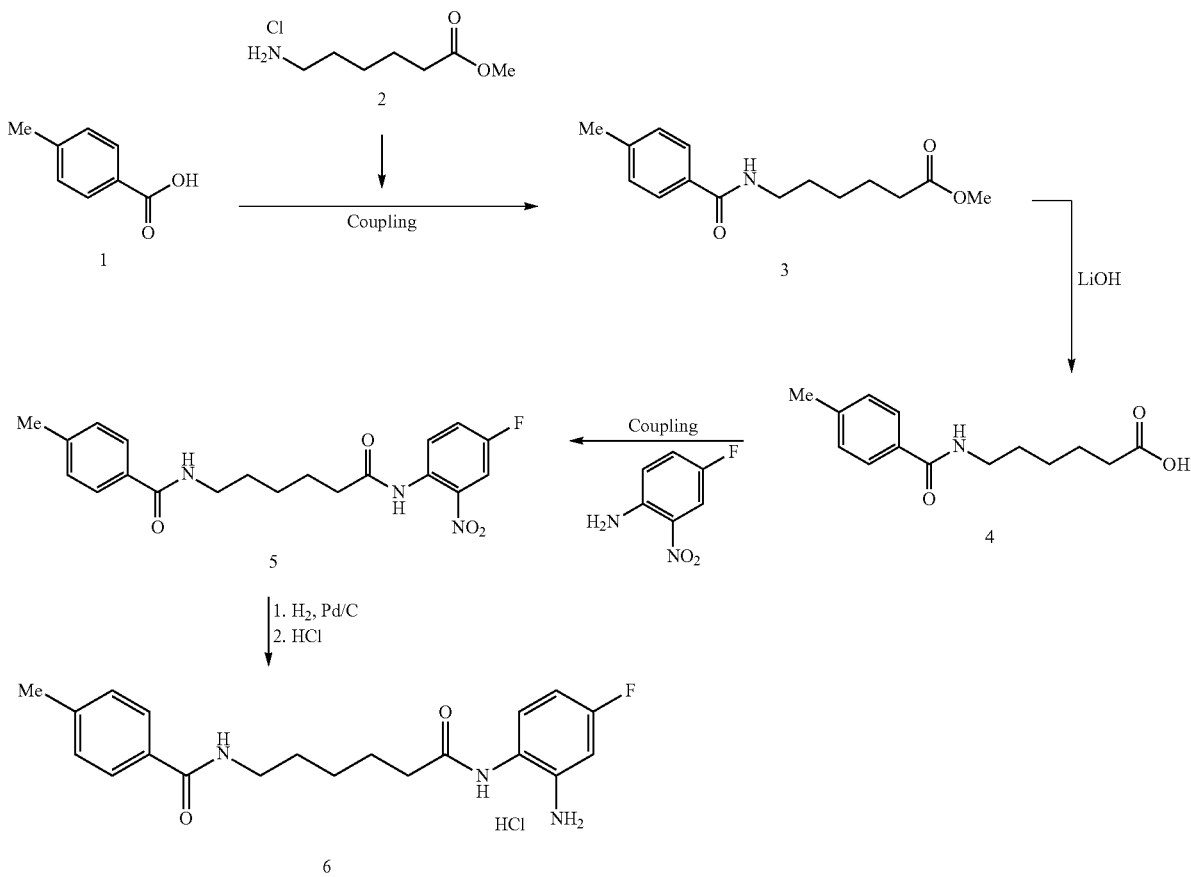

Example 10. Synthesis of R04

N-(2-amino-4-fluorophenyl)-6-[2-(4-morpholinyl)acetamido]hexanamide

This compound was made by the procedure shown below, starting, in part, from an intermediate from the synthesis of R02.

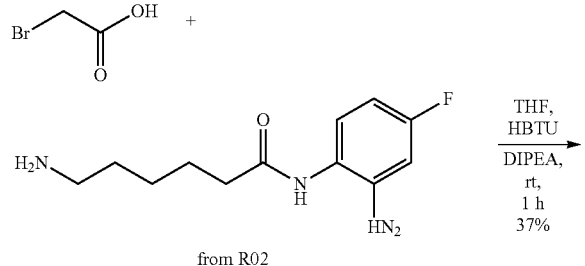

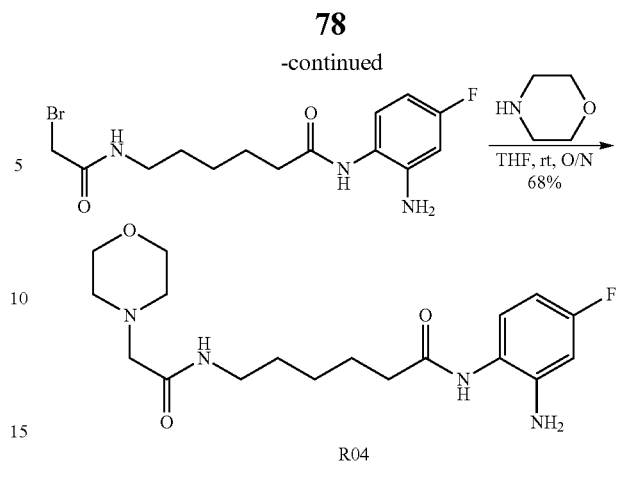

Example 11. Synthesis of R06

N-(6-(2-amino-5-fluorophenylamino)-6-oxohexyl)-4-fluorobenzamide

This compound was made by the procedure shown below.

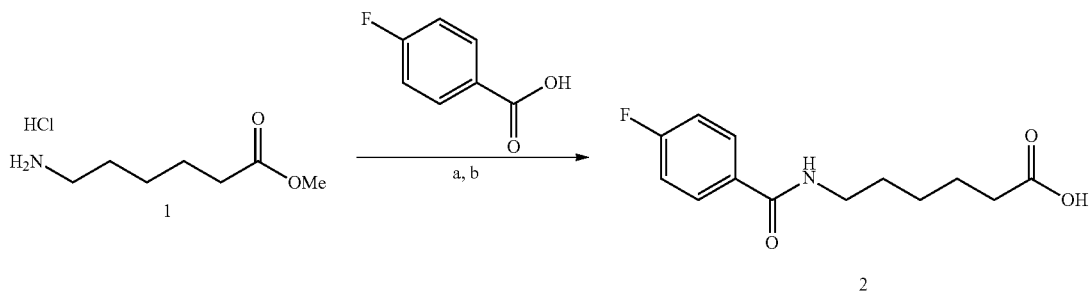

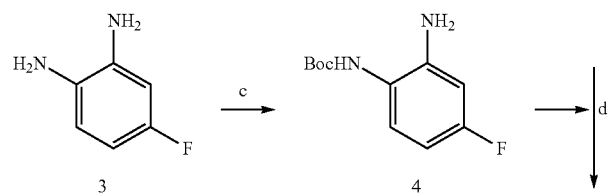

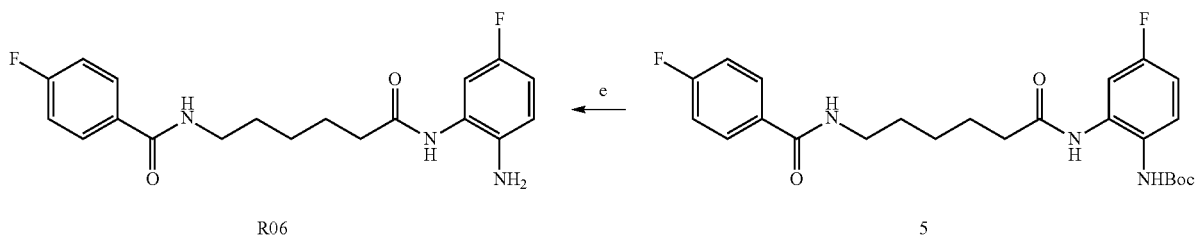

Reagents and Conditions: a) EDCI, HOBt, DIEA, DCM. b) LiOH. c) Boc$_2$O, heat. d) HATU, DIEA, DCM. e) TFA, then NaHCO$_3$

Example 12. Synthesis of R07

N-(6-(2-amino-4-fluorophenylamino)-6-oxohexyl)-4-fluorobenzamide

This compound was made by the procedure shown below. Step c) uses 4-fluorophenylenediamine.

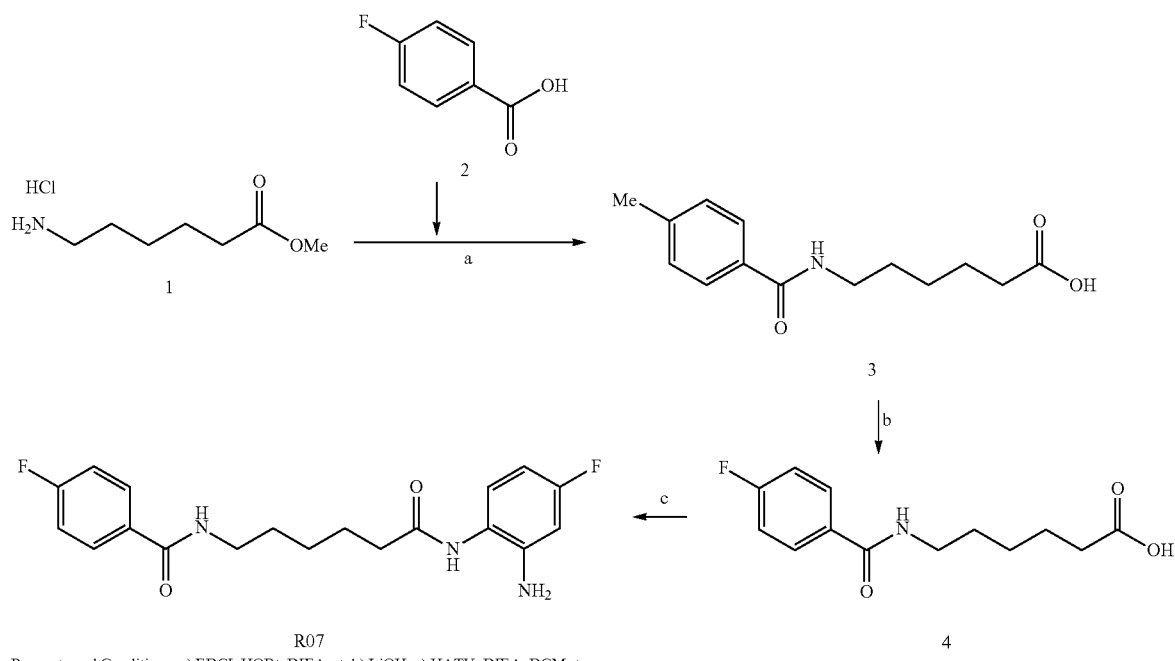

Reagents and Conditions: a) EDCI, HOBt, DIEA, rt. b) LiOH. c) HATU, DIEA, DCM rt

Example 13. Synthesis of R08

N-(2-aminophenyl)-6-(4-fluorophenylsulfonamido)hexanamide

This compound was made by the procedure shown below.

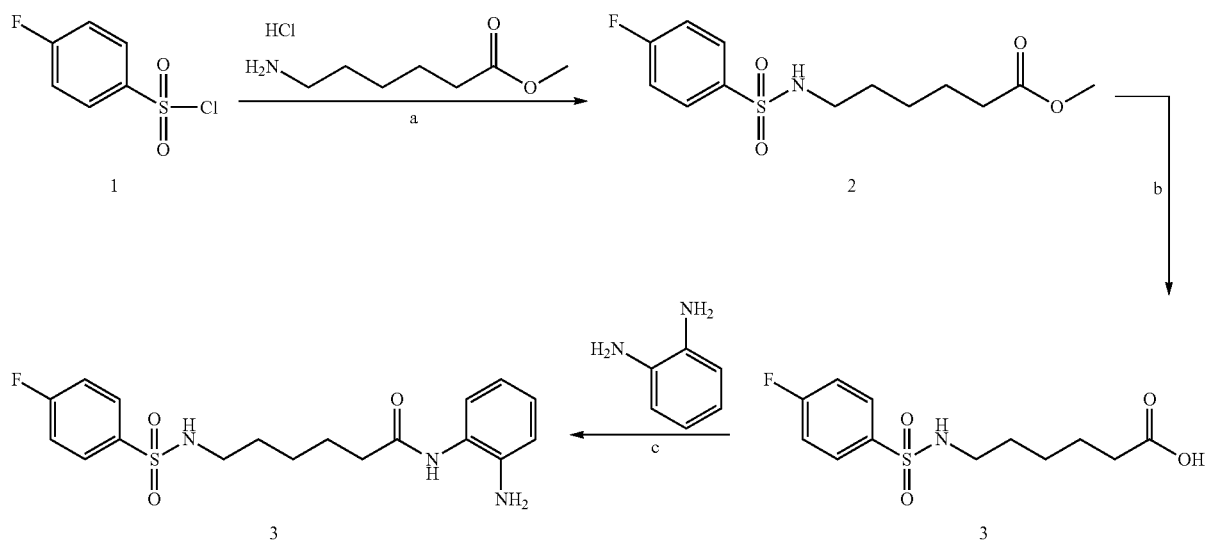

Reagents and Conditions: a) DIEA, CH$_2$Cl$_2$, rt. b) LiOH, MeOH, rt. c) EDCI, HOBT, DIEA, DCM, rt

Example 14. Synthesis of R09
N-(2-amino-4-fluorophenyl)-6-(4-fluorophenylsulfonamido)hexanamide
This compound was made by the procedure shown below.
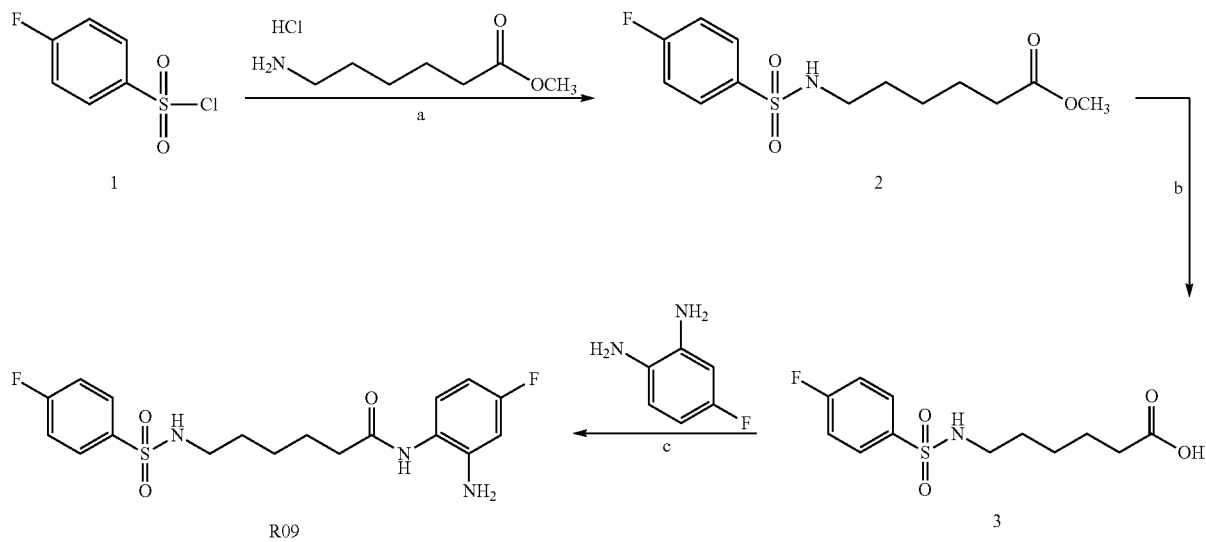
Reagents and Conditions: a) DIEA, CH$_2$Cl$_2$, rt. b) LiOH, MeOH, rt. c) EDCI, HOBT, DIEA, DCM, rt
Example 16. Synthesis of R11
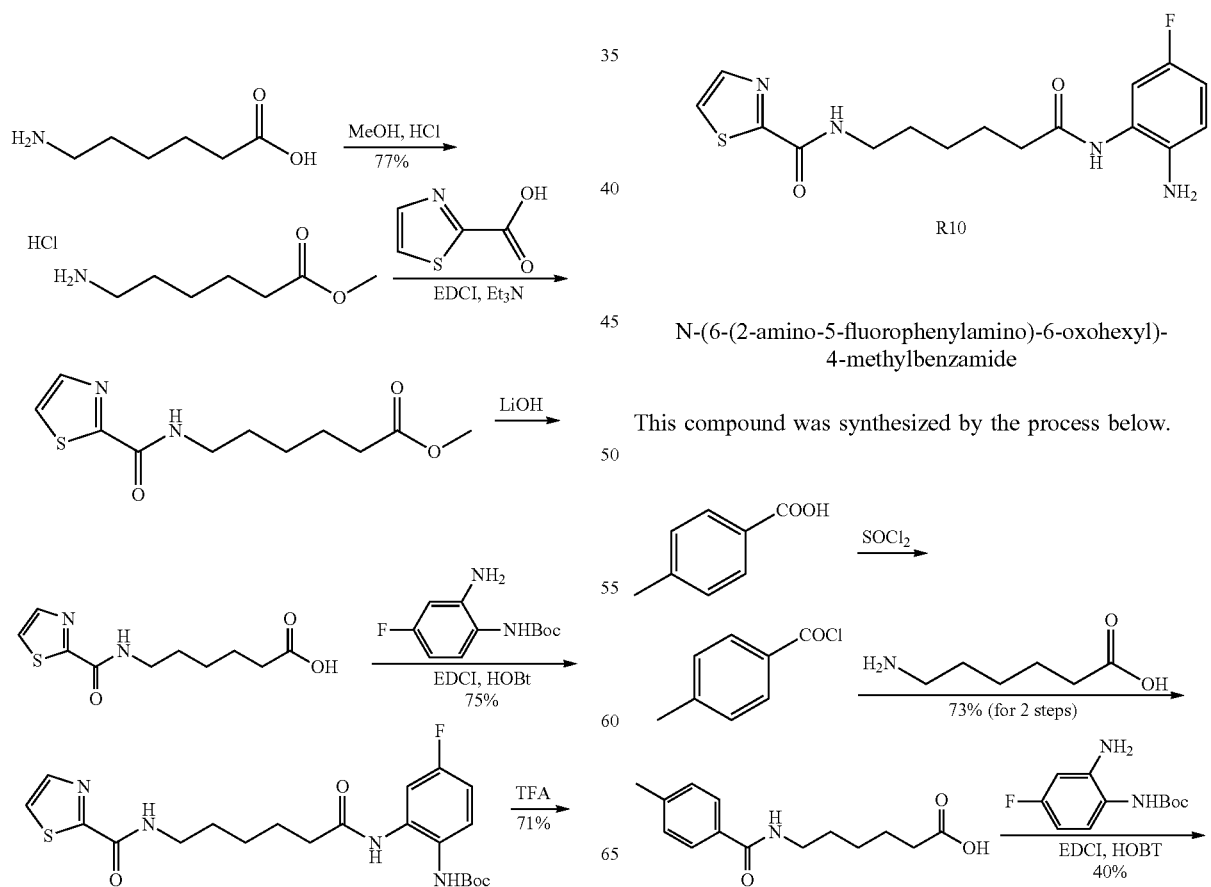
N-(6-(2-amino-5-fluorophenylamino)-6-oxohexyl)-4-methylbenzamide
This compound was synthesized by the process below.

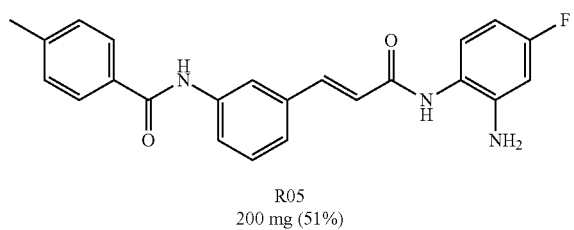
R05
200 mg (51%)
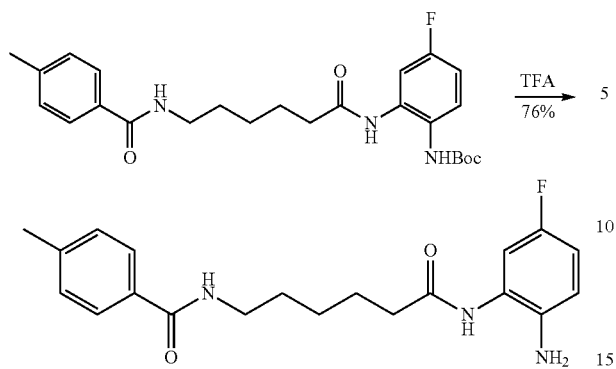
R11
Example 17. Synthesis of R05
(E)-N-(3-(3-(2-amino-4-fluorophenylamino)-3-oxo-prop-1-enyl)phenyl)-4-methylbenzamide
This compound was synthesized by the process below.
Example 18. Synthesis of R06
N-(2-amino-4-fluorophenyl)-6-(1,3-dioxoisoindolin-2-yl)hexanamide
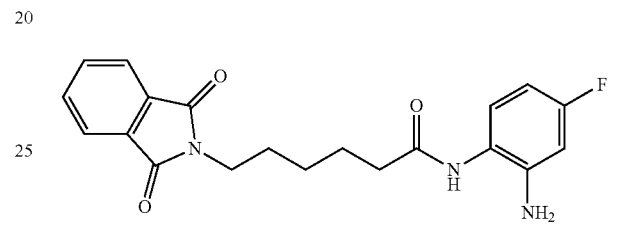
The title compound was made by following general Scheme 1A to give Example R06 LC-MS: Obs'd m/z=370.1 [M+H]; Calc'd=370.1 [M+H]
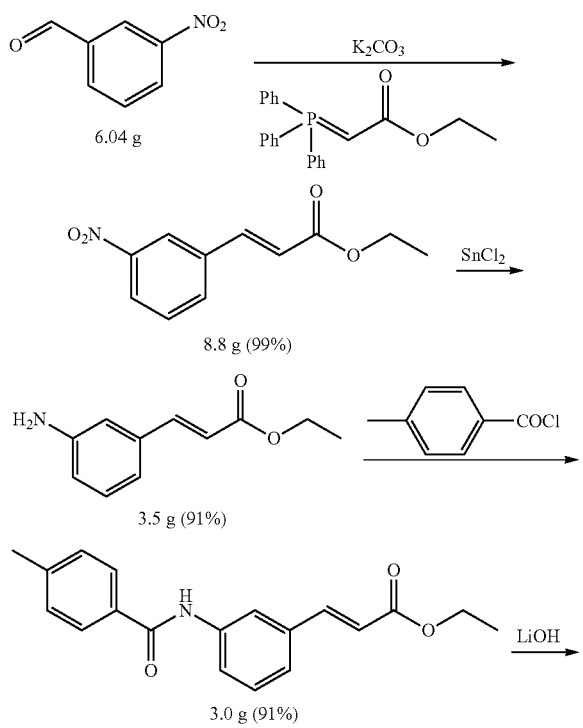
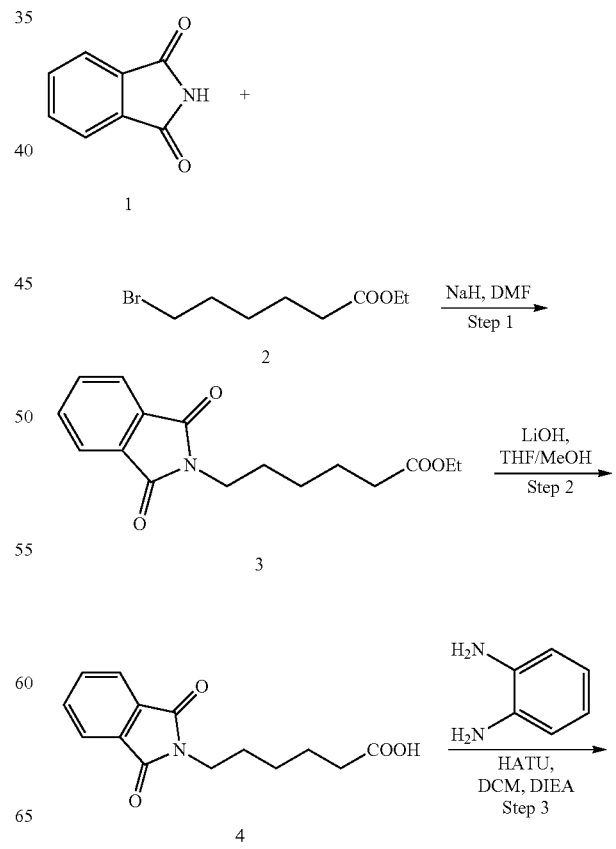

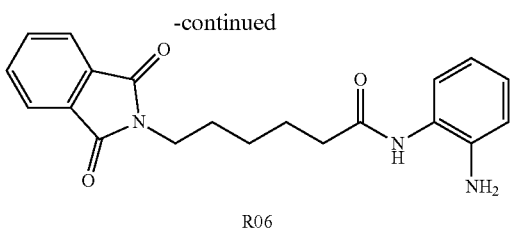

R06

Example 19. Synthesis of R07

(E)-N-(2-aminophenyl)-6-(1,3-dioxoisoindolin-2-yl)hex-2-en amide

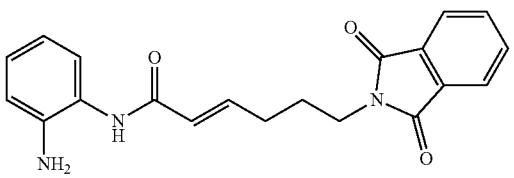 [SMILES: Nc1ccccc1NC(=O)/C=C/CCCN1C(=O)c2ccccc2C1=O]

The title compound was made as described in general Scheme 5.

Scheme 5

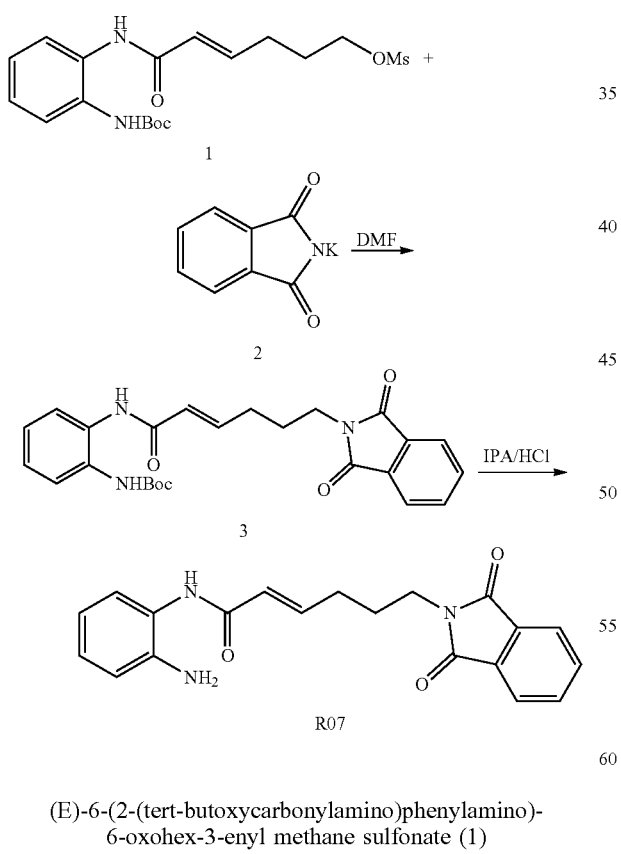

(E)-6-(2-(tert-butoxycarbonylamino)phenylamino)-6-oxohex-3-enyl methane sulfonate (1)

To a solution of (E)-tert-butyl 2-(6-hydroxyhex-2-enamido)phenylcarbamate (398 mg, 1 mmol) and triethylamine (151.5 mg, 1.5 mmol) in DCM (10 mL) was added methanesulfonyl chloride (127.6 mg, 1.1 mmol) at 0° C. and stirred for 0.5 hour, then the reaction was stirred at room temperature for 1 hr, then water (10 mL) was added, the mixture was extracted with DCM (3×20 mL), the combined organic layers were washed with brine, dried over $Na_2SO_4$ and concentrated to give the desired compound of (E)-6-(2-(tert-butoxycarbonyl amino)phenylamino)-6-oxohex-3-enyl methanesulfonate (358 mg, yield 90%) as oil after purification by column chromatography (eluent: PE:EA=10:1). LC-MS found 399 $(M+H)^+$.

(E)-tert-butyl2-(6-(1,3-dioxoisoindolin-2-yl)hex-2-enamido)phenylcarbamate (3)

To a solution of (E)-6-(2-(tert-butoxycarbonylamino)phenylamino)-6-oxohex-4-enyl methanesulfonate (1) (200 mg, 0.5 mmol) in DMF was added potassium 1,3-dioxoisoindolin-2-ide (111 mg, 0.6 mmol), the mixture was stirred at RT for 12 hours. The mixture was poured into 100 mL water, then extracted with MTBE (25 mL×2), and the organic layers were washed with water (25 mL×3) and brine (3×20 mL), dried over $Na_2SO_4$ and concentrated to give the desired compound of (E)-tert-butyl 2-(6-(1,3-dioxoisoindolin-2-yl)hex-2-enamido)phenylcarbamate (3) (135 mg, yield 60%) as a yellow oil after purification by column chromatography on silica gel (eluent: PE:EA=1:1). LC-MC found 450 $(M+H)^+$.

(E)-N-(2-aminophenyl)-6-(1,3-dioxoisoindolin-2-yl)hex-2-en amide (R07)

To a solution of (E)-tert-butyl 2-(6-(1,3-dioxoisoindolin-2-yl)hex-2-enamido)phenylcarbamate (3) (135 mg, 0.3 mmol) in propan-2-ol (10 mL). The mixture was stirred at 0° C. with HCl gas for 1 hour, To the reaction mixture was added 10% $K_2CO_3$ to adjust the pH value to 7-8, then the mixture was extracted with DCM (3×50 mL), the combined organic layers were washed with brine, dried over $Na_2SO_4$ and concentrated to give the desired compound of (E)-N-(2-aminophenyl)-6-(1,3-dioxoisoindolin-2-yl)hex-2-enamide (40 mg, yield 37%) as an off-white solid after purification by column chromatography (eluent: DCM:MeOH=50:1). $^1$H NMR (300 MHz, DMSO): δ 1.759-1.830 (m, 2H), 2.202-2.271 (m, 2H), 3.495-3.646 (m, 2H), 4.783 (s, 2H) 6.143-6.194 (d, J=15.3 1H), 6.519-6.692 (m, 1H) 6.705-6.914 (m, 4H), 7.206-7.229 (d, 1H), 7.813-7.891 (d, 2H), 8.350 (m, 4H), 9.175 (s, 1H); LC-MS found 350 $(M+H)^+$; HPLC (214 nm, 99%, 254 nm, 99%).

Example 20. Synthesis of R08

(E)-2-(6-(2-aminophenyl)-6-oxohex-3-enyl)isoindoline-1,3-dione

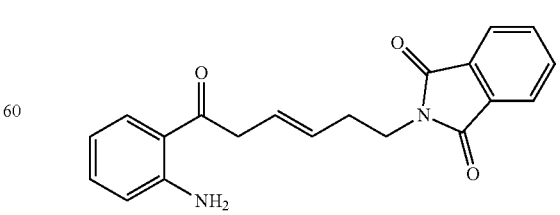

The title compound was made by following general Scheme 5 in a similar manner as described for Example 53 in scheme 5, but starting with (E)-6-(2-(tert-butoxycarbonylamino)phenylamino)-6-oxohex-3-enylmethane sulfonate.

Example 21

Synthesis of the Template (1) with the Saturated Linker ($L^2$)

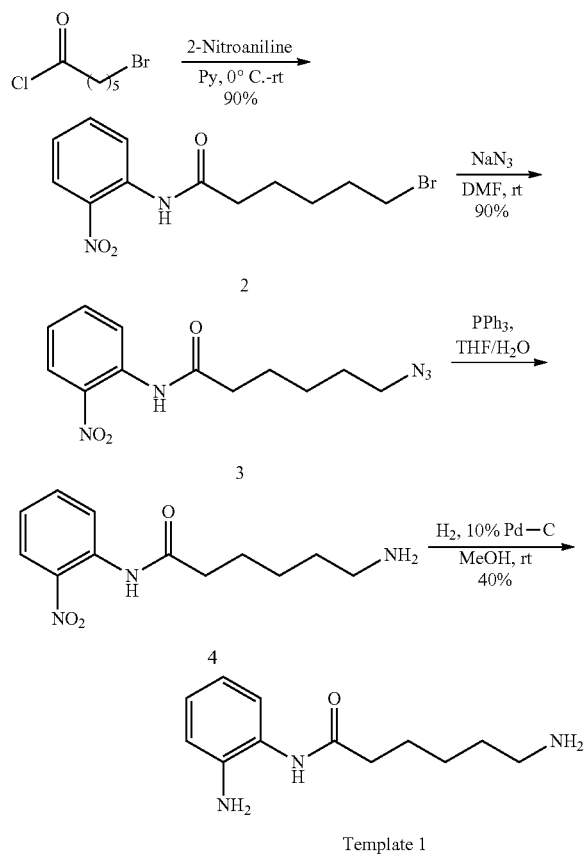

Template 1

Preparation of 6-bromo-N-(2-nitrophenyl)hexanamide (2)

To a solution of 2-nitroaniline (13.82 g, 100 mmol) in pyridine (120 mL) at 0° C. was dropwise added 6-bromohexanoyl chloride (22.6 mL, 32 g, 150 mmol) over 15 minutes. The resulting mixture was stirred for 1.5 hours at the same temperature, then poured into ice-water (500 mL) and extracted with ethyl acetate (2×200 mL). The combined organic phase was washed with aqueous citric acid solution (2×100 mL), water (100 mL) and brine (50 mL). After removal of the solvent, the crude product was passed through a silica gel pad (100 g) and washed with 1:1 mixture of hexane and diethyl ether. Concentration of the appropriate fractions gave 28.4 g of 2 as yellow solid. LC-MS ($M^+$+1) 315

Preparation of 6-azido-N-(2-nitrophenyl)hexanamide (3)

A mixture of 2 (28.4 g, 90 mmol) and sodium azide (12 g, 184 mmol) in DMF (200 mL) was stirred overnight at room temperature. The reaction mixture was poured into ice-water (500 mL) and extracted with ethyl acetate (2×200 mL). The combined organic phase was washed with water (4×100 mL) and brine (50 mL). After removal of the solvent the crude product was passed through a silica gel pad (100 g) and washed with 1:2 mixture of hexane and diethyl ether. Concentration of the appropriate fractions gave 22.5 g of 3 as a pale yellow oil. LC-MS ($M^+$+Na) 300

Preparation of 6-amino-N-(2-nitrophenyl)hexanamide (4)

To a mixture of 3 (13.5 g, 48.7 mmol), THF (100 mL) and water (50 mL) was added triphenyl phosphine (14.05 g, 53.5 mmol). The resulting mixture was stirred at room temperature for 6 hours. The THF and water were removed in vacuo. The residue was dissolved in the minimal amount of dichloromethane and passed through a silica gel pad (50 g) and washed with dichloromethane (500 mL) followed by a 4:1 mixture of dichloromethane-5% ammonia in methanol (500 mL). The appropriate fractions were concentrated and recrystallized from ethyl acetate to yield 6.45 g of 4 as a pale yellow solid.

Preparation of 6-amino-N-(2-aminophenyl)hexanamide (Template 1)

A mixture of 4 (6.40 g, 25.7 mmol), 10% Pd—C (0.5 g), and methanol (200 mL) was stirred under a hydrogen balloon at room temperature for 3 hours. The catalyst was filtered off and washed with additional methanol. Solvent was removed in vacuo to give 5.8 g of Template 1 as an off white solid LC-MS ($M^+$+1) 222. $^1$H NMR (DMSO-$d_6$) δ 1.34 (m, 4H), 1.57 (m, 2H), 2.29 (t, J=5.4 Hz, 2H), 2.49 (br, s, 2H), 2.54 (t, J=5.4 Hz, 2H), 4.32 (br, s, 2H), 6.52 (dd, J=6 Hz, J=6 Hz, 1H), 6.70 (d, J=6 Hz, 1H), 6.87 (dd, J=6 Hz, J=6 Hz, 1H), 7.15 (d, J=6 Hz, 1H), 9.14 (br, s, 1H).

Example 22. Library Synthesis:

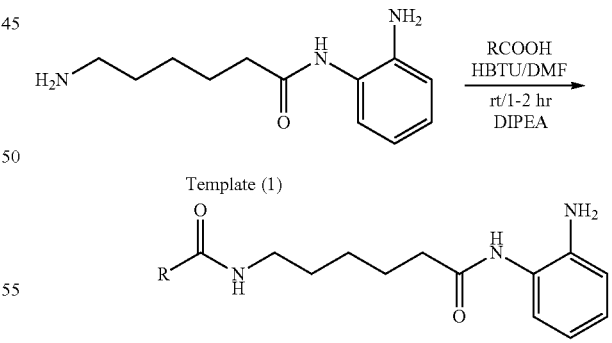

A mixture of acid (300 μmol), HBTU (171 mg, 450 μmol), DIPEA (500 μL), and DMF (1 mL) was stirred at room temperature for 15 minutes. The amine template (66 mg, 300 μmol) was then added and the mixture stirred for an additional 16 hours. DMF was removed in vacuo. Saturated sodium bicarbonate (2 mL) was added and the mixture extracted with ethyl acetate (3×2 mL). The combined organic layer was concentrated in vacuo and submitted for RP-HPLC purification.

Samples were analyzed prior to purification on an XBridge C18 3.5□m, 4.6×50 mm column. Solvents A and B were water with 0.1% NH$_4$OH and acetonitrile with 0.1% NH$_4$OH respectively. The total method time was 6 minutes with a gradient of 5% B to 95% B over 4.33 minutes. Mass spectral data were acquired from 180-850 amu in electrospray positive mode.

Samples were purified on an XBridge Prep C18 5 um OBD 19×100 mm column. Solvents A and B were water with 0.1% NH$_4$OH and acetonitrile with 0.1% NH$_4$OH respectively. The total method time was 10 minutes with a gradient of 10% B to 75% B over 4.63 minutes. Mass spectral data were acquired from 180-850 amu in electrospray positive mode. Note that for individual samples, the gradient was adjusted to optimize separation; the method above was the starting point for all samples.

Samples were analyzed after purification on a Zorbax SB-C18 1.8 □m, 2.1×30 mm column. Solvents A and B were water with 0.1% TFA and acetonitrile with 0.1% TFA respectively. The total method time was 1.70 min with a 1.00 mL/minute flow rate and a gradient of 5% B to 95% B over 1.3 minutes. Mass spectral data were acquired from 100-1000 amu in electrospray positive mode.

Instrumentation: MS—Waters SQ; UV—Waters 2487; ELS—Waters 2424

MS—Waters Acquity SQ Detector; UV—Waters PDA Detector

The following 105 compounds were prepared using the method described above:

R08 to R106 were all prepared using this method (105 compounds in total). LC/MS data for these compounds is listed in Table 6.

Example 23. Synthesis of Compounds with the Unsaturated Linker (L$^2$)

The synthesis of 12 target compounds R107 to R118 involved 12 steps. It was completed using the synthetic method as described in Scheme 2

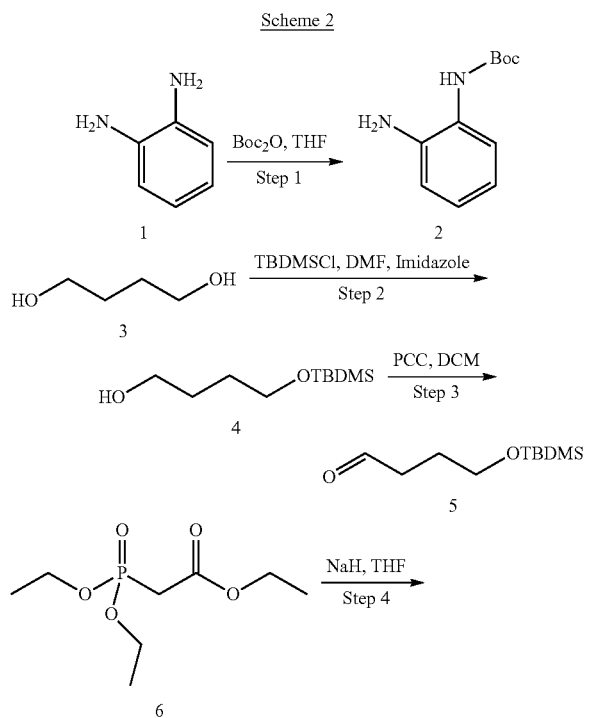

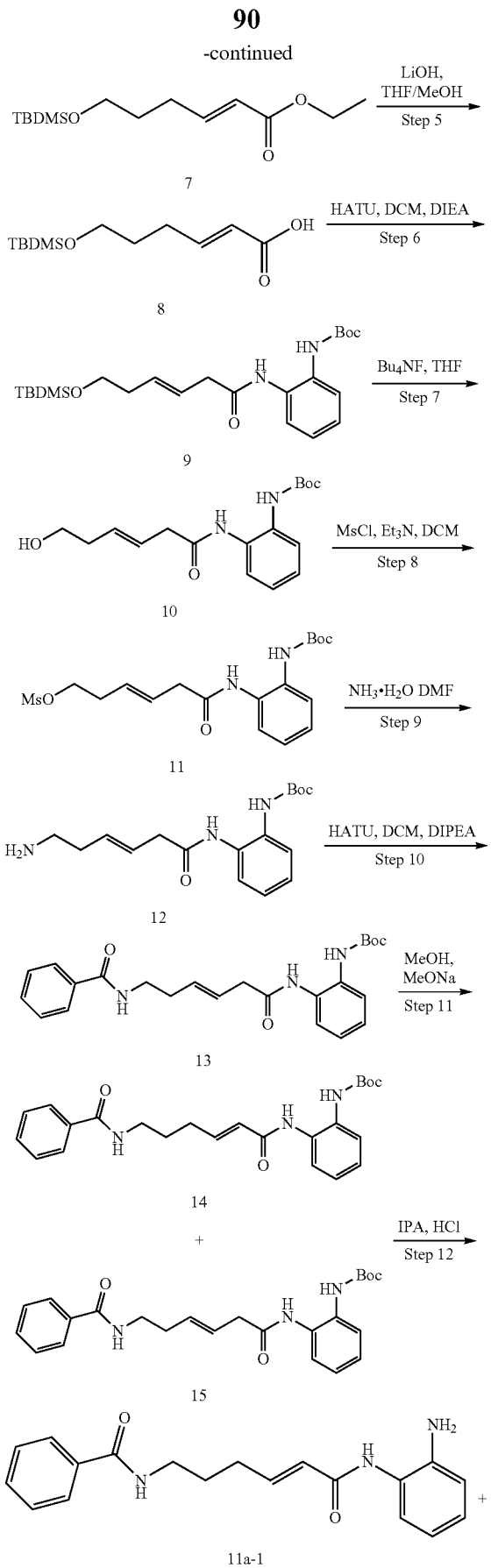

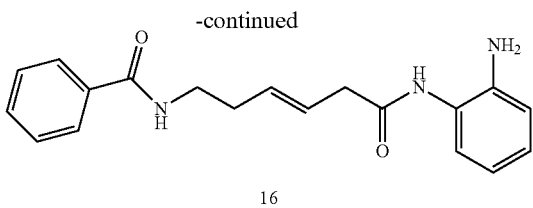

16 tert-butyl 2-aminophenylcarbamate (2)

To the solution of benzene-1,2-diamine (54.0 g, 500 mmol), triethylamine (60.6 g, 600 mmol) in DCM (10 mL) was added (Boc)$_2$O (109 g, 525 mmol), the mixture was stirred for about 1 hr at 0° C., then was warmed at RT for 5 hours. the reaction was washed with water (3×500 mL) and brine (3×500 mL), dried over Na$_2$SO$_4$ and concentrated to give the desired compound of tert-butyl 2-aminophenylcarbamate (2)(69.0 g, yield 66%) as yellow solid which was purified by column chromatography on silica gel (eluent: PE:EA=10:1). $^1$H NMR (300 MHz, CDCl$_3$): δ 1.47 (S, 9H), 5.85 (S, 2H), 6.84 (m, 1H), 6.98 (m, 1H), 7.39 (m, 2H). 9.86 (S, 1H), LC-MS: 209 (M+H)$^+$

4-(tert-butyldimethylsilyloxy)butan-1-ol (4)

To a solution of butane-1,4-diol (180.0 g, 2.0 mol), triethylamine (242.4 g, 2.4 mol) in DCM (1500 mL) was dropwised tert-butylchlorodimethylsilane (306 g, 2.03 mol) in 500 mL DCM, the mixture was stirred for about 1 hr at 0° C., then was warmed at RT for overnight. the reaction was washed with water (500 mL×3) and brine (500×3 mL), dried over Na$_2$SO$_4$ and concentrated to give the desired compound of 4-(tert-butyl dimethylsilyl oxy)butan-1-ol (180.0 g, yield 44%) as yellow oil which was purified by column chromatography on silica gel (eluent: PE:EA=50:1). LC-MC found 205 (M+H)$^+$.

4-(tert-butyldimethylsilyloxy)butanal (5)

To a suspension of PCC (161.5 g, 0.75 mol) in DCM (1000 mL) was added 4-(tert-butyl dimethylsilyl oxy)butan-1-ol (102.0 g, 0.5 mol) in 500 mL of DCM, the mixture was stirred for about 1 hr at 0° C., then was warmed to RT and stirred for 2 hours. Then the mixture was filtered and the filtrate was concentrated in vacuo to give the desired compound of 4-(tert-butyldimethylsilyloxy)butanal (5) (121.2 g, yield 60%) as yellow oil which was purified by column chromatography on silica gel (eluent: PE:EA=50:1). $^1$H NMR (300 MHz, CDCl$_3$): δ 0.04 (S, 6H), 0.0854 (S, 9H), 1.747 (m, 2H), 3.595 (d, J=12 Hz, 1H), 9.677 (d, J=3.3 Hz, 1H); LC-MC found 203 (M+H)+.

(E)-ethyl 6-(tert-butyldimethylsilyloxy)hex-2-enoate (7)

Ethyl 2-(ethoxy(ethoxymethyl)phosphoryl)acetate (75.8 g, 0.3386 mol) was added to NaH (13.5 g, 60%) in 600 mL THF at 0° C., and the solution was warmed at RT for 1 hour, followed by the addition of 4-(tert-butyldimethylsilyloxy)butanal (5) (57.0 g, 0.2822 mol) in THF (200 mL) at 0° C., The mixture was stirred at RT for 2 hours. After removal of the solvent, the residue was dissolved in DCM, and the mixture was washed with water (3×200 mL) and brine (3×200 mL), dried over Na$_2$SO$_4$ and concentrated to give the desired compound of (E)-ethyl 6-(tert-butyldimethylsilyloxy)hex-2-enoate (7) (37.0 g, yield 48%) as yellow oil which was purified by column chromatography on silica gel (eluent: PE:EA=30:1). $^1$H NMR (300 MHz, CDCl$_3$): δ 0.0021 (S, 6H), 0.0857 (S, 9H), 1.197 (t, 3H), 1.600 (m, 2H), 1.197 (t, 3H), 2.240 (q, 2H), 3.586 (t, 2H), 4.098 (q, 2H), 5.832 (d, J=15.6 Hz, 1H), 6.936-6.885 (m, 1H); LC-MS found 273 (M+H)$^+$.

(E)-6-(tert-butyldimethylsilyloxy)hex-2-enoic acid (8)

To a solution of (E)-ethyl 6-(tert-butyldimethylsilyloxy) hex-2-enoate (7) (27.2 g, 0.1 mol) in THF and MeOH was added LiOH (6.6 g, 0.3 mol) in 50 mL H$_2$O, the mixture was stirred at RT for 5 hours. After removal of the solvent, the residue was poured into 3N HCl to the pH value was adjusted to 4-5, then extracted with DCM (250 mL×2), and the organic layers were washed with water (250 mL×3) and brine (3×200 mL), dried over Na$_2$SO$_4$ and concentrated to give the desired compound of (E)-6-(tert-butyldimethylsilyloxy)hex-2-enoic acid (8) (12.1 g, 50%) as a yellow oil after purification by column chromatography on silica gel (eluent: PE:EA=5:1). $^1$H NMR (300 MHz, CDCl$_3$): δ 0.0021 (S, 6H), 0.0857 (S, 9H), 1.600 (m, 2H), 1.197 (t, 3H), 2.240 (q, 2H), 3.586 (t, 2H), 5.832 (d, J=15.6 Hz, 1H), 6.936-6.885 (m, 1H); LC-MS found 245 (M+H)$^+$.

(E)-tert-butyl2-(6-(tert-butyldimethylsilyloxy)hex-3-en amido)phenylcarbamate(9)

A mixture of (E)-6-(tert-butyldimethylsilyloxy)hex-2-enoic acid (12.0 g, 49.2 mmol), HATU (18.69 g, 49.2 mmol), DIEA (30 mL), tert-butyl 2-aminophenylcarbamate (2) (10.23 g, 49.2 mmol) in DCM was stirred at RT for 5 hours, The reaction mixture was poured onto 500 mL of ethyl acetate and 200 mL of water, the organic layer was washed with water (250 mL×3) and brine (3×200 mL), dried over Na$_2$SO$_4$ and concentrated to give the desired compound of (E)-tert-butyl2-(6-(tert-butyldimethylsilyloxy)hex-3-enamido)phenylcarbamate (13.1 g, 44%) as a yellow oil after purification by column chromatography on silica gel (eluent: PE:EA=8:1). LC-MC (M+1) 435 (M+H)$^+$

(E)-tert-butyl 2-(6-hydroxyhex-3-enamido)phenylcarbamate (10)

A TBAF (4.46 g, 17.06 mmol) in THF was added to a solution of (E)-tert-butyl2-(6-(tert-butyldimethylsilyloxy) hex-3-enamido)phenylcarbamate (6.17 g, 14.2 mmol) in THF (180 mL) at 0° C. for 0.5 hour, then the mixture was stirred at RT for 12 hours. The reaction mixture was diluted with ether (500 mL) and washed with brine (3×200 mL), the organic layer was dried over Na$_2$SO$_4$, filtered and concentrated to give the desired compound of (E)-tert-butyl 2-(6-hydroxyhex-3-enamido)phenylcarbamate (10) (2.38 g, 52%) as a yellow oil after purification by column chromatography on silica gel (eluent: PE:EA=1:1). $^1$H NMR (300 MHz, CDCl$_3$): δ 1.475 (S, 9H), 2.292 (q, 2H), 3.096 (d, 2H), 3.652 (t, 2H), 5.655-5.701 (m, 2H), 6.996-7.124 (m, 2H), 7.310-7.380 (m, 2H), 7.482 (d, J=7.8 Hz, 1H), 8.652 (s, 1H); LC-MS found 321 (M+H)$^+$.

(E)-6-(2-(tert-butoxycarbonylamino)phenylamino)-6-oxohex-3-enyl methane sulfonate(11)

To a solution of (E)-tert-butyl 2-(6-hydroxyhex-3-enamido)phenylcarbamate (10) (398 mg, 1 mmol) and triethylamine (151.5 mg, 1.5 mmol) in DCM (10 mL) was added methanesulfonyl chloride (127.6 mg, 1.1 mmol) at 0° C. and stirred for 0.5 hour, then the reaction was stirred at room temperature for 1 hr, then water (10 mL) was added, the mixture was extracted with DCM (3×20 mL), the combined organic layers were washed with brine, dried over $Na_2SO_4$ and concentrated to give the desired compound of (E)-6-(2-(tert-butoxycarbonyl amino)phenylamino)-6-oxohex-3-enyl methanesulfonate (358 mg, yield 90%) as oil after purification by column chromatography (eluent: PE:EA=10:1). LC-MS found 399 (M+H)+.

(E)-tert-butyl 2-(6-aminohex-3-enamido)phenylcarbamate(12)

To a solution of (E)-6-(2-(tert-butoxycarbonyl amino)phenylamino)-6-oxohex-3-enyl methanesulfonate (358 mg, 0.9 mmol) in DMF (5 mL) was added $NH_3.H_2O$ (20 mL) at 0° C. and stirred at the same temperature for 0.5 hour, then the reaction mixture was stirred at room temperature for 12 hr, then water (100 mL) was added, the mixture was extracted with DCM (3×50 mL), the combined organic layers were washed with brine, dried over $Na_2SO_4$ and concentrated to give the desired compound of (E)-tert-butyl 2-(6-aminohex-3-enamido)phenylcarbamate (100 mg, 88%) as a white solid after purification by column chromatography (eluent: DCM:MeOH=50:1).
$^1$H NMR (300 MHz, $CDCl_3$): δ 1.453 (S, 9H), 2.449 (m, 4H), 2.826 (t, 2H), 3.235 (d, 2H), 5.7081 (t, 2H), 6.996-7.124 (m, 2H), 7.054-7.145 (m, 2H), 7.436-7.558 (m, 2H), 8.512 (s, 1H). 8.866 (s, 1H); LC-MS found 320 (M+H)+.

(E)-tert-butyl 2-(6-benzamidohex-3-enamido)phenylcarbamate(13)

A mixture of (E)-tert-butyl 2-(6-aminohex-3-enamido)phenylcarbamate (100 mg, 0.3134 mmol), HATU (119.1 mg, 0.3134 mmol), DIEA (0.25 ml), benzoic acid (38 mg, 03134 mmol) in DCM was stirred at RT for 5 hours, The reaction mixture was poured onto 50 mL of ethyl acetate and 20 mL of water. The organic layers were washed with water (20 mL×3) and brine (3×20 mL), dried over $Na_2SO_4$ and concentrated to give the desired compound of (E)-tert-butyl 2-(6-benzamidohex-3-enamido)phenylcarbamate (86.16 mg, yield 65%) as a white solid after purification by column chromatography on silica gel (eluent: DCM:MeOH=200:1). LC-MS found 424 (M+H)+.

(E)-tert-butyl 2-(6-benzamidohex-2-enamido)phenylcarbamate(14)

To a solution of (E)-tert-butyl 2-(6-benzamidohex-3-enamido)phenylcarbamate (423 mg, 1 mmol) in MeOH was added MeONa (37 mg, 20 mmol), the mixture was stirred for 12 hours. To the reaction mixture was added sat. $NH_4Cl$ solution to adjust the pH value to 7-8, then concentrated, the residue was dissolved in DCM, the organic layer was washed with brine, dried over $Na_2SO_4$ and concentrated to give the desired compound of (E)-tert-butyl 2-(6-benzamidohex-2-enamido)phenylcarbamate (14) (270 mg, 64%) and (E)-tert-butyl 2-(6-benzamidohex-3-enamido)phenylcarbamate (15) (123 mg, 28%) as white solids after purification by column chromatography (eluent: DCM:MeOH=100:1). LC-MS found 424 (M+H)+. Analytical data for compound 14: $^1$H NMR (300 MHz, DMSO): δ 1.504 (s, 9H), 1.791 (m, 2H), 2.308 (m, 2H), 3.465 (m, 2H), 5.988 (d, J=15.6 Hz, 1H), 6.146 (s, 1H), 6.897-6.984 (m, 3H), 7.141-7.165 (m, 2H), 7.418 (s, 1H). 7.515 (s, 1H), 7.4585 (d, 2H). 8.133 (s, 1H).

(E)-N-(6-(2-aminophenylamino)-6-oxohex-4-enyl)benzamide (11a-1) (R118)

To a solution of (E)-tert-butyl 2-(6-benzamidohex-2-enamido)phenylcarbamate (14)(170 mg, 0.402 mmol) in propan-2-ol (10 mL). The mixture was stirred at 0° C. with HCl gas for 1 hour, To the reaction mixture was added 10% $K_2CO_3$ to adjust the pH value to 7-8, then the mixture was extracted with DCM (3×50 mL), the combined organic layers were washed with brine, dried over $Na_2SO_4$ and concentrated to give the desired compound of (E)-N-(6-(2-aminophenylamino)-6-oxohex-4-enyl)benzamide (71.6 mg, yield 62%) as an off-white solid after purification by column chromatography (eluent: DCM:MeOH=50:1). $^1$H NMR (300 MHz, DMSO): δ 1.724 (t, 2H), 2.258 (t, 2H), 3.465 (m, 2H), 4.875 (s, 1H), 6.165-6.216 (d, J=15.3 1H), 6.511-6.991 (m, 4H), 7.232-7.258 (d, 1H), 7.425-7.512 (m, 3H). 7.802-7.852 (m, 2H), 8.507 (s, 1H), 9.200 (s, 1H); LC-MS found 324 (M+H)+; HPLC (214 nm, 99.6%, 254 nm, 100%).

(E)-N-(6-(2-aminophenylamino)-6-oxohex-3-enyl)benzamide(16) (R109)

To a solution of (E)-tert-butyl 2-(6-benzamidohex-3-enamido)phenylcarbamate (15)(130 mg, 0.307 mmol) in propan-2-ol (10 mL) was bubbled HCl gas for 1 hour at 0° C. To the reaction mixture was added 10% $K_2CO_3$ to adjust the pH value to 7-8, then the mixture was extracted with DCM (3×50 mL), the combined organic layers were washed with brine, dried over $Na_2SO_4$ and concentrated to give the desired compound of (E)-N-(6-(2-aminophenylamino)-6-oxohex-3-enyl)benzamide(16) (20 mg, 20%) as an off-white solid after purification by column chromatography (eluent: DCM:MeOH=50:1). $^1$H NMR (300 MHz, DMSO): δ 2.418 (m, 2H), 3.257 (m, 2H), 4.847 (s, 2H), 5.572-5.716 (m, 2H), 6.519-6.570 (m, 1H), 67.424-7.549 (m, 3H), 7.833-7.861 (t, 2H). 8.532-8.576 (t, 2H), 9.149 (s, 1H); LC-MS found 324 (M+H)+; HPLC (214 nm, 98%, 254 nm, 98%).

The same procedure was applied to the preparation of the following compounds:

Example 24. Synthesis of R111

(E)-N-(6-(2-aminophenylamino)-6-oxohex-3-enyl)-3-chlorobenzamide

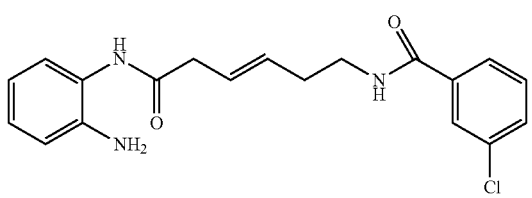 [SMILES: Nc1ccccc1NC(=O)C/C=C/CCNC(=O)c1cccc(Cl)c1]

Isolated yield (10 mg, 13%). $^1$H NMR (300 MHz, DMSO): δ 2.367 (m, 2H), 3.151-3.174 (d, 2H), 4.847 (s, 2H), 5.603-5.765 (m, 2H), 6.513-6.563 (m, 1H), 6.710-6.736 (m, 1H), 6.881-6.931 (m, 1H), 7.121-7.149 (d, 1H), 7.464-7.7.886 (m, 4H). 8.532-8.576 (t, 2H). 8.686 (s, 1H). 9.135 (s, 1H); LC-MS found 359 (M+H)⁺; HPLC (214 nm, 98%, 254 nm, 96%).

Example 25. Synthesis of R115

(E)-N-(6-(2-aminophenylamino)-6-oxohex-4-enyl)-3-chlorobenzamide

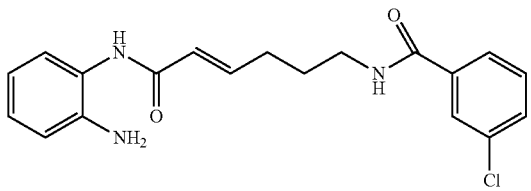 [SMILES: Nc1ccccc1NC(=O)/C=C/CCCNC(=O)c1cccc(Cl)c1]

Isolated yield (45 mg, 45%). ¹H NMR (300 MHz, DMSO): δ 1.704 (t, 2H), 2.258 (m, 2H), 3.465 (m, 2H), 4.862 (s, 1H), 6.155-6.206 (d, J=15.3 1H), 6.547 (t, 1H) 6.709-6.919 (m, 3H), 7.226-7.252 (d, 1H), 7.252-7.608 (m, 2H). 7.792-7.882 (m, 2H). 8.633 (s, 1H). 9.186 (s, 1H); LC-MS found 359 (M+H)⁺; HPLC (214 nm, 100%, 254 100%).

Example 26. Synthesis of R110

(E)-N-(6-(2-aminophenylamino)-6-oxohex-3-enyl)-4-fluorobenzamide

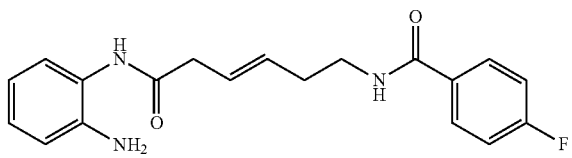 [SMILES: Nc1ccccc1NC(=O)C/C=C/CCNC(=O)c1ccc(F)cc1]

Isolated yield (45 mg, 45%). ¹H NMR (300 MHz, DMSO): δ 2.389 (m, 2H), 3.153-3.176 (d, 2H), 4.847 (s, 2H), 5.603-5.765 (m, 2H), 6.518-6.568 (m, 1H), 6.710-6.736 (d, 1H), 6.909 (t, 1H), 7.121-7.296 (m, 3H), 7.893-7.922 (q, 2H). 8.573 (s, 1H). 9.147 (s, 1H); LC-MS found 342 (M+H)⁺; HPLC (214 nm, 99.8%, 254 nm, 99%).

Example 27. Synthesis of R116

(E)-N-(6-(2-aminophenylamino)-6-oxohex-4-enyl)-4-fluorobenzamide

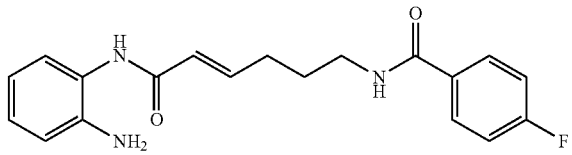 [SMILES: Nc1ccccc1NC(=O)/C=C/CCCNC(=O)c1ccc(F)cc1]

Isolated yield (40 mg, 26%). ¹H NMR (300 MHz, DMSO): δ 1.704 (t, 2H), 2.258 (m, 2H), 3.465 (m, 2H), 4.862 (s, 1H), 6.155-6.206 (d, J=15.3 1H), 6.547 (t, 1H) 6.709-6.919 (m, 3H), 7.226-7.252 (d, 1H), 7.252-7.608 (m, 2H). 7.792-7.882 (m, 2H). 8.633 (s, 1H). 9.186 (s, 1H); LC-MS found 342 (M+H)⁺; HPLC (214 nm, 97%, 254 nm, 96%).

Example 28. Synthesis of R108

(E)-N-(6-(2-aminophenylamino)-6-oxohex-3-enyl)-4-methoxybenzamide

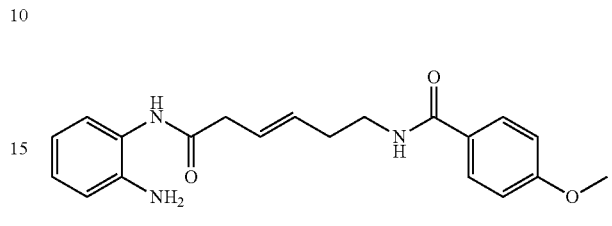

Isolated yield (10 mg, 13%). ¹H NMR (300 MHz, DMSO): δ 2.356-2.378 (d, 2H), 3.153-3.176 (d, 2H), 3.805 (s, 3H). 4.847 (s, 2H), 5.598-5.765 (m, 2H), 6.518-6.568 (m, 1H), 6.710-6.736 (d, 1H), 6.885-6.948 (m, 3H), 6.948-7.157 (t, 1H). 7.811-7.840 (d, 2H), 8.390 (s, 1H). 9.147 (s, 1H). LC-MS found 354 (M+H)⁺; HPLC (214 nm, 100%, 254 nm, 99%).

Example 29. Synthesis of R114

(E)-N-(6-(2-aminophenylamino)-6-oxohex-4-enyl)-4-methoxybenzamide

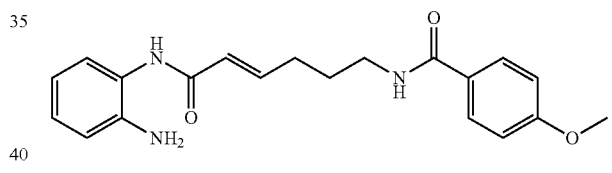

Isolated yield (40 mg, 26%). ¹H NMR (300 MHz, DMSO): δ 1.639-1.733 (q, 2H), 2.202-2.271 (q, 2H), 3.182-3.333 (m, 2H), 3.794 (s, 3H), 4.815 (s, 2H) 6.150-6.201 (d, J=15.3 1H), 6.542 (t, 1H) 6.706-6.912 (m, 4H), 7.226-7.252 (d, 1H), 7.802-7.831 (d, 2H). 8.350 (s, 1H). 9.175 (s, 1H); LC-MS found 354 (M+H)⁺; HPLC (214 nm, 96%, 254 nm, 96%).

Example 30. Synthesis of R107

(E)-N-(6-(2-aminophenylamino)-6-oxohex-3-enyl)-4-methylbenzamide

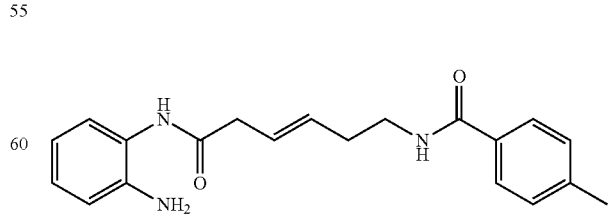

Isolated yield (60 mg, 77%). ¹H NMR (300 MHz, DMSO): δ 2.401-2.431 (d, 5H), 3.201-3.285 (t, 2H), 4.897 (s, 2H), 6.590 (m, 1H), 6.761-6.785 (m, 1H), 6.957 (m, 1H), 7.185-7.310 (m, 3H), 7.789-7.816 (d, 2H), 8.511 (s, 1H). 9.187 (s, 1H); LC-MS found 338 (M+H)+; HPLC (214 nm, 100%, 254 nm, 100%).

Example 31. Synthesis of R07

(E)-N-(2-aminophenyl)-6-(1,3-dioxoisoindolin-2-yl)hex-2-enamide

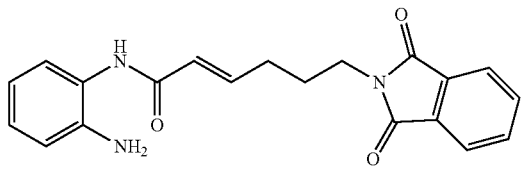 [SMILES: Nc1ccccc1NC(=O)/C=C/CCCN1C(=O)c2ccccc2C1=O]

Isolated yield (60 mg, 37%). $^1$H NMR (300 MHz, DMSO): δ 1.759-1.830 (m, 2H), 2.202-2.271 (m, 2H), 3.495-3.646 (m, 2H), 4.783 (s, 2H) 6.143-6.194 (d, J=15.3 1H), 6.519-6.692 (m, 1H) 6.705-6.914 (m, 4H), 7.206-7.229 (d, 1H), 7.813-7.891 (d, 2H), 8.350 (m, 4H), 9.175 (s, 1H); LC-MS found 350 (M+H)+; HPLC (214 nm, 99%, 254 nm, 99%).

Example 32. Synthesis of Boc-protected R107

(E)-tert-butyl 2-(6-(4-methylbenzamido)hex-3-enamido)phenylcarbamate

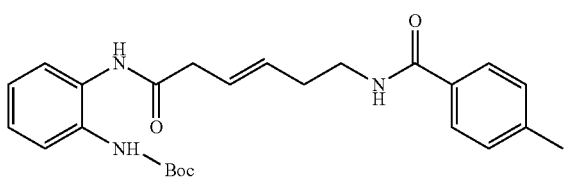 [SMILES: Cc1ccc(C(=O)NCC/C=C/CC(=O)Nc2ccccc2NC(=O)OC(C)(C)C)cc1]

Isolated yield (300 mg, 52%). $^1$H NMR (300 MHz, CDCl$_3$) δ 1.48 (s, 9H), 2.33 (s, 3H), 2.45 (m, J=6.6 Hz, 2H), 3.19 (d, J=6.6 Hz, 2H), 3.49 (m, J=6.3 Hz, 2H), 5.73 (m, 2H), 6.97-7.16 (m, 6H), 7.39 (d, J=7.8 Hz, 1H), 7.45 (d, J=7.8 Hz, 1H), 7.60 (d, J=8.4 Hz, 2H); LC-MS found 438 (M+H)+.

Example 33. Synthesis of Boc-protected R117

(E)-tert-butyl 2-(6-(4-methylbenzamido)hex-2-enamido)phenylcarbamate

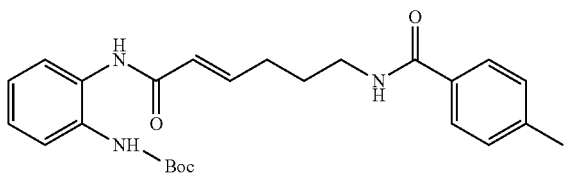 [SMILES: Cc1ccc(C(=O)NCCC/C=C/C(=O)Nc2ccccc2NC(=O)OC(C)(C)C)cc1]

Isolated yield (100 mg, 52%). $^1$H NMR (300 MHz, CDCl$_3$) δ 1.48 (s, 9H), 1.68 (m, J=7.2 Hz, 2H), 2.21 (m, J=7.2 Hz, 2H), 2.37 (s, 3H), 3.39 (m, J=6.9 Hz, 2H), 5.96 (d, J=15.3 Hz, 1H), 6.49 (b, 1H), 7.15-7.16 (m, 6H), 7.39 (m, 1H), 7.48 (b, 1H), 7.67 (d, J=8.1 Hz, 2H); LC-MS found 438 (M+H)+.

Example 34. Synthesis of R117

(E)-N-(6-(2-aminophenylamino)-6-oxohex-4-enyl)-4-methylbenzamide

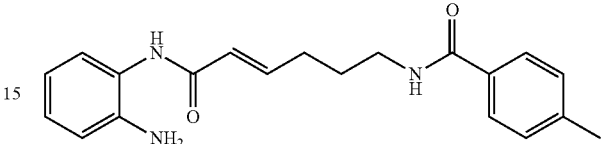

Isolated yield (50 mg, 65%). $^1$H NMR (300 MHz, DMSO-d$_6$) δ1.69 (m, J=6.9 Hz, 2H), 2.25 (m, J=6.9 Hz, 2H), 2.35 (s, 3H), 3.29 (m, J=6.9 Hz, 2H), 4.88 (b, 2H), 6.18 (d, J=15 Hz, 1H), 6.55 (t, J=7.5 Hz, 1H), 6.83 (m, 3H), 7.26 (d, J=8.4 Hz, 2H), 7.75 (d, J=8.4 Hz, 2H), 8.41 (b, 1H), 8.41 (b, 1H), 9.16 (b, 1H); LC-MS found 338 (M+H)+; HPLC (214 nm, 99%, 254 nm, 99%).

Example 35. Synthesis of Boc-Protected R113

(E)-tert-butyl 2-(6-(4-(dimethylamino)benzamido)hex-2-enamido)phenylcarbamate

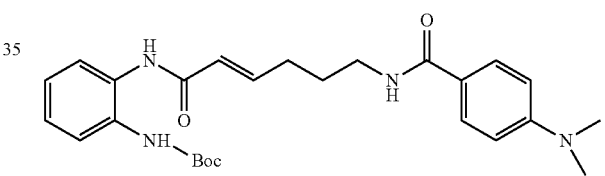

Isolated yield (75 mg, 50%). $^1$H NMR (300 MHz, CDCl$_3$) δ 1.50 (s, 9H), 1.78 (m, J=7.2 Hz, 2H), 2.26 (m, J=7.2 Hz, 2H), 3.0 (s, 6H), 3.45 (m, J=7.2 Hz, 2H), 6.02 (d, J=15.3 Hz, 1H), 6.22 (b, 1H), 6.65 (d, J=7.5 Hz, 2H), 6.98-7.16 (m, 3H), 7.48 (m, 2H), 7.68 (d, J=7.5 Hz, 2H); LC-MS found 467 (M+H)+.

Example 36. Synthesis of R113

(E)-N-(6-(2-aminophenylamino)-6-oxohex-4-enyl)-4-(dimethylamino)benzamide

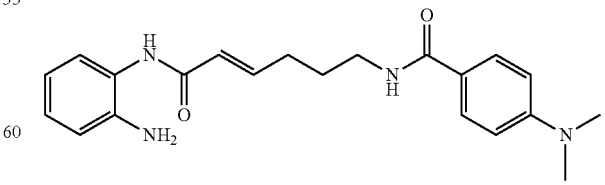

Isolated yield (16 mg, 33%). $^1$H NMR (300 MHz, DMSO-d$_6$) δ1.72 (m, J=6.9 Hz, 2H), 2.26 (m, J=6.9 Hz, 2H), 2.97 (s, 6H), 3.29 (m, J=6.9 Hz, 2H), 5.0 (b, 2H), 6.22 (d, J=15 Hz, 1H), 6.55 (t, J=7.5 Hz, 1H), 6.70-6.92 (m, 5H), 7.28 (d, J=8.4 Hz, 1H), 7.75 (d, J=9 Hz, 2H), 8.24 (b, 1H), 9.20 (s, 1H); LC-MS found 367 (M+H)⁺; HPLC (214 nm, 91%, 254 nm, 100%).

Example 37. Synthesis of Boc-Protected INT R112

(E)-tert-butyl 2-(6-(4-morpholinobenzamido)hex-3-enamido)phenylcarbamate

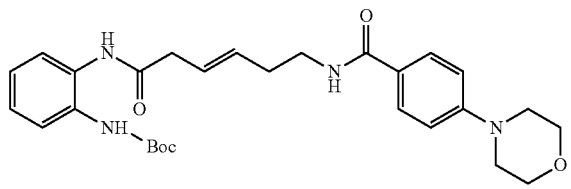 [SMILES: CC(C)(C)OC(=O)Nc1ccccc1NC(=O)C/C=C/CCNC(=O)c1ccc(N2CCOCC2)cc1]

Isolated yield (350 mg, 55%). ¹H NMR (300 MHz, CDCl₃) δ 1.49 (s, 9H), 2.46 (m, J=6.6 Hz, 2H), 3.18 (m, 6H), 3.46 (d, J=6.6 Hz, 2H), 3.83 (m, 4H), 5.73 (m, 2H), 6.70 (d, J=9 Hz 2H), 6.83 (b, 1H), 7.06-7.16 (m, 3H), 7.47 (m, 2H), 7.60 (d, J=9 Hz, 2H); LC-MS found 508 (M+H)⁺.

Example 38. Synthesis of Boc-Protected R112

(E)-tert-butyl 2-(6-(4-morpholinobenzamido)hex-2-enamido)phenylcarbamate

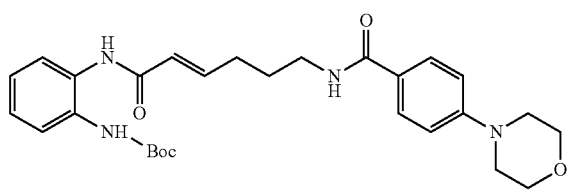 [SMILES: CC(C)(C)OC(=O)Nc1ccccc1NC(=O)/C=C/CCCNC(=O)c1ccc(N2CCOCC2)cc1]

Isolated yield (90 mg, 45%). ¹H NMR (300 MHz, CDCl₃) δ 1.50 (s, 9H), 1.78 (m, J=7.2 Hz, 2H), 2.26 (m, J=7.2 Hz, 2H), 3.22 (m, 4H), 3.45 (m, J=7.2 Hz, 2H), 3.85 (m, 4H), 6.02 (d, J=15.3 Hz, 1H), 6.22 (b, 1H), 6.65 (d, J=7.5 Hz, 2H), 6.98-7.16 (m, 2H), 7.48 (m, 2H), 7.68 (d, J=7.5 Hz, 2H); LC-MS found 508 (M+H)⁺.

Example 39. Synthesis of R112

(E)-N-(6-(2-aminophenylamino)-6-oxohex-4-enyl)-4-morpholinobenzamide

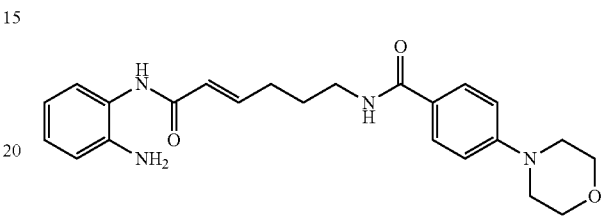

Isolated yield (60 mg, 80%). ¹H NMR (300 MHz, DMSO-d₆) δ 1.72 (m, J=6.9 Hz, 2H), 2.26 (m, J=6.9 Hz, 2H), 3.29 (m, 6H), 3.73 (m, 4H), 4.86 (b, 2H), 6.22 (d, J=15 Hz, 1H), 6.55 (t, J=7.5 Hz, 1H), 6.70-6.92 (m, 5H), 7.28 (d, J=8.4 Hz, 1H), 7.75 (d, J=9 Hz, 2H), 8.24 (b, 1H), 9.20 (s, 1H); LC-MS found 409 (M+H)⁺; HPLC (214 nm, 99%, 254 nm, 99%).

Example 40. Additional HDAC3 Inhibitors

Additional HDAC3 inhibitors were identified as in Example 4. The activities of the compounds to inhibit HDAC1 and HDAC3 are listed in Table 6.

TABLE 6

Activity of Additional HDAC3 Inhibitors

Record 1

| Structure | 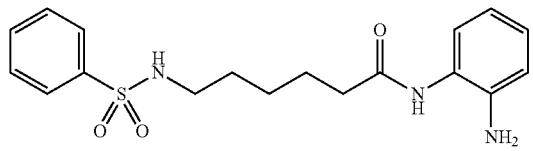 [SMILES: Nc1ccccc1NC(=O)CCCCCNS(=O)(=O)c1ccccc1] |
|---|---|
| Comp id | R119 |
| HDAC1 IC50 (nM) | 7000 |
| HDAC3 IC50 (nM) | 1100 |
| Chemical_name | N-(2-aminophenyl)-6-(phenylsulfonamido)hexanamide |
| LC/MS Calc'd (M + H) | |
| LC/MS Obsv'd (M + H) | |

TABLE 6-continued

Activity of Additional HDAC3 Inhibitors

Record 2

Structure 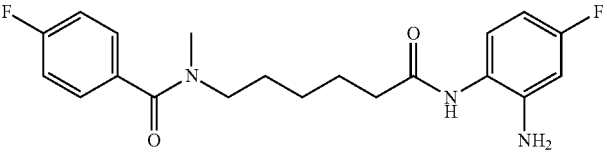 [SMILES: CN(CCCCCC(=O)Nc1ccc(F)cc1N)C(=O)c1ccc(F)cc1]

| | |
|---|---|
| Comp id | R120 |
| HDAC1 IC50 (nM) | 31170 |
| HDAC3 IC50 (nM) | 9322 |
| Chemical_name | N-(6-(2-amino-4-fluorophenylamino)-6-oxohexyl)-4-fluoro-N-methylbenzamide |
| LC/MS Calc'd (M + H) | 376.4 |
| LC/MS Obsv'd (M + H) | 376.1 |

Record 3

Structure 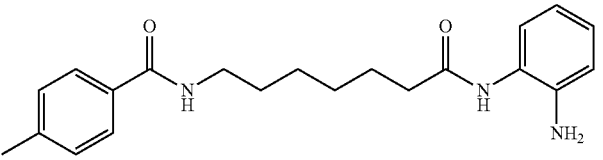 [SMILES: Cc1ccc(C(=O)NCCCCCCC(=O)Nc2ccccc2N)cc1]

| | |
|---|---|
| Comp id | R121 |
| HDAC1 IC50 (nM) | 190 |
| HDAC3 IC50 (nM) | 653 |
| Chemical_name | N-(7-(2-aminophenylamino)-7-oxoheptyl)-4-methylbenzamide |
| LC/MS Calc'd (M + H) | 354.5 |
| LC/MS Obsv'd (M + H) | 354.1 |

Record 4

Structure 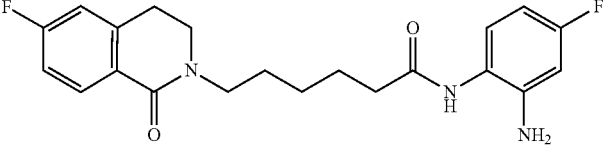 [SMILES: Nc1cc(F)ccc1NC(=O)CCCCCN1CCc2cc(F)ccc2C1=O]

| | |
|---|---|
| Comp id | R122 |
| HDAC1 IC50 (nM) | 9366 |
| HDAC3 IC50 (nM) | 1411 |
| Chemical_name | N-(2-amino-4-fluorophenyl)-6-(6-fluoro-1-oxo-3,4-dihydroisoquinolin-2(1H)-yl)hexanamide |
| LC/MS Calc'd (M + H) | 388.4 |
| LC/MS Obsv'd (M + H) | 388.4 |

Record 5

Structure 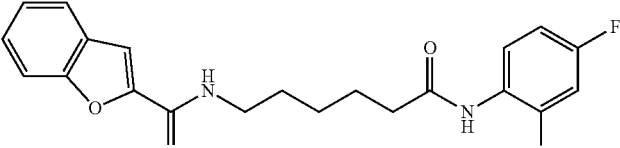

| | |
|---|---|
| Comp id | R123 |
| HDAC1 IC50 (nM) | 760 |
| HDAC3 IC50 (nM) | 480 |
| Chemical_name | N-(6-(2-amino-4-fluorophenylamino)-6-oxohexyl)benzofuran-2-carboxamide |
| LC/MS Calc'd (M + H) | 384.4 |
| LC/MS Obsv'd (M + H) | 384.1 |

TABLE 6-continued

Activity of Additional HDAC3 Inhibitors

Record 6

Structure

| Comp id | R124 |
|---|---|
| HDAC1 IC50 (nM) | 1000 |
| HDAC3 IC50 (nM) | 70 |
| Chemical_name | N-(6-(4-fluoro-2-hydroxyphenylamino)-6-oxohexyl)-4-methylbenzamide |
| LC/MS Calc'd (M + H) | 359.4 |
| LC/MS Obsv'd (M + H) | 359.1 |

Record 7

Structure

| Comp id | R125 |
|---|---|
| HDAC1 IC50 (nM) | 3890 |
| HDAC3 IC50 (nM) | 2010 |
| Chemical_name | N-(6-(2-amino-4-fluorophenylamino)-6-oxohexyl)picolinamide |
| LC/MS Calc'd (M + H) | 345.4 |
| LC/MS Obsv'd (M + H) | 345.1 |

Record 8

Structure

| Comp id | R126 |
|---|---|
| HDAC1 IC50 (nM) | 18000 |
| HDAC3 IC50 (nM) | 3000 |
| Chemical_name | N-(6-(2-amino-4-fluorophenylamino)-6-oxohexyl)nicotinamide |
| LC/MS Calc'd (M + H) | 345.4 |
| LC/MS Obsv'd (M + H) | 345.1 |

Record 9

Structure

| Comp id | R127 |
|---|---|
| HDAC1 IC50 (nM) | 300 |
| HDAC3 IC50 (nM) | 1000 |
| Chemical_name | N-(6-(2-amino-5-methoxyphenylamino)-6-oxohexyl)-4-methylbenzamide |
| LC/MS Calc'd (M + H) | 370.5 |
| LC/MS Obsv'd (M + H) | 370.2 |

TABLE 6-continued

Activity of Additional HDAC3 Inhibitors

Record 10

Structure

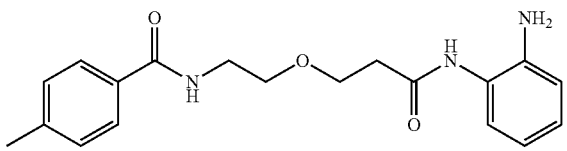 [SMILES: Cc1ccc(C(=O)NCCOCCC(=O)Nc2ccccc2N)cc1]

| | |
|---|---|
| Comp id | R128 |
| HDAC1 IC50 (nM) | 30690 |
| HDAC3 IC50 (nM) | 4451 |
| Chemical_name | N-(2-(3-(2-aminophenylamino)-3-oxopropoxy)ethyl)-4-methylbenzamide |
| LC/MS Calc'd (M + H) | 342.4 |
| LC/MS Obsv'd (M + H) | 342.1 |

Record 11

Structure

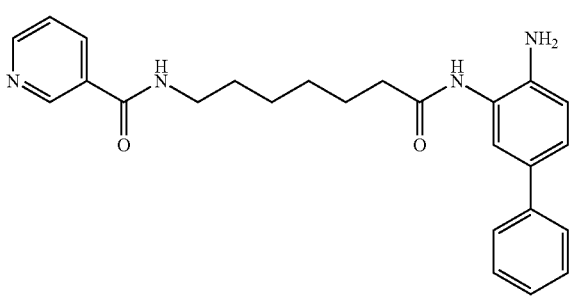 [SMILES: Nc1ccc(-c2ccccc2)cc1NC(=O)CCCCCCNC(=O)c1cccnc1]

| | |
|---|---|
| Comp id | R129 |
| HDAC1 IC50 (nM) | 66 |
| HDAC3 IC50 (nM) | 20000 |
| Chemical_name | N-(7-(4-aminobiphenyl-3-ylamino)-7-oxoheptyl)nicotinamide |
| LC/MS Calc'd (M + H) | 417.5 |
| LC/MS Obsv'd (M + H) | 417.1 |

Record 12

Structure

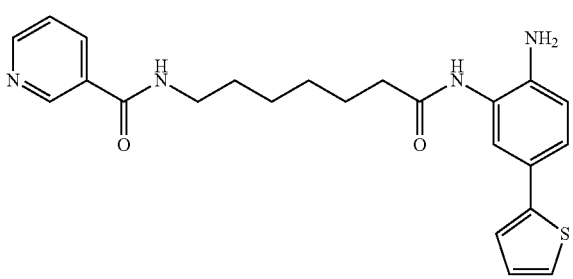 [SMILES: Nc1ccc(-c2cccs2)cc1NC(=O)CCCCCCNC(=O)c1cccnc1]

| | |
|---|---|
| Comp id | R130 |
| HDAC1 IC50 (nM) | 21 |
| HDAC3 IC50 (nM) | 20000 |
| Chemical_name | N-(7-(2-amino-5-(thiophen-2-yl)phenylamino)-7-oxoheptyl)nicotinamide |
| LC/MS Calc'd (M + H) | 423.5 |
| LC/MS Obsv'd (M + H) | 423.1 |

TABLE 6-continued

Activity of Additional HDAC3 Inhibitors

Record 13

Structure 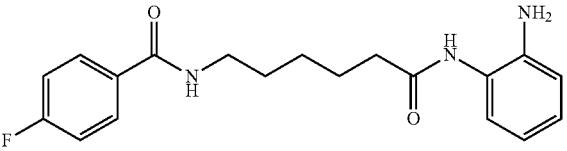 [SMILES: Nc1ccccc1NC(=O)CCCCCNC(=O)c1ccc(F)cc1]

| | |
|---|---|
| Comp id | R131 |
| HDAC1 IC50 (nM) | 1800 |
| HDAC3 IC50 (nM) | 700 |
| Chemical_name | N-(6-(2-aminophenylamino)-6-oxohexyl)-4-fluorobenzamide |
| LC/MS Calc'd (M + H) | 344.4 |
| LC/MS Obsv'd (M + H) | 344.1 |

Record 14

Structure 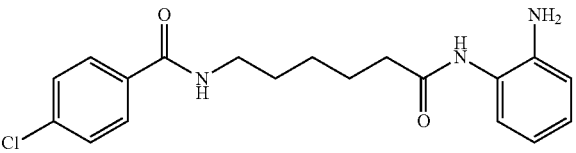 [SMILES: Nc1ccccc1NC(=O)CCCCCNC(=O)c1ccc(Cl)cc1]

| | |
|---|---|
| Comp id | R132 |
| HDAC1 IC50 (nM) | 700 |
| HDAC3 IC50 (nM) | 300 |
| Chemical_name | N-(6-(2-aminophenylamino)-6-oxohexyl)-4-chlorobenzamide |
| LC/MS Calc'd (M + H) | 360.9 |
| LC/MS Obsv'd (M + H) | 360 |

Record 15

Structure 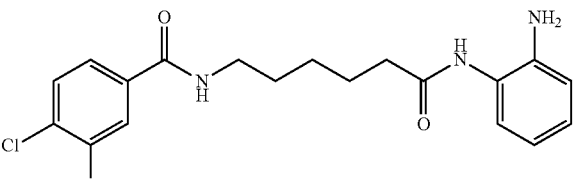

| | |
|---|---|
| Comp id | R133 |
| HDAC1 IC50 (nM) | 382 |
| HDAC3 IC50 (nM) | 200 |
| Chemical_name | N-(6-(2-aminophenylamino)-6-oxohexyl)-3,4-dichlorobenzamide |
| LC/MS Calc'd (M + H) | 395.3 |
| LC/MS Obsv'd (M + H) | 395 |

Record 16

Structure 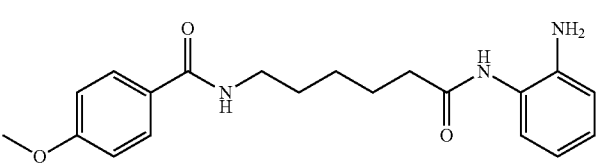 [SMILES: COc1ccc(C(=O)NCCCCCC(=O)Nc2ccccc2N)cc1]

| | |
|---|---|
| Comp id | R134 |
| HDAC1 IC50 (nM) | 1700 |
| HDAC3 IC50 (nM) | 300 |
| Chemical_name | N-(6-(2-aminophenylamino)-6-oxohexyl)-4-methoxybenzamide |
| LC/MS Calc'd (M + H) | 356.4 |
| LC/MS Obsv'd (M + H) | 356.1 |

TABLE 6-continued

Activity of Additional HDAC3 Inhibitors

Record 17

Structure

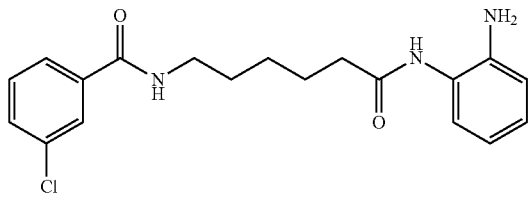 [SMILES: Nc1ccccc1NC(=O)CCCCCNC(=O)c1cccc(Cl)c1]

| | |
|---|---|
| Comp id | R135 |
| HDAC1 IC50 (nM) | 2000 |
| HDAC3 IC50 (nM) | 400 |
| Chemical_name | N-(6-(2-aminophenylamino)-6-oxohexyl)-3-chlorobenzamide |
| LC/MS Calc'd (M + H) | 360.9 |
| LC/MS Obsv'd (M + H) | 360.2 |

Record 18

Structure

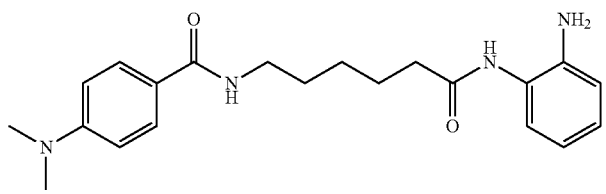 [SMILES: CN(C)c1ccc(C(=O)NCCCCCC(=O)Nc2ccccc2N)cc1]

| | |
|---|---|
| Comp id | R136 |
| HDAC1 IC50 (nM) | 1000 |
| HDAC3 IC50 (nM) | 200 |
| Chemical_name | N-(6-(2-aminophenylamino)-6-oxohexyl)-4-(dimethylamino)benzamide |
| LC/MS Calc'd (M + H) | 369.5 |
| LC/MS Obsv'd (M + H) | 369.1 |

Record 19

Structure

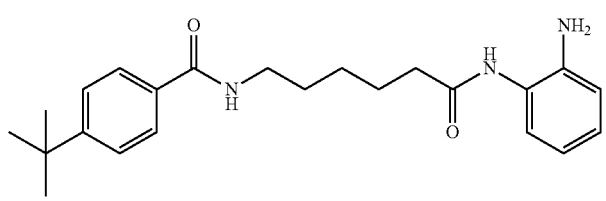 [SMILES: CC(C)(C)c1ccc(C(=O)NCCCCCC(=O)Nc2ccccc2N)cc1]

| | |
|---|---|
| Comp id | R137 |
| HDAC1 IC50 (nM) | 600 |
| HDAC3 IC50 (nM) | 400 |
| Chemical_name | N-(6-(2-aminophenylamino)-6-oxohexyl)-4-tert-butylbenzamide |
| LC/MS Calc'd (M + H) | 382.5 |
| LC/MS Obsv'd (M + H) | 382.2 |

TABLE 6-continued

Activity of Additional HDAC3 Inhibitors

Record 20

Structure

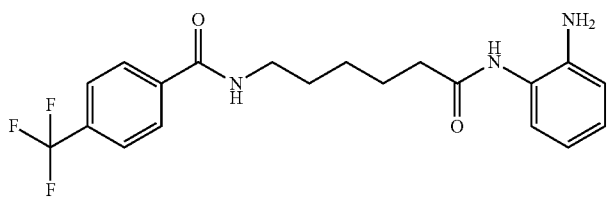 [SMILES: Nc1ccccc1NC(=O)CCCCCNC(=O)c1ccc(C(F)(F)F)cc1]

| | |
|---|---|
| Comp id | R138 |
| HDAC1 IC50 (nM) | 1100 |
| HDAC3 IC50 (nM) | 600 |
| Chemical_name | N-(6-(2-aminophenylamino)-6-oxohexyl)-4-(trifluoromethyl)benzamide |
| LC/MS Calc'd (M + H) | 394.4 |
| LC/MS Obsv'd (M + H) | 394 |

Record 21

Structure

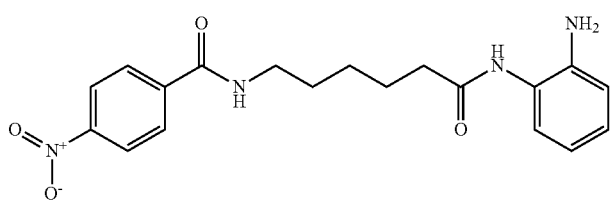 [SMILES: Nc1ccccc1NC(=O)CCCCCNC(=O)c1ccc([N+](=O)[O-])cc1]

| | |
|---|---|
| Comp id | R139 |
| HDAC1 IC50 (nM) | 1200 |
| HDAC3 IC50 (nM) | 500 |
| Chemical_name | N-(6-(2-aminophenylamino)-6-oxohexyl)-4-nitrobenzamide |
| LC/MS Calc'd (M + H) | 371.4 |
| LC/MS Obsv'd (M + H) | 371.1 |

Record 22

Structure

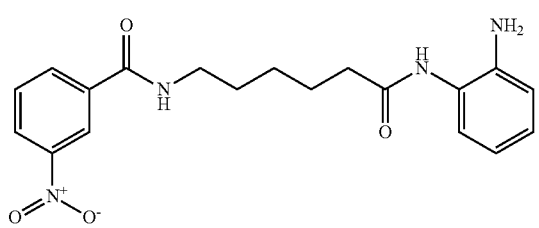 [SMILES: Nc1ccccc1NC(=O)CCCCCNC(=O)c1cccc([N+](=O)[O-])c1]

| | |
|---|---|
| Comp id | R140 |
| HDAC1 IC50 (nM) | 800 |
| HDAC3 IC50 (nM) | 500 |
| Chemical_name | N-(6-(2-aminophenylamino)-6-oxohexyl)-3-nitrobenzamide |
| LC/MS Calc'd (M + H) | 371.4 |
| LC/MS Obsv'd (M + H) | 371.1 |

TABLE 6-continued

Activity of Additional HDAC3 Inhibitors

Record 23

Structure

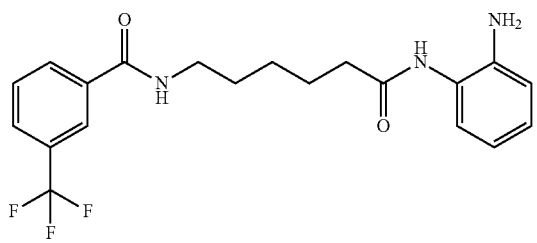 [SMILES: Nc1ccccc1NC(=O)CCCCCNC(=O)c1cccc(C(F)(F)F)c1]

| | |
|---|---|
| Comp id | R141 |
| HDAC1 IC50 (nM) | 700 |
| HDAC3 IC50 (nM) | 400 |
| Chemical_name | N-(6-(2-aminophenylamino)-6-oxohexyl)-3-(trifluoromethyl)benzamide |
| LC/MS Calc'd (M + H) | 394.4 |
| LC/MS Obsv'd (M + H) | 394.1 |

Record 24

Structure

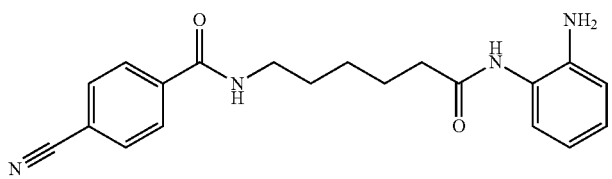 [SMILES: N#Cc1ccc(C(=O)NCCCCCC(=O)Nc2ccccc2N)cc1]

| | |
|---|---|
| Comp id | R142 |
| HDAC1 IC50 (nM) | 700 |
| HDAC3 IC50 (nM) | 400 |
| Chemical_name | N-(6-(2-aminophenylamino)-6-oxohexyl)-4-cyanobenzamide |
| LC/MS Calc'd (M + H) | 351.4 |
| LC/MS Obsv'd (M + H) | 351.1 |

Record 25

Structure

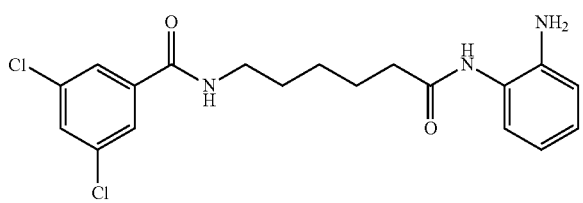 [SMILES: Nc1ccccc1NC(=O)CCCCCNC(=O)c1cc(Cl)cc(Cl)c1]

| | |
|---|---|
| Comp id | R143 |
| HDAC1 IC50 (nM) | 400 |
| HDAC3 IC50 (nM) | 300 |
| Chemical_name | N-(6-(2-aminophenylamino)-6-oxohexyl)-3,5-dichlorobenzamide |
| LC/MS Calc'd (M + H) | 395.3 |
| LC/MS Obsv'd (M + H) | 394.1 |

TABLE 6-continued

Activity of Additional HDAC3 Inhibitors

Record 26

Structure

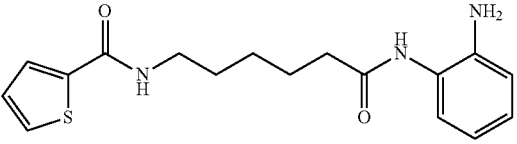

| | |
|---|---|
| Comp id | R144 |
| HDAC1 IC50 (nM) | 649 |
| HDAC3 IC50 (nM) | 221 |
| Chemical_name | N-(6-(2-aminophenylamino)-6-oxohexyl)thiophene-2-carboxamide |
| LC/MS Calc'd (M + H) | 332.4 |
| LC/MS Obsv'd (M + H) | 332 |

Record 27

Structure

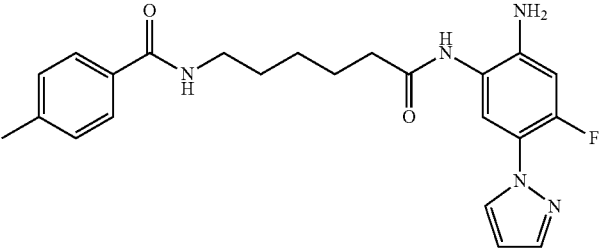 [SMILES: Cc1ccc(C(=O)NCCCCCC(=O)Nc2cc(-n3cccn3)c(F)cc2N)cc1]

| | |
|---|---|
| Comp id | R145 |
| HDAC1 IC50 (nM) | 442 |
| HDAC3 IC50 (nM) | 20000 |
| Chemical_name | N-(6-(2-amino-4-fluoro-5-(1H-pyrazol-1-yl)phenylamino)-6-oxohexyl)-4-methylbenzamide |
| LC/MS Calc'd (M + H) | 424.5 |
| LC/MS Obsv'd (M + H) | 424.2 |

Record 28

Structure

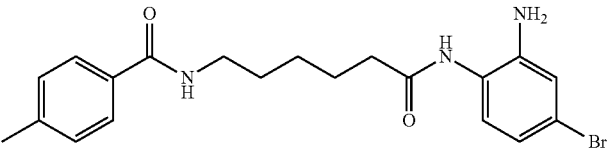 [SMILES: Cc1ccc(C(=O)NCCCCCC(=O)Nc2ccc(Br)cc2N)cc1]

| | |
|---|---|
| Comp id | R146 |
| HDAC1 IC50 (nM) | 84000 |
| HDAC3 IC50 (nM) | 16000 |
| Chemical_name | N-(6-(2-amino-4-bromophenylamino)-6-oxohexyl)-4-methylbenzamide |
| LC/MS Calc'd (M + H) | 419.3 |
| LC/MS Obsv'd (M + H) | 419.9 |

Record 29

Structure

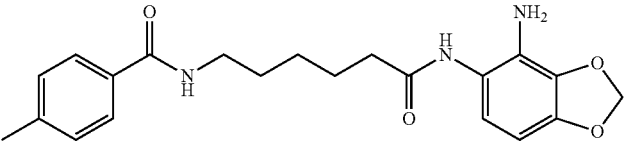 [SMILES: Cc1ccc(C(=O)NCCCCCC(=O)Nc2ccc3c(c2N)OCO3)cc1]

| | |
|---|---|
| Comp id | R147 |
| HDAC1 IC50 (nM) | 2890 |
| HDAC3 IC50 (nM) | 2254 |
| Chemical_name | N-(6-(4-aminobenzo[d][1,3]dioxol-5-ylamino)-6-oxohexyl)-4-methylbenzamide |
| LC/MS Calc'd (M + H) | 384.4 |
| LC/MS Obsv'd (M + H) | 384.1 |

TABLE 6-continued

Activity of Additional HDAC3 Inhibitors

Record 30

Structure 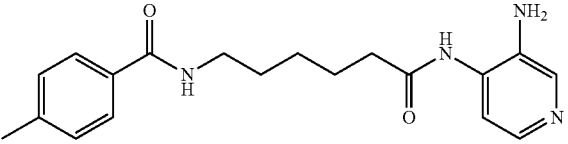 [SMILES: Cc1ccc(C(=O)NCCCCCC(=O)Nc2ccncc2N)cc1]

| | |
|---|---|
| Comp id | R148 |
| HDAC1 IC50 (nM) | 23170 |
| HDAC3 IC50 (nM) | 7934 |
| Chemical_name | N-(6-(3-aminopyridin-4-ylamino)-6-oxohexyl)-4-methylbenzamide |
| LC/MS Calc'd (M + H) | 341.4 |
| LC/MS Obsv'd (M + H) | 342.2 |

Record 31

Structure 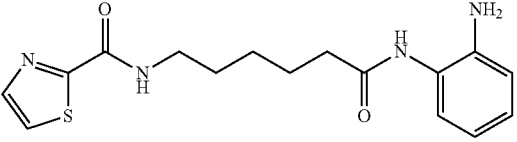 [SMILES: Nc1ccccc1NC(=O)CCCCCNC(=O)c1nccs1]

| | |
|---|---|
| Comp id | R149 |
| HDAC1 IC50 (nM) | 973 |
| HDAC3 IC50 (nM) | 1082 |
| Chemical_name | N-(6-(2-aminophenylamino)-6-oxohexyl)thiazole-2-carboxamide |
| LC/MS Calc'd (M + H) | 333.4 |
| LC/MS Obsv'd (M + H) | 333.1 |

Record 32

Structure 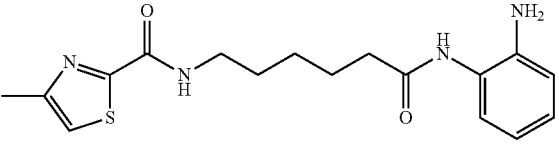 [SMILES: Cc1csc(C(=O)NCCCCCC(=O)Nc2ccccc2N)n1]

| | |
|---|---|
| Comp id | R150 |
| HDAC1 IC50 (nM) | 721 |
| HDAC3 IC50 (nM) | 129 |
| Chemical_name | N-(6-(2-aminophenylamino)-6-oxohexyl)-4-methylthiazole-2-carboxamide |
| LC/MS Calc'd (M + H) | 347.4 |
| LC/MS Obsv'd (M + H) | 347.2 |

Record 33

Structure 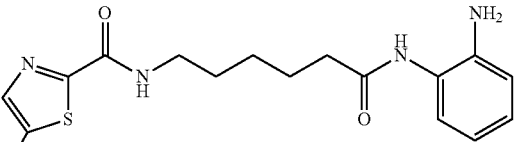

| | |
|---|---|
| Comp id | R151 |
| HDAC1 IC50 (nM) | 816 |
| HDAC3 IC50 (nM) | 989 |
| Chemical_name | N-(6-(2-aminophenylamino)-6-oxohexyl)-5-methylthiazole-2-carboxamide |
| LC/MS Calc'd (M + H) | 347.4 |
| LC/MS Obsv'd (M + H) | 347.1 |

TABLE 6-continued

Activity of Additional HDAC3 Inhibitors

Record 34

Structure 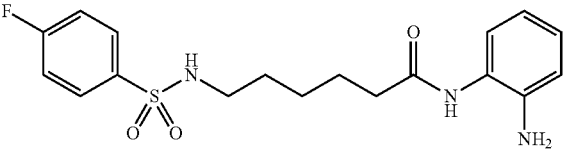 [SMILES: Nc1ccccc1NC(=O)CCCCCNS(=O)(=O)c1ccc(F)cc1]

| | |
|---|---|
| Comp id | R152 |
| HDAC1 IC50 (nM) | 4595 |
| HDAC3 IC50 (nM) | 4000 |
| Chemical_name | N-(2-aminophenyl)-6-(4-fluorophenylsulfonamido)hexanamide |
| LC/MS Calc'd (M + H) | |
| LC/MS Obsv'd (M + H) | |

Record 35

Structure 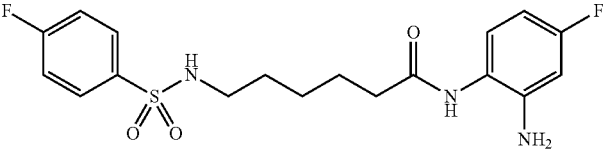 [SMILES: Nc1cc(F)ccc1NC(=O)CCCCCNS(=O)(=O)c1ccc(F)cc1]

| | |
|---|---|
| Comp id | R153 |
| HDAC1 IC50 (nM) | 30000 |
| HDAC3 IC50 (nM) | 6000 |
| Chemical_name | N-(2-amino-4-fluorophenyl)-6-(4-fluorophenylsulfonamido)hexanamide |
| LC/MS Calc'd (M + H) | |
| LC/MS Obsv'd (M + H) | |

Record 36

Structure 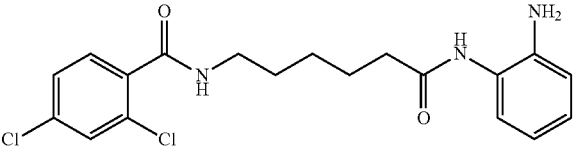 [SMILES: Nc1ccccc1NC(=O)CCCCCNC(=O)c1ccc(Cl)cc1Cl]

| | |
|---|---|
| Comp id | R154 |
| HDAC1 IC50 (nM) | 2270 |
| HDAC3 IC50 (nM) | 605 |
| Chemical_name | N-(6-(2-aminophenylamino)-6-oxohexyl)-2,4-dichlorobenzamide |
| LC/MS Calc'd (M + H) | 395.3 |
| LC/MS Obsv'd (M + H) | 394 |

Record 37

Structure 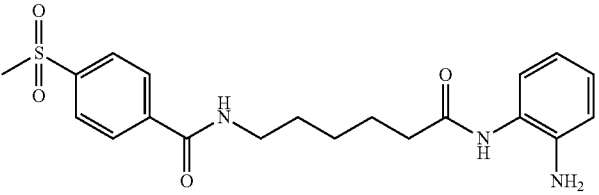 [SMILES: CS(=O)(=O)c1ccc(C(=O)NCCCCCC(=O)Nc2ccccc2N)cc1]

| | |
|---|---|
| Comp id | R155 |
| HDAC1 IC50 (nM) | 570 |
| HDAC3 IC50 (nM) | 1255 |
| Chemical_name | N-(6-(2-aminophenylamino)-6-oxohexyl)-4-(methylsulfonyl)benzamide |
| LC/MS Calc'd (M + H) | 404.5 |
| LC/MS Obsv'd (M + H) | 405 |

TABLE 6-continued

Activity of Additional HDAC3 Inhibitors

Record 38

Structure

| Comp id | R156 |
| --- | --- |
| HDAC1 IC50 (nM) | 1104 |
| HDAC3 IC50 (nM) | 1190 |
| Chemical_name | N-(6-(2-aminophenylamino)-6-oxohexyl)-4-sulfamoylbenzamide |
| LC/MS Calc'd (M + H) | 405.5 |
| LC/MS Obsv'd (M + H) | 405 |

Record 39

Structure

| Comp id | R157 |
| --- | --- |
| HDAC1 IC50 (nM) | 1260 |
| HDAC3 IC50 (nM) | 1404 |
| Chemical_name | N-(6-(2-aminophenylamino)-6-oxohexyl)isonicotinamide |
| LC/MS Calc'd (M + H) | 327.4 |
| LC/MS Obsv'd (M + H) | 327.1 |

Record 40

Structure

| Comp id | R158 |
| --- | --- |
| HDAC1 IC50 (nM) | 2045 |
| HDAC3 IC50 (nM) | 1686 |
| Chemical_name | N-(6-(2-aminophenylamino)-6-oxohexyl)pyrazine-2-carboxamide |
| LC/MS Calc'd (M + H) | 328.4 |
| LC/MS Obsv'd (M + H) | 328.2 |

Record 41

Structure

| Comp id | R159 |
| --- | --- |
| HDAC1 IC50 (nM) | 2565 |
| HDAC3 IC50 (nM) | 2377 |
| Chemical_name | N-(6-(2-aminophenylamino)-6-oxohexyl)pyridazine-4-carboxamide |
| LC/MS Calc'd (M + H) | 328.4 |
| LC/MS Obsv'd (M + H) | 328.1 |

TABLE 6-continued

Activity of Additional HDAC3 Inhibitors

Record 42

Structure 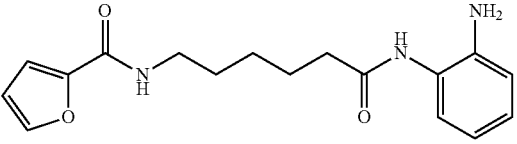 [SMILES: Nc1ccccc1NC(=O)CCCCCNC(=O)c1ccco1]

| | |
|---|---|
| Comp id | R160 |
| HDAC1 IC50 (nM) | 990 |
| HDAC3 IC50 (nM) | 331 |
| Chemical_name | N-(6-(2-aminophenylamino)-6-oxohexyl)furan-2-carboxamide |
| LC/MS Calc'd (M + H) | 316.4 |
| LC/MS Obsv'd (M + H) | 316.1 |

Record 43

Structure 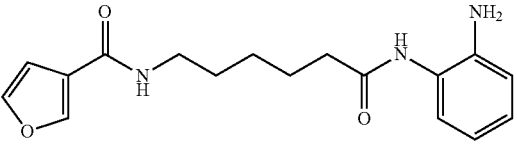 [SMILES: Nc1ccccc1NC(=O)CCCCCNC(=O)c1ccsc1]

| | |
|---|---|
| Comp id | R161 |
| HDAC1 IC50 (nM) | 1240 |
| HDAC3 IC50 (nM) | 386 |
| Chemical_name | N-(6-(2-aminophenylamino)-6-oxohexyl)furan-3-carboxamide |
| LC/MS Calc'd (M + H) | 316.4 |
| LC/MS Obsv'd (M + H) | 316.1 |

Record 44

Structure 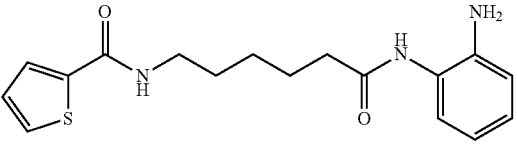

| | |
|---|---|
| Comp id | R162 |
| HDAC1 IC50 (nM) | 664 |
| HDAC3 IC50 (nM) | 200 |
| Chemical_name | N-(6-(2-aminophenylamino)-6-oxohexyl)thiophene-2-carboxamide |
| LC/MS Calc'd (M + H) | 332.4 |
| LC/MS Obsv'd (M + H) | 332 |

Record 45

Structure 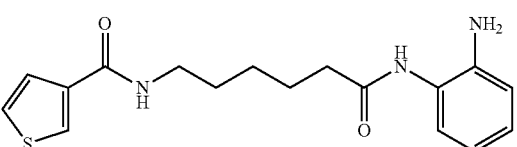

| | |
|---|---|
| Comp id | R163 |
| HDAC1 IC50 (nM) | 760 |
| HDAC3 IC50 (nM) | 233 |
| Chemical_name | N-(6-(2-aminophenylamino)-6-oxohexyl)thiophene-3-carboxamide |
| LC/MS Calc'd (M + H) | 332.4 |
| LC/MS Obsv'd (M + H) | 332.1 |

TABLE 6-continued

Activity of Additional HDAC3 Inhibitors

Record 46

Structure 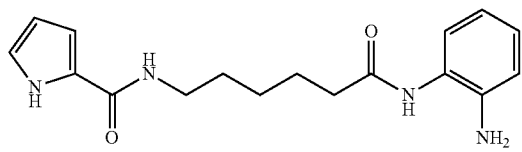 [SMILES: Nc1ccccc1NC(=O)CCCCCNC(=O)c1ccc[nH]1]

| | |
|---|---|
| Comp id | R164 |
| HDAC1 IC50 (nM) | 463 |
| HDAC3 IC50 (nM) | 460 |
| Chemical_name | N-(6-(2-aminophenylamino)-6-oxohexyl)-1H-pyrrole-2-carboxamide |
| LC/MS Calc'd (M + H) | 315.4 |
| LC/MS Obsv'd (M + H) | 315.1 |

Record 47

Structure 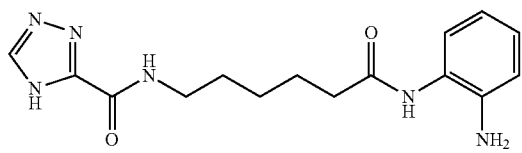 [SMILES: Nc1ccccc1NC(=O)CCCCCNC(=O)c1nnc[nH]1]

| | |
|---|---|
| Comp id | R165 |
| HDAC1 IC50 (nM) | 2689 |
| HDAC3 IC50 (nM) | 1589 |
| Chemical_name | N-(6-(2-aminophenylamino)-6-oxohexyl)-4H-1,2,4-triazole-3-carboxamide |
| LC/MS Calc'd (M + H) | 317.4 |
| LC/MS Obsv'd (M + H) | |

Record 48

Structure 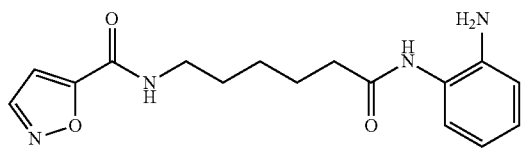 [SMILES: Nc1ccccc1NC(=O)CCCCCNC(=O)c1ccno1]

| | |
|---|---|
| Comp id | R166 |
| HDAC1 IC50 (nM) | 1372 |
| HDAC3 IC50 (nM) | 2323 |
| Chemical_name | N-(6-(2-aminophenylamino)-6-oxohexyl)isoxazole-5-carboxamide |
| LC/MS Calc'd (M + H) | 317.4 |
| LC/MS Obsv'd (M + H) | 317.1 |

Record 49

Structure 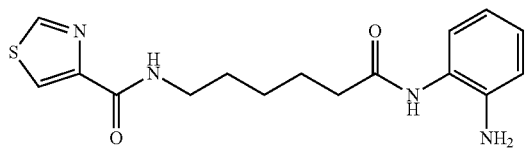 [SMILES: Nc1ccccc1NC(=O)CCCCCNC(=O)c1cscn1]

| | |
|---|---|
| Comp id | R167 |
| HDAC1 IC50 (nM) | 1039 |
| HDAC3 IC50 (nM) | 841 |
| Chemical_name | N-(6-(2-aminophenylamino)-6-oxohexyl)thiazole-4-carboxamide |
| LC/MS Calc'd (M + H) | 333.4 |
| LC/MS Obsv'd (M + H) | 333.1 |

TABLE 6-continued

Activity of Additional HDAC3 Inhibitors

Record 50

Structure

| Comp id | R168 |
| --- | --- |
| HDAC1 IC50 (nM) | 238 |
| HDAC3 IC50 (nM) | 979 |
| Chemical_name | N-(6-(2-aminophenylamino)-6-oxohexyl)-2-(piperidin-1-yl)isonicotinamide |
| LC/MS Calc'd (M + H) | 410.5 |
| LC/MS Obsv'd (M + H) | 410.1 |

Record 51

Structure

| Comp id | R169 |
| --- | --- |
| HDAC1 IC50 (nM) | 388 |
| HDAC3 IC50 (nM) | 181 |
| Chemical_name | N-(6-(2-aminophenylamino)-6-oxohexyl)-3-phenyl-1H-pyrazole-5-carboxamide |
| LC/MS Calc'd (M + H) | 392.5 |
| LC/MS Obsv'd (M + H) | 392.2 |

Record 52

Structure

| Comp id | R170 |
| --- | --- |
| HDAC1 IC50 (nM) | 754 |
| HDAC3 IC50 (nM) | 585 |
| Chemical_name | N-(6-(2-aminophenylamino)-6-oxohexyl)-2,3-dihydrobenzo[b][1,4]dioxine-6-carboxamide |
| LC/MS Calc'd (M + H) | 384.4 |
| LC/MS Obsv'd (M + H) | 384.1 |

Record 53

Structure

| Comp id | R171 |
| --- | --- |
| HDAC1 IC50 (nM) | 418 |
| HDAC3 IC50 (nM) | 308 |
| Chemical_name | N-(6-(2-aminophenylamino)-6-oxohexyl)benzofuran-2-carboxamide |
| LC/MS Calc'd (M + H) | 366.4 |
| LC/MS Obsv'd (M + H) | 366.1 |

TABLE 6-continued

Activity of Additional HDAC3 Inhibitors

Record 54

Structure 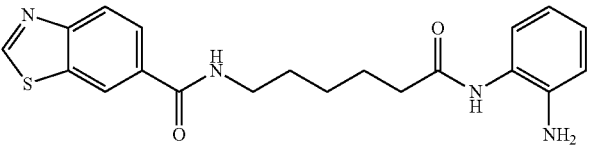 [SMILES: Nc1ccccc1NC(=O)CCCCCNC(=O)c1ccc2ncsc2c1]

| | |
|---|---|
| Comp id | R172 |
| HDAC1 IC50 (nM) | 433 |
| HDAC3 IC50 (nM) | 326 |
| Chemical_name | N-(6-(2-aminophenylamino)-6-oxohexyl)benzo[d]thiazole-6-carboxamide |
| LC/MS Calc'd (M + H) | 383.5 |
| LC/MS Obsv'd (M + H) | 383.2 |

Record 55

Structure 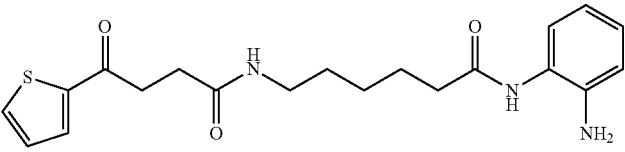 [SMILES: Nc1ccccc1NC(=O)CCCCCNC(=O)CCC(=O)c1cccs1]

| | |
|---|---|
| Comp id | R173 |
| HDAC1 IC50 (nM) | 780 |
| HDAC3 IC50 (nM) | 694 |
| Chemical_name | N-(2-aminophenyl)-6-(4-oxo-4-(thiophen-2-yl)butanamido)hexanamide |
| LC/MS Calc'd (M + H) | 388.5 |
| LC/MS Obsv'd (M + H) | 388 |

Record 56

Structure 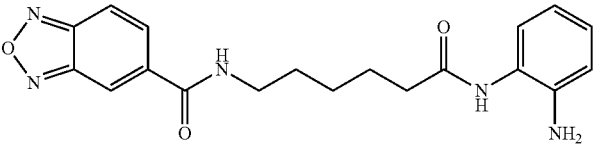 [SMILES: Nc1ccccc1NC(=O)CCCCCNC(=O)c1ccc2nonc2c1]

| | |
|---|---|
| Comp id | R174 |
| HDAC1 IC50 (nM) | 1238 |
| HDAC3 IC50 (nM) | 1153 |
| Chemical_name | N-(6-(2-aminophenylamino)-6-oxohexyl)benzo[c][1,2,5]oxadiazole-5-carboxamide |
| LC/MS Calc'd (M + H) | 368.4 |
| LC/MS Obsv'd (M + H) | 368.2 |

Record 57

Structure 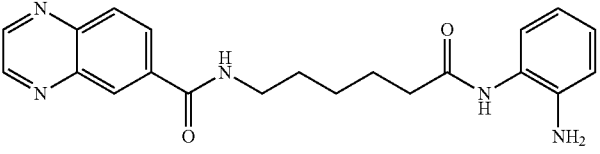 [SMILES: Nc1ccccc1NC(=O)CCCCCNC(=O)c1ccc2nccnc2c1]

| | |
|---|---|
| Comp id | R175 |
| HDAC1 IC50 (nM) | 1027 |
| HDAC3 IC50 (nM) | 841 |
| Chemical_name | N-(6-(2-aminophenylamino)-6-oxohexyl)quinoxaline-6-carboxamide |
| LC/MS Calc'd (M + H) | 378.4 |
| LC/MS Obsv'd (M + H) | 378.3 |

TABLE 6-continued

Activity of Additional HDAC3 Inhibitors

Record 58

Structure 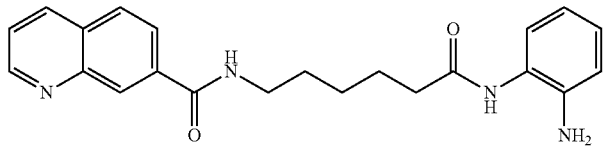 [SMILES: Nc1ccccc1NC(=O)CCCCCNC(=O)c1ccc2cccnc2c1]

| | |
|---|---|
| Comp id | R176 |
| HDAC1 IC50 (nM) | 617 |
| HDAC3 IC50 (nM) | 946 |
| Chemical_name | N-(6-(2-aminophenylamino)-6-oxohexyl)quinoline-7-carboxamide |
| LC/MS Calc'd (M + H) | 377.5 |
| LC/MS Obsv'd (M + H) | 377.1 |

Record 59

Structure 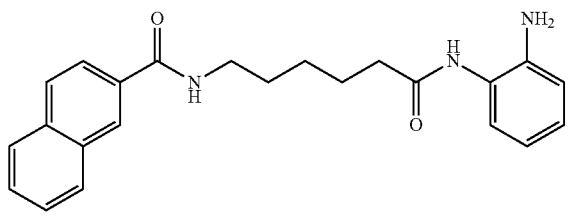 [SMILES: Nc1ccccc1NC(=O)CCCCCNC(=O)c1ccc2ccccc2c1]

| | |
|---|---|
| Comp id | R177 |
| HDAC1 IC50 (nM) | 187 |
| HDAC3 IC50 (nM) | 137 |
| Chemical_name | N-(6-(2-aminophenylamino)-6-oxohexyl)-2-naphthamide |
| LC/MS Calc'd (M + H) | 376.5 |
| LC/MS Obsv'd (M + H) | 376.1 |

Record 60

Structure 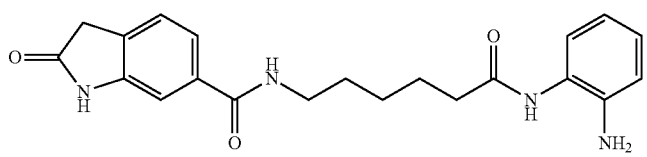 [SMILES: Nc1ccccc1NC(=O)CCCCCNC(=O)c1ccc2c(c1)NC(=O)C2]

| | |
|---|---|
| Comp id | R178 |
| HDAC1 IC50 (nM) | 725 |
| HDAC3 IC50 (nM) | 559 |
| Chemical_name | N-(6-(2-aminophenylamino)-6-oxohexyl)-2-oxoindoline-6-carboxamide |
| LC/MS Calc'd (M + H) | 381.4 |
| LC/MS Obsv'd (M + H) | 381.1 |

TABLE 6-continued

Activity of Additional HDAC3 Inhibitors

Record 61

Structure 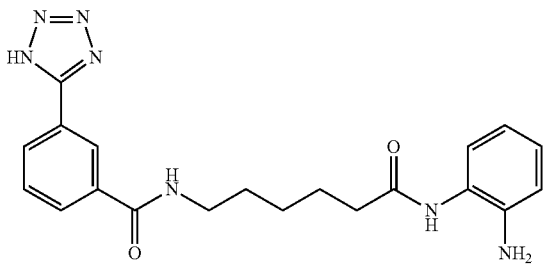 [SMILES: Nc1ccccc1NC(=O)CCCCCNC(=O)c1cccc(-c2nnn[nH]2)c1]

| | |
|---|---|
| Comp id | R179 |
| HDAC1 IC50 (nM) | 466 |
| HDAC3 IC50 (nM) | 900 |
| Chemical_name | N-(6-(2-aminophenylamino)-6-oxohexyl)-3-(1H-tetrazol-5-yl)benzamide |
| LC/MS Calc'd (M + H) | 394.4 |
| LC/MS Obsv'd (M + H) | 394.1 |

Record 62

Structure 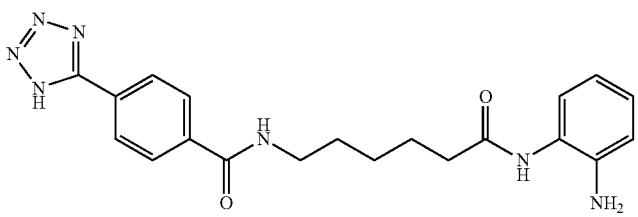 [SMILES: Nc1ccccc1NC(=O)CCCCCNC(=O)c1ccc(-c2nnn[nH]2)cc1]

| | |
|---|---|
| Comp id | R180 |
| HDAC1 IC50 (nM) | 371 |
| HDAC3 IC50 (nM) | 1130 |
| Chemical_name | N-(6-(2-aminophenylamino)-6-oxohexyl)-4-(1H-tetrazol-5-yl)benzamide |
| LC/MS Calc'd (M + H) | 394.4 |
| LC/MS Obsv'd (M + H) | 394 |

Record 63

Structure 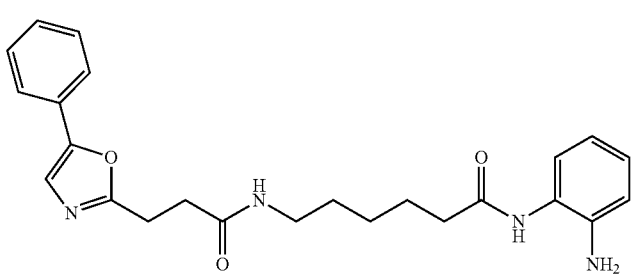 [SMILES: Nc1ccccc1NC(=O)CCCCCNC(=O)CCc1ncc(-c2ccccc2)o1]

| | |
|---|---|
| Comp id | R181 |
| HDAC1 IC50 (nM) | 312 |
| HDAC3 IC50 (nM) | 284 |
| Chemical_name | N-(2-aminophenyl)-6-(3-(5-phenyloxazol-2-yl)propanamido)hexanamide |
| LC/MS Calc'd (M + H) | 421.5 |
| LC/MS Obsv'd (M + H) | 421.1 |

TABLE 6-continued

Activity of Additional HDAC3 Inhibitors

Record 64

Structure 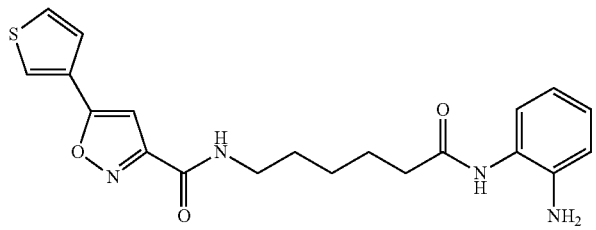 [SMILES: Nc1ccccc1NC(=O)CCCCCNC(=O)c1cc(-c2ccsc2)on1]

| | |
|---|---|
| Comp id | R182 |
| HDAC1 IC50 (nM) | 484 |
| HDAC3 IC50 (nM) | 752 |
| Chemical_name | N-(6-(2-aminophenylamino)-6-oxohexyl)-5-(thiophen-3-yl)isoxazole-3-carboxamide |
| LC/MS Calc'd (M + H) | 399.5 |
| LC/MS Obsv'd (M + H) | 399.1 |

Record 65

Structure 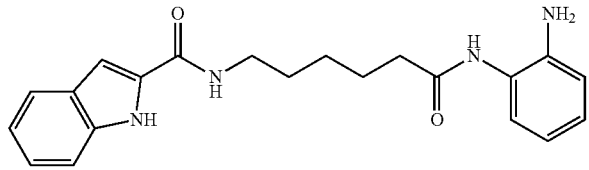 [SMILES: Nc1ccccc1NC(=O)CCCCCNC(=O)c1cc2ccccc2[nH]1]

| | |
|---|---|
| Comp id | R183 |
| HDAC1 IC50 (nM) | 95 |
| HDAC3 IC50 (nM) | 33 |
| Chemical_name | N-(6-(2-aminophenylamino)-6-oxohexyl)-1H-indole-2-carboxamide |
| LC/MS Calc'd (M + H) | 365.4 |
| LC/MS Obsv'd (M + H) | 365.1 |

Record 66

Structure 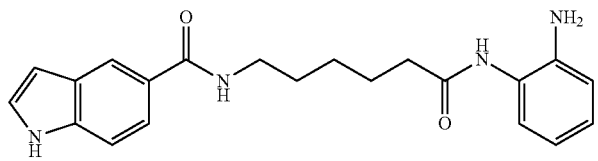 [SMILES: Nc1ccccc1NC(=O)CCCCCNC(=O)c1ccc2[nH]ccc2c1]

| | |
|---|---|
| Comp id | R184 |
| HDAC1 IC50 (nM) | 105 |
| HDAC3 IC50 (nM) | 57 |
| Chemical_name | N-(6-(2-aminophenylamino)-6-oxohexyl)-1H-indole-5-carboxamide |
| LC/MS Calc'd (M + H) | 365.4 |
| LC/MS Obsv'd (M + H) | 365.1 |

Record 67

Structure 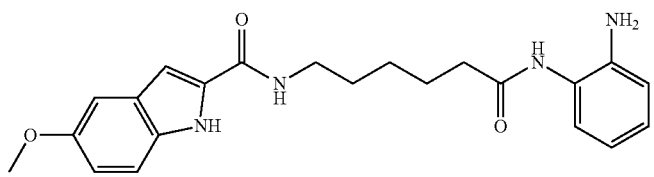 [SMILES: COc1ccc2[nH]c(C(=O)NCCCCCC(=O)Nc3ccccc3N)cc2c1]

| | |
|---|---|
| Comp id | R185 |
| HDAC1 IC50 (nM) | 258 |
| HDAC3 IC50 (nM) | 31 |
| Chemical_name | N-(6-(2-aminophenylamino)-6-oxohexyl)-5-methoxy-1H-indole-2-carboxamide |
| LC/MS Calc'd (M + H) | 395.5 |
| LC/MS Obsv'd (M + H) | 395.1 |

TABLE 6-continued

Activity of Additional HDAC3 Inhibitors

Record 68

Structure 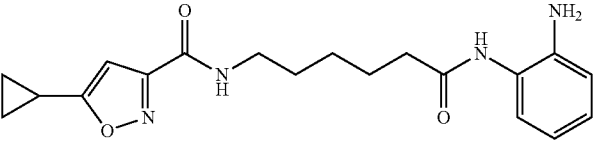 [SMILES: Nc1ccccc1NC(=O)CCCCCNC(=O)c1cc(C2CC2)on1]

| | |
|---|---|
| Comp id | R186 |
| HDAC1 IC50 (nM) | 673 |
| HDAC3 IC50 (nM) | 190 |
| Chemical_name | N-(6-(2-aminophenylamino)-6-oxohexyl)-5-cyclopropylisoxazole-3-carboxamide |
| LC/MS Calc'd (M + H) | 357.4 |
| LC/MS Obsv'd (M + H) | 357.1 |

Record 69

Structure 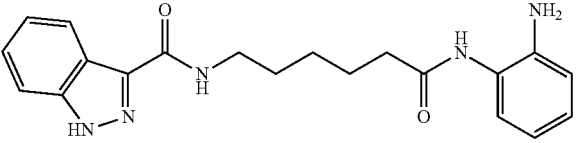 [SMILES: Nc1ccccc1NC(=O)CCCCCNC(=O)c1n[nH]c2ccccc12]

| | |
|---|---|
| Comp id | R187 |
| HDAC1 IC50 (nM) | 107 |
| HDAC3 IC50 (nM) | 92 |
| Chemical_name | N-(6-(2-aminophenylamino)-6-oxohexyl)-1H-indazole-3-carboxamide |
| LC/MS Calc'd (M + H) | 366.4 |
| LC/MS Obsv'd (M + H) | 366.1 |

Record 70

Structure 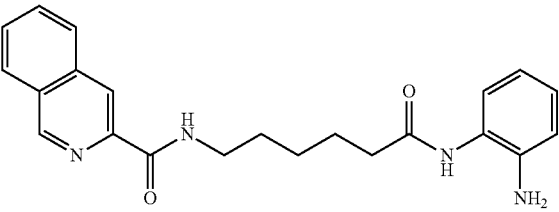 [SMILES: Nc1ccccc1NC(=O)CCCCCNC(=O)c1cc2ccccc2cn1]

| | |
|---|---|
| Comp id | R188 |
| HDAC1 IC50 (nM) | 264 |
| HDAC3 IC50 (nM) | 314 |
| Chemical_name | N-(6-(2-aminophenylamino)-6-oxohexyl)isoquinoline-3-carboxamide |
| LC/MS Calc'd (M + H) | 377.5 |
| LC/MS Obsv'd (M + H) | 377.1 |

Record 71

Structure 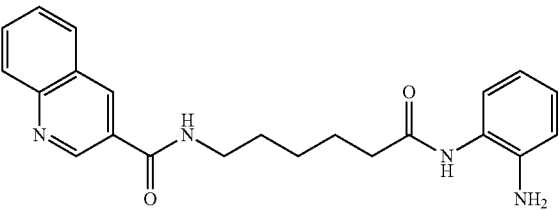 [SMILES: Nc1ccccc1NC(=O)CCCCCNC(=O)c1cnc2ccccc2c1]

| | |
|---|---|
| Comp id | R189 |
| HDAC1 IC50 (nM) | 479 |
| HDAC3 IC50 (nM) | 424 |
| Chemical_name | N-(6-(2-aminophenylamino)-6-oxohexyl)quinoline-3-carboxamide |
| LC/MS Calc'd (M + H) | 377.5 |
| LC/MS Obsv'd (M + H) | 377.1 |

TABLE 6-continued

Activity of Additional HDAC3 Inhibitors

Record 72

Structure 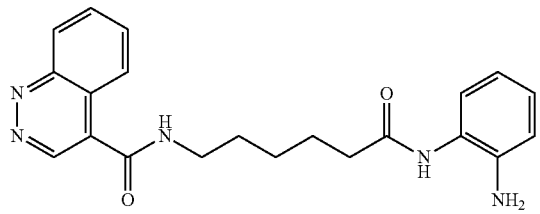 [SMILES: Nc1ccccc1NC(=O)CCCCCNC(=O)c1cnnc2ccccc12]

| | |
|---|---|
| Comp id | R190 |
| HDAC1 IC50 (nM) | 4312 |
| HDAC3 IC50 (nM) | 1940 |
| Chemical_name | N-(6-(2-aminophenylamino)-6-oxohexyl)cinnoline-4-carboxamide |
| LC/MS Calc'd (M + H) | 378.4 |
| LC/MS Obsv'd (M + H) | 378.1 |

Record 73

Structure 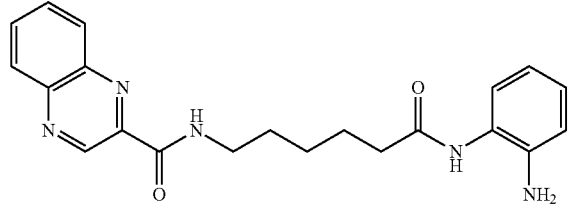

| | |
|---|---|
| Comp id | R191 |
| HDAC1 IC50 (nM) | 388 |
| HDAC3 IC50 (nM) | 456 |
| Chemical_name | N-(6-(2-aminophenylamino)-6-oxohexyl)quinoxaline-2-carboxamide |
| LC/MS Calc'd (M + H) | 378.4 |
| LC/MS Obsv'd (M + H) | 378.1 |

Record 74

Structure 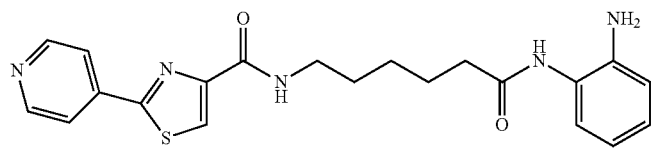 [SMILES: Nc1ccccc1NC(=O)CCCCCNC(=O)c1csc(-c2ccncc2)n1]

| | |
|---|---|
| Comp id | R192 |
| HDAC1 IC50 (nM) | 300 |
| HDAC3 IC50 (nM) | 100 |
| Chemical_name | N-(6-(2-aminophenylamino)-6-oxohexyl)-2-(pyridin-4-yl)thiazole-4-carboxamide |
| LC/MS Calc'd (M + H) | 410.5 |
| LC/MS Obsv'd (M + H) | 410 |

TABLE 6-continued

Activity of Additional HDAC3 Inhibitors

Record 75

Structure 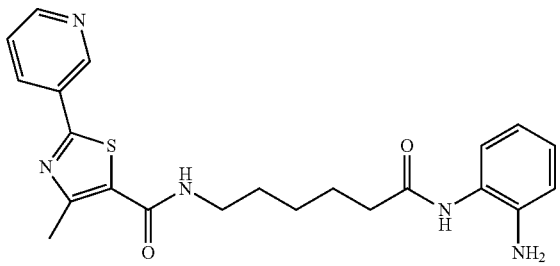 [SMILES: Cc1nc(-c2cccnc2)sc1C(=O)NCCCCCC(=O)Nc1ccccc1N]

| | |
|---|---|
| Comp id | R193 |
| HDAC1 IC50 (nM) | 352 |
| HDAC3 IC50 (nM) | 856 |
| Chemical_name | N-(6-(2-aminophenylamino)-6-oxohexyl)-4-methyl-2-(pyridin-3-yl)thiazole-5-carboxamide |
| LC/MS Calc'd (M + H) | 424.5 |
| LC/MS Obsv'd (M + H) | 424 |

Record 76

Structure 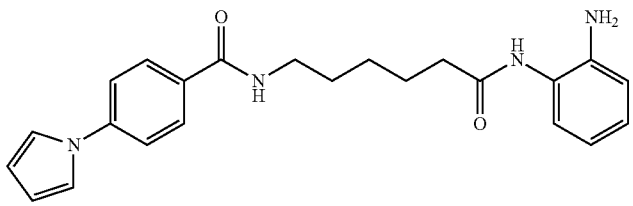 [SMILES: Nc1ccccc1NC(=O)CCCCCNC(=O)c1ccc(-n2cccc2)cc1]

| | |
|---|---|
| Comp id | R194 |
| HDAC1 IC50 (nM) | 258 |
| HDAC3 IC50 (nM) | 185 |
| Chemical_name | N-(6-(2-aminophenylamino)-6-oxohexyl)-4-(1H-pyrrol-1-yl)benzamide |
| LC/MS Calc'd (M + H) | 391.5 |
| LC/MS Obsv'd (M + H) | 391.1 |

Record 77

Structure 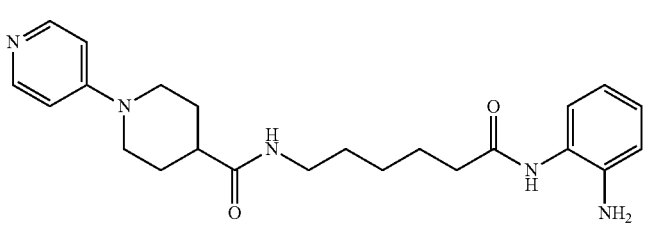 [SMILES: Nc1ccccc1NC(=O)CCCCCNC(=O)C1CCN(c2ccncc2)CC1]

| | |
|---|---|
| Comp id | R195 |
| HDAC1 IC50 (nM) | 1725 |
| HDAC3 IC50 (nM) | 955 |
| Chemical_name | N-(6-(2-aminophenylamino)-6-oxohexyl)-1-(pyridin-4-yl)piperidine-4-carboxamide |
| LC/MS Calc'd (M + H) | 410.5 |
| LC/MS Obsv'd (M + H) | 410.1 |

TABLE 6-continued

Activity of Additional HDAC3 Inhibitors

Record 78

Structure

| | |
|---|---|
| Comp id | R196 |
| HDAC1 IC50 (nM) | 483 |
| HDAC3 IC50 (nM) | 185 |
| Chemical_name | N-(6-(2-aminophenylamino)-6-oxohexyl)-4-methyl-2-(pyridin-2-yl)thiazole-5-carboxamide |
| LC/MS Calc'd (M + H) | 424.5 |
| LC/MS Obsv'd (M + H) | 424 |

Record 79

Structure

| | |
|---|---|
| Comp id | R197 |
| HDAC1 IC50 (nM) | 38950 |
| HDAC3 IC50 (nM) | 6954 |
| Chemical_name | N-(5-(2-aminophenylamino)-5-oxopentyl)-5-methylthiazole-2-carboxamide |
| LC/MS Calc'd (M + H) | 333.4 |
| LC/MS Obsv'd (M + H) | 333 |

Record 80

Structure

| | |
|---|---|
| Comp id | R198 |
| HDAC1 IC50 (nM) | 25070 |
| HDAC3 IC50 (nM) | 9191 |
| Chemical_name | N-(5-(2-aminophenylamino)-5-oxopentyl)-2,6-dimethoxynicotinamide |
| LC/MS Calc'd (M + H) | 373.4 |
| LC/MS Obsv'd (M + H) | 373.1 |

Record 81

Structure

| | |
|---|---|
| Comp id | R199 |
| HDAC1 IC50 (nM) | 18910 |
| HDAC3 IC50 (nM) | 11950 |
| Chemical_name | N-(5-(2-aminophenylamino)-5-oxopentyl)-4-(methylsulfonyl)benzamide |
| LC/MS Calc'd (M + H) | 390.5 |
| LC/MS Obsv'd (M + H) | 390 |

TABLE 6-continued

Activity of Additional HDAC3 Inhibitors

Record 82

Structure 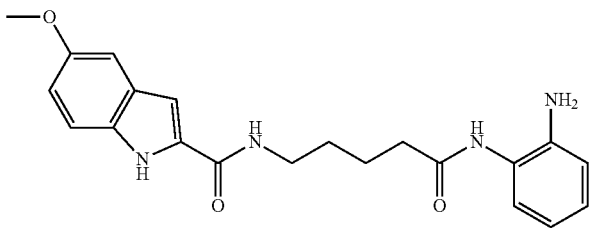 [SMILES: COc1ccc2[nH]c(C(=O)NCCCCC(=O)Nc3ccccc3N)cc2c1]

| | |
|---|---|
| Comp id | R200 |
| HDAC1 IC50 (nM) | 3709 |
| HDAC3 IC50 (nM) | 878 |
| Chemical_name | N-(5-(2-aminophenylamino)-5-oxopentyl)-5-methoxy-1H-indole-2-carboxamide |
| LC/MS Calc'd (M + H) | 381.4 |
| LC/MS Obsv'd (M + H) | 381.1 |

Record 83

Structure 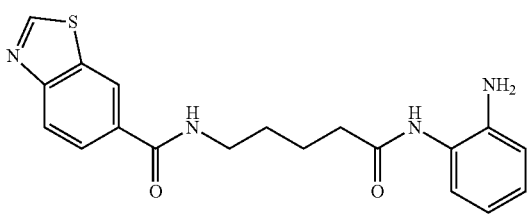 [SMILES: Nc1ccccc1NC(=O)CCCCNC(=O)c1ccc2ncsc2c1]

| | |
|---|---|
| Comp id | R201 |
| HDAC1 IC50 (nM) | 11390 |
| HDAC3 IC50 (nM) | 8608 |
| Chemical_name | N-(5-(2-aminophenylamino)-5-oxopentyl)benzo[d]thiazole-6-carboxamide |
| LC/MS Calc'd (M + H) | 369.5 |
| LC/MS Obsv'd (M + H) | 369 |

Record 84

Structure 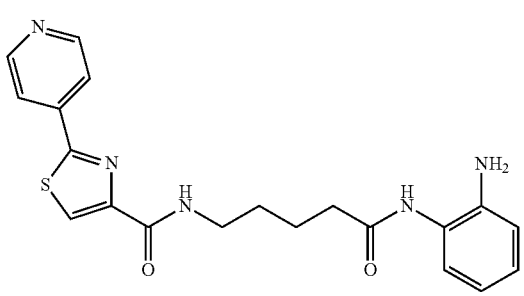 [SMILES: Nc1ccccc1NC(=O)CCCCNC(=O)c1csc(-c2ccncc2)n1]

| | |
|---|---|
| Comp id | R202 |
| HDAC1 IC50 (nM) | 2766 |
| HDAC3 IC50 (nM) | 829 |
| Chemical_name | N-(5-(2-aminophenylamino)-5-oxopentyl)-2-(pyridin-4-yl)thiazole-4-carboxamide |
| LC/MS Calc'd (M + H) | 396.5 |
| LC/MS Obsv'd (M + H) | 396 |

TABLE 6-continued

Activity of Additional HDAC3 Inhibitors

Record 85

Structure  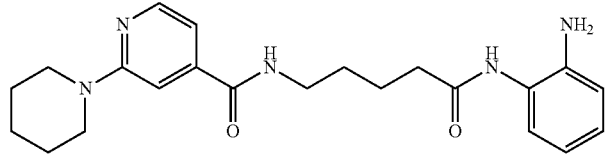 [SMILES: Nc1ccccc1NC(=O)CCCCNC(=O)c1ccnc(N2CCCCC2)c1]

| | |
|---|---|
| Comp id | R203 |
| HDAC1 IC50 (nM) | 18240 |
| HDAC3 IC50 (nM) | 7455 |
| Chemical_name | N-(5-(2-aminophenylamino)-5-oxopentyl)-2-(piperidin-1-yl)isonicotinamide |
| LC/MS Calc'd (M + H) | 396.5 |
| LC/MS Obsv'd (M + H) | 396.1 |

Record 86

Structure  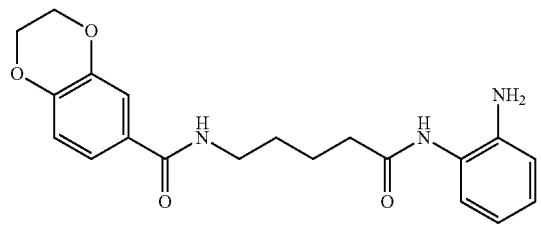 [SMILES: Nc1ccccc1NC(=O)CCCCNC(=O)c1ccc2c(c1)OCCO2]

| | |
|---|---|
| Comp id | R204 |
| HDAC1 IC50 (nM) | 4615 |
| HDAC3 IC50 (nM) | 1931 |
| Chemical_name | N-(5-(2-aminophenylamino)-5-oxopentyl)-2,3-dihydrobenzo[b][1,4]dioxine-6-carboxamide |
| LC/MS Calc'd (M + H) | 370.4 |
| LC/MS Obsv'd (M + H) | 370.1 |

Record 87

Structure  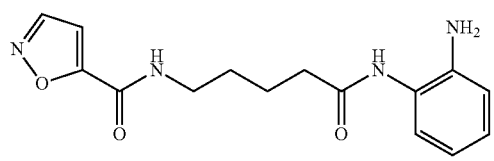 [SMILES: Nc1ccccc1NC(=O)CCCCNC(=O)c1ccno1]

| | |
|---|---|
| Comp id | R205 |
| HDAC1 IC50 (nM) | 32850 |
| HDAC3 IC50 (nM) | 21420 |
| Chemical_name | N-(5-(2-aminophenylamino)-5-oxopentyl)isoxazole-5-carboxamide |
| LC/MS Calc'd (M + H) | 303.3 |
| LC/MS Obsv'd (M + H) | 303.1 |

TABLE 6-continued

Activity of Additional HDAC3 Inhibitors

Record 88

Structure

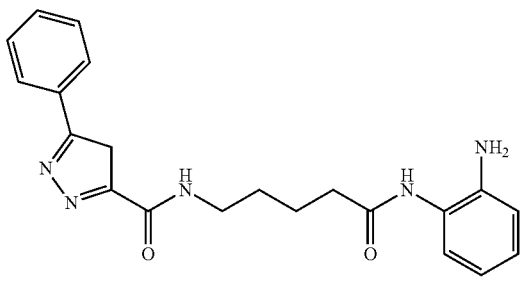 [SMILES: Nc1ccccc1NC(=O)CCCCNC(=O)C1=NN=C(c2ccccc2)C1]

| | |
|---|---|
| Comp id | R206 |
| HDAC1 IC50 (nM) | 2026 |
| HDAC3 IC50 (nM) | 1303 |
| Chemical_name | N-(5-(2-aminophenylamino)-5-oxopentyl)-5-phenyl-4H-pyrazole-3-carboxamide |
| LC/MS Calc'd (M + H) | 378.4 |
| LC/MS Obsv'd (M + H) | 378.1 |

Record 89

Structure

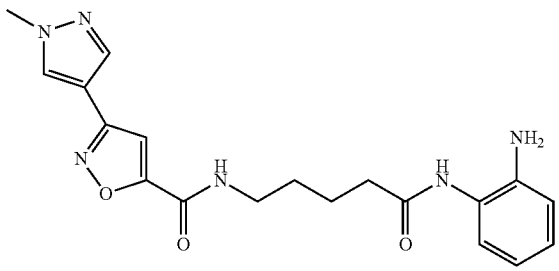 [SMILES: Cn1cc(-c2cc(C(=O)NCCCCC(=O)Nc3ccccc3N)on2)cn1]

| | |
|---|---|
| Comp id | R207 |
| HDAC1 IC50 (nM) | 7274 |
| HDAC3 IC50 (nM) | 6383 |
| Chemical_name | N-(5-(2-aminophenylamino)-5-oxopentyl)-3-(1-methyl-1H-pyrazol-4-yl)isoxazole-5-carboxamide |
| LC/MS Calc'd (M + H) | 383.4 |
| LC/MS Obsv'd (M + H) | 383.1 |

Record 90

Structure

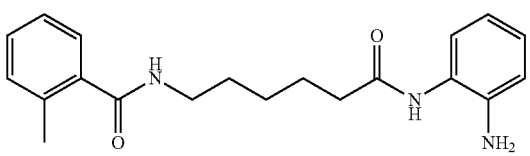 [SMILES: Cc1ccccc1C(=O)NCCCCCC(=O)Nc1ccccc1N]

| | |
|---|---|
| Comp id | R08 |
| HDAC1 IC50 (nM) | |
| HDAC3 IC50 (nM) | 716 |
| Chemical_name | N-(6-(2-aminophenylamino)-6-oxohexyl)-2-methylbenzamide |
| LC/MS Calc'd (M + H) | 340.4 |
| LC/MS Obsv'd (M + H) | 340.2 |

TABLE 6-continued

Activity of Additional HDAC3 Inhibitors

Record 91

Structure 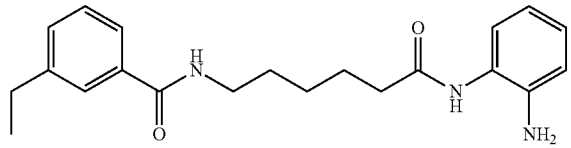 [SMILES: CCc1cccc(C(=O)NCCCCCC(=O)Nc2ccccc2N)c1]

| | |
|---|---|
| Comp id | R09 |
| HDAC1 IC50 (nM) | |
| HDAC3 IC50 (nM) | 121 |
| Chemical_name | N-(6-(2-aminophenylamino)-6-oxohexyl)-3-ethylbenzamide |
| LC/MS Calc'd (M + H) | 354.5 |
| LC/MS Obsv'd (M + H) | 354.2 |

Record 92

Structure 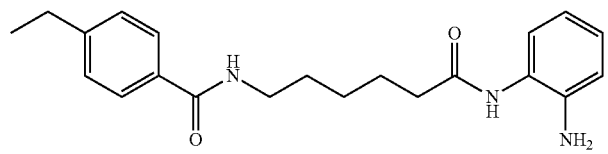 [SMILES: CCc1ccc(C(=O)NCCCCCC(=O)Nc2ccccc2N)cc1]

| | |
|---|---|
| Comp id | R10 |
| HDAC1 IC50 (nM) | |
| HDAC3 IC50 (nM) | 183 |
| Chemical_name | N-(6-(2-aminophenylamino)-6-oxohexyl)-4-ethylbenzamide |
| LC/MS Calc'd (M + H) | 354.5 |
| LC/MS Obsv'd (M + H) | 354.2 |

Record 93

Structure 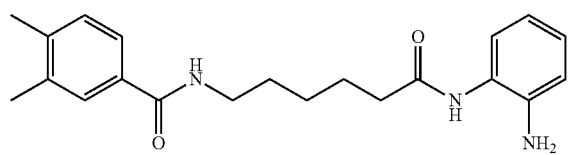 [SMILES: Cc1ccc(C(=O)NCCCCCC(=O)Nc2ccccc2N)cc1C]

| | |
|---|---|
| Comp id | R11 |
| HDAC1 IC50 (nM) | |
| HDAC3 IC50 (nM) | 144 |
| Chemical_name | N-(6-(2-aminophenylamino)-6-oxohexyl)-3,4-dimethylbenzamide |
| LC/MS Calc'd (M + H) | 354.5 |
| LC/MS Obsv'd (M + H) | 354.2 |

Record 94

Structure 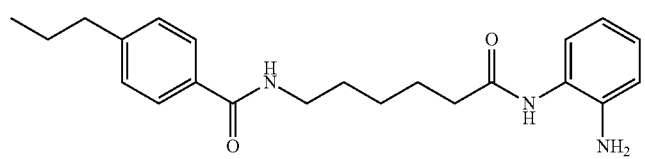 [SMILES: CCCc1ccc(C(=O)NCCCCCC(=O)Nc2ccccc2N)cc1]

| | |
|---|---|
| Comp id | R12 |
| HDAC1 IC50 (nM) | |
| HDAC3 IC50 (nM) | 127 |
| Chemical_name | N-(6-(2-aminophenylamino)-6-oxohexyl)-4-propylbenzamide |
| LC/MS Calc'd (M + H) | 368.5 |
| LC/MS Obsv'd (M + H) | 368.2 |

TABLE 6-continued

Activity of Additional HDAC3 Inhibitors

Record 95

Structure 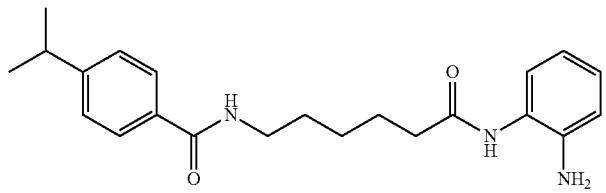 [SMILES: CC(C)c1ccc(C(=O)NCCCCCC(=O)Nc2ccccc2N)cc1]

| | |
|---|---|
| Comp id | R13 |
| HDAC1 IC50 (nM) | |
| HDAC3 IC50 (nM) | 147 |
| Chemical_name | N-(6-(2-aminophenylamino)-6-oxohexyl)-4-isopropylbenzamide |
| LC/MS Calc'd (M + H) | 368.5 |
| LC/MS Obsv'd (M + H) | 368.2 |

Record 96

Structure 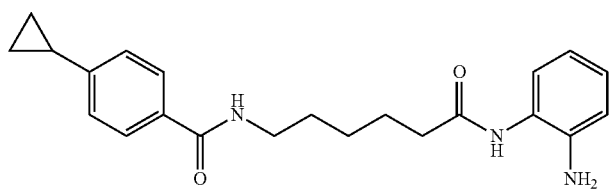 [SMILES: Nc1ccccc1NC(=O)CCCCCNC(=O)c1ccc(C2CC2)cc1]

| | |
|---|---|
| Comp id | R14 |
| HDAC1 IC50 (nM) | |
| HDAC3 IC50 (nM) | 104 |
| Chemical_name | N-(6-(2-aminophenylamino)-6-oxohexyl)-4-cyclopropylbenzamide |
| LC/MS Calc'd (M + H) | 366.5 |
| LC/MS Obsv'd (M + H) | 366.2 |

Record 97

Structure 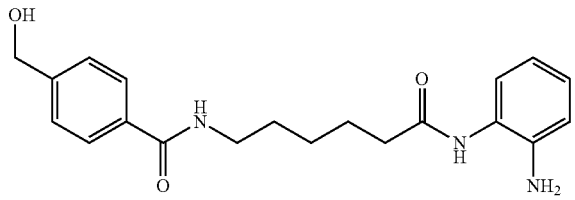 [SMILES: Nc1ccccc1NC(=O)CCCCCNC(=O)c1ccc(CO)cc1]

| | |
|---|---|
| Comp id | R15 |
| HDAC1 IC50 (nM) | |
| HDAC3 IC50 (nM) | 315 |
| Chemical_name | N-(6-(2-aminophenylamino)-6-oxohexyl)-4-(hydroxymethyl)benzamide |
| LC/MS Calc'd (M + H) | 356.4 |
| LC/MS Obsv'd (M + H) | 356.2 |

Record 98

Structure 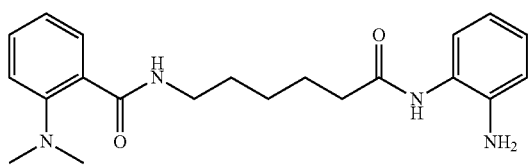 [SMILES: CN(C)c1ccccc1C(=O)NCCCCCC(=O)Nc1ccccc1N]

| | |
|---|---|
| Comp id | R16 |
| HDAC1 IC50 (nM) | |
| HDAC3 IC50 (nM) | 387 |
| Chemical_name | N-(6-(2-aminophenylamino)-6-oxohexyl)-2-(dimethylamino)benzamide |
| LC/MS Calc'd (M + H) | 369.5 |
| LC/MS Obsv'd (M + H) | 369.2 |

TABLE 6-continued

Activity of Additional HDAC3 Inhibitors

Record 99

Structure 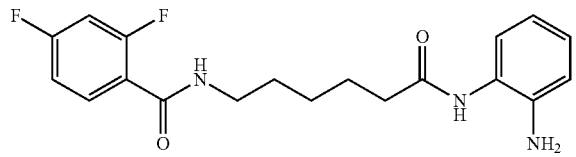 [SMILES: Nc1ccccc1NC(=O)CCCCCNC(=O)c1ccc(F)cc1F]

| | |
|---|---|
| Comp id | R17 |
| HDAC1 IC50 (nM) | |
| HDAC3 IC50 (nM) | 486 |
| Chemical_name | N-(6-(2-aminophenylamino)-6-oxohexyl)-2,4-difluorobenzamide |
| LC/MS Calc'd (M + H) | 362.4 |
| LC/MS Obsv'd (M + H) | 362.1 |

Record 100

Structure 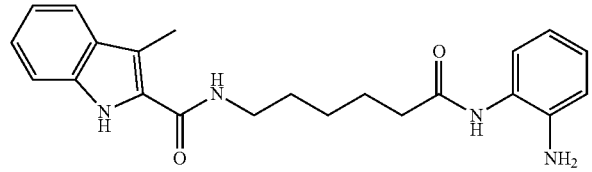 [SMILES: Cc1c(C(=O)NCCCCCC(=O)Nc2ccccc2N)[nH]c2ccccc12]

| | |
|---|---|
| Comp id | R18 |
| HDAC1 IC50 (nM) | 371 |
| HDAC3 IC50 (nM) | 40 |
| Chemical_name | N-(6-(2-aminophenylamino)-6-oxohexyl)-3-methyl-1H-indole-2-carboxamide |
| LC/MS Calc'd (M + H) | 379.5 |
| LC/MS Obsv'd (M + H) | 379.2 |

Record 101

Structure 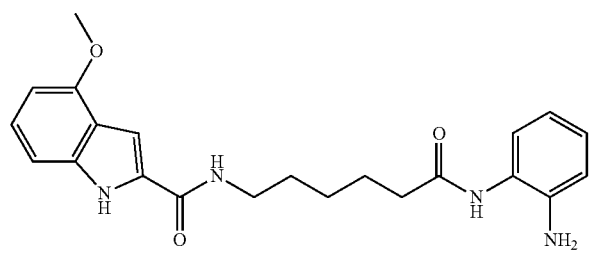 [SMILES: COc1cccc2[nH]c(C(=O)NCCCCCC(=O)Nc3ccccc3N)cc12]

| | |
|---|---|
| Comp id | R19 |
| HDAC1 IC50 (nM) | 299 |
| HDAC3 IC50 (nM) | 36 |
| Chemical_name | N-(6-(2-aminophenylamino)-6-oxohexyl)-4-methoxy-1H-indole-2-carboxamide |
| LC/MS Calc'd (M + H) | 395.5 |
| LC/MS Obsv'd (M + H) | 395.2 |

TABLE 6-continued

Activity of Additional HDAC3 Inhibitors

Record 102

Structure

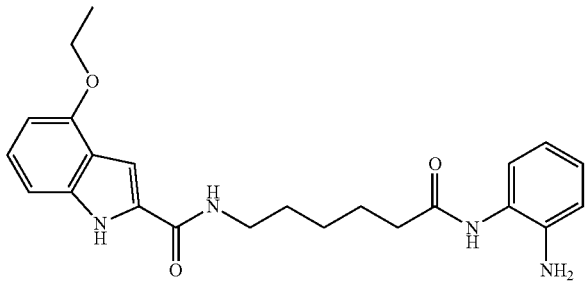 [SMILES: CCOc1cccc2[nH]c(C(=O)NCCCCCC(=O)Nc3ccccc3N)cc12]

| | |
|---|---|
| Comp id | R20 |
| HDAC1 IC50 (nM) | 262 |
| HDAC3 IC50 (nM) | 72 |
| Chemical_name | N-(6-(2-aminophenylamino)-6-oxohexyl)-4-ethoxy-1H-indole-2-carboxamide |
| LC/MS Calc'd (M + H) | 409.5 |
| LC/MS Obsv'd (M + H) | 409.2 |

Record 103

Structure

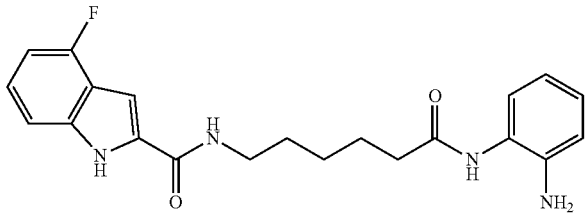

| | |
|---|---|
| Comp id | R21 |
| HDAC1 IC50 (nM) | 436 |
| HDAC3 IC50 (nM) | 60 |
| Chemical_name | N-(6-(2-aminophenylamino)-6-oxohexyl)-4-fluoro-1H-indole-2-carboxamide |
| LC/MS Calc'd (M + H) | 383.4 |
| LC/MS Obsv'd (M + H) | 383.2 |

Record 104

Structure

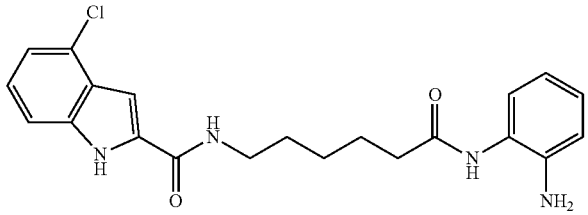 [SMILES: Nc1ccccc1NC(=O)CCCCCNC(=O)c1cc2c(Cl)cccc2[nH]1]

| | |
|---|---|
| Comp id | R22 |
| HDAC1 IC50 (nM) | 254 |
| HDAC3 IC50 (nM) | 28 |
| Chemical_name | N-(6-(2-aminophenylamino)-6-oxohexyl)-4-chloro-1H-indole-2-carboxamide |
| LC/MS Calc'd (M + H) | 399.9 |
| LC/MS Obsv'd (M + H) | 399.1 |

TABLE 6-continued

Activity of Additional HDAC3 Inhibitors

Record 105

Structure 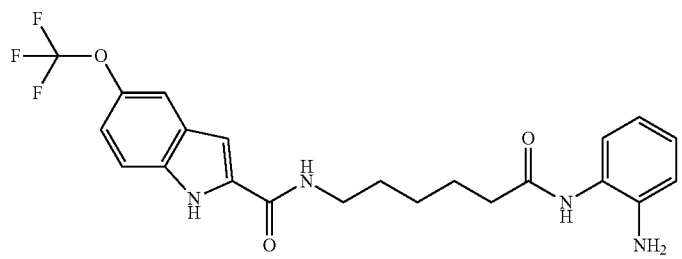 [SMILES: Nc1ccccc1NC(=O)CCCCCNC(=O)c1cc2cc(OC(F)(F)F)ccc2[nH]1]

| | |
|---|---|
| Comp id | R23 |
| HDAC1 IC50 (nM) | 550 |
| HDAC3 IC50 (nM) | 20 |
| Chemical_name | N-(6-(2-aminophenylamino)-6-oxohexyl)-5-(trifluoromethoxy)-1H-indole-2-carboxamide |
| LC/MS Calc'd (M + H) | 449.4 |
| LC/MS Obsv'd (M + H) | 449.2 |

Record 106

Structure 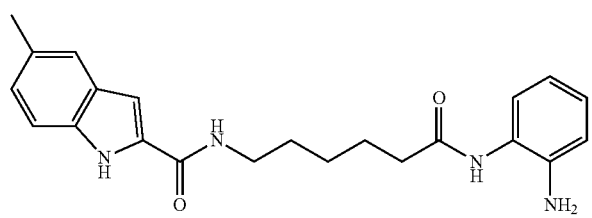 [SMILES: Cc1ccc2[nH]c(C(=O)NCCCCCC(=O)Nc3ccccc3N)cc2c1]

| | |
|---|---|
| Comp id | R24 |
| HDAC1 IC50 (nM) | 426 |
| HDAC3 IC50 (nM) | 27 |
| Chemical_name | N-(6-(2-aminophenylamino)-6-oxohexyl)-5-methyl-1H-indole-2-carboxamide |
| LC/MS Calc'd (M + H) | 379.5 |
| LC/MS Obsv'd (M + H) | 379.2 |

Record 107

Structure 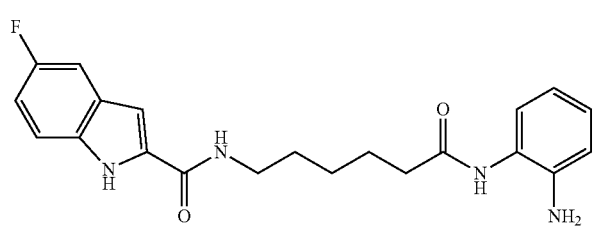 [SMILES: Nc1ccccc1NC(=O)CCCCCNC(=O)c1cc2cc(F)ccc2[nH]1]

| | |
|---|---|
| Comp id | R25 |
| HDAC1 IC50 (nM) | 384 |
| HDAC3 IC50 (nM) | 57 |
| Chemical_name | N-(6-(2-aminophenylamino)-6-oxohexyl)-5-fluoro-1H-indole-2-carboxamide |
| LC/MS Calc'd (M + H) | 383.4 |
| LC/MS Obsv'd (M + H) | 383.2 |

TABLE 6-continued

Activity of Additional HDAC3 Inhibitors

Record 108

Structure

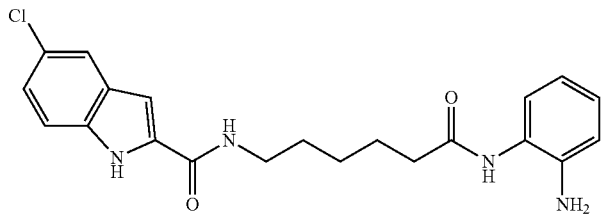 [SMILES: Nc1ccccc1NC(=O)CCCCCNC(=O)c1cc2cc(Cl)ccc2[nH]1]

| | |
|---|---|
| Comp id | R26 |
| HDAC1 IC50 (nM) | 203 |
| HDAC3 IC50 (nM) | 20 |
| Chemical_name | N-(6-(2-aminophenylamino)-6-oxohexyl)-5-chloro-1H-indole-2-carboxamide |
| LC/MS Calc'd (M + H) | 399.9 |
| LC/MS Obsv'd (M + H) | 399.1 |

Record 109

Structure

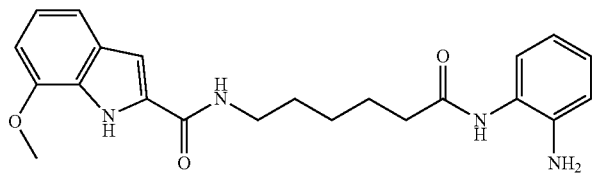 [SMILES: COc1cccc2cc(C(=O)NCCCCCC(=O)Nc3ccccc3N)[nH]c12]

| | |
|---|---|
| Comp id | R27 |
| HDAC1 IC50 (nM) | 392 |
| HDAC3 IC50 (nM) | 55 |
| Chemical_name | N-(6-(2-aminophenylamino)-6-oxohexyl)-7-methoxy-1H-indole-2-carboxamide |
| LC/MS Calc'd (M + H) | 395.5 |
| LC/MS Obsv'd (M + H) | 395.2 |

Record 110

Structure

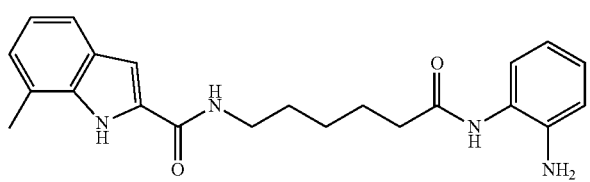

| | |
|---|---|
| Comp id | R28 |
| HDAC1 IC50 (nM) | 59 |
| HDAC3 IC50 (nM) | 32 |
| Chemical_name | N-(6-(2-aminophenylamino)-6-oxohexyl)-7-methyl-1H-indole-2-carboxamide |
| LC/MS Calc'd (M + H) | 379.5 |
| LC/MS Obsv'd (M + H) | 379.2 |

TABLE 6-continued

Activity of Additional HDAC3 Inhibitors

Record 111

Structure

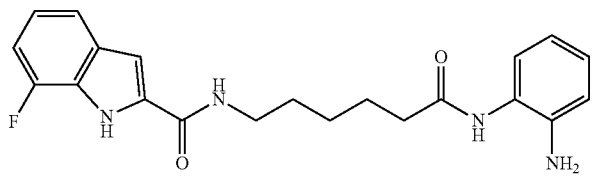 [SMILES: Nc1ccccc1NC(=O)CCCCCNC(=O)c1cc2cccc(F)c2[nH]1]

| | |
|---|---|
| Comp id | R29 |
| HDAC1 IC50 (nM) | 79 |
| HDAC3 IC50 (nM) | 41 |
| Chemical_name | N-(6-(2-aminophenylamino)-6-oxohexyl)-7-fluoro-1H-indole-2-carboxamide |
| LC/MS Calc'd (M + H) | 383.4 |
| LC/MS Obsv'd (M + H) | 383.2 |

Record 112

Structure

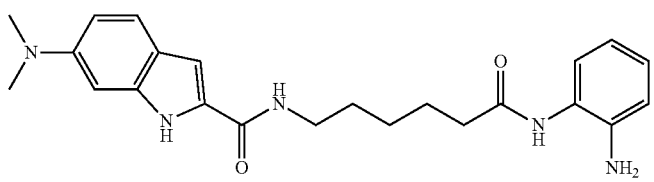

| | |
|---|---|
| Comp id | R30 |
| HDAC1 IC50 (nM) | 81 |
| HDAC3 IC50 (nM) | 115 |
| Chemical_name | N-(6-(2-aminophenylamino)-6-oxohexyl)-6-(dimethylamino)-1H-indole-2-carboxamide |
| LC/MS Calc'd (M + H) | 408.5 |
| LC/MS Obsv'd (M + H) | 408.2 |

Record 113

Structure

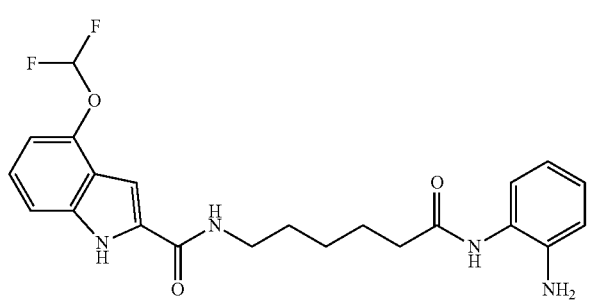 [SMILES: Nc1ccccc1NC(=O)CCCCCNC(=O)c1cc2c(OC(F)F)cccc2[nH]1]

| | |
|---|---|
| Comp id | R31 |
| HDAC1 IC50 (nM) | 41 |
| HDAC3 IC50 (nM) | 52 |
| Chemical_name | N-(6-(2-aminophenylamino)-6-oxohexyl)-4-(difluoromethoxy)-1H-indole-2-carboxamide |
| LC/MS Calc'd (M + H) | 431.4 |
| LC/MS Obsv'd (M + H) | 431.2 |

TABLE 6-continued

Activity of Additional HDAC3 Inhibitors

Record 114

Structure

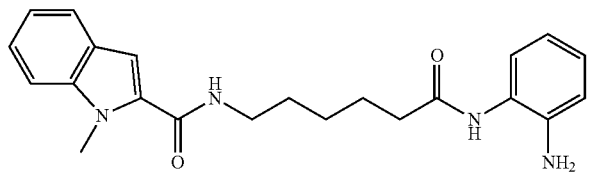 [SMILES: Cn1c(C(=O)NCCCCCC(=O)Nc2ccccc2N)cc2ccccc21]

| | |
|---|---|
| Comp id | R32 |
| HDAC1 IC50 (nM) | 135 |
| HDAC3 IC50 (nM) | 113 |
| Chemical_name | N-(6-(2-aminophenylamino)-6-oxohexyl)-1-methyl-1H-indole-2-carboxamide |
| LC/MS Calc'd (M + H) | 379.5 |
| LC/MS Obsv'd (M + H) | 379.2 |

Record 115

Structure

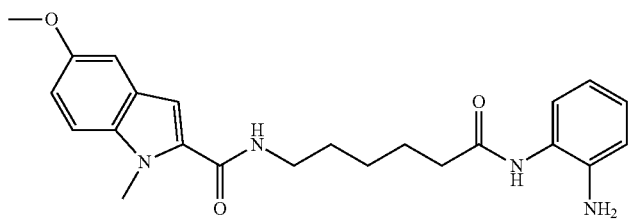 [SMILES: COc1ccc2c(c1)cc(C(=O)NCCCCCC(=O)Nc1ccccc1N)n2C]

| | |
|---|---|
| Comp id | R33 |
| HDAC1 IC50 (nM) | 95 |
| HDAC3 IC50 (nM) | 108 |
| Chemical_name | N-(6-(2-aminophenylamino)-6-oxohexyl)-5-methoxy-1-methyl-1H-indole-2-carboxamide |
| LC/MS Calc'd (M + H) | 409.5 |
| LC/MS Obsv'd (M + H) | 409.2 |

Record 116

Structure

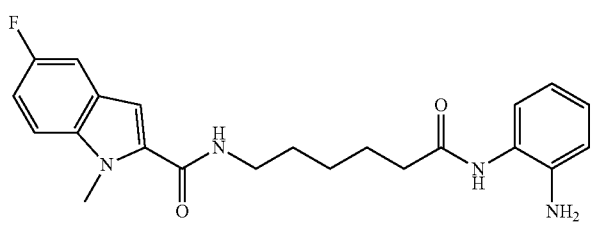 [SMILES: Cn1c(C(=O)NCCCCCC(=O)Nc2ccccc2N)cc2cc(F)ccc21]

| | |
|---|---|
| Comp id | R34 |
| HDAC1 IC50 (nM) | 81 |
| HDAC3 IC50 (nM) | 77 |
| Chemical_name | N-(6-(2-aminophenylamino)-6-oxohexyl)-5-fluoro-1-methyl-1H-indole-2-carboxamide |
| LC/MS Calc'd (M + H) | 397.5 |
| LC/MS Obsv'd (M + H) | 397.2 |

TABLE 6-continued

Activity of Additional HDAC3 Inhibitors

Record 117

Structure

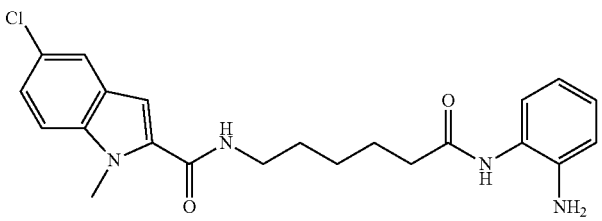 [SMILES: Cn1c(C(=O)NCCCCCC(=O)Nc2ccccc2N)cc2cc(Cl)ccc21]

| | |
|---|---|
| Comp id | R35 |
| HDAC1 IC50 (nM) | 61 |
| HDAC3 IC50 (nM) | 58 |
| Chemical_name | N-(6-(2-aminophenylamino)-6-oxohexyl)-5-chloro-1-methyl-1H-indole-2-carboxamide |
| LC/MS Calc'd (M + H) | 413.9 |
| LC/MS Obsv'd (M + H) | 413.2 |

Record 118

Structure

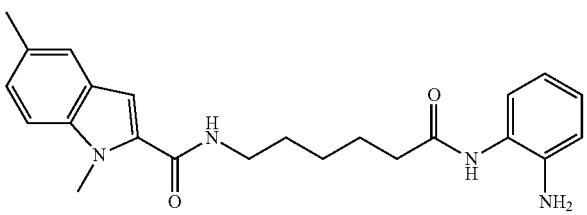 [SMILES: Cc1ccc2c(c1)cc(C(=O)NCCCCCC(=O)Nc1ccccc1N)n2C]

| | |
|---|---|
| Comp id | R36 |
| HDAC1 IC50 (nM) | 93 |
| HDAC3 IC50 (nM) | 92 |
| Chemical_name | N-(6-(2-aminophenylamino)-6-oxohexyl)-1,5-dimethyl-1H-indole-2-carboxamide |
| LC/MS Calc'd (M + H) | 393.5 |
| LC/MS Obsv'd (M + H) | 393.2 |

Record 119

Structure

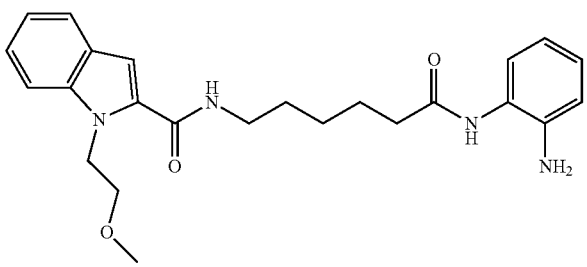 [SMILES: COCCn1c(C(=O)NCCCCCC(=O)Nc2ccccc2N)cc2ccccc21]

| | |
|---|---|
| Comp id | R37 |
| HDAC1 IC50 (nM) | 195 |
| HDAC3 IC50 (nM) | 143 |
| Chemical_name | N-(6-(2-aminophenylamino)-6-oxohexyl)-1-(2-methoxyethyl)-1H-indole-2-carboxamide |
| LC/MS Calc'd (M + H) | 423.5 |
| LC/MS Obsv'd (M + H) | 423.2 |

TABLE 6-continued

Activity of Additional HDAC3 Inhibitors

Record 120

Structure

| Comp id | R38 |
|---|---|
| HDAC1 IC50 (nM) | 3756 |
| HDAC3 IC50 (nM) | 585 |
| Chemical_name | N-(6-(2-aminophenylamino)-6-oxohexyl)-2-ethylbenzamide |
| LC/MS Calc'd (M + H) | 354.5 |
| LC/MS Obsv'd (M + H) | 354.2 |

Record 121

Structure

| Comp id | R39 |
|---|---|
| HDAC1 IC50 (nM) | 585 |
| HDAC3 IC50 (nM) | 131 |
| Chemical_name | N-(6-(2-aminophenylamino)-6-oxohexyl)-3-(dimethylamino)benzamide |
| LC/MS Calc'd (M + H) | 369.5 |
| LC/MS Obsv'd (M + H) | |

Record 122

Structure

| Comp id | R40 |
|---|---|
| HDAC1 IC50 (nM) | 196 |
| HDAC3 IC50 (nM) | 46 |
| Chemical_name | N-(6-(2-aminophenylamino)-6-oxohexyl)-7-methoxy-1H-indole-3-carboxamide |
| LC/MS Calc'd (M + H) | 395.5 |
| LC/MS Obsv'd (M + H) | 395.2 |

Record 123

Structure

| Comp id | R41 |
|---|---|
| HDAC1 IC50 (nM) | 378 |
| HDAC3 IC50 (nM) | 66 |
| Chemical_name | N-(6-(2-aminophenylamino)-6-oxohexyl)-1-methyl-1H-indole-6-carboxamide |
| LC/MS Calc'd (M + H) | 379.5 |
| LC/MS Obsv'd (M + H) | 379.2 |

TABLE 6-continued

Activity of Additional HDAC3 Inhibitors

Record 124

Structure 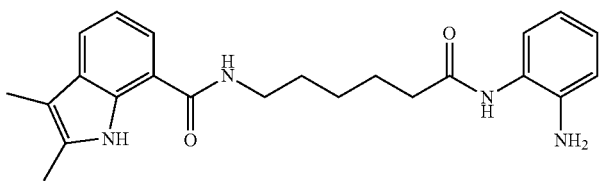 [SMILES: Cc1[nH]c2c(C(=O)NCCCCCC(=O)Nc3ccccc3N)cccc2c1C]

| | |
|---|---|
| Comp id | R42 |
| HDAC1 IC50 (nM) | 207 |
| HDAC3 IC50 (nM) | 47 |
| Chemical_name | N-(6-(2-aminophenylamino)-6-oxohexyl)-2,3-dimethyl-1H-indole-7-carboxamide |
| LC/MS Calc'd (M + H) | 393.5 |
| LC/MS Obsv'd (M + H) | 393.2 |

Record 125

Structure 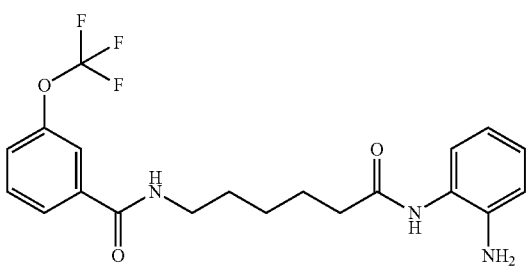 [SMILES: Nc1ccccc1NC(=O)CCCCCNC(=O)c1cccc(OC(F)(F)F)c1]

| | |
|---|---|
| Comp id | R43 |
| HDAC1 IC50 (nM) | 468 |
| HDAC3 IC50 (nM) | 79 |
| Chemical_name | N-(6-(2-aminophenylamino)-6-oxohexyl)-3-(trifluoromethoxy)benzamide |
| LC/MS Calc'd (M + H) | 410.4 |
| LC/MS Obsv'd (M + H) | 410.2 |

Record 126

Structure 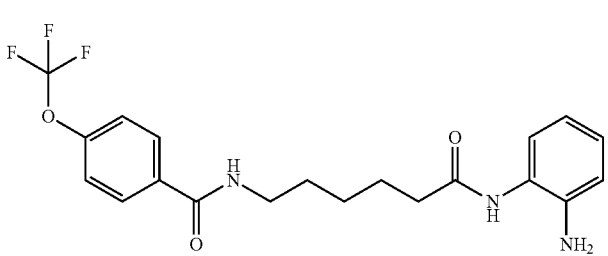 [SMILES: Nc1ccccc1NC(=O)CCCCCNC(=O)c1ccc(OC(F)(F)F)cc1]

| | |
|---|---|
| Comp id | R44 |
| HDAC1 IC50 (nM) | 501 |
| HDAC3 IC50 (nM) | 133 |
| Chemical_name | N-(6-(2-aminophenylamino)-6-oxohexyl)-4-(trifluoromethoxy)benzamide |
| LC/MS Calc'd (M + H) | 410.4 |
| LC/MS Obsv'd (M + H) | 410.2 |

TABLE 6-continued

Activity of Additional HDAC3 Inhibitors

Record 127

Structure 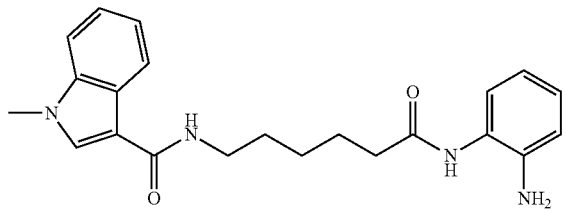

| | |
|---|---|
| Comp id | R45 |
| HDAC1 IC50 (nM) | 174 |
| HDAC3 IC50 (nM) | 56 |
| Chemical_name | N-(6-(2-aminophenylamino)-6-oxohexyl)-1-methyl-1H-indole-3-carboxamide |
| LC/MS Calc'd (M + H) | 379.5 |
| LC/MS Obsv'd (M + H) | 379.2 |

Record 128

Structure 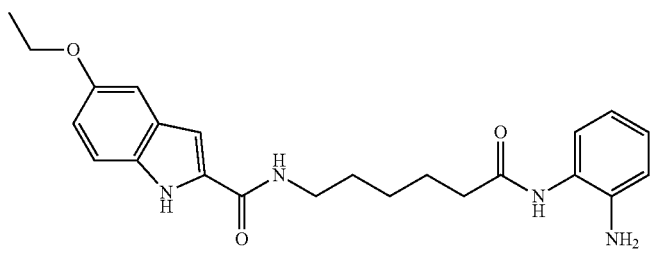

| | |
|---|---|
| Comp id | R46 |
| HDAC1 IC50 (nM) | 359 |
| HDAC3 IC50 (nM) | 49 |
| Chemical_name | N-(6-(2-aminophenylamino)-6-oxohexyl)-5-ethoxy-1H-indole-2-carboxamide |
| LC/MS Calc'd (M + H) | 409.5 |
| LC/MS Obsv'd (M + H) | |

Record 129

Structure 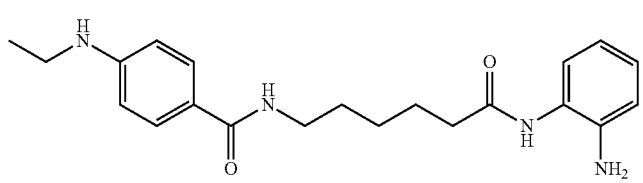 [SMILES: CCNc1ccc(C(=O)NCCCCCC(=O)Nc2ccccc2N)cc1]

| | |
|---|---|
| Comp id | R47 |
| HDAC1 IC50 (nM) | 403 |
| HDAC3 IC50 (nM) | 80 |
| Chemical_name | N-(6-(2-aminophenylamino)-6-oxohexyl)-4-(ethylamino)benzamide |
| LC/MS Calc'd (M + H) | 369.5 |
| LC/MS Obsv'd (M + H) | 369.2 |

TABLE 6-continued

Activity of Additional HDAC3 Inhibitors

Record 130

Structure 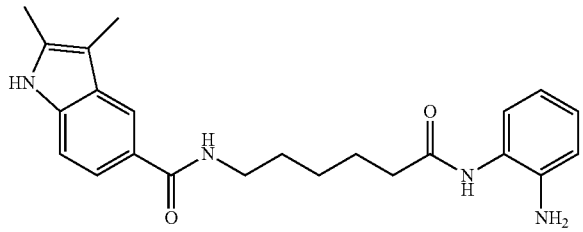 [SMILES: Cc1[nH]c2ccc(C(=O)NCCCCCC(=O)Nc3ccccc3N)cc2c1C]

| | |
|---|---|
| Comp id | R48 |
| HDAC1 IC50 (nM) | 270 |
| HDAC3 IC50 (nM) | 41 |
| Chemical_name | N-(6-(2-aminophenylamino)-6-oxohexyl)-2,3-dimethyl-1H-indole-5-carboxamide |
| LC/MS Calc'd (M + H) | 393.5 |
| LC/MS Obsv'd (M + H) | |

Record 131

Structure 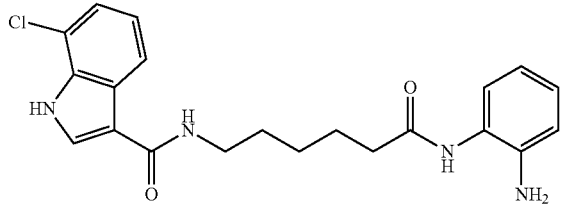 [SMILES: Nc1ccccc1NC(=O)CCCCCNC(=O)c1c[nH]c2c(Cl)cccc12]

| | |
|---|---|
| Comp id | R49 |
| HDAC1 IC50 (nM) | 172 |
| HDAC3 IC50 (nM) | 35 |
| Chemical_name | N-(6-(2-aminophenylamino)-6-oxohexyl)-7-chloro-1H-indole-3-carboxamide |
| LC/MS Calc'd (M + H) | 399.9 |
| LC/MS Obsv'd (M + H) | 399.2 |

Record 132

Structure 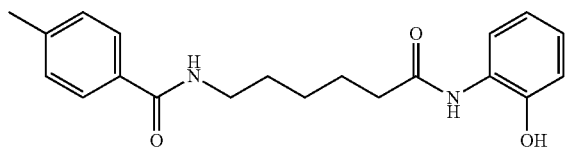 [SMILES: Cc1ccc(C(=O)NCCCCCC(=O)Nc2ccccc2O)cc1]

| | |
|---|---|
| Comp id | R50 |
| HDAC1 IC50 (nM) | 224 |
| HDAC3 IC50 (nM) | 220 |
| Chemical_name | N-(6-(2-hydroxyphenylamino)-6-oxohexyl)-4-methylbenzamide |
| LC/MS Calc'd (M + H) | 341.4 |
| LC/MS Obsv'd (M + H) | 341.2 |

TABLE 6-continued

Activity of Additional HDAC3 Inhibitors

Record 133

Structure 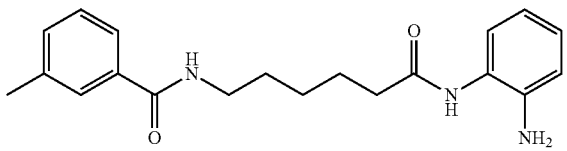

| | |
|---|---|
| Comp id | R52 |
| HDAC1 IC50 (nM) | 527 |
| HDAC3 IC50 (nM) | 58 |
| Chemical_name | N-(6-(2-aminophenylamino)-6-oxohexyl)-3-methylbenzamide |
| LC/MS Calc'd (M + H) | 340.4 |
| LC/MS Obsv'd (M + H) | 340.3 |

Record 134

Structure 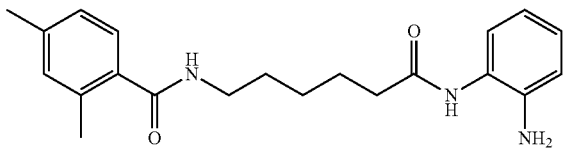 [SMILES: Cc1ccc(C(=O)NCCCCCC(=O)Nc2ccccc2N)c(C)c1]

| | |
|---|---|
| Comp id | R53 |
| HDAC1 IC50 (nM) | 2143 |
| HDAC3 IC50 (nM) | 277 |
| Chemical_name | N-(6-(2-aminophenylamino)-6-oxohexyl)-2,4-dimethylbenzamide |
| LC/MS Calc'd (M + H) | 354.4 |
| LC/MS Obsv'd (M + H) | 354.2 |

Record 135

Structure 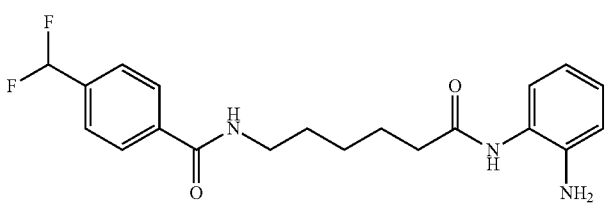 [SMILES: Nc1ccccc1NC(=O)CCCCCNC(=O)c1ccc(C(F)F)cc1]

| | |
|---|---|
| Comp id | R54 |
| HDAC1 IC50 (nM) | 362 |
| HDAC3 IC50 (nM) | 158 |
| Chemical_name | N-(6-(2-aminophenylamino)-6-oxohexyl)-4-(difluoromethyl)benzamide |
| LC/MS Calc'd (M + H) | 376.4 |
| LC/MS Obsv'd (M + H) | 376.2 |

Record 136

Structure 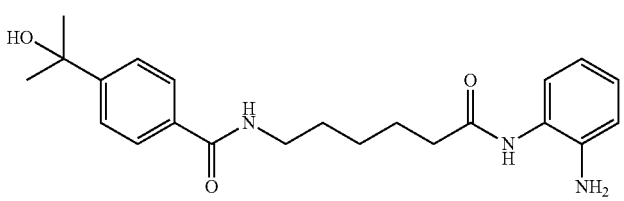 [SMILES: CC(C)(O)c1ccc(C(=O)NCCCCCC(=O)Nc2ccccc2N)cc1]

| | |
|---|---|
| Comp id | R55 |
| HDAC1 IC50 (nM) | 402 |
| HDAC3 IC50 (nM) | 254 |
| Chemical_name | N-(6-(2-aminophenylamino)-6-oxohexyl)-4-(2-hydroxypropan-2-yl)benzamide |
| LC/MS Calc'd (M + H) | 384.5 |
| LC/MS Obsv'd (M + H) | 384.3 |

TABLE 6-continued

Activity of Additional HDAC3 Inhibitors

Record 137

Structure 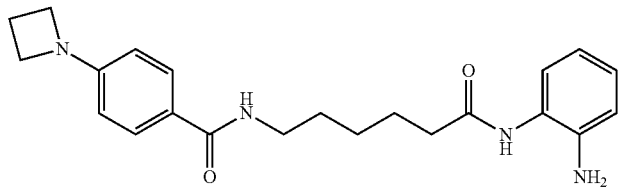 [SMILES: Nc1ccccc1NC(=O)CCCCCNC(=O)c1ccc(N2CCC2)cc1]

| | |
|---|---|
| Comp id | R56 |
| HDAC1 IC50 (nM) | 272 |
| HDAC3 IC50 (nM) | 86 |
| Chemical_name | N-(6-(2-aminophenylamino)-6-oxohexyl)-4-(azetidin-1-yl)benzamide |
| LC/MS Calc'd (M + H) | 381.5 |
| LC/MS Obsv'd (M + H) | 381.3 |

Record 138

Structure 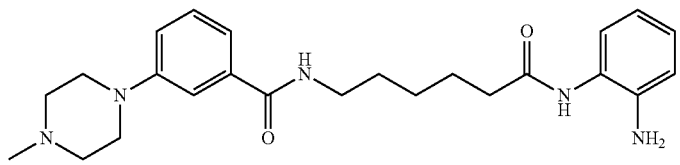 [SMILES: CN1CCN(c2cccc(C(=O)NCCCCCC(=O)Nc3ccccc3N)c2)CC1]

| | |
|---|---|
| Comp id | R57 |
| HDAC1 IC50 (nM) | 365 |
| HDAC3 IC50 (nM) | 66 |
| Chemical_name | N-(6-(2-aminophenylamino)-6-oxohexyl)-3-(4-methylpiperazin-1-yl)benzamide |
| LC/MS Calc'd (M + H) | 424.6 |
| LC/MS Obsv'd (M + H) | 424.3 |

Record 139

Structure 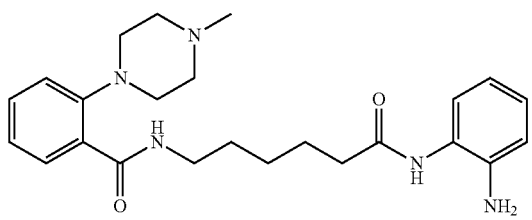 [SMILES: CN1CCN(c2ccccc2C(=O)NCCCCCC(=O)Nc2ccccc2N)CC1]

| | |
|---|---|
| Comp id | R58 |
| HDAC1 IC50 (nM) | 3581 |
| HDAC3 IC50 (nM) | 636 |
| Chemical_name | N-(6-(2-aminophenylamino)-6-oxohexyl)-2-(4-methylpiperazin-1-yl)benzamide |
| LC/MS Calc'd (M + H) | 424.6 |
| LC/MS Obsv'd (M + H) | 424.3 |

TABLE 6-continued

Activity of Additional HDAC3 Inhibitors

Record 140

Structure

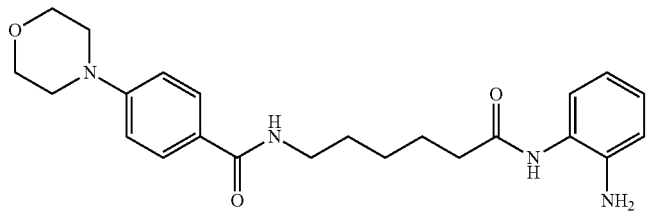 [SMILES: Nc1ccccc1NC(=O)CCCCCNC(=O)c1ccc(N2CCOCC2)cc1]

| | |
|---|---|
| Comp id | R59 |
| HDAC1 IC50 (nM) | 334 |
| HDAC3 IC50 (nM) | 103 |
| Chemical_name | N-(6-(2-aminophenylamino)-6-oxohexyl)-4-morpholinobenzamide |
| LC/MS Calc'd (M + H) | 411.5 |
| LC/MS Obsv'd (M + H) | 411.3 |

Record 141

Structure

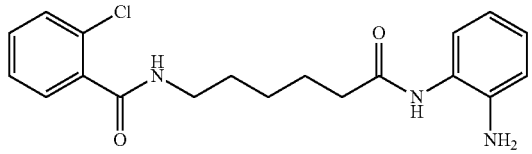 [SMILES: Nc1ccccc1NC(=O)CCCCCNC(=O)c1ccccc1Cl]

| | |
|---|---|
| Comp id | R60 |
| HDAC1 IC50 (nM) | 2035 |
| HDAC3 IC50 (nM) | 442 |
| Chemical_name | N-(6-(2-aminophenylamino)-6-oxohexyl)-2-chlorobenzamide |
| LC/MS Calc'd (M + H) | 360.9 |
| LC/MS Obsv'd (M + H) | 360.2 |

Record 142

Structure

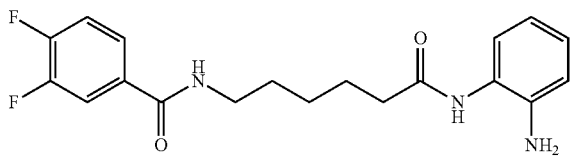 [SMILES: Nc1ccccc1NC(=O)CCCCCNC(=O)c1ccc(F)c(F)c1]

| | |
|---|---|
| Comp id | R61 |
| HDAC1 IC50 (nM) | 772 |
| HDAC3 IC50 (nM) | 123 |
| Chemical_name | N-(6-(2-aminophenylamino)-6-oxohexyl)-3,4-difluorobenzamide |
| LC/MS Calc'd (M + H) | 362.5 |
| LC/MS Obsv'd (M + H) | 362.2 |

Record 143

Structure

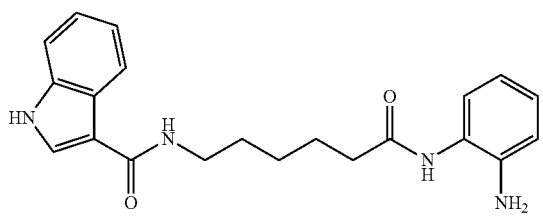 [SMILES: Nc1ccccc1NC(=O)CCCCCNC(=O)c1c[nH]c2ccccc12]

| | |
|---|---|
| Comp id | R62 |
| HDAC1 IC50 (nM) | 246 |
| HDAC3 IC50 (nM) | 33 |
| Chemical_name | N-(6-(2-aminophenylamino)-6-oxohexyl)-1H-indole-3-carboxamide |
| LC/MS Calc'd (M + H) | 365.4 |
| LC/MS Obsv'd (M + H) | 365.2 |

TABLE 6-continued

Activity of Additional HDAC3 Inhibitors

Record 144

Structure

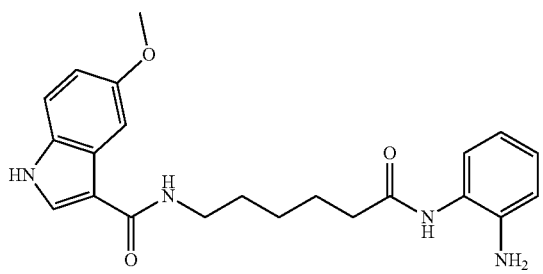 [SMILES: COc1ccc2[nH]cc(C(=O)NCCCCCC(=O)Nc3ccccc3N)c2c1]

| | |
|---|---|
| Comp id | R63 |
| HDAC1 IC50 (nM) | 218 |
| HDAC3 IC50 (nM) | 39 |
| Chemical_name | N-(6-(2-aminophenylamino)-6-oxohexyl)-5-methoxy-1H-indole-3-carboxamide |
| LC/MS Calc'd (M + H) | 395.5 |
| LC/MS Obsv'd (M + H) | 395.3 |

Record 145

Structure

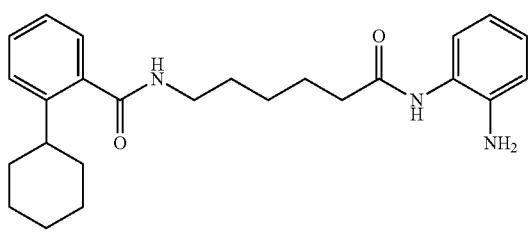 [SMILES: Nc1ccccc1NC(=O)CCCCCNC(=O)c1ccccc1C1CCCCC1]

| | |
|---|---|
| Comp id | R64 |
| HDAC1 IC50 (nM) | 2768 |
| HDAC3 IC50 (nM) | 1302 |
| Chemical_name | N-(6-(2-aminophenylamino)-6-oxohexyl)-2-cyclohexylbenzamide |
| LC/MS Calc'd (M + H) | 408.5 |
| LC/MS Obsv'd (M + H) | 408.3 |

Record 146

Structure

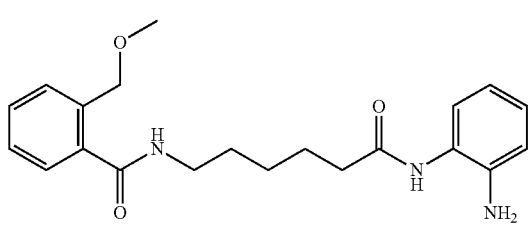 [SMILES: COCc1ccccc1C(=O)NCCCCCC(=O)Nc1ccccc1N]

| | |
|---|---|
| Comp id | R65 |
| HDAC1 IC50 (nM) | 3278 |
| HDAC3 IC50 (nM) | 1475 |
| Chemical_name | N-(6-(2-aminophenylamino)-6-oxohexyl)-2-(methoxymethyl)benzamide |
| LC/MS Calc'd (M + H) | 370.5 |
| LC/MS Obsv'd (M + H) | 370.3 |

TABLE 6-continued

Activity of Additional HDAC3 Inhibitors

Record 147

Structure 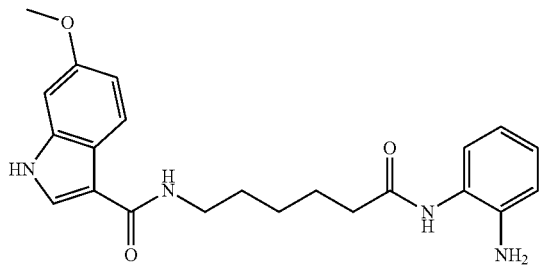 [SMILES: COc1ccc2c(C(=O)NCCCCCC(=O)Nc3ccccc3N)c[nH]c2c1]

| | |
|---|---|
| Comp id | R66 |
| HDAC1 IC50 (nM) | 248 |
| HDAC3 IC50 (nM) | 38 |
| Chemical_name | N-(6-(2-aminophenylamino)-6-oxohexyl)-6-methoxy-1H-indole-3-carboxamide |
| LC/MS Calc'd (M + H) | 395.5 |
| LC/MS Obsv'd (M + H) | 395.2 |

Record 148

Structure 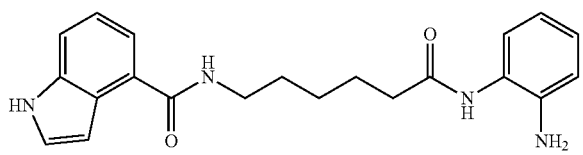 [SMILES: Nc1ccccc1NC(=O)CCCCCNC(=O)c1cccc2[nH]ccc12]

| | |
|---|---|
| Comp id | R67 |
| HDAC1 IC50 (nM) | 524 |
| HDAC3 IC50 (nM) | 72 |
| Chemical_name | N-(6-(2-aminophenylamino)-6-oxohexyl)-1H-indole-4-carboxamide |
| LC/MS Calc'd (M + H) | 365.4 |
| LC/MS Obsv'd (M + H) | 365.2 |

Record 149

Structure 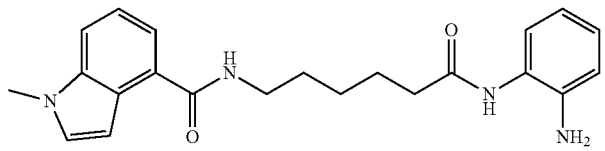 [SMILES: Cn1ccc2c(C(=O)NCCCCCC(=O)Nc3ccccc3N)cccc21]

| | |
|---|---|
| Comp id | R68 |
| HDAC1 IC50 (nM) | 448 |
| HDAC3 IC50 (nM) | 85 |
| Chemical_name | N-(6-(2-aminophenylamino)-6-oxohexyl)-1-methyl-1H-indole-4-carboxamide |
| LC/MS Calc'd (M + H) | 379.5 |
| LC/MS Obsv'd (M + H) | 379.3 |

Record 150

Structure 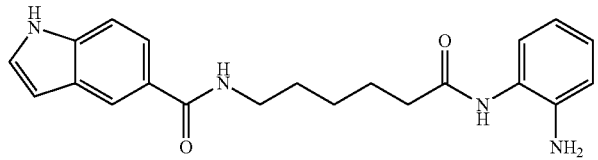 [SMILES: Nc1ccccc1NC(=O)CCCCCNC(=O)c1ccc2[nH]ccc2c1]

| | |
|---|---|
| Comp id | R69 |
| HDAC1 IC50 (nM) | 210 |
| HDAC3 IC50 (nM) | 31 |
| Chemical_name | N-(6-(2-aminophenylamino)-6-oxohexyl)-1H-indole-5-carboxamide |
| LC/MS Calc'd (M + H) | 365.4 |
| LC/MS Obsv'd (M + H) | 365.2 |

TABLE 6-continued

Activity of Additional HDAC3 Inhibitors

Record 151

Structure

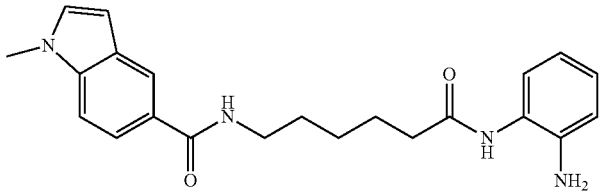 [SMILES: Cn1ccc2cc(C(=O)NCCCCCC(=O)Nc3ccccc3N)ccc21]

| | |
|---|---|
| Comp id | R70 |
| HDAC1 IC50 (nM) | 218 |
| HDAC3 IC50 (nM) | 33 |
| Chemical_name | N-(6-(2-aminophenylamino)-6-oxohexyl)-1-methyl-1H-indole-5-carboxamide |
| LC/MS Calc'd (M + H) | 379.5 |
| LC/MS Obsv'd (M + H) | 379.3 |

Record 152

Structure

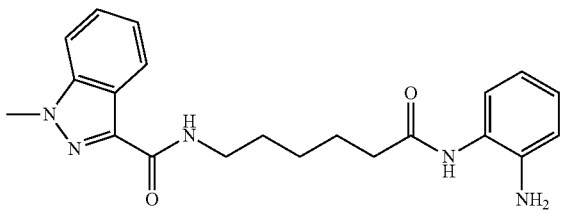 [SMILES: Cn1nc(C(=O)NCCCCCC(=O)Nc2ccccc2N)c2ccccc21]

| | |
|---|---|
| Comp id | R71 |
| HDAC1 IC50 (nM) | 299 |
| HDAC3 IC50 (nM) | 54 |
| Chemical_name | N-(6-(2-aminophenylamino)-6-oxohexyl)-1-methyl-1H-indazole-3-carboxamide |
| LC/MS Calc'd (M + H) | 380.5 |
| LC/MS Obsv'd (M + H) | 380.2 |

Record 153

Structure

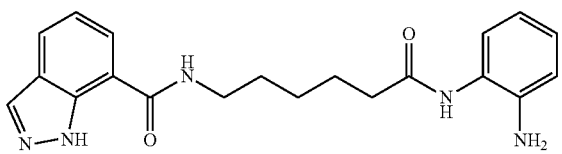 [SMILES: Nc1ccccc1NC(=O)CCCCCNC(=O)c1cccc2cn[nH]c12]

| | |
|---|---|
| Comp id | R72 |
| HDAC1 IC50 (nM) | 371 |
| HDAC3 IC50 (nM) | 99 |
| Chemical_name | N-(6-(2-aminophenylamino)-6-oxohexyl)-1H-indazole-7-carboxamide |
| LC/MS Calc'd (M + H) | 366.4 |
| LC/MS Obsv'd (M + H) | 366.2 |

TABLE 6-continued

Activity of Additional HDAC3 Inhibitors

Record 154

Structure 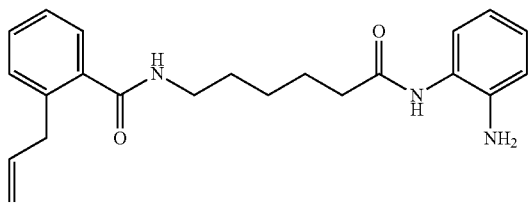 [SMILES: C=CCc1ccccc1C(=O)NCCCCCC(=O)Nc1ccccc1N]

| | |
|---|---|
| Comp id | R73 |
| HDAC1 IC50 (nM) | 2698 |
| HDAC3 IC50 (nM) | 847 |
| Chemical_name | 2-allyl-N-(6-(2-aminophenylamino)-6-oxohexyl)benzamide |
| LC/MS Calc'd (M + H) | 366.5 |
| LC/MS Obsv'd (M + H) | 366.1 |

Record 155

Structure 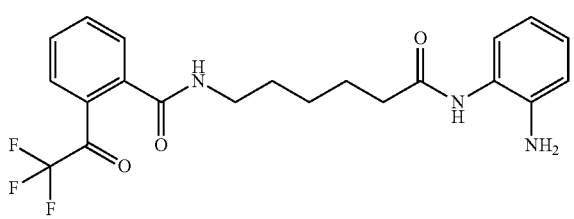 [SMILES: Nc1ccccc1NC(=O)CCCCCNC(=O)c1ccccc1C(=O)C(F)(F)F]

| | |
|---|---|
| Comp id | R74 |
| HDAC1 IC50 (nM) | 26490 |
| HDAC3 IC50 (nM) | 37910 |
| Chemical_name | N-(6-(2-aminophenylamino)-6-oxohexyl)-2-(2,2,2-trifluoroacetyl)benzamide |
| LC/MS Calc'd (M + H) | 422.4 |
| LC/MS Obsv'd (M + H) | 422.2 |

Record 156

Structure 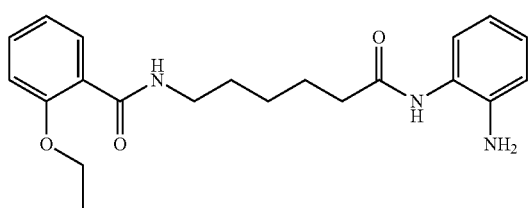 [SMILES: CCOc1ccccc1C(=O)NCCCCCC(=O)Nc1ccccc1N]

| | |
|---|---|
| Comp id | R75 |
| HDAC1 IC50 (nM) | 549 |
| HDAC3 IC50 (nM) | 338 |
| Chemical_name | N-(6-(2-aminophenylamino)-6-oxohexyl)-2-ethoxybenzamide |
| LC/MS Calc'd (M + H) | 370.5 |
| LC/MS Obsv'd (M + H) | 370.3 |

TABLE 6-continued

Activity of Additional HDAC3 Inhibitors

Record 157

Structure
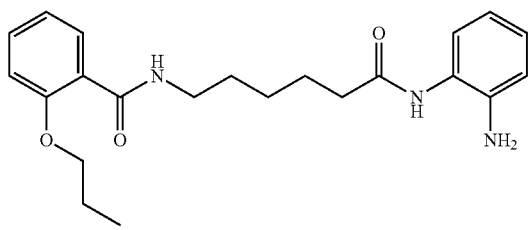 [SMILES: CCCOc1ccccc1C(=O)NCCCCCC(=O)Nc1ccccc1N]

| | |
|---|---|
| Comp id | R76 |
| HDAC1 IC50 (nM) | 399 |
| HDAC3 IC50 (nM) | 135 |
| Chemical_name | N-(6-(2-aminophenylamino)-6-oxohexyl)-2-propoxybenzamide |
| LC/MS Calc'd (M + H) | 384.5 |
| LC/MS Obsv'd (M + H) | 384.3 |

Record 158

Structure
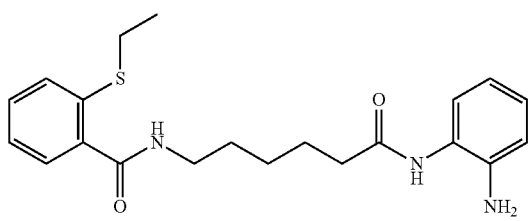 [SMILES: CCSc1ccccc1C(=O)NCCCCCC(=O)Nc1ccccc1N]

| | |
|---|---|
| Comp id | R77 |
| HDAC1 IC50 (nM) | 1333 |
| HDAC3 IC50 (nM) | 381 |
| Chemical_name | N-(6-(2-aminophenylamino)-6-oxohexyl)-2-(ethylthio)benzamide |
| LC/MS Calc'd (M + H) | 386.5 |
| LC/MS Obsv'd (M + H) | 386.2 |

Record 159

Structure
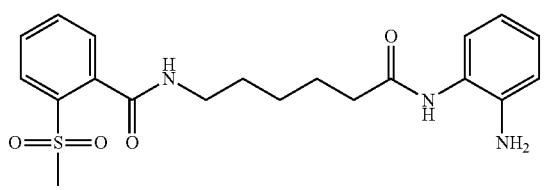 [SMILES: CS(=O)(=O)c1ccccc1C(=O)NCCCCCC(=O)Nc1ccccc1N]

| | |
|---|---|
| Comp id | R78 |
| HDAC1 IC50 (nM) | 4447 |
| HDAC3 IC50 (nM) | 1242 |
| Chemical_name | N-(6-(2-aminophenylamino)-6-oxohexyl)-2-(methylsulfonyl)benzamide |
| LC/MS Calc'd (M + H) | 404.5 |
| LC/MS Obsv'd (M + H) | 404.2 |

TABLE 6-continued

Activity of Additional HDAC3 Inhibitors

Record 160

Structure 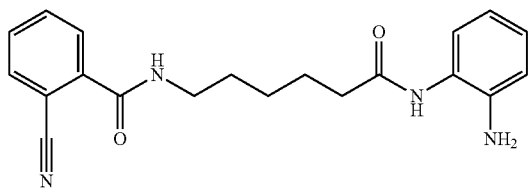 [SMILES: N#Cc1ccccc1C(=O)NCCCCCC(=O)Nc1ccccc1N]

| | |
|---|---|
| Comp id | R79 |
| HDAC1 IC50 (nM) | 426 |
| HDAC3 IC50 (nM) | 86 |
| Chemical_name | N-(6-(2-aminophenylamino)-6-oxohexyl)-2-cyanobenzamide |
| LC/MS Calc'd (M + H) | 351.4 |
| LC/MS Obsv'd (M + H) | 351.2 |

Record 161

Structure 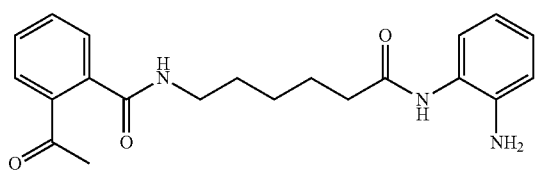 [SMILES: CC(=O)c1ccccc1C(=O)NCCCCCC(=O)Nc1ccccc1N]

| | |
|---|---|
| Comp id | R80 |
| HDAC1 IC50 (nM) | 2644 |
| HDAC3 IC50 (nM) | 741 |
| Chemical_name | 2-acetyl-N-(6-(2-aminophenylamino)-6-oxohexyl)benzamide |
| LC/MS Calc'd (M + H) | 368.4 |
| LC/MS Obsv'd (M + H) | 350.2 |

Record 162

Structure 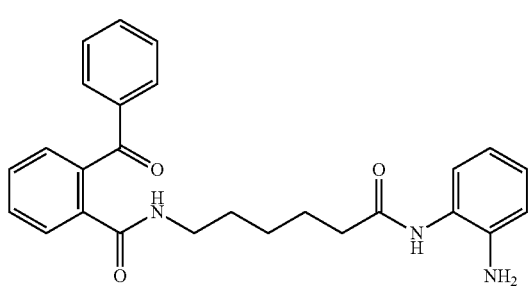 [SMILES: Nc1ccccc1NC(=O)CCCCCNC(=O)c1ccccc1C(=O)c1ccccc1]

| | |
|---|---|
| Comp id | R81 |
| HDAC1 IC50 (nM) | 2720 |
| HDAC3 IC50 (nM) | 279 |
| Chemical_name | N-(6-(2-aminophenylamino)-6-oxohexyl)-2-benzoylbenzamide |
| LC/MS Calc'd (M + H) | 430.5 |
| LC/MS Obsv'd (M + H) | 429.8 |

TABLE 6-continued

Activity of Additional HDAC3 Inhibitors

Record 163

Structure 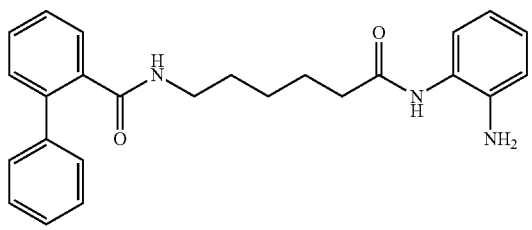 [SMILES: Nc1ccccc1NC(=O)CCCCCNC(=O)c1ccccc1-c1ccccc1]

| | |
|---|---|
| Comp id | R82 |
| HDAC1 IC50 (nM) | 5732 |
| HDAC3 IC50 (nM) | 697 |
| Chemical_name | N-(6-(2-aminophenylamino)-6-oxohexyl)biphenyl-2-carboxamide |
| LC/MS Calc'd (M + H) | 402.5 |
| LC/MS Obsv'd (M + H) | 402.3 |

Record 164

Structure 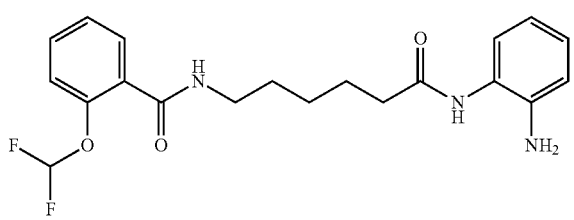 [SMILES: Nc1ccccc1NC(=O)CCCCCNC(=O)c1ccccc1OC(F)F]

| | |
|---|---|
| Comp id | R83 |
| HDAC1 IC50 (nM) | 1479 |
| HDAC3 IC50 (nM) | 214 |
| Chemical_name | N-(6-(2-aminophenylamino)-6-oxohexyl)-2-(difluoromethoxy)benzamide |
| LC/MS Calc'd (M + H) | 392.4 |
| LC/MS Obsv'd (M + H) | 392.2 |

Record 165

Structure 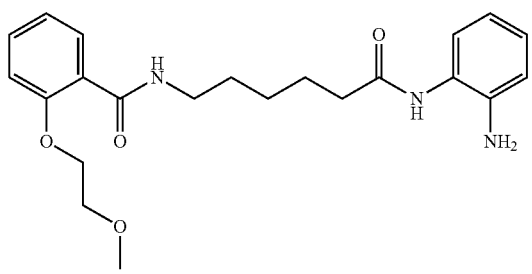 [SMILES: COCCOc1ccccc1C(=O)NCCCCCC(=O)Nc1ccccc1N]

| | |
|---|---|
| Comp id | R84 |
| HDAC1 IC50 (nM) | 2396 |
| HDAC3 IC50 (nM) | 642 |
| Chemical_name | N-(6-(2-aminophenylamino)-6-oxohexyl)-2-(2-methoxyethoxy)benzamide |
| LC/MS Calc'd (M + H) | 400.5 |
| LC/MS Obsv'd (M + H) | 400.3 |

TABLE 6-continued

Activity of Additional HDAC3 Inhibitors

Record 166

Structure

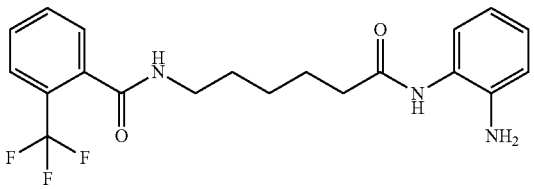 [SMILES: Nc1ccccc1NC(=O)CCCCCNC(=O)c1ccccc1C(F)(F)F]

| | |
|---|---|
| Comp id | R85 |
| HDAC1 IC50 (nM) | 3564 |
| HDAC3 IC50 (nM) | 808 |
| Chemical_name | N-(6-(2-aminophenylamino)-6-oxohexyl)-2-(trifluoromethyl)benzamide |
| LC/MS Calc'd (M + H) | 394.4 |
| LC/MS Obsv'd (M + H) | 394.2 |

Record 167

Structure

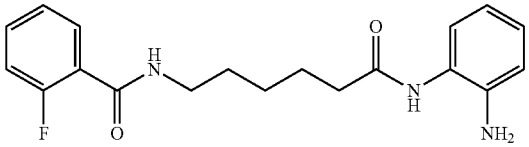

| | |
|---|---|
| Comp id | R86 |
| HDAC1 IC50 (nM) | 1135 |
| HDAC3 IC50 (nM) | 184 |
| Chemical_name | N-(6-(2-aminophenylamino)-6-oxohexyl)-2-fluorobenzamide |
| LC/MS Calc'd (M + H) | 344.4 |
| LC/MS Obsv'd (M + H) | 344.2 |

Record 168

Structure

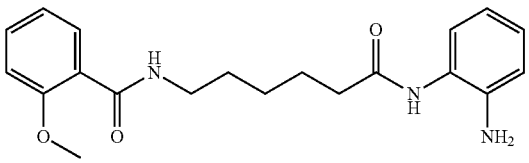 [SMILES: COc1ccccc1C(=O)NCCCCCC(=O)Nc1ccccc1N]

| | |
|---|---|
| Comp id | R87 |
| HDAC1 IC50 (nM) | 674 |
| HDAC3 IC50 (nM) | 86 |
| Chemical_name | N-(6-(2-aminophenylamino)-6-oxohexyl)-2-methoxybenzamide |
| LC/MS Calc'd (M + H) | 356.4 |
| LC/MS Obsv'd (M + H) | 356.2 |

Record 169

Structure

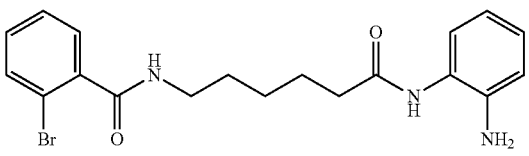 [SMILES: Nc1ccccc1NC(=O)CCCCCNC(=O)c1ccccc1Br]

| | |
|---|---|
| Comp id | R88 |
| HDAC1 IC50 (nM) | 2719 |
| HDAC3 IC50 (nM) | 399 |
| Chemical_name | N-(6-(2-aminophenylamino)-6-oxohexyl)-2-bromobenzamide |
| LC/MS Calc'd (M + H) | 405.3 |
| LC/MS Obsv'd (M + H) | 405.1 |

TABLE 6-continued

Activity of Additional HDAC3 Inhibitors

Record 170

Structure

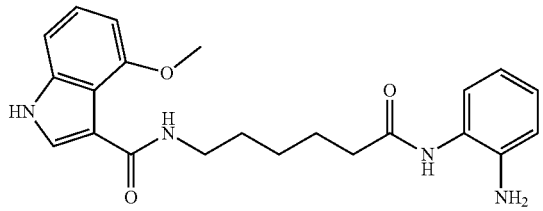 [SMILES: COc1cccc2[nH]cc(C(=O)NCCCCCC(=O)Nc3ccccc3N)c12]

| | |
|---|---|
| Comp id | R89 |
| HDAC1 IC50 (nM) | 197 |
| HDAC3 IC50 (nM) | 58 |
| Chemical_name | N-(6-(2-aminophenylamino)-6-oxohexyl)-4-methoxy-1H-indole-3-carboxamide |
| LC/MS Calc'd (M + H) | 395.5 |
| LC/MS Obsv'd (M + H) | 395.2 |

Record 171

Structure

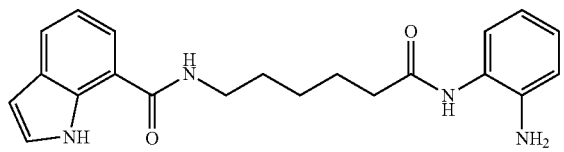

| | |
|---|---|
| Comp id | R90 |
| HDAC1 IC50 (nM) | 278 |
| HDAC3 IC50 (nM) | 36 |
| Chemical_name | N-(6-(2-aminophenylamino)-6-oxohexyl)-1H-indole-7-carboxamide |
| LC/MS Calc'd (M + H) | 365.4 |
| LC/MS Obsv'd (M + H) | 365.3 |

Record 172

Structure

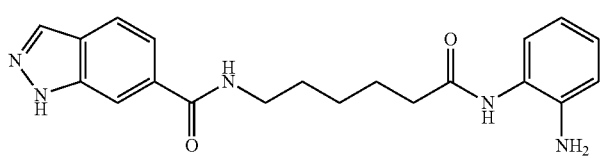 [SMILES: Nc1ccccc1NC(=O)CCCCCNC(=O)c1ccc2cn[nH]c2c1]

| | |
|---|---|
| Comp id | R91 |
| HDAC1 IC50 (nM) | 582 |
| HDAC3 IC50 (nM) | 115 |
| Chemical_name | N-(6-(2-aminophenylamino)-6-oxohexyl)-1H-indazole-6-carboxamide |
| LC/MS Calc'd (M + H) | 366.4 |
| LC/MS Obsv'd (M + H) | 366.2 |

Record 173

Structure

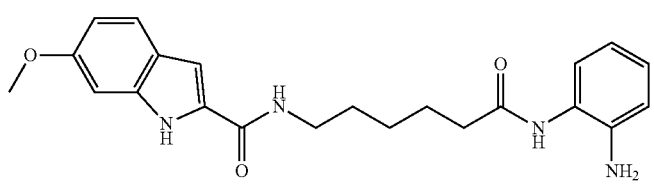 [SMILES: COc1ccc2cc(C(=O)NCCCCCC(=O)Nc3ccccc3N)[nH]c2c1]

| | |
|---|---|
| Comp id | R92 |
| HDAC1 IC50 (nM) | 193 |
| HDAC3 IC50 (nM) | 26 |
| Chemical_name | N-(6-(2-aminophenylamino)-6-oxohexyl)-6-methoxy-1H-indole-2-carboxamide |
| LC/MS Calc'd (M + H) | 395.5 |
| LC/MS Obsv'd (M + H) | 395.2 |

TABLE 6-continued

Activity of Additional HDAC3 Inhibitors

Record 174

| | |
|---|---|
| Structure | (structure image) |
| Comp id | R93 |
| HDAC1 IC50 (nM) | 449 |
| HDAC3 IC50 (nM) | 78 |
| Chemical_name | N-(6-(2-aminophenylamino)-6-oxohexyl)-4-(methylamino)benzamide |
| LC/MS Calc'd (M + H) | 355.4 |
| LC/MS Obsv'd (M + H) | 355.3 |

Record 175

| | |
|---|---|
| Structure | (structure image) |
| Comp id | R94 |
| HDAC1 IC50 (nM) | 315 |
| HDAC3 IC50 (nM) | 78 |
| Chemical_name | N-(6-(2-aminophenylamino)-6-oxohexyl)-4-(cyclopropylamino)benzamide |
| LC/MS Calc'd (M + H) | 381.5 |
| LC/MS Obsv'd (M + H) | 381.3 |

Record 176

| | |
|---|---|
| Structure | (structure image) |
| Comp id | R95 |
| HDAC1 IC50 (nM) | 445 |
| HDAC3 IC50 (nM) | 94 |
| Chemical_name | N-(6-(2-aminophenylamino)-6-oxohexyl)-4-(4-methylpiperazin-1-yl)benzamide |
| LC/MS Calc'd (M + H) | 424.6 |
| LC/MS Obsv'd (M + H) | 424.5 |

Record 177

| | |
|---|---|
| Structure | (structure image) |
| Comp id | R96 |
| HDAC1 IC50 (nM) | 177 |
| HDAC3 IC50 (nM) | 32 |
| Chemical_name | N-(6-(2-aminophenylamino)-6-oxohexyl)-6-methyl-1H-indole-2-carboxamide |
| LC/MS Calc'd (M + H) | 379.5 |
| LC/MS Obsv'd (M + H) | 379.3 |

TABLE 6-continued

Activity of Additional HDAC3 Inhibitors

Record 178

Structure 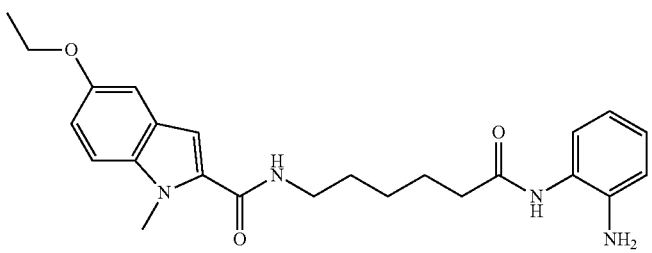 [SMILES: CCOc1ccc2c(c1)cc(C(=O)NCCCCCC(=O)Nc1ccccc1N)n2C]

| | |
|---|---|
| Comp id | R97 |
| HDAC1 IC50 (nM) | 327 |
| HDAC3 IC50 (nM) | 67 |
| Chemical_name | N-(6-(2-aminophenylamino)-6-oxohexyl)-5-ethoxy-1-methyl-1H-indole-2-carboxamide |
| LC/MS Calc'd (M + H) | 423.5 |
| LC/MS Obsv'd (M + H) | 423.3 |

Record 179

Structure 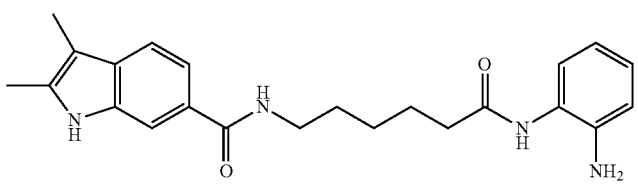 [SMILES: Cc1[nH]c2cc(C(=O)NCCCCCC(=O)Nc3ccccc3N)ccc2c1C]

| | |
|---|---|
| Comp id | R98 |
| HDAC1 IC50 (nM) | 201 |
| HDAC3 IC50 (nM) | 37 |
| Chemical_name | N-(6-(2-aminophenylamino)-6-oxohexyl)-2,3-dimethyl-1H-indole-6-carboxamide |
| LC/MS Calc'd (M + H) | 393.5 |
| LC/MS Obsv'd (M + H) | 393.3 |

Record 180

Structure 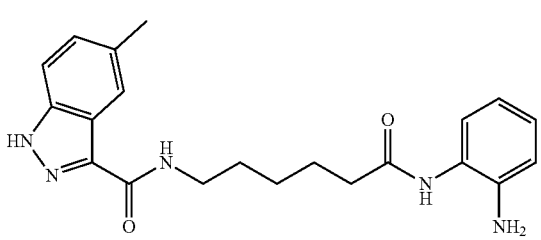 [SMILES: Cc1ccc2[nH]nc(C(=O)NCCCCCC(=O)Nc3ccccc3N)c2c1]

| | |
|---|---|
| Comp id | R99 |
| HDAC1 IC50 (nM) | 220 |
| HDAC3 IC50 (nM) | 45 |
| Chemical_name | N-(6-(2-aminophenylamino)-6-oxohexyl)-5-methyl-1H-indazole-3-carboxamide |
| LC/MS Calc'd (M + H) | 380.5 |
| LC/MS Obsv'd (M + H) | 380.3 |

TABLE 6-continued

Activity of Additional HDAC3 Inhibitors

Record 181

Structure

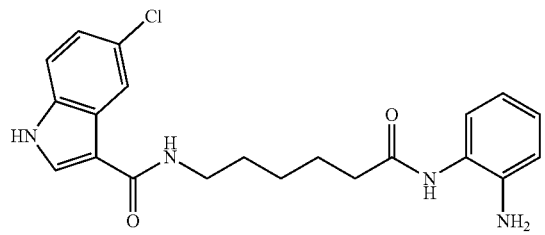 [SMILES: Nc1ccccc1NC(=O)CCCCCNC(=O)c1c[nH]c2ccc(Cl)cc12]

| | |
|---|---|
| Comp id | R100 |
| HDAC1 IC50 (nM) | 263 |
| HDAC3 IC50 (nM) | 48 |
| Chemical_name | N-(6-(2-aminophenylamino)-6-oxohexyl)-5-chloro-1H-indole-3-carboxamide |
| LC/MS Calc'd (M + H) | 399.9 |
| LC/MS Obsv'd (M + H) | 399.2 |

Record 182

Structure

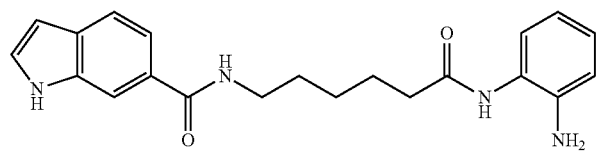

| | |
|---|---|
| Comp id | R101 |
| HDAC1 IC50 (nM) | 234 |
| HDAC3 IC50 (nM) | 41 |
| Chemical_name | N-(6-(2-aminophenylamino)-6-oxohexyl)-1H-indole-6-carboxamide |
| LC/MS Calc'd (M + H) | 365.4 |
| LC/MS Obsv'd (M + H) | 365.3 |

Record 183

Structure

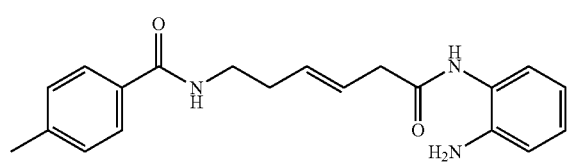 [SMILES: Cc1ccc(C(=O)NCC/C=C/CC(=O)Nc2ccccc2N)cc1]

| | |
|---|---|
| Comp id | R107 |
| HDAC1 IC50 (nM) | |
| HDAC3 IC50 (nM) | 1564 |
| Chemical_name | (E)-N-(6-(2-aminophenylamino)-6-oxohex-3-enyl)-4-methylbenzamide |
| LC/MS Calc'd (M + H) | 338.4 |
| LC/MS Obsv'd (M + H) | 338 |

Record 184

Structure

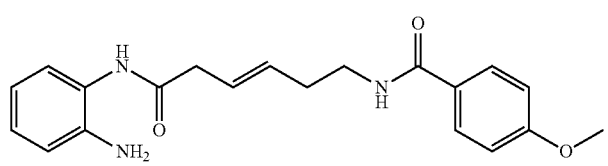 [SMILES: COc1ccc(C(=O)NCC/C=C/CC(=O)Nc2ccccc2N)cc1]

| | |
|---|---|
| Comp id | R108 |
| HDAC1 IC50 (nM) | |
| HDAC3 IC50 (nM) | 1983 |
| Chemical_name | (E)-N-(6-(2-aminophenylamino)-6-oxohex-3-enyl)-4-methoxybenzamide |
| LC/MS Calc'd (M + H) | 354.4 |
| LC/MS Obsv'd (M + H) | 354 |

TABLE 6-continued

Activity of Additional HDAC3 Inhibitors

Record 185

Structure 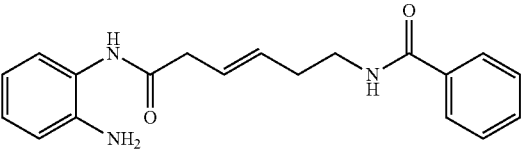 [SMILES: Nc1ccccc1NC(=O)C/C=C/CCNC(=O)c1ccccc1]

| | |
|---|---|
| Comp id | R109 |
| HDAC1 IC50 (nM) | |
| HDAC3 IC50 (nM) | 5782 |
| Chemical_name | (E)-N-(6-(2-aminophenylamino)-6-oxohex-3-enyl)benzamide |
| LC/MS Calc'd (M + H) | 324.4 |
| LC/MS Obsv'd (M + H) | 324 |

Record 186

Structure 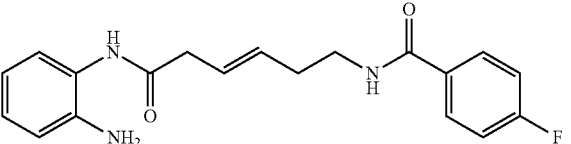

| | |
|---|---|
| Comp id | R110 |
| HDAC1 IC50 (nM) | |
| HDAC3 IC50 (nM) | 4797 |
| Chemical_name | (E)-N-(6-(2-aminophenylamino)-6-oxohex-3-enyl)-4-fluorobenzamide |
| LC/MS Calc'd (M + H) | 342.4 |
| LC/MS Obsv'd (M + H) | 342 |

Record 187

Structure 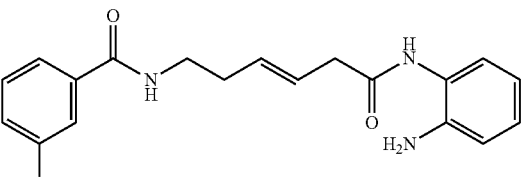

| | |
|---|---|
| Comp id | R111 |
| HDAC1 IC50 (nM) | |
| HDAC3 IC50 (nM) | 953 |
| Chemical_name | (E)-N-(6-(2-aminophenylamino)-6-oxohex-3-enyl)-3-chlorobenzamide |
| LC/MS Calc'd (M + H) | 358.8 |
| LC/MS Obsv'd (M + H) | 359 |

Record 188

Structure 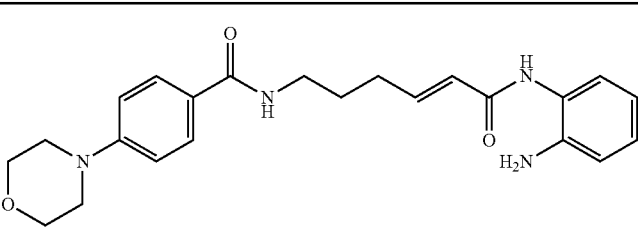

| | |
|---|---|
| Comp id | R112 |
| HDAC1 IC50 (nM) | |
| HDAC3 IC50 (nM) | 485 |
| Chemical_name | (E)-N-(6-(2-aminophenylamino)-6-oxohex-4-enyl)-4-morpholinobenzamide |
| LC/MS Calc'd (M + H) | 409.5 |
| LC/MS Obsv'd (M + H) | 409 |

TABLE 6-continued

Activity of Additional HDAC3 Inhibitors

Record 189

Structure

Comp id: R113
HDAC1 IC50 (nM):
HDAC3 IC50 (nM): 176
Chemical_name: (E)-N-(6-(2-aminophenylamino)-6-oxohex-4-enyl)-4-(dimethylamino)benzamide
LC/MS Calc'd (M + H): 367.5
LC/MS Obsv'd (M + H): 367

Record 190

Structure

Comp id: R114
HDAC1 IC50 (nM):
HDAC3 IC50 (nM): 228
Chemical_name: (E)-N-(6-(2-aminophenylamino)-6-oxohex-4-enyl)-4-methoxybenzamide
LC/MS Calc'd (M + H): 354.4
LC/MS Obsv'd (M + H): 354

Record 191

Structure

Comp id: R115
HDAC1 IC50 (nM):
HDAC3 IC50 (nM): 148
Chemical_name: (E)-N-(6-(2-aminophenylamino)-6-oxohex-4-enyl)-3-chlorobenzamide
LC/MS Calc'd (M + H): 358.8
LC/MS Obsv'd (M + H): 359

Record 192

Structure

Comp id: R116
HDAC1 IC50 (nM):
HDAC3 IC50 (nM): 348
Chemical_name: (E)-N-(6-(2-aminophenylamino)-6-oxohex-4-enyl)-4-fluorobenzamide
LC/MS Calc'd (M + H): 342.4
LC/MS Obsv'd (M + H): 342

TABLE 6-continued

Activity of Additional HDAC3 Inhibitors

Record 193

Structure

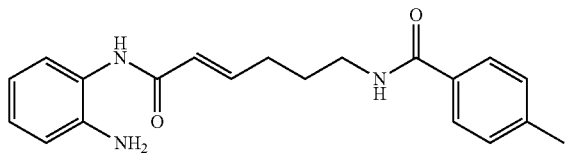 [SMILES: Cc1ccc(C(=O)NCCC/C=C/C(=O)Nc2ccccc2N)cc1]

| | |
|---|---|
| Comp id | R117 |
| HDAC1 IC50 (nM) | |
| HDAC3 IC50 (nM) | 239 |
| Chemical_name | (E)-N-(6-(2-aminophenylamino)-6-oxohex-4-enyl)-4-methylbenzamide |
| LC/MS Calc'd (M + H) | 338.4 |
| LC/MS Obsv'd (M + H) | 338 |

Record 194

Structure

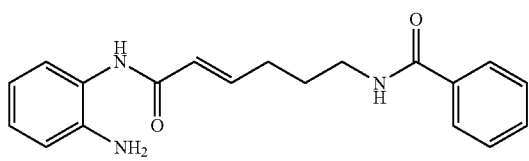 [SMILES: Nc1ccccc1NC(=O)/C=C/CCCNC(=O)c1ccccc1]

| | |
|---|---|
| Comp id | R118 |
| HDAC1 IC50 (nM) | |
| HDAC3 IC50 (nM) | 251 |
| Chemical_name | (E)-N-(6-(2-aminophenylamino)-6-oxohex-4-enyl)benzamide |
| LC/MS Calc'd (M + H) | 324.4 |
| LC/MS Obsv'd (M + H) | 324 |

Record 195

Structure

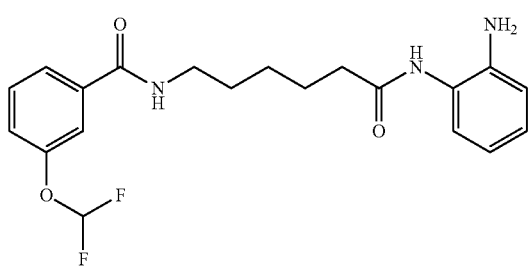 [SMILES: Nc1ccccc1NC(=O)CCCCCNC(=O)c1cccc(OC(F)F)c1]

| | |
|---|---|
| Comp id | R102 |
| HDAC1 IC50 (nM) | |
| HDAC3 IC50 (nM) | 130 |
| Chemical_name | N-(6-(2-aminophenylamino)-6-oxohexyl)-3-(difluoromethoxy)benzamide |
| LC/MS Calc'd (M + H) | 392.4 |
| LC/MS Obsv'd (M + H) | 392.3 |

TABLE 6-continued

Activity of Additional HDAC3 Inhibitors

Record 196

Structure

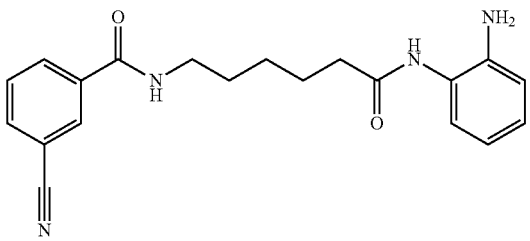 [SMILES: N#Cc1cccc(C(=O)NCCCCCC(=O)Nc2ccccc2N)c1]

| | |
|---|---|
| Comp id | R103 |
| HDAC1 IC50 (nM) | |
| HDAC3 IC50 (nM) | 195 |
| Chemical_name | N-(6-(2-aminophenylamino)-6-oxohexyl)-3-cyanobenzamide |
| LC/MS Calc'd (M + H) | 351.4 |
| LC/MS Obsv'd (M + H) | 351.3 |

Record 197

Structure

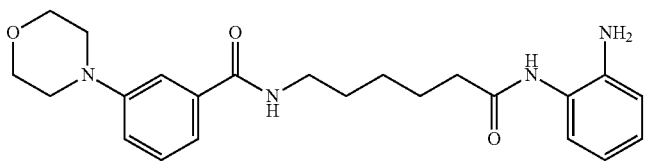 [SMILES: Nc1ccccc1NC(=O)CCCCCNC(=O)c1cccc(N2CCOCC2)c1]

| | |
|---|---|
| Comp id | R104 |
| HDAC1 IC50 (nM) | |
| HDAC3 IC50 (nM) | 279 |
| Chemical_name | N-(6-(2-aminophenylamino)-6-oxohexyl)-3-morpholinobenzamide |
| LC/MS Calc'd (M + H) | 411.5 |
| LC/MS Obsv'd (M + H) | |

Record 198

Structure

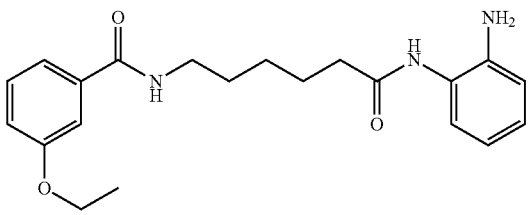 [SMILES: CCOc1cccc(C(=O)NCCCCCC(=O)Nc2ccccc2N)c1]

| | |
|---|---|
| Comp id | R105 |
| HDAC1 IC50 (nM) | |
| HDAC3 IC50 (nM) | 182 |
| Chemical_name | N-(6-(2-aminophenylamino)-6-oxohexyl)-3-ethoxybenzamide |
| LC/MS Calc'd (M + H) | 370.5 |
| LC/MS Obsv'd (M + H) | 370.3 |

TABLE 6-continued

Activity of Additional HDAC3 Inhibitors

Record 199

Structure

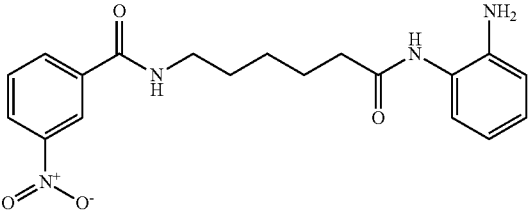 [SMILES: Nc1ccccc1NC(=O)CCCCCNC(=O)c1cccc([N+](=O)[O-])c1]

| Comp id | R106 |
|---|---|
| HDAC1 IC50 (nM) | |
| HDAC3 IC50 (nM) | 254 |
| Chemical_name | N-(6-(2-aminophenylamino)-6-oxohexyl)-3-nitrobenzamide |
| LC/MS Calc'd (M + H) | 371.4 |
| LC/MS Obsv'd (M + H) | 371.3 |

Example 41. Acid Stability

Method

From a DMSO stock solution (10 mM), 1 mL of 100 uM solution of each compound was prepared in 0.01N HCl (pH=2). Immediately after mixing, about 100 uL of each sample was transferred to a HPLC sample vial and run using the standard purity check HPLC/UV method (t=0 data). Then the samples were incubate at 50° C. and tested after 2, 4, and 24 hrs. The percent remaining was calculated using the ratio of area under the peak after incubation time over the initial time (t=0) times 100.

injection. Total RNA from brain stem, heart, and/or cerebellum were extracted. Frataxin mRNA expression was determined by one-step quantitative real-time PCR using the primers 5' CCTGGCCGAGTTCTTTGAAG-3' (SEQ ID NO:1) and 5'-GCCAGATTTGCTTGTTTGG-3' (SEQ ID NO:2).

Frataxin mRNA was significantly lower in the brain, cerebellum, and heart of vehicle-treated knock-in mice than in similarly treated wild-type animals. Treatment with compound R03 increased knock-in frataxin mRNA to levels that do not significantly differ from wild-type, thus demonstrating essentially complete correction of Fxn deficiency in

TABLE 7

Acid Stability Data for Compounds R01 and R117

| | | Acid Stability, pH = 2, 50° C. | |
|---|---|---|---|
| | | % remaining | |
| Structure | Compound ID | t = 4 hr | t = 24 hr |
| 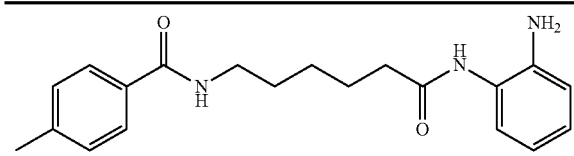 | R01 | 69 | 6 |
| 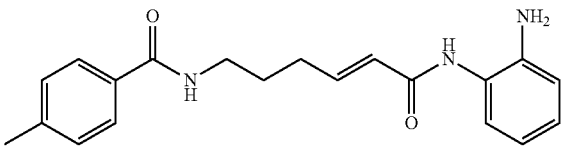 [SMILES: Cc1ccc(C(=O)NCCC/C=C/C(=O)Nc2ccccc2N)cc1] | R117 | 90 | 44 |

Example 42. Compound R03 Increases Frataxin Expression In Vivo

This example demonstrates that compound R03 increases in vivo frataxin expression. A single dose of compound R03 at 50 mg/kg was administered subcutaneously to eight mice per group of knock-in mice homozygous for a $(GAA)_{230}$ repeat in the first intron of the endogenous frataxin gene (Miranda et al., 2002, FEBS Lett., 512:291-297). Brain, heart, and skeletal muscle were recovered 24 hours after the these animals. Western blotting confirmed that increased Fxn mRNA levels resulted in higher frataxin protein level.

Example 43. Compound R03 Alleviates Symptoms in an FRDA Mouse Model

This example demonstrates that compound R03 alleviates symptoms in a mouse model of FRDA. Compound R03 was administered to mice expressing from a yeast artificial chromosome (YAC) a human FXN gene with a GAA repeat expansion (190+90 repeats) and lacking the mouse Fxn gene (FXN⁺, fxn⁻). Production of these mice, known as "YG8 rescue," because the expression of the expanded human FXN gene from the YAC rescues the embryonic lethality of the homozygous Fxn knockout, is described in Al-Mahdawi et al., 2006, Genomics, 88:580-590, which is incorporated herein by reference in its entirety. These YG8 rescue mice present a mild phenotype consistent with less severe, later onset cases of FRDA in humans. The mice have reduced frataxin expression, reduced coordination and locomotor activity, increased weight, impaired aconitase activity, and oxidative stress as compared to wild-type littermate controls. Thus, this model provides a reasonable correlation to the human disorder for the purposes of testing potential new drugs to treat FRDA in humans.

Figure 2:
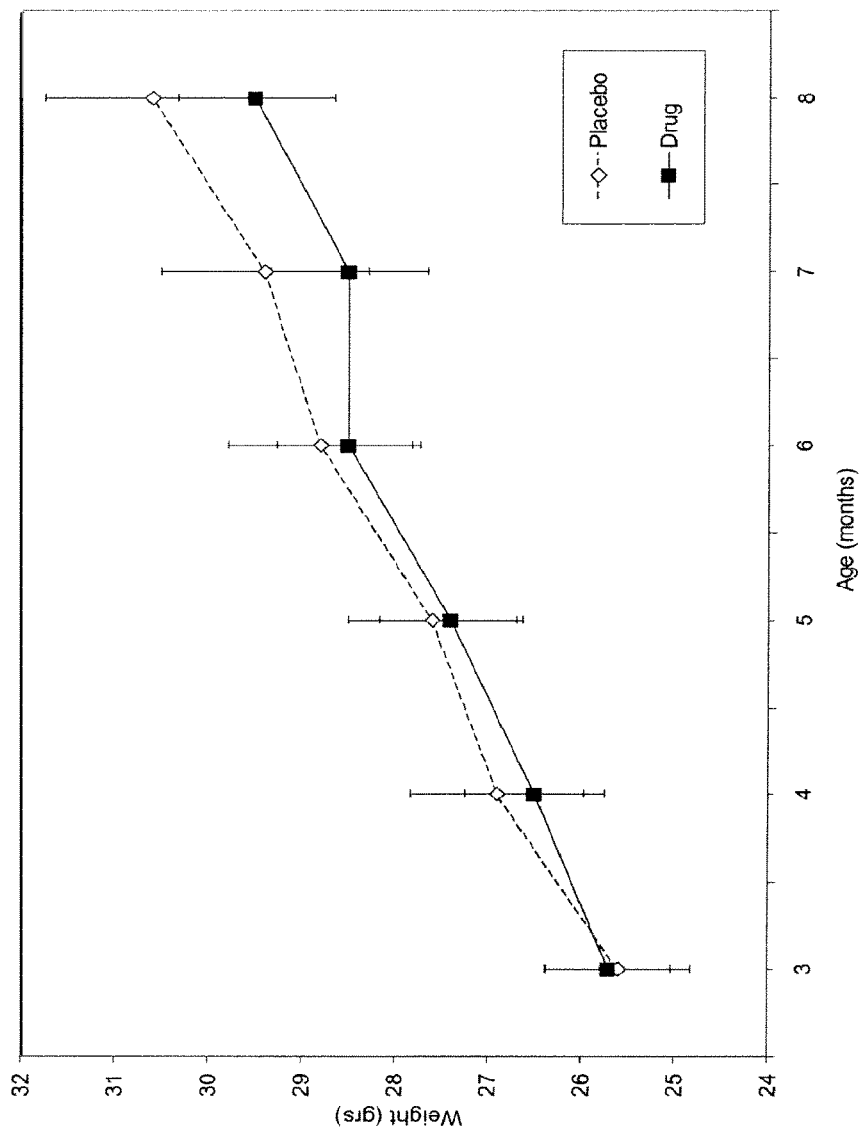
FIG. 2 is a line graph depicting the average weights of $FXN^+$, $fxn^{-/-}$ FRDA model mice treated with compound R03 or vehicle control.

The YG8 rescue mice were treated daily with compound R03 beginning at three months of age, with treatment continuing over a period of five months. The mice were administered subcutaneously 50 mg/kg of compound R03 in vehicle (20% propylene glycol, 20% polyethylene glycol-400, 20% glycerol, 100 mM acetate pH 5.4) or vehicle alone (n=20 per treatment group). Coordination, activity, and weight were assayed at the initiation of treatment and each month thereafter. The average weight of the drug-treated mice was consistently lower than the control mice, although this difference was not significant at any time point (FIG. 2).

Figure 3:
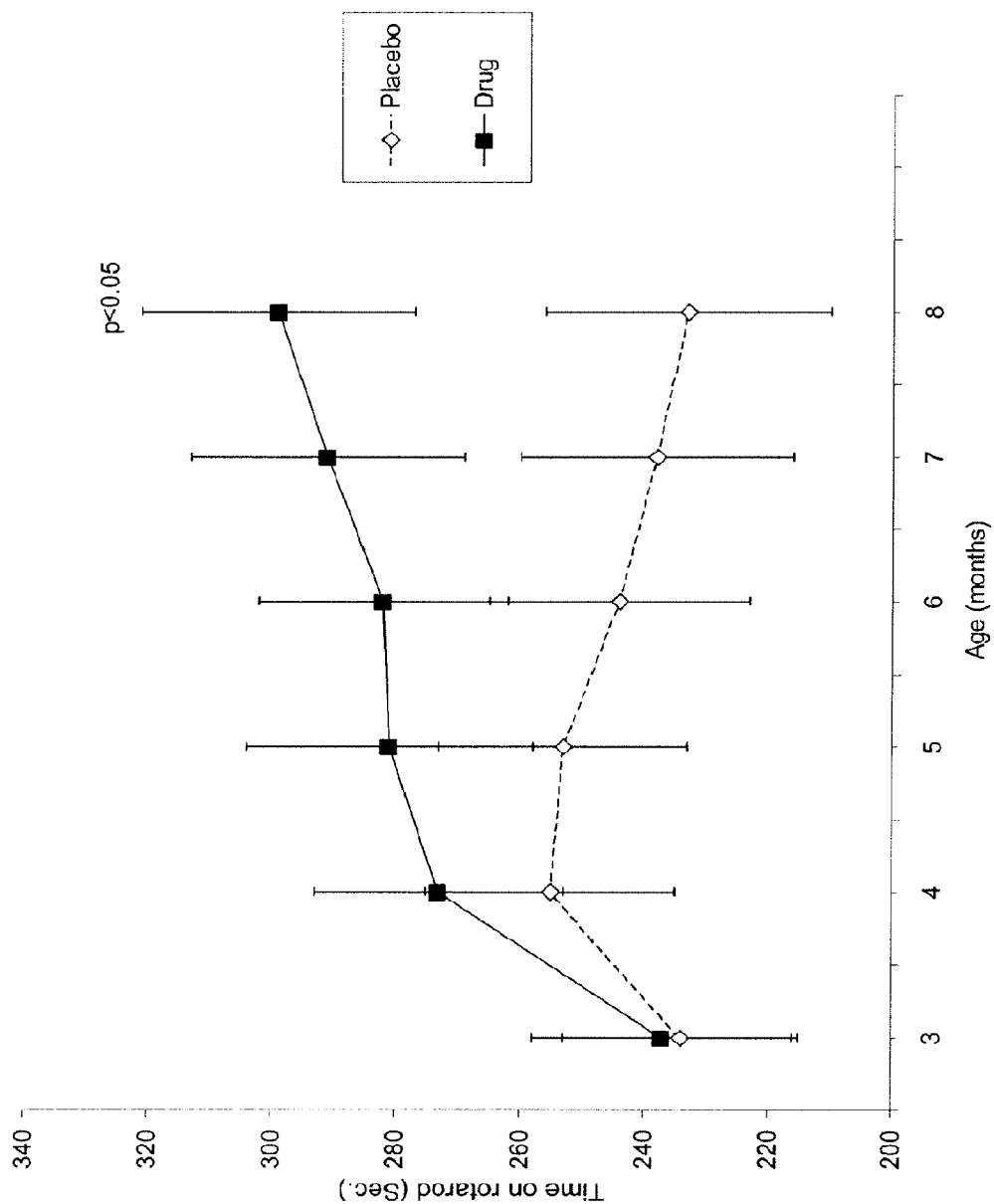
FIG. 3 is a line graph depicting the latency to fall of $FXN^+$, $fxn^{-/-}$ FRDA model mice treated with compound R03 or vehicle control. Eight months, p<0.05.

Coordination was assayed using the rotarod analysis essentially as described in Al-Mahdawi et al. Briefly, treated and control mice were placed on a Ugo-Basille 7650 accelerating rotarod treadmill apparatus. The apparatus was set at a constant rotation speed, and the latency time taken for each mouse to fall from the rod was recorded. The mice performed four trials each, with a 10-minute rest between each trial. The latency to fall increased for the drug-treated mice, whereas the latency to fall for the control mice increased initially and then decreased thereafter (FIG. 3). This experiment indicates that compound R03 was effective to increase coordination of the FRDA model mice.

Figure 4:
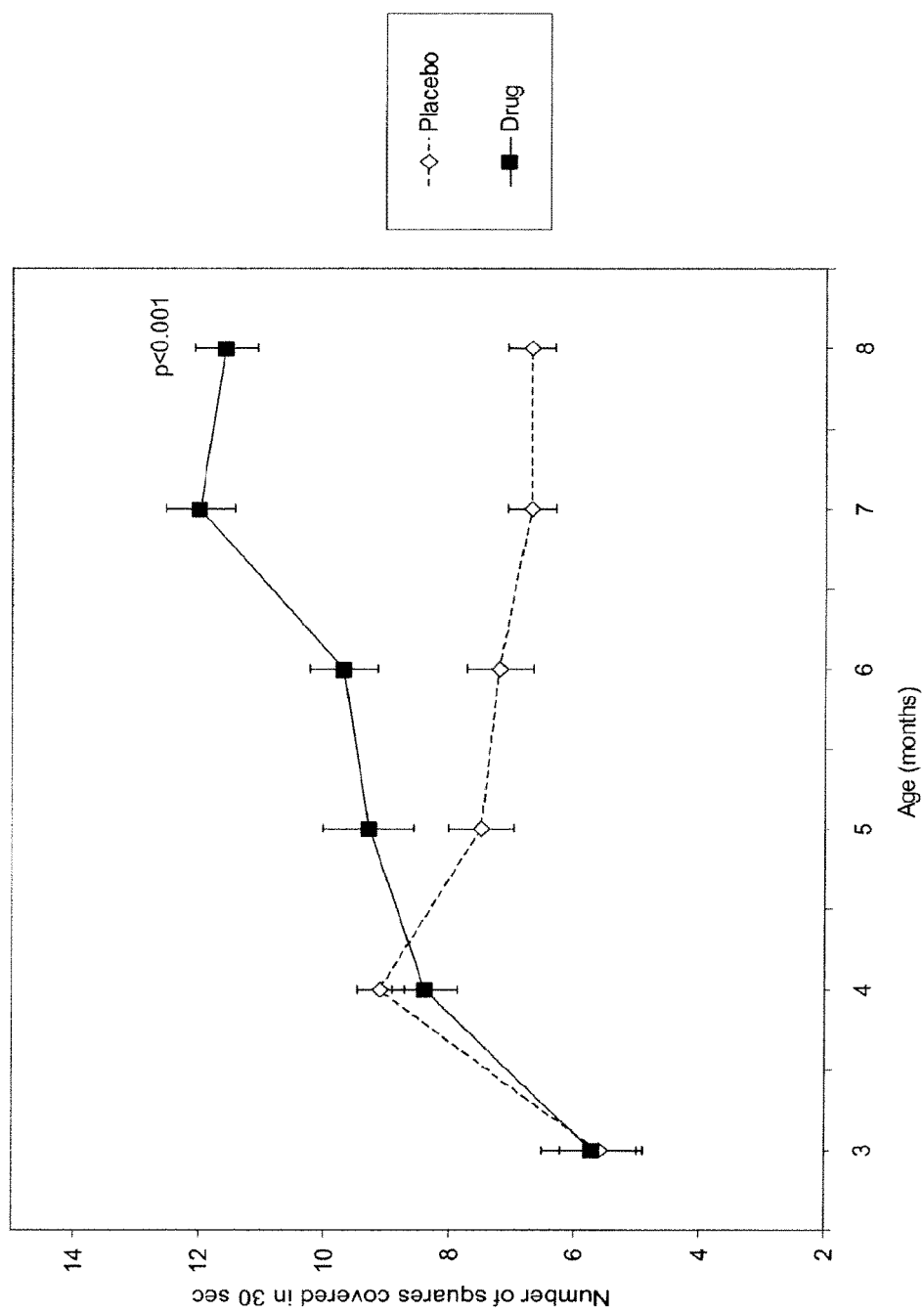
FIG. 4 is a line graph depicting the activity of $FXN^+$, $fxn^{-/-}$ FRDA model mice treated with compound R03 or vehicle control. Eight months, p<0.001.

Activity was assayed by placing the mice in a gridded open-field Persipex box and recording the number of gridded squares entered by each mouse over a 30 second period. Four trials were performed for each mouse at each time point. The number of squares entered per mouse increased over the course of the trial for the drug-treated mice, whereas the activity of the control mice increased initially and then decreased thereafter (FIG. 4). This experiment indicates that compound R03 was effective to increase activity of the FRDA model mice.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating a disorder selected from cutaneous T cell lymphoma, B cell lymphoma, colorectal cancer, psoriasis, rheumatoid arthritis, osteoarthritis, Friedreich's ataxia, myotonic dystrophy, spinal muscular atrophy, fragile X syndrome, Huntington's disease, spinocerebellar ataxia, Kennedy's disease, amyotrophic lateral sclerosis, spinal and bulbar muscular atrophy, and Alzheimer's disease in a patient in need thereof, the method comprising administering to said patient a therapeutically effective amount of a compound having a structure of Formula (I):

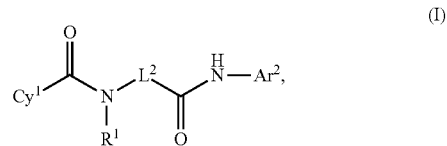

wherein
Ar² is selected from $C_{6-10}$ aryl and benzo[d][1,3]dioxolyl; wherein said $C_{6-10}$ aryl and benzo[d][1,3]dioxolyl are each substituted at one ortho position by $NH_2$ and by m independently selected $R^z$ groups;
L² is selected from straight chain $C_{4-6}$ alkylene and straight chain $C_{4-6}$ alkenylene; wherein 1 or 2 carbon atoms of said straight chain $C_{4-6}$ alkylene, or straight chain $C_{4-6}$ alkenylene is optionally replaced by a group independently selected from —O—, —S—, —S(=O)—, —S(=O)₂—, —C(=O)—, and —NR$^a$—;
each $R^a$ is independently selected from H and $C_{1-3}$ alkyl;
Cy¹ is selected from $C_{6-10}$ aryl and $C_{1-9}$ heteroaryl; each of which is substituted with n independently selected $R^y$ groups;
R¹ is H or $C_{1-4}$ alkyl;
each $R^y$ is independently selected from halogen, cyano, nitro, hydroxyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$ alkylcarbonyl, $C_{1-6}$ haloalkylcarbonyl, $C_{6-10}$ arylcarbonyl, $C_{1-6}$ alkylsulfonyl, sulfonamido, $C_{1-6}$ alkylthio, carbamyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, amino, $C_{1-6}$ alkylamino, di-$C_{1-6}$ alkylamino, $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$ alkylcarbonyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, $C_{1-6}$ alkylamino, di-$C_{1-6}$ alkylamino are each optionally substituted by 1, 2, or 3 independently selected $R^{y'}$ groups; and wherein said $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1, 2, or 3 independently selected $R^{y''}$ groups;
provided that only one $R^y$ is selected from the optionally substituted groups $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;
each $R^z$ is independently selected from halogen, cyano, nitro, hydroxyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{6-10}$ aryloxy, $C_{1-6}$ alkoxycarbonyl, $C_{1-6}$ alkylcarbonyl, carbamyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl) amino, $C_{1-6}$ alkoxycarbonylamino, amino, $C_{1-6}$ alkylamino, di-$C_{1-6}$ alkylamino, $C_{3-7}$ cycloalkyl, $C_{2-6}$ heterocycloalkyl, phenyl, $C_{1-6}$ heteroaryl, $C_{3-7}$ cycloalkyl- $C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$ alkylcarbamyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, $C_{1-6}$ alkylamino, di-$C_{1-6}$ alkylamino are each optionally substituted by 1, 2, or 3 independently selected $R^{z'}$ groups; and wherein said $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1, 2, or 3 independently selected $R^{z''}$ groups;

provided that only one $R^z$ is selected from the optionally substituted groups $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;

each $R^{y'}$ and $R^{z'}$ is independently selected from hydroxyl, cyano, nitro, $C_{1-4}$ alkoxy, $C_{1-4}$ haloalkoxy, amino, $C_{1-4}$ alkylamino, and di-$C_{1-4}$-alkylamino;

each $R^{y'''}$ and $R^{z''}$ is independently selected from halogen, hydroxyl, cyano, nitro, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

n is an integer selected from 0, 1, 2, 3, and 4 when $Cy^1$ is $C_{1-9}$ heteroaryl and n is an integer selected from 1, 2, 3, and 4 when $Cy^1$ is $C_{6-10}$ aryl; and m is an integer selected from 0, 1, 2, and 3;

or pharmaceutically acceptable salt thereof.

2. The method of claim 1, wherein $Cy^1$ is selected from $C_{6-10}$ aryl, which is substituted with n independently selected $R^y$ groups.

3. The method of claim 1, wherein $Cy^1$ is selected from $C_{2-9}$ heteroaryl, which is substituted with n independently selected $R^y$ groups.

4. The method of claim 3, wherein $Cy^1$ is indolyl or indazolyl, each of which is substituted with n independently selected $R^y$ groups.

5. The method of claim 1, wherein $Cy^1$ is phenyl, which is optionally substituted with n independently selected $R^y$ groups.

6. The method of claim 1, wherein $Cy^1$ is $C_{1-6}$ heteroaryl, which is optionally substituted with n independently selected $R^y$ groups.

7. The method of claim 1, wherein $Ar^2$ is phenyl, and said phenyl is substituted at one ortho position by $NH_2$ and by m independently selected $R^z$ groups.

8. The method of claim 7, wherein $R^z$ is selected from halogen, $C_{1-6}$ alkyl, $C_{1-6}$ haloalkyl, $C_{1-6}$ alkoxy, and $C_{1-6}$ haloalkoxy.

9. The method of claim 8, wherein $R^z$ is halogen.

10. The method of claim 4, wherein $L^2$ is straight chain $C_{4-6}$ alkenylene.

11. The method of claim 10, wherein $L^2$ is straight chain $C_{4-6}$ alkenylene having one double bond.

12. The method of claim 1, wherein $R^1$ is hydrogen.

13. The method of claim 1, wherein $Ar^2$ is phenyl; which is substituted at one ortho position by $NH_2$ and by m independently selected $R^z$ groups;

$Cy^1$ is $C_{6-10}$ aryl; which is substituted with n independently selected $R^y$ groups;

each $R^y$ is independently selected from halogen, cyano, nitro, $C_{1-6}$ alkyl, $C_{1-6}$ haloalkyl, $C_{1-6}$ alkoxy, $C_{1-6}$ haloalkoxy, $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{y'}$ groups; and wherein said $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1 or 2 independently selected $R^{y''}$ groups;

provided that only one $R^y$ is selected from the optionally substituted groups $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;

each $R^z$ is independently selected from halogen, cyano, nitro, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{z'}$ groups;

each $R^{y'}$ and $R^{z'}$ is independently selected from hydroxyl, cyano, nitro, $C_{1-4}$ alkoxy, and $C_{1-4}$ haloalkoxy;

each $R^{y''}$ is independently selected from halogen, hydroxyl, cyano, nitro, $C_{1-4}$ alkyl, $C_{1-4}$ haloalkyl, $C_{1-4}$ alkoxy, and $C_{1-4}$ haloalkoxy;

n is an integer selected from 1, 2, and 3; and m is an integer selected from 0, 1, and 2.

14. The method of claim 1, wherein $Ar^2$ is phenyl; which is substituted at one ortho position by $NH_2$ and by m independently selected $R^z$ groups;

$Cy^1$ is $C_{1-9}$ heteroaryl; which is substituted with n independently selected $R^y$ groups;

each $R^y$ is independently selected from halogen, $C_{1-6}$ alkyl, $C_{1-6}$ haloalkyl, $C_{1-6}$ alkoxy, $C_{1-6}$ haloalkoxy, $C_{3-7}$ cycloalkyl, and $C_{2-6}$ heterocycloalkyl; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{y'}$ groups; and wherein said $C_{3-7}$ cycloalkyl and $C_{2-6}$ heterocycloalkyl are each optionally substituted by 1 or 2 independently selected $R^{y''}$ groups;

provided that only one $R^y$ is selected from the optionally substituted groups $C_{3-7}$ cycloalkyl and $C_{2-6}$ heterocycloalkyl;

each $R^z$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1 or 2 independently selected $R^{z'}$ groups;

each $R^{y'}$ and $R^{z'}$ is independently selected from hydroxyl, $C_{1-4}$ alkoxy, and $C_{1-4}$ haloalkoxy;

each $R^{y''}$ is independently selected from halogen, hydroxyl, $C_{1-4}$ alkyl, $C_{1-4}$ haloalkyl, $C_{1-4}$ alkoxy, and $C_{1-4}$ haloalkoxy;

n is an integer selected from 0, 1, and 2; and m is an integer selected from 0, 1 and 2.

15. The method of claim 1, wherein $Ar^2$ is phenyl; which is substituted at one ortho position by $NH_2$ and by m independently selected $R^z$ groups;

$L^2$ is selected from unsubstituted straight chain $C_4$ alkylene, and unsubstituted straight chain $C_5$ alkylene, and unsubstituted straight chain $C_6$ alkylene;

$Cy^1$ is phenyl; which is substituted with 1, 2, or 3 independently selected $R^y$ groups;

each $R^y$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1, 2, or 3 independently selected $R^{y'}$ groups;

each $R^z$ is independently selected from halogen, $C_{1-6}$ alkyl, $C_{1-6}$ haloalkyl, $C_{1-6}$ alkoxy, and $C_{1-6}$ haloalkoxy; wherein said $C_{1-6}$ alkyl, $C_{1-6}$ haloalkyl, $C_{1-6}$ alkoxy, and $C_{1-6}$ haloalkoxy are each optionally substituted by 1 or 2 independently selected $R^{z'}$ groups;

each $R^{y'}$ and $R^{z'}$ is independently selected from hydroxyl, $C_{1-4}$ alkoxy, and $C_{1-4}$ haloalkoxy;

each $R^{y''}$ is independently selected from halogen, hydroxyl, $C_{1-4}$ alkyl, $C_{1-4}$ haloalkyl, $C_{1-4}$ alkoxy, and $C_{1-4}$ haloalkoxy; and m is an integer selected from 0, 1 and 2.

16. The method of claim 1, wherein
$Ar^2$ is phenyl; which is substituted at one ortho position by $NH_2$ and by m independently selected $R^z$ groups;
$L^2$ is —$CH_2CH_2CH_2CH_2CH_2$—;
$Cy^1$ is phenyl; which is substituted with n independently selected $R^y$ groups;
$R^1$ is H;
each $R^y$ is independently selected from halogen and $C_{1-6}$ alkyl;
each $R^z$ is independently selected from halogen; and
m is 0 or 1.

17. The method of claim 1, wherein the compound is selected from the group consisting of:
- N-(6-(2-aminophenylamino)-6-oxohexyl)-4-methylbenzamide;
- N-(6-(2-amino-4-fluorophenylamino)-6-oxohexyl)-4-methylbenzamide;
- N-(6-(2-amino-5-fluorophenylamino)-6-oxohexyl)-4-fluorobenzamide;
- N-(6-(2-amino-4-fluorophenylamino)-6-oxohexyl)-4-fluorobenzamide;
- N-(6-(2-amino-5-fluorophenylamino)-6-oxohexyl)-4-methylbenzamide;
- N-(6-(2-amino-4-fluorophenylamino)-6-oxohexyl)-4-fluoro-N-methylbenzamide;
- N-(5-(2-aminophenylamino)-5-oxopentyl)-4-methylbenzamide;
- N-(7-(2-aminophenylamino)-7-oxoheptyl)-4-methylbenzamide;
- N-(6-(2-amino-5-methoxyphenylamino)-6-oxohexyl)-4-methylbenzamide;
- N-(2-(3-(2-aminophenylamino)-3-oxopropoxy)ethyl)-4-methylbenzamide;
- N-(6-(2-amino-4-fluoro-5-(piperidin-1-yl)phenylamino)-6-oxohexyl)-4-methylbenzamide;
- N-(6-(2-aminophenylamino)-6-oxohexyl)-4-fluorobenzamide;
- N-(6-(2-aminophenylamino)-6-oxohexyl)-4-chlorobenzamide;
- N-(6-(2-aminophenylamino)-6-oxohexyl)-3,4-dichlorobenzamide;
- N-(6-(2-aminophenylamino)-6-oxohexyl)-4-methoxybenzamide;
- N-(6-(2-aminophenylamino)-6-oxohexyl)-3-chlorobenzamide;
- N-(6-(2-aminophenylamino)-6-oxohexyl)-4-(dimethylamino)benzamide;
- N-(6-(2-aminophenylamino)-6-oxohexyl)-4-tert-butylbenzamide;
- N-(6-(2-aminophenylamino)-6-oxohexyl)-4-(trifluoromethyl)benzamide;
- N-(6-(2-aminophenylamino)-6-oxohexyl)-4-nitrobenzamide;
- N-(6-(2-aminophenylamino)-6-oxohexyl)-3-nitrobenzamide;
- N-(6-(2-aminophenylamino)-6-oxohexyl)-3-(trifluoromethyl)benzamide;
- N-(6-(2-aminophenylamino)-6-oxohexyl)-4-cyanobenzamide;
- N-(6-(2-aminophenylamino)-6-oxohexyl)-3,5-dichlorobenzamide;
- N-(6-(2-amino-5-fluoro-4-(piperidin-1-yl)phenylamino)-6-oxohexyl)-4-methylbenzamide;
- N-(6-(2-amino-4-hydroxyphenylamino)-6-oxohexyl)-4-methylbenzamide;
- N-(6-(2,4-diaminophenylamino)-6-oxohexyl)-4-methylbenzamide;
- N-(6-(2-amino-4,5-dimethylphenylamino)-6-oxohexyl)-4-methylbenzamide;
- N-(6-(2-amino-4-chlorophenylamino)-6-oxohexyl)-4-methylbenzamide;
- N-(6-(2-amino-4-fluoro-5-(1H-pyrazol-1-yl)phenylamino)-6-oxohexyl)-4-methylbenzamide;
- N-(6-(2-amino-4-bromophenylamino)-6-oxohexyl)-4-methylbenzamide;
- N-(6-(4-aminobenzo[d][1,3]dioxol-5-ylamino)-6-oxohexyl)-4-methylbenzamide;
- N-(6-(2-amino-4-fluoro-5-morpholinophenylamino)-6-oxohexyl)-4-methylbenzamide;
- N-(6-(3-aminonaphthalen-2-ylamino)-6-oxohexyl)-4-methylbenzamide;
- N-(2-(3-(2-aminophenylamino)-3-oxopropylamino)ethyl)-4-methylbenzamide;
- N-(6-(2-aminophenylamino)-6-oxohexyl)-2,4-dichlorobenzamide;
- N-(6-(2-aminophenylamino)-6-oxohexyl)-4-(methylsulfonyl)benzamide;
- N-(6-(2-aminophenylamino)-6-oxohexyl)-4-sulfamoylbenzamide;
- N-(6-(2-aminophenylamino)-6-oxohexyl)-3-(1H-tetrazol-5-yl)benzamide;
- N-(6-(2-aminophenylamino)-6-oxohexyl)-4-(1H-tetrazol-5-yl)benzamide;
- N-(6-(2-aminophenylamino)-6-oxohexyl)-4-(1H-pyrrol-1-yl)benzamide;
- N-(5-(2-aminophenylamino)-5-oxopentyl)-4-(methylsulfonyl)benzamide;
- N-(6-(2-aminophenylamino)-6-oxohexyl)-2-methylbenzamide;
- N-(6-(2-aminophenylamino)-6-oxohexyl)-3-ethylbenzamide;
- N-(6-(2-aminophenylamino)-6-oxohexyl)-4-ethylbenzamide;
- N-(6-(2-aminophenylamino)-6-oxohexyl)-3,4-dimethylbenzamide;
- N-(6-(2-aminophenylamino)-6-oxohexyl)-4-propylbenzamide;
- N-(6-(2-aminophenylamino)-6-oxohexyl)-4-isopropylbenzamide;
- N-(6-(2-aminophenylamino)-6-oxohexyl)-4-cyclopropylbenzamide;
- N-(6-(2-aminophenylamino)-6-oxohexyl)-4-(hydroxymethyl)benzamide;
- N-(6-(2-aminophenylamino)-6-oxohexyl)-2-(dimethylamino)benzamide;
- N-(6-(2-aminophenylamino)-6-oxohexyl)-2,4-difluorobenzamide;

N-(6-(2-aminophenylamino)-6-oxohexyl)-2-ethylbenzamide;
N-(6-(2-aminophenylamino)-6-oxohexyl)-3-(dimethylamino)benzamide;
N-(6-(2-aminophenylamino)-6-oxohexyl)-3-(trifluoromethoxy)benzamide;
N-(6-(2-aminophenylamino)-6-oxohexyl)-4-(trifluoromethoxy)benzamide;
N-(6-(2-aminophenylamino)-6-oxohexyl)-4-(ethylamino)benzamide;
N-(6-(2-aminophenylamino)-6-oxohexyl)-3-methylbenzamide;
N-(6-(2-aminophenylamino)-6-oxohexyl)-2,4-dimethylbenzamide;
N-(6-(2-aminophenylamino)-6-oxohexyl)-4-(difluoromethyl)benzamide;
N-(6-(2-aminophenylamino)-6-oxohexyl)-4-(2-hydroxypropan-2-yl)benzamide;
N-(6-(2-aminophenylamino)-6-oxohexyl)-4-(azetidin-1-yl)benzamide;
N-(6-(2-aminophenylamino)-6-oxohexyl)-3-(4-methylpiperazin-1-yl)benzamide;
N-(6-(2-aminophenylamino)-6-oxohexyl)-2-(4-methylpiperazin-1-yl)benzamide;
N-(6-(2-aminophenylamino)-6-oxohexyl)-4-morpholinobenzamide;
N-(6-(2-aminophenylamino)-6-oxohexyl)-2-chlorobenzamide;
N-(6-(2-aminophenylamino)-6-oxohexyl)-3,4-difluorobenzamide;
N-(6-(2-aminophenylamino)-6-oxohexyl)-2-cyclohexylbenzamide;
N-(6-(2-aminophenylamino)-6-oxohexyl)-2-(methoxymethyl)benzamide;
2-allyl-N-(6-(2-aminophenylamino)-6-oxohexyl)benzamide;
N-(6-(2-aminophenylamino)-6-oxohexyl)-2-(2,2,2-trifluoroacetyl)benzamide;
N-(6-(2-aminophenylamino)-6-oxohexyl)-2-ethoxybenzamide;
N-(6-(2-aminophenylamino)-6-oxohexyl)-2-propoxybenzamide;
N-(6-(2-aminophenylamino)-6-oxohexyl)-2-(ethylthio)benzamide;
N-(6-(2-aminophenylamino)-6-oxohexyl)-2-(methylsulfonyl)benzamide;
N-(6-(2-aminophenylamino)-6-oxohexyl)-2-cyanobenzamide;
2-acetyl-N-(6-(2-aminophenylamino)-6-oxohexyl)benzamide;
N-(6-(2-aminophenylamino)-6-oxohexyl)-2-benzoylbenzamide;
N-(6-(2-aminophenylamino)-6-oxohexyl)biphenyl-2-carboxamide;
N-(6-(2-aminophenylamino)-6-oxohexyl)-2-(difluoromethoxy)benzamide;
N-(6-(2-aminophenylamino)-6-oxohexyl)-2-(2-methoxyethoxy)benzamide;
N-(6-(2-aminophenylamino)-6-oxohexyl)-2-(trifluoromethyl)benzamide;
N-(6-(2-aminophenylamino)-6-oxohexyl)-2-fluorobenzamide;
N-(6-(2-aminophenylamino)-6-oxohexyl)-2-methoxybenzamide;
N-(6-(2-aminophenylamino)-6-oxohexyl)-2-bromobenzamide;
N-(6-(2-aminophenylamino)-6-oxohexyl)-4-(methylamino)benzamide;
N-(6-(2-aminophenylamino)-6-oxohexyl)-4-(cyclopropylamino)benzamide;
N-(6-(2-aminophenylamino)-6-oxohexyl)-4-(4-methylpiperazin-1-yl)benzamide;
(E)-N-(6-(2-aminophenylamino)-6-oxohex-3-enyl)-4-methylbenzamide;
(E)-N-(6-(2-aminophenylamino)-6-oxohex-3-enyl)-4-methoxybenzamide;
(E)-N-(6-(2-aminophenylamino)-6-oxohex-3-enyl)-4-fluorobenzamide;
(E)-N-(6-(2-aminophenylamino)-6-oxohex-3-enyl)-3-chlorobenzamide;
(E)-N-(6-(2-aminophenylamino)-6-oxohex-4-enyl)-4-morpholinobenzamide;
(E)-N-(6-(2-aminophenylamino)-6-oxohex-4-enyl)-4-(dimethylamino)benzamide;
(E)-N-(6-(2-aminophenylamino)-6-oxohex-4-enyl)-4-methoxybenzamide;
(E)-N-(6-(2-aminophenylamino)-6-oxohex-4-enyl)-3-chlorobenzamide;
(E)-N-(6-(2-aminophenylamino)-6-oxohex-4-enyl)-4-fluorobenzamide;
(E)-N-(6-(2-aminophenylamino)-6-oxohex-4-enyl)-4-methylbenzamide;
N-(6-(2-aminophenylamino)-6-oxohexyl)-3-(difluoromethoxy)benzamide;
N-(6-(2-aminophenylamino)-6-oxohexyl)-3-cyanobenzamide;
N-(6-(2-aminophenylamino)-6-oxohexyl)-3-morpholinobenzamide;
N-(6-(2-aminophenylamino)-6-oxohexyl)-3-ethoxybenzamide; and
N-(6-(2-aminophenylamino)-6-oxohexyl)-3-nitrobenzamide;

or a pharmaceutically acceptable salt thereof.

18. The method of claim 1, wherein the compound is selected from the group consisting of:
N-(2-amino-4-fluorophenyl)-6-(thiazol-2-ylcarbonylamino)hexanamide;
N-(2-amino-5-fluorophenyl)-6-(thiazol-2-ylcarbonylamino)hexanamide;
N-(6-(2-amino-4-fluorophenylamino)-6-oxohexyl)benzofuran-2-carboxamide;
N-(6-(2-amino-4-fluorophenylamino)-6-oxohexyl)picolinamide;
N-(6-(2-amino-4-fluorophenylamino)-6-oxohexyl)nicotinamide;
N-(6-(2-amino-5-phenoxyphenylamino)-6-oxohexyl)nicotinamide;
N-(7-(4-aminobiphenyl-3-ylamino)-7-oxoheptyl)nicotinamide;
N-(7-(2-amino-5-(thiophen-2-yl)phenylamino)-7-oxoheptyl)nicotinamide;
N-(6-(2-aminophenylamino)-6-oxohexyl)thiophene-2-carboxamide;
N-(6-(2-aminophenylamino)-6-oxohexyl)thiazole-2-carboxamide;
N-(6-(2-aminophenylamino)-6-oxohexyl)-4-methylthiazole-2-carboxamide;
N-(6-(2-aminophenylamino)-6-oxohexyl)-5-methylthiazole-2-carboxamide;
N-(6-(2-aminophenylamino)-6-oxohexyl)isonicotinamide;
N-(6-(2-aminophenylamino)-6-oxohexyl)pyrazine-2-carboxamide;

N-(6-(2-aminophenylamino)-6-oxohexyl)pyridazine-4-carboxamide;
N-(6-(2-aminophenylamino)-6-oxohexyl)furan-2-carboxamide;
N-(6-(2-aminophenylamino)-6-oxohexyl)furan-3-carboxamide;
N-(6-(2-aminophenylamino)-6-oxohexyl)thiophene-2-carboxamide;
N-(6-(2-aminophenylamino)-6-oxohexyl)thiophene-3-carboxamide;
N-(6-(2-aminophenylamino)-6-oxohexyl)-1H-pyrrole-2-carboxamide;
N-(6-(2-aminophenylamino)-6-oxohexyl)-4H-1,2,4-triazole-3-carboxamide;
N-(6-(2-aminophenylamino)-6-oxohexyl)isoxazole-5-carboxamide;
N-(6-(2-aminophenylamino)-6-oxohexyl)thiazole-4-carboxamide;
N-(6-(2-aminophenylamino)-6-oxohexyl)-2-(piperidin-1-yl)isonicotinamide;
N-(6-(2-aminophenylamino)-6-oxohexyl)-3-phenyl-1H-pyrazole-5-carboxamide;
N-(6-(2-aminophenylamino)-6-oxohexyl)benzofuran-2-carboxamide;
N-(6-(2-aminophenylamino)-6-oxohexyl)benzo[d]thiazole-6-carboxamide;
N-(6-(2-aminophenylamino)-6-oxohexyl)benzo[c][1,2,5]oxadiazole-5-carboxamide;
N-(6-(2-aminophenylamino)-6-oxohexyl)quinoxaline-6-carboxamide;
N-(6-(2-aminophenylamino)-6-oxohexyl)quinoline-7-carboxamide;
N-(6-(2-aminophenylamino)-6-oxohexyl)-5-(thiophen-3-yl)isoxazole-3-carboxamide;
N-(6-(2-aminophenylamino)-6-oxohexyl)-1H-indole-2-carboxamide;
N-(6-(2-aminophenylamino)-6-oxohexyl)-1H-indole-5-carboxamide;
N-(6-(2-aminophenylamino)-6-oxohexyl)-5-methoxy-1H-indole-2-carboxamide;
N-(6-(2-aminophenylamino)-6-oxohexyl)-5-cyclopropylisoxazole-3-carboxamide;
N-(6-(2-aminophenylamino)-6-oxohexyl)-1H-indazole-3-carboxamide;
N-(6-(2-aminophenylamino)-6-oxohexyl)isoquinoline-3-carboxamide;
N-(6-(2-aminophenylamino)-6-oxohexyl)quinoline-3-carboxamide;
N-(6-(2-aminophenylamino)-6-oxohexyl)cinnoline-4-carboxamide;
N-(6-(2-aminophenylamino)-6-oxohexyl)quinoxaline-2-carboxamide;
N-(6-(2-aminophenylamino)-6-oxohexyl)-2-(pyridin-4-yl)thiazole-4-carboxamide;
N-(6-(2-aminophenylamino)-6-oxohexyl)-4-methyl-2-(pyridin-3-yl)thiazole-5-carboxamide;
N-(6-(2-aminophenylamino)-6-oxohexyl)-4-methyl-2-(pyridin-2-yl)thiazole-5-carboxamide;
N-(5-(2-aminophenylamino)-5-oxopentyl)-5-methylthiazole-2-carboxamide;
N-(5-(2-aminophenylamino)-5-oxopentyl)-2,6-dimethoxynicotinamide;
N-(5-(2-aminophenylamino)-5-oxopentyl)-5-methoxy-1H-indole-2-carboxamide;
N-(5-(2-aminophenylamino)-5-oxopentyl)benzo[d]thiazole-6-carboxamide;
N-(5-(2-aminophenylamino)-5-oxopentyl)-2-(pyridin-4-yl)thiazole-4-carboxamide;
N-(5-(2-aminophenylamino)-5-oxopentyl)-2-(piperidin-1-yl)isonicotinamide;
N-(5-(2-aminophenylamino)-5-oxopentyl)isoxazole-5-carboxamide;
N-(5-(2-aminophenylamino)-5-oxopentyl)-5-phenyl-4H-pyrazole-3-carboxamide;
N-(5-(2-aminophenylamino)-5-oxopentyl)-3-(1-methyl-1H-pyrazol-4-yl)isoxazole-5-carboxamide;
N-(6-(2-aminophenylamino)-6-oxohexyl)-3-methyl-1H-indole-2-carboxamide;
N-(6-(2-aminophenylamino)-6-oxohexyl)-4-methoxy-1H-indole-2-carboxamide;
N-(6-(2-aminophenylamino)-6-oxohexyl)-4-ethoxy-1H-indole-2-carboxamide;
N-(6-(2-aminophenylamino)-6-oxohexyl)-4-fluoro-1H-indole-2-carboxamide;
N-(6-(2-aminophenylamino)-6-oxohexyl)-4-chloro-1H-indole-2-carboxamide;
N-(6-(2-aminophenylamino)-6-oxohexyl)-5-methyl-1H-indole-2-carboxamide;
N-(6-(2-aminophenylamino)-6-oxohexyl)-5-cloro-1H-indole-2-carboxamide;
N-(6-(2-aminophenylamino)-6-oxohexyl)-7-methoxy-1H-indole-2-carboxamide;
N-(6-(2-aminophenylamino)-6-oxohexyl)-7-methy-1H-indole-2-carboxamide;
N-(6-(2-aminophenylamino)-6-oxohexyl)-7-fluoro-1H-indole-2-carboxamide;
N-(6-(2-aminophenylamino)-6-oxohexyl)-6-(dimethylamino)-1H-indole-2-carboxamide;
N-(6-(2-aminophenylamino)-6-oxohexyl)-4-(difluoromethoxy)-1H-indole-2-carboxamide;
N-(6-(2-aminophenylamino)-6-oxohexyl)-1-methyl-1H-indole-2-carboxamide;
N-(6-(2-aminophenylamino)-6-oxohexyl)-5-methoxy-1-methyl-1H-indole-2-carboxamide;
N-(6-(2-aminophenylamino)-6-oxohexyl)-5-fluoro-1-methyl-1H-indole-2-carboxamide;
N-(6-(2-aminophenylamino)-6-oxohexyl)-5-chloro-1-methyl-1H-indole-2-carboxamide;
N-(6-(2-aminophenylamino)-6-oxohexyl)-1,5-dimethyl-1H-indole-2-carboxamide;
N-(6-(2-aminophenylamino)-6-oxohexyl)-1-(2-methoxyethyl)-1H-indole-2-carboxamide;
N-(6-(2-aminophenylamino)-6-oxohexyl)-7-methoxy-1H-indole-3-carboxamide;
N-(6-(2-aminophenylamino)-6-oxohexyl)-1-methyl-1H-indole-6-carboxamide;
N-(6-(2-aminophenylamino)-6-oxohexyl)-2,3-dimethyl-1H-indole-7-carboxamide;
N-(6-(2-aminophenylamino)-6-oxohexyl)-1-methyl-1H-indole-3-carboxamide;
N-(6-(2-aminophenylamino)-6-oxohexyl)-5-ethoxy-1H-indole-2-carboxamide;
N-(6-(2-aminophenylamino)-6-oxohexyl)-2,3-dimethyl-1H-indole-5-carboxamide;
N-(6-(2-aminophenylamino)-6-oxohexyl)-7-chloro-1H-indole-3-carboxamide;
N-(6-(2-aminophenylamino)-6-oxohexyl)-1H-indole-3-carboxamide;
N-(6-(2-aminophenylamino)-6-oxohexyl)-5-methoxy-1H-indole-3-carboxamide;
N-(6-(2-aminophenylamino)-6-oxohexyl)-6-methoxy-1H-indole-3-carboxamide;
N-(6-(2-aminophenylamino)-6-oxohexyl)-1H-indole-4-carboxamide;
N-(6-(2-aminophenylamino)-6-oxohexyl)-1-methyl-1H-indole-4-carboxamide;

N-(6-(2-aminophenylamino)-6-oxohexyl)-1H-indole-5-carboxamide;
N-(6-(2-aminophenylamino)-6-oxohexyl)-1-methyl-1H-indole-5-carboxamide;
N-(6-(2-aminophenylamino)-6-oxohexyl)-1-methyl-1H-indazole-3-carboxamide;
N-(6-(2-aminophenylamino)-6-oxohexyl)-1H-indazole-7-carboxamide;
N-(6-(2-aminophenylamino)-6-oxohexyl)-4-methoxy-1H-indole-3-carboxamide;
N-(6-(2-aminophenylamino)-6-oxohexyl)-1H-indole-7-carboxamide;
N-(6-(2-aminophenylamino)-6-oxohexyl)-1H-indazole-6-carboxamide;
N-(6-(2-aminophenylamino)-6-oxohexyl)-6-methoxy-1H-indole-2-carboxamide;
N-(6-(2-aminophenylamino)-6-oxohexyl)-6-methyl-1H-indole-2-carboxamide;
N-(6-(2-aminophenylamino)-6-oxohexyl)-5-ethoxy-1-methyl-1H-indole-2-carboxamide;
N-(6-(2-aminophenylamino)-6-oxohexyl)-2,3-dimethyl-1H-indole-6-carboxamide;
N-(6-(2-aminophenylamino)-6-oxohexyl)-5-methyl-1H-indazole-3-carboxamide;
N-(6-(2-aminophenylamino)-6-oxohexyl)-5-chloro-1H-indole-3-carboxamide; and
N-(6-(2-aminophenylamino)-6-oxohexyl)-1H-indole-6-carboxamide;
or a pharmaceutically acceptable salt thereof.

19. A method of treating Friedreich's ataxia in a patient in need thereof, the method comprising administering to said patient a therapeutically effective amount of a compound having a structure of Formula (I):

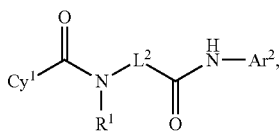

wherein
$Ar^2$ is selected from $C_{6-10}$ aryl and benzo[d][1,3]dioxolyl; wherein said $C_{6-10}$ aryl and benzo[d][1,3]dioxolyl are each substituted at one ortho position by $NH_2$ and by m independently selected $R^z$ groups;
$L^2$ is selected from straight chain $C_{4-6}$ alkylene and straight chain $C_{4-6}$ alkenylene; wherein 1 or 2 carbon atoms of said straight chain $C_{4-6}$ alkylene, or straight chain $C_{4-6}$ alkenylene is optionally replaced by a group independently selected from —O—, —S—, —S(=O)—, —S(=O)$_2$—, —C(=O)—, and —NR$^a$—;
each $R^a$ is independently selected from H and $C_{1-3}$ alkyl;
$Cy^1$ is selected from $C_{6-10}$ aryl and $C_{1-9}$ heteroaryl; each of which is substituted with n independently selected $R^y$ groups;
$R^1$ is H or $C_{1-4}$ alkyl;
each $R^y$ is independently selected from halogen, cyano, nitro, hydroxyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$ alkylcarbonyl, $C_{1-6}$ haloalkylcarbonyl, $C_{6-10}$ arylcarbonyl, $C_{1-6}$ alkylsulfonyl, sulfonamido, $C_{1-6}$ alkylthio, carbamyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, amino, $C_{1-6}$ alkylamino, di-$C_{1-6}$ alkylamino, $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$ alkylcarbonyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, $C_{1-6}$ alkylamino, di-$C_{1-6}$ alkylamino are each optionally substituted by 1, 2, or 3 independently selected $R^{y'}$ groups; and wherein said $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1, 2, or 3 independently selected $R^{y''}$ groups;
provided that only one $R^y$ is selected from the optionally substituted groups $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;
each $R^z$ is independently selected from halogen, cyano, nitro, hydroxyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{6-10}$ aryloxy, $C_{1-6}$ alkoxycarbonyl, $C_{1-6}$ alkylcarbonyl, carbamyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, amino, $C_{1-6}$ alkylamino, di-$C_{1-6}$ alkylamino, $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl; wherein said $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxycarbonyl, $C_{1-6}$ alkylcarbonyl, $C_{1-6}$ alkylcarbamyl, di-$C_{1-6}$ alkylcarbamyl, $C_{1-6}$ alkylcarbonylamino, $C_{1-6}$ alkylcarbonyl-($C_{1-4}$-alkyl)amino, $C_{1-6}$ alkoxycarbonylamino, $C_{1-6}$ alkylamino, di-$C_{1-6}$ alkylamino are each optionally substituted by 1, 2, or 3 independently selected $R^{z'}$ groups; and wherein said $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl are each optionally substituted by 1, 2, or 3 independently selected $R^{z''}$ groups;
provided that only one R is selected from the optionally substituted groups $C_{3-7}$ cycloalkyl, $C_{2-6}$ heterocycloalkyl, phenyl, $C_{1-6}$ heteroaryl, $C_{3-7}$ cycloalkyl-$C_{1-4}$-alkyl, $C_{2-6}$ heterocycloalkyl-$C_{1-4}$-alkyl, phenyl-$C_{1-4}$-alkyl, and $C_{1-6}$ heteroaryl-$C_{1-4}$-alkyl;
each $R^{y'}$ and $R^{z'}$ is independently selected from hydroxyl, cyano, nitro, $C_{1-4}$ alkoxy, $C_{1-4}$ haloalkoxy, amino, $C_{1-4}$ alkylamino, and di-$C_{1-4}$-alkylamino;
each $R^{y''}$ and $R^{z''}$ is independently selected from halogen, hydroxyl, cyano, nitro, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;
n is an integer selected from 0, 1, 2, 3, and 4 when $Cy^1$ is $C_{1-9}$ heteroaryl and n is an integer selected from 1, 2, 3, and 4 when $Cy^1$ is $C_{6-10}$ aryl; and
m is an integer selected from 0, 1, 2, and 3;
or pharmaceutically acceptable salt thereof.

* * * * *

UNITED STATES PATENT AND TRADEMARK OFFICE
CERTIFICATE OF CORRECTION

PATENT NO. : 9,796,664 B2  
APPLICATION NO. : 14/993621  
DATED : October 24, 2017  
INVENTOR(S) : James R. Rusche et al.

Page 1 of 1

It is certified that error appears in the above-identified patent and that said Letters Patent is hereby corrected as shown below:

In the Claims

At Column 219, Line 55, "claim 4," should be -- claim 1, --.

At Column 226, after Line 19, insert -- N-( 6-(2-aminophenylamino )-6-oxohexyl)-5-(trifluoromethoxy )-1H-indole-2-carboxamide; --.

At Column 226, after Line 21, insert -- N-( 6-(2-aminophenylamino )-6-oxohexyl)-5-fluoro-1H-indole-2-carboxamide; --.

At Column 226, Line 22, "cloro" should be -- chloro --.

At Column 228, Line 49, "R" should be -- Rz --.

Signed and Sealed this  
Nineteenth Day of June, 2018

Andrei Iancu  
*Director of the United States Patent and Trademark Office*